(12) United States Patent
Billen et al.

(10) Patent No.: US 7,968,584 B2
(45) Date of Patent: *Jun. 28, 2011

(54) SUBSTITUTED ARYLPYRAZOLES

(75) Inventors: Denis Billen, Sandwich (GB); Jessica Boyle, Sandwich (GB); Douglas James Critcher, Sandwich (GB); David Morris Gethin, Sandwich (GB); Kim Thomas Hall, Sandwich (GB); Graham Michael Kyne, Sandwich (GB)

(73) Assignees: Pfizer Inc., New York, NY (US); Pfizer Products Inc., Groton, CT (US)

( * ) Notice: Subject to any disclaimer, the term of this patent is extended or adjusted under 35 U.S.C. 154(b) by 196 days.

This patent is subject to a terminal disclaimer.

(21) Appl. No.: 12/407,365

(22) Filed: Mar. 19, 2009

(65) Prior Publication Data

US 2009/0186924 A1    Jul. 23, 2009

Related U.S. Application Data

(62) Division of application No. 11/453,053, filed on Jun. 14, 2006, now Pat. No. 7,538,134.

(60) Provisional application No. 60/690,651, filed on Jun. 15, 2005.

(51) Int. Cl.
 *A61K 31/415*  (2006.01)
 *C07D 231/10*  (2006.01)

(52) U.S. Cl. ............... 514/406; 548/373.1; 548/377.1; 514/403

(58) Field of Classification Search ........... 548/373.1, 548/377.1; 514/403, 406
See application file for complete search history.

(56) References Cited

U.S. PATENT DOCUMENTS

| | | | |
|---|---|---|---|
| 6,090,394 A | 7/2000 | Banks | |
| 6,106,864 A | 8/2000 | Dolan et al. | |
| 6,268,509 B1 | 7/2001 | Banks | |
| 7,435,753 B2 | 10/2008 | Billen et al. | |
| 7,514,464 B2 * | 4/2009 | Billen et al. | 514/406 |
| 7,538,134 B2 * | 5/2009 | Billen et al. | 514/406 |
| 7,645,786 B2 * | 1/2010 | Billen et al. | 514/406 |
| 2004/0013980 A1 | 1/2004 | Hatakeyama et al. | |

FOREIGN PATENT DOCUMENTS

| | | |
|---|---|---|
| EP | 0 605 469 | 2/1998 |
| EP | 0 959 071 | 11/1999 |
| EP | 0 933 363 | 8/2003 |
| WO | 91/11172 | 8/1991 |
| WO | 92/06973 | 4/1992 |
| WO | 93/06089 | 4/1993 |
| WO | 94/02518 | 2/1994 |
| WO | 97/07102 | 2/1997 |
| WO | 98/04530 | 2/1998 |
| WO | 98/24767 | 6/1998 |
| WO | 98/55148 | 10/1998 |
| WO | 00/35298 | 6/2000 |
| WO | 2005/060749 | 7/2005 |
| WO | 2005/090313 | 9/2005 |

OTHER PUBLICATIONS

Haleblian, "Characterization of Habits and Crystalline Modification of Solids and Their Pharmaceutical Applications", Journal of Pharmaceutical Sciences, 64(8):1269-1288, 1975.

Dolbier et al., "Trimethylsilyl fluorosulfonyldifluoroacetate (TFDA): a new, highly efficient difluorocarbene reagent", Journal of Fluorine Chemistry, 125:459-469, 2004.

Finnin and Morgan, "Transdermal Penetration Enhancers: Applications, Limitations, and Potential", Journal of Pharmaceutical Sciences, 88(10):955-958, 1999.

Verma and Garg, "Current Status of Drug Delivery Technologies and Future Directions", Pharmaceutical Technology On-Line, 25(2):1-14, 2001.

* cited by examiner

*Primary Examiner* — Golam M Shameem
(74) *Attorney, Agent, or Firm* — Paul M. Misiak

(57) ABSTRACT

This invention relates to a range of 1-aryl-4-cyclopropylpyrazoles in which the cyclopropyl ring is substituted at the angular position, and pharmaceutically acceptable salts and solvates thereof, to compositions comprising such compounds, processes to their synthesis and their use as parasiticides.

3 Claims, No Drawings

SUBSTITUTED ARYLPYRAZOLES

CROSS-REFERENCE TO RELATED APPLICATIONS

This application is a Divisional Application of application Ser. No. 11/453,053, filed Jun. 14, 2006, now allowed, which claims the benefit of U.S. Provisional Application Ser. No. 60/690,651, filed Jun. 15, 2005, which is incorporated herein by reference in its entirety.

FIELD OF THE INVENTION

This invention relates to pyrazole derivatives having parasiticidal properties. The compounds of interest are C4-(cyclopropyl)arylpyrazoles and, more particularly, the invention relates to 1-aryl-4-cyclopropylpyrazoles in which the cyclopropyl ring is substituted at the angular position. Such compounds are useful for having parasiticidal properties.

BACKGROUND OF THE INVENTION

International Patent Application Publication No. (WO) 98/24767, European Patent Application Publication No. (EP) 933363, European Patent Application Publication No. (EP) 959071 and International Patent Application Publication No. (WO) 2005/060749 all describe arylpyrazoles having parasiticidal activity for the control of arthropods.

However, the prior art compounds do not always demonstrate good activity or a long duration of action against parasites. Similarly, some of the prior art parasiticidal agents are useful only for a narrow spectrum of parasites. In some cases this may be attributed to the low bioavailability of the compounds in the treated animal and this can also lead to poor activity. It is an aim of the present invention to overcome various disadvantages of, or improve on, the properties of prior art compounds. Thus it is an aim of the invention to provide an arylpyrazole which has the same or improved activity relative to prior art compounds against parasites. It is a further aim of the present invention to provide arylpyrazole compounds with improved bioavailability whilst maintaining or improving their activity. The compounds of the present invention have especially good ability to control a broad spectrum of arthropods as shown by the results of tests demonstrating their potency and efficacy. In particular, the compounds of the present invention are significantly more active against fleas than similar prior art compounds.

It is a further aim to provide compounds with a long duration of action. Surprisingly it has been found that improving the bioavailability of the compounds does not negatively impact their duration of action. The extended duration of action is generally attributed to an extended half life of the compound in vivo in the host mammal.

It is also desirable that the compounds of the present invention should have an improved pharmacokinetic profile, improved safety, improved persistence and improved solubility.

SUMMARY OF THE INVENTION

Thus, according to the present invention, there is provided a compound of formula (I):

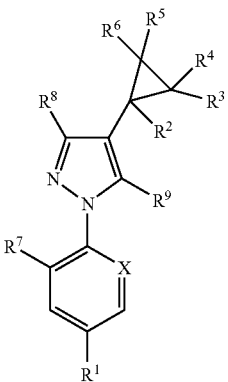

wherein:
X is selected from $CR^{10}$ or N;
$R^1$ is selected from halo, cyano, hydroxy, $C_{1-6}$ alkyl, $C_{1-6}$ alkoxy, $C_{1-6}$ alkanoyl, $C_{1-6}$ haloalkyl, $C_{1-6}$ haloalkoxy, $C_{1-6}$ haloalkanoyl, amino, $C_{1-6}$ alkyl amino, di $C_{1-6}$ alkyl amino, het, phenyl, $SF_5$ and $S(O)_n R^{11}$;
$R^2$ is selected from cyano, hydroxy, C(O)OH, het, phenyl, $S(O)_n R^{11}$, $C(O)NR^a R^b$ and $C(S)NR^a R^b$;
or $R^2$ is selected from $C_{3-8}$ cycloalkyl, $C_{3-8}$ cycloalkyl$C_{1-6}$ alkyl, $C_{2-6}$ alkenyl, $C_{2-6}$ alkynyl, $C_{1-6}$ alkanoyl, $C(O)OC_{1-6}$ alkyl, amino, $C_{1-6}$ alkyl amino, and di $C_{1-6}$ alkyl amino each of which may be optionally and independently further substituted by one or more substituents selected from, where chemically possible, cyano, nitro, halo, oxo, hydroxy, C(O)OH, $C(O)NR^c R^d$, $NR^c C(O)R^d$, $C_{1-6}$ alkyl, $C_{2-6}$ alkenyl, $C_{2-6}$ alkynyl, $C_{3-8}$ cycloalkyl, $C_{3-8}$ cycloalkyl$C_{1-6}$ alkyl, $C_{3-8}$ cycloalkyl$C_{1-6}$ haloalkyl, $C_{1-6}$ alkoxy, $C_{1-6}$ alkanoyl, —C(O)$OC_{1-6}$ alkyl, $C_{1-6}$ haloalkyl, $C_{3-8}$ halocycloalkyl, $C_{1-6}$ haloalkoxy, $C_{1-6}$ haloalkanoyl, —C(O)$OC_{1-6}$ haloalkyl, amino, $NR^c R^d$, het, phenyl and $S(O)_n R^{11}$;
$R^a$ and $R^b$ are independently selected from hydrogen, het, phenyl, and $S(O)_n R^{11}$;
or either one or both of $R^a$ and $R^b$ are independently selected from $C_{1-6}$ alkyl, $C_{2-6}$ alkenyl, $C_{3-8}$ cycloalkyl, $C_{3-8}$ cycloalkyl$C_{1-6}$ alkyl, $C_{1-6}$ alkanoyl, and $C(O)OC_{1-6}$ alkyl, each of which $R^a$ or $R^b$ may be optionally and independently further substituted by one or more substituents selected from, where chemically possible, cyano, nitro, halo, oxo, hydroxy, C(O)OH, $C(O)NR^c R^d$, $NR^c C(O)R^d$, $C_{1-6}$ alkyl, $C_{2-6}$ alkenyl, $C_{2-6}$ alkynyl, $C_{3-8}$ cycloalkyl, $C_{3-8}$ cycloalkyl$C_{1-6}$ alkyl, $C_{3-8}$ cycloalkyl$C_{1-6}$ haloalkyl, $C_{1-6}$ alkoxy, $C_{1-6}$ alkanoyl, —C(O)$OC_{1-6}$ alkyl, $C_{1-6}$ haloalkyl, $C_{3-8}$ halocycloalkyl, $C_{1-6}$ haloalkoxy, $C_{1-6}$ haloalkanoyl, —C(O)$OC_{1-6}$ haloalkyl, amino, $NR^c R^d$, het, phenyl and $S(O)_n R^{11}$;
or $R^a$ and $R^b$ together with the N atom to which they are attached may form a three to seven-membered saturated, partially saturated, unsaturated or aromatic heterocyclic ring which may optionally contain one or more further N, O or S atoms and which may be optionally further substituted by one or more substituents selected from, where chemically possible, cyano, nitro, halo, oxo, hydroxy, C(O)OH, $C(O)NR^c R^d$, $NR^c C(O)R^d$, $C_{1-6}$ alkyl, $C_{2-6}$ alkenyl, $C_{2-6}$ alkynyl, $C_{3-8}$ cycloalkyl, $C_{3-8}$ cycloalkyl$C_{1-6}$ alkyl, $C_{3-8}$ cycloalkyl$C_{1-6}$ haloalkyl, $C_{1-6}$ alkoxy, $C_{1-6}$ alkanoyl, —C(O)$OC_{1-6}$ alkyl, $C_{1-6}$ haloalkyl, $C_{3-8}$ halocycloalkyl, $C_{1-6}$ haloalkoxy, $C_{1-6}$ haloalkanoyl, —C(O)$OC_{1-6}$ haloalkyl, amino, $NR^c R^d$, het, phenyl and $S(O)_n R^{11}$;
or $R^2$ and $R^e$ together with the N atom to which $R^e$ is attached may form a six to seven-membered saturated, partially saturated, or unsaturated heterocyclic ring which may optionally contain one or more further N, O or S atoms and which may be optionally further substituted by one or more substituents selected from, where chemically possible, cyano, nitro, halo, oxo, hydroxy, C(O)OH, C(O)NR$^c$R$^d$, NR$^c$C(O)R$^d$, C$_{1-6}$ alkyl, C$_{2-6}$ alkenyl, C$_{2-6}$ alkynyl, C$_{3-8}$ cycloalkyl, C$_{3-8}$ cycloalkylC$_{1-6}$ alkyl, C$_{3-8}$ cycloalkylC$_{1-6}$ haloalkyl, C$_{1-6}$ alkoxy, C$_{1-6}$ alkanoyl, —C(O)OC$_{1-6}$ alkyl, C$_{1-6}$ haloalkyl, C$_{3-8}$ halocycloalkyl, C$_{1-6}$ haloalkoxy, C$_{1-6}$ haloalkanoyl, —C(O)OC$_{1-6}$ haloalkyl, amino, NR$^c$R$^d$, het, phenyl and S(O)$_n$R$^{11}$;

R$^3$, R$^4$, R$^5$ and R$^6$ are independently selected from hydrogen, halo, cyano, hydroxy, C(O)OH, nitro, phenyl, and S(O)$_n$R$^{11}$; or either one or more of R$^3$, R$^4$, R$^5$ and R$^6$ are independently selected from C$_{1-4}$ alkyl, C(O)NR$^c$R$^d$, C(S)NR$^c$R$^d$, C$_{1-4}$ alkoxy, C$_{1-4}$ alkanoyl, C(O)OC$_{1-4}$ alkyl, amino which R$^3$, R$^4$, R$^5$ and R$^6$ may be optionally and independently further substituted by one or more substituents selected from, where chemically possible, cyano, nitro, halo, hydroxy, C$_{1-4}$ alkyl and amino;

and where not more than two of R$^3$, R$^4$, R$^5$ and R$^6$ are selected from cyano, hydroxy, C(O)OH, nitro, phenyl, S(O)$_n$R$^{11}$, C(O)NR$^c$R$^d$, C(S)NR$^c$R$^d$, C$_{1-4}$ alkoxy, C$_{1-4}$ alkanoyl, C(O)OC$_{1-4}$ alkyl, and amino;

R$^7$ is selected from halo, C$_{1-6}$ alkyl and C$_{1-6}$ alkoxy where, when R$^7$ is C$_{1-6}$ alkyl or C$_{1-6}$ alkoxy, R$^7$ may be optionally substituted with one or more halo substituents;

R$^8$ is selected from hydrogen, cyano, hydroxy, C(O)OH, nitro, halo, het, phenyl and S(O)$_n$R$^{11}$;
or R$^8$ is selected from C$_{1-6}$ alkyl, C$_{2-6}$ alkenyl, C$_{2-6}$ alkynyl, C$_{3-8}$ cycloalkyl, C$_{3-8}$ cycloalkylC$_{1-6}$ alkyl, C$_{1-6}$ alkoxy, C$_{1-6}$ alkanoyl, and C(O)OC$_{1-6}$ alkyl, which R$^8$ may be optionally and independently further substituted by one or more substituents selected from, where chemically possible, cyano, nitro, halo, oxo, hydroxy, C(O)OH, C(O)NR$^c$R$^d$, NR$^c$C(O)R$^d$, C$_{1-6}$ alkyl, C$_{2-6}$ alkenyl, C$_{2-6}$ alkynyl, C$_{3-8}$ cycloalkyl, C$_{3-8}$ cycloalkylC$_{1-6}$ alkyl, C$_{3-8}$ cycloalkylC$_{1-6}$ haloalkyl, C$_{1-6}$ alkoxy, C$_{1-6}$ alkanoyl, —C(O)OC$_{1-6}$ alkyl, C$_{1-6}$ haloalkyl, C$_{3-8}$ halocycloalkyl, C$_{1-6}$ haloalkoxy, C$_{1-6}$ haloalkanoyl, —C(O)OC$_{1-6}$ haloalkyl, amino, NR$^c$R$^d$, het, phenyl and S(O)$_n$R$^{11}$;
or R$^8$ is amino, which R$^8$ may be optionally and independently further substituted by one or more substituents selected from, where chemically possible, C(O)OH, C(O)NR$^c$R$^d$, NR$^c$C(O)R$^d$, C$_{1-6}$ alkyl, C$_{2-6}$ alkenyl, C$_{2-6}$ alkynyl, C$_{3-8}$ cycloalkyl, C$_{3-8}$ cycloalkylC$_{1-6}$ alkyl, C$_{3-8}$ cycloalkylC$_{1-6}$ haloalkyl, C$_{1-6}$ alkoxy, C$_{1-6}$ alkanoyl, —C(O)OC$_{1-6}$ alkyl, C$_{1-6}$ haloalkyl, C$_{3-8}$ halocycloalkyl, C$_{1-6}$ haloalkoxy, C$_{1-6}$ haloalkanoyl, —C(O)OC$_{1-6}$ haloalkyl, het, phenyl and S(O)$_n$R$^{11}$;

R$^9$ is selected from hydrogen, halo, cyano, hydroxy, C(O)OH, nitro, het, phenyl, S(O)$_n$R$^{11}$ and NR$^e$R$^f$;
or R$^9$ is selected from C$_{1-6}$ alkyl, C$_{2-6}$ alkenyl, C$_{2-6}$ alkynyl, C$_{3-8}$ cycloalkyl, C$_{3-8}$ cycloalkylC$_{1-6}$ alkyl, C$_{1-6}$ alkoxy, C$_{3-8}$ cycloalkylC$_{1-6}$ alkoxy, C$_{1-6}$ alkanoyl, C(O)OC$_{1-6}$ alkyl, which R$^9$ may be optionally and independently further substituted by one or more substituents selected from, where chemically possible, cyano, nitro, halo, oxo, hydroxy, C(O)OH, C(O)NR$^c$R$^d$, NR$^c$C(O)R$^d$C$_{1-6}$ alkyl, C$_{2-6}$ alkenyl, C$_{2-6}$ alkynyl, C$_{3-8}$ cycloalkyl, C$_{3-8}$ cycloalkylC$_{1-6}$ alkyl, C$_{3-8}$ cycloalkylC$_{1-6}$ haloalkyl, C$_{1-6}$ alkoxy, C$_{1-6}$ alkanoyl, —C(O)OC$_{1-6}$ alkyl, C$_{1-6}$ haloalkyl, C$_{3-8}$ halocycloalkyl, C$_{1-6}$ haloalkoxy, C$_{1-6}$ haloalkanoyl, —C(O)OC$_{1-6}$ haloalkyl, amino, NR$^c$R$^d$, het, phenyl and S(O)$_n$R$^{11}$;

R$^e$ and R$^f$ are independently selected from hydrogen, het, phenyl and S(O)$_n$R$^{11}$;

or either one or both of R$^e$ and R$^f$ are independently selected from C$_{1-6}$ alkyl, C$_{2-6}$ alkenyl, C$_{3-8}$ cycloalkyl, C$_{3-8}$ cycloalkylC$_{1-6}$ alkyl, C$_{1-6}$ alkanoyl, C(O)OC$_{1-6}$ alkyl, —C(O)OC$_{1-6}$ alkylC$_{3-8}$ cycloalkyl, —C(O)OC$_{3-8}$ cycloalkyl, each of which R$^e$ or R$^f$ may be optionally and independently further substituted by one or more substituents selected from, where chemically possible, cyano, nitro, halo, oxo, hydroxy, C(O)OH, C(O)NR$^c$R$^d$, NR$^c$C(O)R$^d$, C$_{1-6}$ alkyl, C$_{2-6}$ alkenyl, C$_{2-6}$ alkynyl, C$_{3-8}$ cycloalkyl, C$_{3-8}$ cycloalkylC$_{1-6}$ alkyl, C$_{3-8}$ cycloalkylC$_{1-6}$ haloalkyl, C$_{1-6}$ alkoxy, C$_{1-6}$ alkanoyl, —C(O)OC$_{1-6}$ alkyl, C$_{1-6}$ haloalkyl, C$_{3-8}$ halocycloalkyl, C$_{1-6}$ haloalkoxy, C$_{1-6}$ haloalkanoyl, —C(O)OC$_{1-6}$ haloalkyl, amino, NR$^c$R$^d$, het, phenyl and S(O)$_n$R$^{11}$;

or R$^e$ and R$^f$ together with the N atom to which they are attached may form a three to seven-membered saturated, partially saturated, unsaturated or aromatic heterocyclic ring which may optionally contain one or more further N, O or S atoms and which may be optionally further substituted by one or more substituents selected from, where chemically possible, cyano, nitro, halo, oxo, hydroxy, C(O)OH, C(O)NR$^c$R$^d$, NR$^c$C(O)R$^d$, C$_{1-6}$ alkyl, C$_{2-6}$ alkenyl, C$_{2-6}$ alkynyl, C$_{3-8}$ cycloalkyl, C$_{3-8}$ cycloalkylC$_{1-6}$ alkyl, C$_{3-8}$ cycloalkylC$_{1-6}$ haloalkyl, C$_{1-6}$ alkoxy, C$_{1-6}$ alkanoyl, —C(O)OC$_{1-6}$ alkyl, C$_{1-6}$ haloalkyl, C$_{3-8}$ halocycloalkyl, C$_{1-6}$ haloalkoxy, C$_{1-6}$ haloalkanoyl, —C(O)OC$_{1-6}$ haloalkyl, amino, NR$^c$R$^d$, het, phenyl and S(O)$_n$R$^{11}$;

or R$^e$ and R$^f$ together with the atoms to which they are attached may form a six to seven-membered heterocyclic ring as previously described;

R$^{10}$ is selected from halo, C$_{1-6}$ alkyl and C$_{1-6}$ alkoxy and where when R$^{10}$ is C$_{1-6}$ alkyl or C$_{1-6}$ alkoxy it may optionally be substituted with one or more halo substituents;

each of R$^c$ and R$^d$ are independently selected from hydrogen, C$_{1-6}$ alkyl, C$_{2-6}$ alkenyl, C$_{3-8}$ cycloalkyl, C$_{3-8}$ cycloalkylC$_{1-6}$ alkyl, C$_{1-6}$ haloalkyl, C$_{3-8}$ cycloalkylC$_{1-6}$ haloalkyl, C$_{1-6}$ alkanoyl, C$_{1-6}$ haloalkanoyl, C(O)OC$_{1-6}$ alkyl, het, phenyl and S(O)$_n$R$^{11}$;

or R$^c$ and R$^d$ together with the N atom to which at least one of them is attached may form a three to seven-membered saturated, partially saturated, unsaturated or aromatic heterocyclic ring which may optionally contain one or more further N, O or S atoms;

each n is independently 0, 1 or 2;

each R$^{11}$ is independently selected from hydrogen, hydroxy, C$_{1-6}$ alkyl, C$_{1-6}$ haloalkyl, amino, C$_{1-6}$ alkyl amino and di C$_{1-6}$ alkyl amino;

each phenyl may be optionally substituted by one or more further substituents selected from the group consisting of halo, cyano, nitro, hydroxy, C$_{1-6}$ alkyl, C$_{1-6}$ haloalkyl, C$_{1-6}$ alkoxy, C$_{1-6}$ haloalkoxy, amino, C$_{1-6}$ alkyl amino, di C$_{1-6}$ alkyl amino, —NHS(O)$_n$R$^{11}$, and S(O)$_n$R$^{11}$; and each het independently represents a four to seven membered heterocyclic ring, which is aromatic or non-aromatic, unsaturated, partially saturated or saturated and which contains one or more heteroatoms selected from nitrogen, N-oxide, oxygen, sulphur and wherein said heterocyclic ring is optionally substituted, where the valence allows, with one or more substituents selected from halo, cyano, nitro, C$_{1-6}$ alkyl, C$_{1-6}$ haloalkyl, C$_{1-6}$ alkoxy, OC(O)C$_{1-6}$ alkyl, C$_{1-6}$ alkanoyl, C(O)OC$_{1-6}$ alkyl and NR$^g$R$^h$ where R$^g$ and R$^h$ are independently selected from hydrogen, C$_{1-6}$ alkyl and C$_{2-6}$ alkenyl, and where each of the above groups may include one or more optional substituents where chemically possible independently selected from cyano, nitro, halo, oxo, hydroxy, C(O)OH, C(O)NR$^c$R$^d$, NR$^c$C(O)R$^d$, C$_{1-6}$ alkyl, C$_{2-6}$ alkenyl, C$_{2-6}$ alkynyl, C$_{3-8}$ cycloalkyl, C$_{3-8}$ cycloalkylC$_{1-6}$ alkyl, C$_{3-8}$ cycloalkylC$_{1-6}$ haloalkyl, C$_{1-6}$ alkoxy, C$_{1-6}$ alkanoyl, —C(O)

$OC_{1-6}$ alkyl, $C_{1-6}$ haloalkyl, $C_{3-8}$ halocycloalkyl, $C_{1-6}$ haloalkoxy, $C_{1-6}$ haloalkanoyl, —$C(O)OC_{1-6}$ haloalkyl, amino, $C_{1-6}$ alkyl amino, di $C_{1-6}$ alkyl amino, phenyl and $S(O)_nR^{11}$;

or a pharmaceutically acceptable salt or a prodrug thereof.

Preferably, $R^1$ is selected from: cyano; $C_{1-6}$ haloalkyl, for example, trifluoromethyl or i-$C_3F_7$; $C_{1-6}$ haloalkoxy, for example, difluoromethoxy or trifluoromethoxy; $SF_5$; and $S(O)_nR^{11}$ where, for example, $R^{11}$ is $C_{1-6}$ haloalkyl to form, for example, (trifluoromethyl)thio, (trifluoromethyl)sulphinyl or (trifluoromethyl)sulphonyl. More preferably $R^1$ is selected from $C_{1-6}$ haloalkyl, for example, trifluoromethyl, $C_{1-6}$ haloalkoxy for example difluoromethoxy and trifluoromethoxy, and $SF_5$. Even more preferably $R^1$ is selected from $CF_3$, $OCF_3$, or $SF_5$. Most preferably $R^1$ is $SF_5$.

Suitably, $R^2$ is selected from: cyano; C(O)OH; het, eg 1-oxa-3,4-diazolyl or thiazolyl, which het may in turn be substituted with $C_{1-6}$ alkyl, eg methyl or ethyl to form, for example, 5-methyl-1-3,4-oxadiazol-2-yl; and $S(O)_nR^{11}$ where $R^{11}$ is selected from $C_{1-6}$ alkyl, eg methyl or ethyl to form, for example, methylthio, methylsulphinyl or methylsulphonyl, amino to form, for example, aminosulphonyl, and di $C_{1-6}$ alkyl amino, eg dimethylamino to form, for example, (dimethylamino)sulphonyl; $C(O)OC_{1-6}$ alkyl, eg methoxycarbonyl or ethoxycarbonyl, which $C(O)OC_{1-6}$ alkyl may in turn be optionally substituted with halo, eg chloro or fluoro to form, for example, fluoromethoxycarbonyl or trifluoromethoxycarbonyl; and amino.

Equally suitably $R^2$ is selected from $C(O)NR^aR^b$ and $C(S)NR^aR^b$ where $R^a$ and $R^b$ are independently selected from: hydrogen to form, for example, aminocarbonyl or aminocarbonothioyl; $S(O)_nR^{11}$ where $R^{11}$ is $C_{1-6}$ alkyl, eg methyl or ethyl to form, for example, [(methylsulphonyl)amino]carbonyl; and $C_{3-8}$ cycloalkyl, eg cyclopropyl to form, for example, (cyclopropylamino)carbonyl. Equally suitably $R^a$ and $R^b$ are independently selected from $C_{1-6}$ alkyl, eg methyl, ethyl, propyl, isopropyl or isobutyl to form, for example, (methylamino)carbonyl, (dimethylamino)carbonyl, (ethylamino)carbonyl, (propylamino)carbonyl, (isopropylamino)carbonyl, or (isobutylamino)carbonyl, which $C_{1-6}$ alkyl may in turn be optionally substituted with one or more substituents selected from: halo eg fluoro to form, for example, [(trifluoromethyl)amino]carbonyl or [(2,2,2-trifluoroethyl)amino]carbonyl; hydroxy to form, for example, [(2-hydroxyethyl)amino]carbonyl or [(2-hydroxy-2-methylpropyl)amino]carbonyl; $C_{1-6}$ alkoxy to form, for example, [(1-methoxyethyl)amino]carbonyl or [(1-isopropoxypropyl)amino]carbonyl; $C_{3-8}$ cycloalkyl, eg cyclopropyl to form, for example, [(cyclopropylmethyl)amino]carbonyl; or het, eg pyridinyl to form, for example, [(pyridin-2-ylmethyl)amino]carbonyl, [(pyridin-3-ylmethyl)amino]carbonyl, or [(pyridin-4-ylmethyl)amino]carbonyl, or 1, 2, 4 triazolyl to form, for example, [(4H-1,2,4-triazol-3-ylmethyl)amino]carbonyl, which 1,2,4 triazolyl may optionally be further substituted with, for example, $C_{1-6}$ alkyl eg methyl to form, for example, {[(5-methyl-4H-1,2,4-triazol-3-yl)methyl]amino}carbonyl.

Where $R^a$ and $R^b$ together with the N atom to which they are attached form a three to seven-membered saturated, partially saturated, unsaturated or aromatic heterocyclic ring which may optionally contain one or more further N, O or S atoms, the ring is suitably a saturated pyrrolidinyl ring.

Where $R^2$ and $R^e$ together with the N atom to which $R^e$ is attached form a six to seven-membered saturated, partially saturated, or unsaturated heterocyclic ring which may optionally contain one or more further N, O or S atoms it is preferred that $R^2$ is selected from $C(O)NR^aR^b$ and $C(S)NR^aR^b$ wherein it is then $R^a$ and $R^e$ together with the N atoms to which they are attached form a six to seven-membered saturated, partially saturated, or unsaturated heterocyclic ring which may optionally contain one or more further N, O or S atoms. Suitably the ring is a partially unsaturated 1,3-diazepanyl which may be further substituted by $C_{1-6}$ alkyl, eg methyl to form, for example, a 7'-methyl-5'-oxo-5',6',7',8'-tetrahydropyrazolo[3,4-d][1,3]diazepine.

DETAILED DESCRIPTION OF THE INVENTION

Preferably $R^2$ is selected from: cyano; C(O)OH; het, eg 1-oxa-3,4-diazolyl or thiazolyl, which 1-oxa-3,4-diazolyl may in turn be substituted with $C_{1-6}$ alkyl, eg methyl; $S(O)_nR^{11}$ where $R^{11}$ is selected from $C_{1-6}$ alkyl, eg methyl or ethyl, amino, and di $C_{1-6}$ alkyl amino; $C(O)OC_{1-6}$ alkyl, eg methoxycarbonyl or ethoxycarbonyl, which $C(O)OC_{1-6}$ alkyl may in turn be optionally substituted with halo, eg chloro or fluoro; and amino. Further preferred compounds include those where $R^2$ is selected from $C(O)NR^aR^b$ band $C(S)NR^aR^b$ where $R^a$ and $R^b$ are independently selected from: hydrogen; $S(O)_nR^{11}$ where $R^{11}$ is $C_{1-6}$ alkyl, eg methyl or ethyl; $C_{3-8}$ cycloalkyl eg cyclopropyl; and $C_{1-6}$ alkyl, eg methyl, ethyl, isopropyl or isobutyl which $C_{1-6}$ alkyl may in turn be optionally substituted with one or more groups selected from halo eg fluoro, hydroxy, $C_{1-6}$ alkoxy, $C_{3-8}$ cycloalkyl, eg cyclopropyl, or het, eg pyridinyl, or 1, 2, 4 triazolyl which 1, 2, 4 triazolyl may optionally be further substituted with, for example, $C_{1-6}$ alkyl eg methyl.

Even more preferably $R^2$ is selected from: cyano; $S(O)_nR^{11}$ where $R^{11}$ is $C_{1-6}$ alkyl, eg methyl or ethyl; and $C(O)NR^aR^b$, where $R^a$ is hydrogen and $R^b$ is selected from hydrogen, and $C_{1-6}$ alkyl eg methyl or isopropyl, which $C_{1-6}$ alkyl may be optionally substituted with het, eg pyridinyl to form, for example, [(pyridin-4-ylmethyl)amino]carbonyl.

Most preferably, $R^2$ is $C(O)NR^aR^b$ where both of $R^a$ and $R^b$ are hydrogen.

Suitably $R^3$, $R^4$, $R^5$ and $R^6$ are each independently selected from: hydrogen; halo, eg chloro or fluoro; or $C_{1-4}$ alkyl, eg methyl, which $C_{1-4}$ alkyl is optionally substituted by 1 to 5 halo groups independently selected from chloro or fluoro to form, for example, trifluoromethyl. Preferably, $R^3$ and $R^4$ are independently selected from: hydrogen; chloro; fluoro; and $C_{1-4}$ alkyl, eg methyl which $C_{1-4}$ alkyl is optionally substituted by 1 to 5 halo groups and both $R^5$ and $R^6$ are hydrogen. More preferably, both $R^3$ and $R^4$ are the same as each other and are selected from: hydrogen; fluoro; chloro; and methyl and both $R^5$ and $R^6$ are hydrogen. Most preferably, both $R^3$ and $R^4$ are the same as each other and are selected from: hydrogen; fluoro; and chloro and both $R^5$ and $R^6$ are hydrogen.

Suitable compounds include those where, when $R^7$ is halo, preferred halo substituents are fluoro, chloro or bromo. Further suitable compounds include those where, when $R^7$ is selected from $C_{1-6}$ alkyl or $C_{1-6}$ alkoxy where the $C_{1-6}$ alkyl or $C_{1-6}$ alkoxy are optionally substituted with one or more halo substituents, preferred halo substituents are fluoro, chloro or bromo. Preferably $R^7$ is selected from chloro, or fluoro. Most preferably $R^7$ is chloro.

Suitably, $R^8$ is selected from: cyano; halo, eg chloro or fluoro; $C_{1-6}$ alkyl, eg methyl or ethyl which $C_{1-6}$ alkyl may optionally be substituted with one or more fluoro groups to form, for example, trifluoromethyl; and $C_{1-6}$ alkanoyl, eg acetyl or propanoyl which $C_{1-6}$ alkanoyl may optionally be substituted by one or more substituents independently selected from $S(O)_nR^{11}$ eg where $R^{11}$ is $C_{1-6}$ alkyl, eg methyl or ethyl to form, for example, (methylthio)carbonyl, halo eg chloro or fluoro, to form for example trifluoroacetyl, or $C_{1-6}$ alkoxy to form, for example 2-ethoxy-2-oxoethyl.

Preferably, $R^8$ is selected from: cyano; $C_{1-6}$ alkyl, eg methyl which $C_{1-6}$ alkyl may optionally be substituted with one or more fluoro groups; and $C_{1-6}$ alkanoyl, eg acetyl which $C_{1-6}$ alkanoyl may optionally be substituted by $S(O)_nR^{11}$, eg where $R^{11}$ is $C_{1-6}$ alkyl. Most preferably, $R^8$ is cyano.

Suitably $R^9$ is selected from: hydrogen; hydroxy; cyano; halo, eg chloro or fluoro; het, eg pyrazinyl, imidazolyl, or pyridinyl to form, for example, pyridin-2-yl or pyridin-4-yl, where suitably the pyridinyl may be further substituted with, eg oxy to form, for example, 1-hydroxy-pyridinyl; phenyl which phenyl may in turn be optionally substituted by one or more substituents selected from: halo, eg chloro or fluoro to form, for example, 4-fluorophenyl or 3,4-difluorophenyl, and $S(O)_nR^{11}$, eg where $R^{11}$ is methyl to form, for example, 4-(methylsulphonyl)phenyl; and $S(O)_nR^{11}$, eg where $R^{11}$ is methyl to form, for example, methylthio, methylsulphinyl, or methylsulphonyl.

Further suitable compounds include those where $R^9$ is $C_{1-6}$ alkyl, eg methyl, ethyl, isopropyl, or t-butyl which $C_{1-6}$ alkyl may in turn optionally be substituted by one or more substituents selected from: halo, eg fluoro or chloro to form, for example, difluoromethyl, trifluoromethyl or trifluoroethyl; $C_{1-6}$ alkyl, eg t-butyl to form, for example, t-butylmethyl; $C_{3-8}$ cycloalkyl, eg cyclopropyl, cyclopentyl or cyclohexyl to form, for example, cyclopropylmethyl, cyclopentylmethyl, cyclohexylmethyl or cyclopropylethyl; $C_{1-6}$ alkoxy, eg methoxy or ethoxy to form, for example, methoxymethyl, methoxyethyl, ethoxymethyl or ethoxyethyl; het, eg pyrazinyl to form, for example, pyrazinylmethyl or pyrazinylethyl, imidazolyl to form, for example, (1H-imidazolyl)methyl or (1H-imidazolyl)ethyl, 1,2,4-triazolyl to form, for example, (4H-1,2,4-triazol-3-yl methyl or (4H-1,2,4-triazol-3-yl)ethyl, or pyridinyl to form, for example, pyridin-2-ylmethyl, pyridin-2-ylethyl, pyridin-4-ylmethyl or pyridin-4-ylethyl, where suitably the pyridinyl may be further substituted with, eg oxy to form, for example, (1-hydroxy-pyridinyl)methyl or (1-hydroxy-pyridinyl)ethyl; phenyl to form, for example, benzyl or phenylethyl which phenyl may in turn be optionally substituted by one or more substituents selected from halo, eg chloro or fluoro to form, for example, 4-fluorobenzyl, (4-fluorophenyl)ethyl, 3,4-difluorobenzyl or (3,4-difluorophenyl) ethyl, $C_{1-4}$ alkyl optionally substituted by one or more halo groups, eg chloro or fluoro to form, for example, (trifluoromethyl)benzyl or [(trifluoromethyl)phenyl]ethyl, or $S(O)_nR^{11}$, eg where $R^{11}$ is methyl to form, for example, 4-(methylsulphonyl)benzyl or [4-(methylsulphonyl)phenyl]ethyl; —C(O) $OC_{1-6}$ alkyl eg ethoxycarbonyl to form, for example, 2-ethoxy-2-oxoethyl; amino to form for example aminomethyl or aminoethyl; $C_{1-6}$ alkyl amino, eg methylamino to form, for example, (methylamino)methyl, (methylamino)ethyl, (ethylamino)methyl or (ethylamino)ethyl; and $S(O)_nR^{11}$, eg where $R^{11}$ is methyl to form, for example, (methylthio) methyl, (methylthio)ethyl, (methylsulphinyl)methyl, (methylsulphinyl)ethyl, (methylsulphonyl)methyl, or (methylsulphonyl)ethyl.

Further suitable compounds include those where $R^9$ is selected from: $C_{2-6}$ alkenyl, eg ethenyl which $C_{2-6}$ alkenyl may be further substituted with het eg pyrazinyl, 1,3,4-triazolyl, imidazolyl, or pyridinyl, or phenyl which phenyl may be further substituted by for example halo, eg chloro or fluoro to form, for example, 4-fluorophenyl or 3,4-difluorophenyl, $C_{1-4}$ alkyl optionally substituted by one or more halo groups, eg chloro or fluoro to form, for example, trifluoromethylphenyl, or $S(O)_nR^{11}$, eg where $R^{11}$ is methyl to form, for example, 4-(methylsulphonyl)phenyl; $C_{3-8}$ cycloalkyl, eg cyclopropyl, cyclobutyl, cyclopentyl or cyclohexyl, which $C_{3-8}$ cycloalkyl may be optionally substituted with one or more groups selected from halo, eg fluoro or chloro, cyano, and hydroxy; and $C_{3-8}$ cycloalkyl$C_{1-6}$ alkyl, eg cyclopropylmethyl or cyclopropylethyl, which $C_{3-8}$ cycloalkyl$C_{1-6}$ alkyl may be optionally substituted with one or more groups selected from halo eg fluoro or chloro, to form, for example, (1-fluorocyclopropyl)methyl, $C_{1-6}$ alkyl eg methyl or ethyl to form, for example, (1-methylcyclopropyl)methyl or (1-ethylcyclopropyl)methyl, and $C_{1-6}$ haloalkyl to form, for example, [(1-trifluoromethyl)cyclopropyl]methyl.

Equally suitably $R^9$ is $C_{1-6}$ alkoxy, eg methoxy, ethoxy, isopropoxy or t-butoxy which $C_{1-6}$ alkoxy may in turn optionally be substituted by one or more substituents selected from: halo, eg fluoro or chloro to form, for example, trifluoromethoxy or trifluoroethoxy; $C_{1-6}$ alkyl, eg t-butyl to form, for example, t-butylmethoxy; $C_{3-8}$ cycloalkyl, eg cyclopropyl, cyclopentyl or cyclohexyl to form, for example, cyclopropylmethoxy, cyclopentylmethoxy, cyclohexylmethoxy or cyclopropylethoxy; het, eg pyrazinyl to form, for example, pyrazinylmethoxy, imidazolyl to form, for example, (1H-imidazolyl)methoxy, 1,3,4-triazolyl to form, for example, (4H-1,2,4-triazol-3-yl)methoxy or (4H-1,2,4-triazol-3-yl) ethoxy, or pyridinyl to form, for example, pyridin-2-ylmethoxy or pyridin-4-ylmethoxy, where suitably the pyridinyl may be further substituted with, eg oxy to form, for example, (1-hydroxypyridinyl)methoxy; phenyl to form, for example, benzyloxy which phenyl may in turn be optionally substituted by one or more substituents selected from halo, eg chloro or fluoro to form, for example, (4-fluorobenzyl)oxy or (3,4-difluorobenzyl)oxy, $C_{1-4}$ alkyl optionally substituted by one or more halo groups, eg chloro or fluoro to form, for example, [(trifluoromethyl)benzyl]oxy, and $S(O)_nR^{11}$, eg where $R^{11}$ is methyl to form, for example, [4-(methylsulphonyl)benzyl]oxy; and —C(O)O$C_{1-6}$ alkyl, eg ethoxycarbonyl to form, for example, 2-ethoxy-2-oxoethyl.

Equally suitably $R^9$ is $C_{3-8}$ cycloalkyl$C_{1-6}$ alkoxy eg cyclopropylmethoxy or cyclopropylethoxy which $C_{3-8}$ cycloalkyl$C_{1-6}$ alkoxy may be optionally substituted with one or more groups selected from: halo eg fluoro or chloro, to form for example (1-fluorocyclopropyl)methoxy; $C_{1-6}$ alkyl eg methyl or ethyl to form, for example (1-methylcyclopropyl)methoxy or (1-ethylcyclopropyl)methoxy; or $C_{1-6}$ haloalkyl to form, for example, [1-(trifluoromethyl)cyclopropyl]methoxy.

Still further suitable compounds include those where $R^9$ is $NR^eR^f$ and where each of $R^e$ and $R^f$ are hydrogen to form, for example, amino.

Still further suitable compounds include those where $R^9$ is $NR^eR^f$ and where each of $R^e$ or $R^f$ are independently selected from hydrogen and $C_{1-6}$ alkyl, eg methyl, ethyl, n-propyl, isopropyl, n-butyl, t-butyl, or n-pentyl to form, for example, methylamino, dimethylamino, ethylamino, propylamino, isopropylamino, butylamino, t-butylamino, or pentylamino which $C_{1-6}$ alkyl may in turn be substituted with one or more substituents selected from: cyano to form, for example, (2-cyanoethyl)amino; halo, eg fluoro or chloro to form, for example, (fluoroethyl)amino, (2-fluoro-2-methyl)propylamino, (trifluoromethyl)amino, (trifluoroethyl)amino, (2-fluoroethyl)amino, (3,3,3-trifluoropropyl)amino, (4,4,4-trifluorobutyl)amino, or (5,5,5-trifluoropentyl)amino; C(O) OH to form, for example, (3-carboxypropyl)amino; C(O) $NR^cR^d$ where $R^c$ or $R^d$ are independently selected from the group consisting of hydrogen to form, for example, 2-carbamoyl-ethylamino, 3-carbamoyl-propylamino, or 4-carbamoyl-butylaminoamino, $C_{3-8}$ cycloalkyl$C_{1-6}$ alkyl eg cyclopropylmethyl to form, for example, (2-cyclopropylmethyl-carbamoyl)ethylamino, or $C_{1-6}$ haloalkyl eg trifluoroethyl to form, for example, (trifluoroethyl-carbamoyl)ethylamino; $C_{1-6}$ alkyl, eg methyl, isopropyl, t-butyl to form, for example, isopropylmethylamino, or t-butylmethylamino; $C_{1-6}$ alkoxy, eg methoxy, ethoxy or isopropoxy to form, for example, (2-methoxyethyl)(methyl)amino or (2-isopropoxyethyl)amino; het, eg pyrazinyl to form, for example, pyrazinylmethylamino, imidazolyl to form, for example, (1H-imidazol-2-yl)methylamino, 1,2,4-triazolyl to form, for example, (4H-1,2,4-triazol-3-yl)methylamino, (4H-1,2,4-triazol-3-yl)ethylamino, or (4H-1,2,4-triazol-1-yl)ethylamino, isoxaolyl to form, for example, isoxazol-3-ylmethylamino, thiazolyl to form, for example, 1,3-thiazol-2-ylmethylamino or 1,3-thiazol-4-ylmethylamino which thiazolyl may be optionally further substituted with halo, eg chloro to form, for example, [(2-chloro-1,3-thiazol-4-yl)methyl]amino, pyrazolyl to form, for example, (1H-pyrazol-4-ylmethyl)amino or (1H-pyrazol-4-ylethyl)amino which pyrazolyl may be optionally further substituted with one or more substituents selected from $C_{1-6}$alkyl, eg methyl, or halo, eg chloro, to form, for example, [(1-methyl-1H-pyrazol-4-yl)ethyl]amino, or [(1-methyl-3-methyl-5-chloro-1H-pyrazol-4-yl)methyl]amino, tretrahydropyranyl to form, for example, (tetrahydro-2H-pyran-4-ylmethyl)amino, or pyridinyl to form, for example, (pyridin-2-ylmethyl)amino or (pyridin-4-ylmethyl)amino, where suitably the pyridinyl may be further substituted with, eg oxy to form, for example, [(1-hydroxypyridin-4-yl)methyl]amino; phenyl to form, for example, benzylamino which phenyl may in turn be optionally substituted by one or more substituents selected from halo, eg chloro or fluoro to form, for example, (4-fluorobenzyl)amino or (3,4-difluorobenzyl)amino, $C_{1-6}$ alkyl optionally substituted by one or more halo groups, eg chloro or fluoro to form, for example, (trifluoromethylbenzyl)amino, $S(O)_nR^{11}$, eg where $R^{11}$ is methyl to form, for example, [(4-methylsulphonyl)benzyl]amino, or where $R^{11}$ is $C_{1-6}$ alkyl amino eg N-methyl to form, for example, {4-[(methylsulphonyl)amino]benzyl}aminoamino, $-NHS(O)_nR^{11}$, eg where $R^{11}$ is methyl to form, for example, {4-[(methylamino)sulphonyl]benzyl}aminoamino; and $S(O)_nR^{11}$ eg where $R^{11}$ is methyl to form, for example, 3-(S-methyl thio ether) propyl amino.

Yet further suitable compounds include those where $R^e$ is independently selected from hydrogen or $C_{1-6}$ alkyl, eg methyl and $R^f$ is independently selected from: $C_{3-8}$ cycloalkyl, eg cyclopropyl to form, for example, cyclopropylamino; and $C_{3-8}$ cycloalkyl$C_{1-6}$ alkyl eg cyclopropylmethyl, cyclopropylethyl, cyclobutylmethyl, cyclopentylmethyl or cyclohexylmethyl to form, for example, (cyclopropylmethyl)amino, (cyclopropylmethyl)(methyl)amino, (cyclopropylethyl)amino, (cyclobutylmethyl)amino, (cyclopentylmethyl)amino or (cyclohexylmethyl)amino, which $C_{3-8}$ cycloalkyl$C_{1-6}$ alkyl may be optionally substituted with one or more groups selected from: halo eg fluoro or chloro, to form for example [(1-fluorocyclopropyl)methyl]amino; $C_{1-6}$ alkyl eg methyl or ethyl to form, for example, [(1-methylcyclopropyl)methyl]amino or [(1-ethylcyclopropyl)methyl]amino; $C_{1-6}$ haloalkyl eg trifluoromethyl to form, for example, [(1-trifluoromethylcyclopropyl)methyl]amino; amino to form, for example, [(1-aminocyclopropyl)methyl]amino; $C(O)NR^cR^d$ where $R^c$ and $R^d$ are hydrogen to form, for example, {[1-(aminocarbonyl)cyclopropyl]methyl}amino; $NR^cR^d$ where $R^c$ or $R^d$ are independently selected from the group consisting of hydrogen, $C(O)OC_{1-6}$ alkyl eg t-butoxycarbonyl, or $S(O)_nR^{11}$ where $R^{11}$ is methyl to form, for example, {{1-[(t-butoxycarbonyl)amino]cyclopropyl}methyl}amino, or {{1-[(methylsulphonyl)amino]cyclopropyl}methyl}amino.

Yet further suitable compounds include those where $R^e$ is independently selected from hydrogen or $C_{1-6}$ alkyl, eg methyl and $R^f$ is independently selected from: $-C(O)OC_{1-6}$ alkyl, eg methoxycarbonyl, ethoxycarbonyl or isopropoxycarbonyl to form, for example, (methoxycarbonyl)amino, (ethoxycarbonyl)amino, (isopropoxycarbonyl)amino or (methyl)(isopropoxycarbonyl)amino; $-C(O)OC_{3-8}$ cycloalkyl eg cyclobutoxycarbonyl to form, for example, (cyclobutyloxycarbonyl)amino or (methyl)(cyclobutyloxycarbonyl) amino; and $-C(O)O\ C_{1-6}$ alkyl$C_{3-8}$ cycloalkyl eg cyclopropylmethoxycarbonyl to from, for example, [(cyclopropylmethoxy)carbonyl]amino or (methyl) [(cyclopropylmethoxy)carbonyl]amino, which $-C(O)OC_{1-6}$ alkyl$C_{3-8}$ cycloalkyl may be further optionally substituted by, for example, $C_{1-6}$ haloalkyl eg fluoromethyl to form, for example, {{[1-(fluoromethyl)cyclopropyl]methoxy}carbonyl}amino.

Preferably $R^9$ is selected from: hydrogen; halo, eg chloro; $C_{1-6}$ alkyl, eg methyl, which $C_{1-6}$ alkyl may in turn optionally be substituted by one or more substituents selected from halo, eg fluoro to form, for example, difluoromethyl, or $C_{1-6}$ alkoxy, eg methoxy to form, for example, methoxymethyl; $C_{2-6}$ alkenyl, eg ethenyl; $C_{3-8}$ cycloalkyl$C_{1-6}$ alkoxy eg cyclopropylmethoxy; and $S(O)_nR^{11}$, eg where $R^{11}$ is methyl to form, for example, methylthio, methylsulphinyl, or methylsulphonyl.

Equally preferred compounds include those where $R^9$ is $NR^eR^f$ where each of $R^e$ or $R^f$ are independently selected from hydrogen and $C_{1-6}$ alkyl, eg methyl, ethyl, n-propyl, isopropyl, n-butyl, t-butyl, or n-pentyl which $C_{1-6}$ alkyl may in turn be substituted with one or more substituents selected from: cyano; halo, eg fluoro; $C(O)OH$; $C(O)NR^cR^d$ where $R^c$ or $R^d$ are independently selected from the group consisting of hydrogen, $C_{3-8}$ cycloalkyl$C_{1-6}$ alkyl eg cyclopropylmethyl, or $C_{1-6}$ haloalkyl eg trifluoroethyl; $C_{1-6}$ alkyl, eg methyl, isopropyl, t-butyl; $C_{1-6}$ alkoxy, eg methoxy, ethoxy or isopropoxy; het, eg pyrazinyl, imidazolyl, 1,2,4-triazolyl, isoxaolyl, thiazolyl which thiazolyl may be optionally further substituted with halo, eg chloro, pyrazolyl which pyrazolyl may be optionally further substituted with $C_{1-6}$alkyl, eg methyl or halo, eg chloro, tretrahydropyranyl, or pyridinyl where suitably the pyridinyl may be further substituted with eg oxy; phenyl which phenyl may in turn be optionally substituted by one or more substituents selected from halo, eg fluoro, $C_{1-6}$ alkyl optionally substituted by one or more halo groups, eg fluoro, $S(O)_nR^{11}$, eg where $R^{11}$ is methyl or where $R^{11}$ is $C_{1-6}$ alkyl amino eg N-methyl, $-NHS(O)_nR^{11}$, eg where $R^{11}$ is methyl; and $S(O)_nR^{11}$ eg where $R^{11}$ is methyl.

Equally preferred compounds include those where $R^9$ is $NR^eR^f$ where $R^e$ is hydrogen or $C_{1-6}$ alkyl, eg methyl and $R^f$ is $C_{3-8}$ cycloalkyl$C_{1-6}$ alkyl eg cyclopropylmethyl, cyclopropylethyl, cyclobutylmethyl, cyclopentylmethyl or cyclohexylmethyl, which $C_{3-8}$ cycloalkyl$C_{1-6}$ alkyl may be optionally substituted with one or more groups selected from: $C_{1-6}$ alkyl eg methyl; amino; $C(O)NR^cR^d$ where $R^c$ and $R^d$ are both hydrogen; and $NR^cR^d$ where $R^c$ and $R^d$ are independently selected from the group consisting of hydrogen, $C(O)OC_{1-6}$ alkyl eg t-butoxy carbonyl, and $S(O)_nR^{11}$ where $R^{11}$ is methyl.

Equally preferred compounds include those where $R^9$ is $NR^eR^f$ where $R^e$ is hydrogen or $C_{1-6}$ alkyl, eg methyl and $R^f$ is selected from: $-C(O)OC_{1-6}$ alkyl, eg methoxycarbonyl, ethoxycarbonyl or isopropoxycarbonyl; $-C(O)OC_{3-8}$ cycloalkyl eg cyclobutoxycarbonyl; and $-C(O)OC_{1-6}$ alkyl$C_{3-8}$ cycloalkyl eg cyclopropylmethoxycarbonyl, which $-C(O)OC_{1-6}$ alkyl$C_{3-8}$ cycloalkyl may be further optionally substituted by, for example, $C_{1-6}$ haloalkyl eg fluoromethyl.

Even more preferably $R^9$ is selected from: halo eg chloro; $C_{1-6}$ alkyl, eg methyl, which $C_{1-6}$ alkyl may in turn optionally be substituted by halo, eg fluoro; $NR^eR^f$ where each of $R^e$ or $R^f$ is independently selected from hydrogen, $C_{1-6}$ alkyl, eg methyl, ethyl, n-propyl, isopropyl, n-butyl, t-butyl, n-pentyl which $C_{1-6}$ alkyl may in turn be substituted with one or more substituents selected from cyano, halo, eg fluoro, C(O)$NR^cR^d$ where $R^c$ and $R^d$ are both hydrogen, het, eg 1,2,4-triazolyl, or $S(O)_nR^{11}$ eg where $R^{11}$ is methyl; $C_{3-8}$ cycloalkyl$C_{1-6}$ alkyl eg cyclopropylmethyl, cyclopropylethyl, which $C_{3-8}$ cycloalkyl$C_{1-6}$ alkyl may be optionally substituted with C(O)$NR^cR^d$ where $R^c$ and $R^d$ are both hydrogen; —C(O)O$C_{1-6}$ alkyl, eg methoxycarbonyl, ethoxycarbonyl or isopropoxycarbonyl; and —C(O)O$C_{1-6}$ alkyl$C_{3-8}$ cycloalkyl eg cyclopropylmethoxycarbonyl.

Most preferably $R^9$ is selected from: chloro; methyl; difluoromethyl; amino; methylamino; (2-cyanoethyl)amino; isobutylamino; (2-fluoroethyl)amino; (2-fluoro-2-methylpropyl)amino; carbamoylmethylamino; (1,2,4-triazol-1yl)ethylamino; [3-(methylthio)propyl]amino; (cyclopropylmethyl)amino; (methyl)(cyclopropylmethyl)amino; {[1-(aminocarbonyl)cyclopropyl]methyl}amino; (methoxycarbonyl)amino; (ethoxycarbonyl)amino; (isopropoxycarbonyl)amino; (methyl)(ethoxycarbonyl)amino; and [(cyclopropylmethoxy)carbonyl]amino.

Preferably X is $CR^{10}$. Suitable compounds include those where, when $R^{10}$ is halo, preferred halo substituents are fluoro, chloro or bromo. Further suitable compounds include those where, when $R^{10}$ is selected from $C_{1-6}$ alkyl or $C_{1-6}$ alkoxy where the $C_{1-6}$ alkyl or $C_{1-6}$ alkoxy are optionally substituted with one or more halo substituents, preferred halo substituents are fluoro, chloro or bromo. Preferably $R^{10}$ is selected from chloro, or fluoro. Most preferably $R^{10}$ is chloro. Other preferred compounds are those in which $R^7$ and $R^{10}$ are the same. More preferably, both $R^7$ and $R^{10}$ are Cl.

A further group of suitable compounds of the present invention are those of formula (I) where: $R^1$, $R^3$-$R^{11}$, X, $R^c$, $R^d$, n, and het are all as defined for formula (I) above; and $R^2$ is selected from cyano, hydroxy, C(O)OH, het, $S(O)_nR^{11}$, C(O)$NR^aR^b$ and C(S)$NR^aR^b$; or $R^2$ is selected from $C_{1-6}$ alkanoyl, C(O)O$C_{1-6}$ alkyl, and amino, each of which may be optionally and independently further substituted by one or more substituents selected from, where chemically possible, cyano, nitro, halo, oxo, hydroxy, C(O)OH, C(O)$NR^cR^d$, $NR^c$C(O)$R^d$, $C_{1-6}$ alkyl, $C_{2-6}$ alkenyl, $C_{2-6}$ alkynyl, $C_{3-8}$ cycloalkyl, $C_{3-8}$ cycloalkyl$C_{1-6}$ alkyl, $C_{3-8}$ cycloalkyl$C_{1-6}$ haloalkyl, $C_{1-6}$ alkoxy, $C_{1-6}$ alkanoyl, —C(O)O$C_{1-6}$ alkyl, $C_{1-6}$ haloalkyl, $C_{3-8}$ halocycloalkyl, $C_{1-6}$ haloalkoxy, $C_{1-6}$ haloalkanoyl, —C(O)O$C_{1-6}$ haloalkyl, amino, $NR^cR^d$, het, phenyl and $S(O)_nR^{11}$; where $R^a$ and $R^b$ are independently selected from hydrogen, het, phenyl, and $S(O)_nR^{11}$; or either one or both of $R^a$ and $R^b$ are independently selected from $C_{1-6}$ alkyl, $C_{3-8}$ cycloalkyl, $C_{3-8}$ cycloalkyl$C_{1-6}$ alkyl, each of which $R^a$ or $R^b$ may be optionally and independently further substituted by one or more substituents selected from, where chemically possible, cyano, nitro, halo, oxo, hydroxy, C(O)OH, C(O)$NR^cR^d$, $NR^c$C(O)$R^d$, $C_{1-6}$ alkyl, $C_{2-6}$ alkenyl, $C_{2-6}$ alkynyl, $C_{3-8}$ cycloalkyl, $C_{3-8}$ cycloalkyl$C_{1-6}$ alkyl, $C_{3-8}$ cycloalkyl$C_{1-6}$ haloalkyl, $C_{1-6}$ alkoxy, $C_{1-6}$ alkanoyl, —C(O)O$C_{1-6}$ alkyl, $C_{1-6}$ haloalkyl, $C_{3-8}$ halocycloalkyl, $C_{1-6}$ haloalkoxy, $C_{1-6}$ haloalkanoyl, —C(O)O$C_{1-6}$ haloalkyl, amino, $NR^cR^d$, het, phenyl and $S(O)_nR^{11}$; or $R^a$ and $R^b$ together with the N atom to which they are attached may form a three to seven-membered saturated, partially saturated, or unsaturated or aromatic heterocyclic ring which may optionally contain one or more further N, O or S atoms and which may be optionally further substituted by one or more substituents selected from, where chemically possible, cyano, nitro, halo, oxo, hydroxy, C(O)OH, C(O)$NR^cR^d$, $NR^c$C(O)$R^d$, $C_{1-6}$ alkyl, $C_{2-6}$ alkenyl, $C_{2-6}$ alkynyl, $C_{3-8}$ cycloalkyl, $C_{3-8}$ cycloalkyl$C_{1-6}$ alkyl, $C_{3-8}$ cycloalkyl$C_{1-6}$ haloalkyl, $C_{1-6}$ alkoxy, $C_{1-6}$ alkanoyl, —C(O)O$C_{1-6}$ alkyl, $C_{1-6}$ haloalkyl, $C_{3-8}$ halocycloalkyl, $C_{1-6}$ haloalkoxy, $C_{1-6}$ haloalkanoyl, —C(O)O$C_{1-6}$ haloalkyl, amino, $NR^cR^d$, het, phenyl and $S(O)_nR^{11}$;
or a pharmaceutically acceptable salt or a prodrug thereof.

Preferably, in these compounds of formula (I): $R^1$ is selected from $CF_3$, $OCF_3$, or $SF_5$; both $R^3$ and $R^4$ are the same as each other and are selected from: hydrogen; fluoro; and chloro and both $R^5$ and $R^6$ are hydrogen; $R^7$ is chloro; $R^8$ is cyano; and X is $CR^{10}$ where $R^{10}$ is chloro.

A yet further group of suitable compounds of the present invention are those of formula (I) where:
$R^1$-$R^8$, X, $R^c$, $R^d$, n, $R^{10}$-$R^{11}$, and het are all as defined for formula (I) above; and
$R^9$ is selected from hydrogen, halo, and $S(O)_nR^{11}$;
or $R^9$ is selected from $C_{1-6}$ alkyl, $C_{3-8}$ cycloalkyl$C_{1-6}$ alkoxy, which $R^9$ may be optionally and independently further substituted by one or more substituents selected from, where chemically possible, cyano, nitro, halo, oxo, hydroxy, C(O)OH, C(O)$NR^cR^d$, $NR^c$C(O)$R^d$, $C_{1-6}$ alkyl, $C_{2-6}$ alkenyl, $C_{2-6}$ alkynyl, $C_{3-8}$ cycloalkyl, $C_{3-8}$ cycloalkyl$C_{1-6}$ alkyl, $C_{3-8}$ cycloalkyl$C_{1-6}$ haloalkyl, $C_{1-6}$ alkoxy, $C_{1-6}$ alkanoyl, —C(O)O$C_{1-6}$ alkyl, $C_{1-6}$ haloalkyl, $C_{3-8}$ halocycloalkyl, $C_{1-6}$ haloalkoxy, $C_{1-6}$ haloalkanoyl, —C(O)O$C_{1-6}$ haloalkyl, amino, $NR^cR^d$, het, phenyl and $S(O)_nR^{11}$;
or $R^9$ is $NR^eR^f$ where $R^e$ and $R^f$ are independently selected from hydrogen; or either one or both of $R^e$ and $R^f$ are independently selected from $C_{1-6}$ alkyl, $C_{3-8}$ cycloalkyl$C_{1-6}$ alkyl, C(O)O$C_{1-6}$ alkyl, —C(O)O$C_{1-6}$ alkyl$C_{3-8}$ cycloalkyl, —C(O)O$C_{3-8}$ cycloalkyl, each of which $R^e$ or $R^f$ may be optionally and independently further substituted by one or more substituents selected from, where chemically possible, cyano, nitro, halo, oxo, hydroxy, C(O)OH, C(O)$NR^cR^d$, $NR^c$C(O)$R^d$, $C_{1-6}$ alkyl, $C_{2-6}$ alkenyl, $C_{2-6}$ alkynyl, $C_{3-8}$ cycloalkyl, $C_{3-8}$ cycloalkyl$C_{1-6}$ alkyl, $C_{3-8}$ cycloalkyl$C_{1-6}$ haloalkyl, $C_{1-6}$ alkoxy, $C_{1-6}$ alkanoyl, —C(O)O$C_{1-6}$ alkyl, $C_{1-6}$ haloalkyl, $C_{3-8}$ halocycloalkyl, $C_{1-6}$ haloalkoxy, $C_{1-6}$ haloalkanoyl, —C(O)O$C_{1-6}$ haloalkyl, amino, $NR_cR^d$, het, phenyl and $S(O)_nR^{11}$; or a pharmaceutically acceptable salt or a prodrug thereof.

Preferably, in these compounds of formula (I): $R^1$ is selected from $CF_3$, $OCF_3$, or $SF_5$; both $R^3$ and $R^4$ are the same as each other and are selected from: hydrogen; fluoro; and chloro and both $R^5$ and $R^6$ are hydrogen; $R^7$ is chloro; $R^8$ is cyano; and X is $CR^{10}$ where $R^{10}$ is chloro.

A still further of suitable compounds of the present invention are those of formula (I) where:
$R^1$, $R^3$-$R^8$, X, $R^c$, $R^d$, n, $R^{10}$-$R^{11}$, and het are all as defined for formula (I) above; $R^2$ is selected from cyano, hydroxy, C(O)OH, het, $S(O)_nR^{11}$, C(O)$NR^aR^b$ and C(S)$NR^aR^b$;
or $R^2$ is selected from $C_{1-6}$ alkanoyl, C(O)O$C_{1-6}$ alkyl, and amino, each of which may be optionally and independently further substituted by one or more substituents selected from, where chemically possible, cyano, nitro, halo, oxo, hydroxy, C(O)OH, C(O)$NR^cR^d$, $NR^c$C(O)$R^d$, $C_{1-6}$ alkyl, $C_{2-6}$ alkenyl, $C_{2-6}$ alkynyl, $C_{3-8}$ cycloalkyl, $C_{3-8}$ cycloalkyl$C_{1-6}$ alkyl, $C_{3-8}$ cycloalkyl$C_{1-6}$ haloalkyl, $C_{1-6}$ alkoxy, $C_{1-6}$ alkanoyl, —C(O)O$C_{1-6}$ alkyl, $C_{1-6}$ haloalkyl, $C_{3-8}$ halocycloalkyl, $C_{1-6}$ haloalkoxy, $C_{1-6}$ haloalkanoyl, —C(O)O$C_{1-6}$ haloalkyl, amino, $NR^cR^d$, het, phenyl and $S(O)_nR^{11}$; where $R^a$ and $R^b$ are independently selected from hydrogen, het, phenyl, and $S(O)_nR^{11}$; or either one or both of $R^a$ and $R^b$ are independently selected from $C_{1-6}$ alkyl, $C_{3-8}$ cycloalkyl, $C_{3-8}$ cycloalkylC$_{1-6}$ alkyl, each of which R$^a$ or R$^b$ may be optionally and independently further substituted by one or more substituents selected from, where chemically possible, cyano, nitro, halo, oxo, hydroxy, C(O)OH, C(O)NR$^c$R$^d$, NR$^c$-C(O)R$^d$, C$_{1-6}$ alkyl, C$_{2-6}$ alkenyl, C$_{2-6}$ alkynyl, C$_{3-8}$ cycloalkyl, C$_{3-8}$ cycloalkylC$_{1-6}$ alkyl, C$_{3-8}$ cycloalkylC$_{1-6}$ haloalkyl, C$_{1-6}$ alkoxy, C$_{1-6}$ alkanoyl, —C(O)OC$_{1-6}$ alkyl, C$_{1-6}$ haloalkyl, C$_{3-8}$ halocycloalkyl, C$_{1-6}$ haloalkoxy, C$_{1-6}$ haloalkanoyl, —C(O)OC$_{1-6}$ haloalkyl, amino, NR$^c$R$^d$, het, phenyl and S(O)$_n$R$^{11}$; or R$^a$ and R$^b$ together with the N atom to which they are attached may form a three to seven-membered saturated, partially saturated, or unsaturated or aromatic heterocyclic ring which may optionally contain one or more further N, O or S atoms and which may be optionally further substituted by one or more substituents selected from, where chemically possible, cyano, nitro, halo, oxo, hydroxy, C(O)OH, C(O)NR$^c$R$^d$, NR$^c$C(O)R$^d$, C$_{1-6}$ alkyl, C$_{2-6}$ alkenyl, C$_{2-6}$ alkynyl, C$_{3-8}$ cycloalkyl, C$_{3-8}$ cycloalkylC$_{1-6}$ alkyl, C$_{3-8}$ cycloalkylC$_{1-6}$ haloalkyl, C$_{1-6}$ alkoxy, C$_{1-6}$ alkanoyl, —C(O)OC$_{1-6}$ alkyl, C$_{1-6}$ haloalkyl, C$_{3-8}$ halocycloalkyl, C$_{1-6}$ haloalkoxy, C$_{1-6}$ haloalkanoyl, —C(O)OC$_{1-6}$ haloalkyl, amino, NR$^c$R$^d$, het, phenyl and S(O)$_n$R$^{11}$;

R$^9$ is selected from hydrogen, halo, and S(O)$_n$R$^{11}$;

or R$^9$ is selected from C$_{1-6}$ alkyl, C$_{3-8}$ cycloalkylC$_{1-6}$ alkoxy, which R$^9$ may be optionally and independently further substituted by one or more substituents selected from, where chemically possible, cyano, nitro, halo, oxo, hydroxy, C(O)OH, C(O)NR$^c$R$^d$, NR$^c$C(O)R$^d$, C$_{1-6}$ alkyl, C$_{2-6}$ alkenyl, C$_{2-6}$ alkynyl, C$_{3-8}$ cycloalkyl, C$_{3-8}$ cycloalkylC$_{1-6}$ alkyl, C$_{3-8}$ cycloalkylC$_{1-6}$ haloalkyl, C$_{1-6}$ alkoxy, C$_{1-6}$ alkanoyl, —C(O)OC$_{1-6}$ alkyl, C$_{1-6}$ haloalkyl, C$_{3-8}$ halocycloalkyl, C$_{1-6}$ haloalkoxy, C$_{1-6}$ haloalkanoyl, —C(O)OC$_{1-6}$ haloalkyl, amino, NR$^c$R$^d$, het, phenyl and S(O)$_n$R$^{11}$;

or R$^9$ is NR$^e$R$^f$ where R$^e$ and R$^f$ are independently selected from hydrogen; or either one or both of R$^e$ and R$^f$ are independently selected from C$_{1-6}$ alkyl, C$_{3-8}$ cycloalkylC$_{1-6}$ alkyl, C(O)OC$_{1-6}$ alkyl, —C(O)OC$_{1-6}$ alkylC$_{3-8}$ cycloalkyl, —C(O)OC$_{3-8}$ cycloalkyl, each of which R$^e$ or R$^f$ may be optionally and independently further substituted by one or more substituents selected from, where chemically possible, cyano, nitro, halo, oxo, hydroxy, C(O)OH, C(O)NR$^c$R$^d$, NR$^c$C(O)R$^d$, C$_{1-6}$ alkyl, C$_{2-6}$ alkenyl, C$_{2-6}$ alkynyl, C$_{3-8}$ cycloalkyl, C$_{3-8}$ cycloalkylC$_{1-6}$ alkyl, C$_{3-8}$ cycloalkylC$_{1-6}$ haloalkyl, C$_{1-6}$ alkoxy, C$_{1-6}$ alkanoyl, —C(O)OC$_{1-6}$ alkyl, C$_{1-6}$ haloalkyl, C$_{3-8}$ halocycloalkyl, C$_{1-6}$ haloalkoxy, C$_{1-6}$ haloalkanoyl, —C(O)OC$_{1-6}$ haloalkyl, amino, NR$^c$R$^d$, het, phenyl and S(O)$_n$R$^{11}$; or a pharmaceutically acceptable salt or a prodrug thereof.

Preferably, in these compounds of formula (I): R$^1$ is selected from CF$_3$, OCF$_3$, or SF$_5$; both R$^3$ and R$^4$ are the same as each other and are selected from: hydrogen; fluoro; and chloro and both R$^5$ and R$^6$ are hydrogen; R$^7$ is chloro; R$^8$ is cyano; and X is CR$^{10}$ where R$^{10}$ is chloro.

An even further group of suitable compounds of the present invention are those of formula (I) below:
R$^1$-R$^2$, R$^7$-R$^9$, X, R$^c$, R$^d$, n, R$^{11}$ and het are all as defined for formula (I) above; and
R$^3$, R$^4$, R$^5$ and R$^6$ are independently selected from hydrogen, halo, cyano, hydroxy, C(O)OH, nitro, phenyl, and S(O)$_n$R$^{11}$; or either one or more of R$^3$, R$^4$, R$^5$ and R$^6$ are independently selected from C$_{1-4}$ alkyl, C(O)NR$^c$R$^d$, C(S)NR$^c$R$^d$, C$_{1-4}$ alkoxy, C$_{1-4}$ alkanoyl, C(O)OC$_{1-4}$ alkyl, amino which R$^3$, R$^4$, R$^5$ and R$^6$ may be optionally and independently further substituted by one or more substituents selected from, where chemically possible, cyano, nitro, halo, hydroxy, C$_{1-4}$ alkyl and amino;

and where not more than two of R$^3$, R$^4$, R$^5$ and R$^6$ are selected from cyano, hydroxy, C(O)OH, nitro, phenyl, S(O)$_n$R$^{11}$, C(O)NR$^c$R$^d$, C(S)NR$^c$R$^d$, C$_{1-4}$ alkoxy, C$_{1-4}$ alkanoyl, C(O)OC$_{1-4}$ alkyl, and amino;

or a pharmaceutically acceptable salt or a prodrug thereof.

Preferably, in these compounds of formula (I): R$^1$ is selected from CF$_3$, OCF$_3$, or SF$_5$; R$^7$ is chloro; R$^8$ is cyano; and X is CR$^{10}$ where R$^{10}$ is chloro.

Preferred individual compounds of the invention are selected from:

5-amino-1-[2,6-dichloro-4-pentafluorothiophenyl]-4-[1-(methylsulfonyl)cyclopropyl]-1H-pyrazole-3-carbonitrile;

1-{5-amino-3-cyano-1-[2,6-dichloro-4-(trifluoromethyl)phenyl]-1H-pyrazol-4-yl}cyclopropanecarboxamide;

methyl 1-{5-amino-3-cyano-1-[2,6-dichloro-4-(trifluoromethyl)phenyl]-1H-pyrazol-4-yl}cyclopropane-carboxylate;

5-amino-1-[2,6-dichloro-4-(trifluoromethyl)phenyl]-4-[2,2-difluoro-1-(methylsulfonyl)cyclopropyl]-1H-pyrazole-3-carbonitrile;

1-{5-amino-3-cyano-1-[2,6-dichloro-4-(trifluoromethyl)phenyl]-1H-pyrazol-4-yl}-N,N-dimethylcyclopropanecarboxamide;

5-amino-1-[2,6-dichloro-4-(trifluoromethyl)phenyl]-4-[1-(methylsulfonyl)cyclopropyl]-1H-pyrazole-3-carbonitrile;

5-amino-4-(1-amino-2,2-difluorocyclopropyl)-1-[2,6-dichloro-4-(trifluoromethyl)phenyl]-1H-pyrazole-3-carbonitrile;

1-{5-amino-3-cyano-1-[2,6-dichloro-4-(trifluoromethyl)phenyl]-1H-pyrazol-4-yl}-2,2-difluoro-N,N-dimethyl-cyclopropanesulfonamide;

5-amino-1-[2,6-dichloro-4-(trifluoromethyl)phenyl]-4-[1-(pyrrolidin-1-ylcarbonyl)cyclopropyl]-1H-pyrazole-3-carbonitrile;

5-amino-4-(1-cyanocyclopropyl)-1-[2,6-dichloro-4-(trifluoromethyl)phenyl]-1H-pyrazole-3-carbonitrile;

5-amino-4-(1-cyanocyclopropyl)-1-[2,6-dichloro-4-pentafluorothiophenyl]-1H-pyrazole-3-carbonitrile;

1-{5-amino-3-cyano-1-[2,6-dichloro-4-(trifluoromethyl)phenyl]-1H-pyrazol-4-yl}-2,2-difluorocyclopropanesulfonamide;

1-{5-amino-3-cyano-1-[2,6-dichloro-4-pentafluorothiophenyl]-1H-pyrazol-4-yl}cyclopropanecarboxamide;

1-{3-cyano-1-[2,6-dichloro-4-pentafluorothiophenyl]-5-(isobutylamino)-1H-pyrazol-4-yl}cyclopropanecarboxamide;

1-{5-amino-3-cyano-1-[2,6-dichloro-4-pentafluorothiophenyl]-1H-pyrazol-4-yl}-N-isopropylcyclopropanecarboxamide;

1-{3-cyano-1-[2,6-dichloro-4-pentafluorothiophenyl]-5-[(2-fluoroethyl)amino]-1H-pyrazol-4-yl}cyclopropane-carboxamide;

1-{5-[(2-amino-2-oxoethyl)amino]-3-cyano-1-[2,6-dichloro-4-pentafluorothiophenyl]-1H-pyrazol-4-yl}-cyclopropanecarboxamide;

1-{5-amino-3-cyano-1-[2,6-dichloro-4-pentafluorothiophenyl]-1H-pyrazol-4-yl}-2,2-dichlorocyclopropane-carboxamide;

1-{3-cyano-5-[(cyclopropylmethyl)amino]-1-[2,6-dichloro-4-pentafluorothiophenyl]-1H-pyrazol-4-yl}-N-(pyridin-4-ylmethyl)cyclopropanecarboxamide;

isopropyl {4-[1-(aminocarbonyl)cyclopropyl]-3-cyano-1-[2,6-dichloro-4-pentafluorothiophenyl]-1H-pyrazol-5-yl}carbamate;

1-(3-cyano-1-[2,6-dichloro-4-pentafluorothiophenyl]-5-{[2-(1H-1,2,4-triazol-1-yl)ethyl]amino}-1H-pyrazol-4-yl)cyclopropanecarboxamide;

1-{3-cyano-5-[(2-cyanoethyl)amino]-1-[2,6-dichloro-4-pentafluorothiophenyl]-1H-pyrazol-4-yl}cyclopropanecarboxamide;

1-(5-amino-3-cyano-1-{2,6-dichloro-4-[1,2,2,2-tetrafluoro-1-(trifluoromethyl)ethyl]phenyl}-1H-pyrazol-4-yl)cyclopropanecarboxamide;

1-(3-cyano-1-[2,6-dichloro-4-pentafluorothiophenyl]-5-{[3-(methylthio)propyl]amino}-1H-pyrazol-4-yl)-cyclopropanecarboxamide;

1-{3-cyano-5-[(cyclopropylmethyl)amino]-1-[2,6-dichloro-4-pentafluorothiophenyl]-1H-pyrazol-4-yl}-N-[(5-methyl-4H-1,2,4-triazol-3-yl)methyl]cyclopropanecarboxamide;

1-{3-cyano-5-[(cyclopropylmethyl)(methyl)amino]-1-[2,6-dichloro-4-pentafluorothiophenyl]-1H-pyrazol-4-yl}cyclopropanecarboxamide;

[1-(fluoromethyl)cyclopropyl]methyl {4-[1-(aminocarbonyl)cyclopropyl]-3-cyano-1-[2,6-dichloro-4-pentafluorothiophenyl]-1H-pyrazol-5-yl}carbamate;

1-{3-cyano-1-[2,6-dichloro-4-pentafluorothiophenyl]-5-(methylamino)-1H-pyrazol-4-yl}-2,2-difluorocyclopropanecarboxamide;

1-{3-cyano-1-[2,6-dichloro-4-pentafluorothiophenyl]-5-[(3,3,3-trifluoropropyl)amino]-1H-pyrazol-4-yl}cyclopropanecarboxamide;

1-(5-{[(2-chloro-1,3-thiazol-5-yl)methyl]amino}-3-cyano-1-[2,6-dichloro-4-pentafluorothiophenyl]-1H-pyrazol-4-yl)cyclopropanecarboxamide;

1-{3-cyano-1-[2,6-dichloro-4-pentafluorothiophenyl]-5-[(isoxazol-5-ylmethyl)amino]-1H-pyrazol-4-yl}cyclopropanecarboxamide;

N~3~-{4-[1-(aminocarbonyl)cyclopropyl]-3-cyano-1-[2,6-dichloro-4-pentafluorothiophenyl]-1H-pyrazol-5-yl}-beta-alaninamide;

1-{3-cyano-1-[2,6-dichloro-4-pentafluorothiophenyl]-5-[(5,5,5-trifluoropentyl)amino]-1H-pyrazol-4-yl}cyclopropanecarboxamide;

1-{3-cyano-1-[2,6-dichloro-4-pentafluorothiophenyl]-5-(propylamino)-1H-pyrazol-4-yl}cyclopropanecarboxamide;

1-{3-cyano-5-[(cyclobutylmethyl)amino]-1-[2,6-dichloro-4-pentafluorothiophenyl]-1H-pyrazol-4-yl}cyclopropanecarboxamide;

1-{3-cyano-1-[2,6-dichloro-4-pentafluorothiophenyl]-5-(dimethylamino)-1H-pyrazol-4-yl}cyclopropanecarboxamide;

ethyl {4-[1-(aminocarbonyl)cyclopropyl]-3-cyano-1-[2,6-dichloro-4-(trifluoromethoxy)phenyl]-1H-pyrazol-5-yl}carbamate;

2,2-dichloro-1-{3-cyano-1-[2,6-dichloro-4-pentafluorothiophenyl]-5-(methylamino)-1H-pyrazol-4-yl}cyclopropanecarboxamide;

1-{5-amino-3-cyano-1-[2,6-dichloro-4-(trifluoromethoxy)phenyl]-1H-pyrazol-4-yl}-2,2-dichlorocyclopropanecarboxamide;

1-{3-cyano-5-({2-[(cyclopropylmethyl)amino]-2-oxoethyl}amino)-1-[2,6-dichloro-4-pentafluorothiophenyl]-1H-pyrazol-4-yl}cyclopropanecarboxamide;

1-{5-[(4-amino-4-oxobutyl)amino]-3-cyano-1-[2,6-dichloro-4-pentafluorothiophenyl]-1H-pyrazol-4-yl}cyclopropanecarboxamide;

1-{3-cyano-1-[2,6-dichloro-4-pentafluorothiophenyl]-5-[(1,3-thiazol-2-ylmethyl)amino]-1H-pyrazol-4-yl}-cyclopropanecarboxamide;

1-{3-cyano-5-[(cyclopropylmethyl)amino]-1-[2,6-dichloro-4-pentafluorothiophenyl]-1H-pyrazol-4-yl}-N-(2-methoxyethyl)cyclopropanecarboxamide;

1-{3-cyano-5-[(cyclopropylmethyl)amino]-1-[2,6-dichloro-4-pentafluorothiophenyl]-1H-pyrazol-4-yl}-N-(2-hydroxyethyl)cyclopropanecarboxamide;

1-{3-cyano-5-[(cyclopropylmethyl)amino]-1-[2,6-dichloro-4-pentafluorothiophenyl]-1H-pyrazol-4-yl}-N-(pyridin-2-ylmethyl)cyclopropanecarboxamide;

1-{3-cyano-5-[(cyclopropylmethyl)amino]-1-[2,6-dichloro-4-pentafluorothiophenyl]-1H-pyrazol-4-yl}-N-(pyridin-3-ylmethyl)cyclopropanecarboxamide;

1-{3-cyano-5-[(cyclopropylmethyl)amino]-1-[2,6-dichloro-4-pentafluorothiophenyl]-1H-pyrazol-4-yl}-N-(2-hydroxy-2-methylpropyl)cyclopropanecarboxamide;

1-(3-cyano-1-[2,6-dichloro-4-pentafluorothiophenyl]-5-{[2-(1-methyl-1H-pyrazol-4-yl)ethyl]amino}-1H-pyrazol-4-yl)cyclopropanecarboxamide;

1-{3-cyano-1-[2,6-dichloro-4-pentafluorothiophenyl]-5-(dimethylamino)-1H-pyrazol-4-yl}-2,2-difluorocyclopropanecarboxamide;

1-{3-cyano-1-[2,6-dichloro-4-pentafluorothiophenyl]-5-(methylthio)-1H-pyrazol-4-yl}cyclopropanecarboxamide;

1-{3-cyano-1-[2,6-dichloro-4-pentafluorothiophenyl]-5-[(2-methoxyethyl)(methyl)amino]-1H-pyrazol-4-yl}cyclopropanecarboxamide;

1-(5-{[(5-chloro-1,3-dimethyl-1H-pyrazol-4-yl)methyl]amino}-3-cyano-1-[2,6-dichloro-4-pentafluorothiophenyl]-1H-pyrazol-4-yl)cyclopropanecarboxamide;

1-{5-amino-3-cyano-1-[2,6-dichloro-4-pentafluorothiophenyl]-1H-pyrazol-4-yl}-2,2-difluorocyclopropanecarboxamide;

1-{5-amino-3-cyano-1-[2,6-dichloro-4-(trifluoromethoxy)phenyl]-1H-pyrazol-4-yl}cyclopropanecarboxamide;

1-{5-amino-3-cyano-1-[2,6-dichloro-4-(trifluoromethyl)phenyl]-1H-pyrazol-4-yl}-2,2-difluorocyclopropane-carboxamide;

1-{5-amino-3-cyano-1-[2,6-dichloro-4-pentafluorothiophenyl]-1H-pyrazol-4-yl}-N-methylcyclopropane-carboxamide;

1-{5-amino-3-cyano-1-[2,6-dichloro-4-(trifluoromethyl)phenyl]-1H-pyrazol-4-yl}-N-cyclopropylcyclopropanecarboxamide;

1-{5-amino-3-cyano-1-[2,6-dichloro-4-(trifluoromethyl)phenyl]-1H-pyrazol-4-yl}-N-(cyclopropylmethyl)-cyclopropanecarboxamide;

1-{5-amino-3-cyano-1-[2,6-dichloro-4-(trifluoromethyl)phenyl]-1H-pyrazol-4-yl}-N-pyridin-2-ylcyclopropanecarboxamide;

1-{5-amino-1-[2,6-dichloro-4-(trifluoromethyl)phenyl]-3-(trifluoromethyl)-1H-pyrazol-4-yl}cyclopropane-carboxamide;

1-(3-cyano-1-[2,6-dichloro-4-(trifluoromethyl)phenyl]-5-{[(1E)-(dimethylamino)methylene]amino}-1H-pyrazol-4-yl)cyclopropanecarboxamide;

1-{5-amino-3-cyano-1-[2,6-dichloro-4-pentafluorothiophenyl]-1H-pyrazol-4-yl}-N-(2,2,2-trifluoroethyl)-cyclopropanecarboxamide;

1-{3-cyano-1-[2,6-dichloro-4-(trifluoromethoxy)phenyl]-5-(methylamino)-1H-pyrazol-4-yl}-2,2-difluoro-cyclopropanecarboxamide;

1-{3-cyano-1-[2,6-dichloro-4-(trifluoromethoxy)phenyl]-5-(methylamino)-1H-pyrazol-4-yl}cyclopropane-carboxamide;

1-{3-cyano-5-[(cyclopropylmethyl)amino]-1-[2,6-dichloro-4-(trifluoromethyl)phenyl]-1H-pyrazol-4-yl}-N-methyl-cyclopropanecarboxamide;
1-{5-amino-3-cyano-1-[2,6-dichloro-4-(trifluoromethyl)phenyl]-1H-pyrazol-4-yl}-2,2-dimethylcyclopropane-carboxamide;
1-{3-cyano-1-[2,6-dichloro-4-pentafluorothiophenyl]-5-[(4H-1,2,4-triazol-3-ylmethyl)amino]-1H-pyrazol-4-yl}cyclopropanecarboxamide;
1-(3-cyano-1-[2,6-dichloro-4-pentafluorothiophenyl]-5-{[(1-methylcyclopropyl)methyl]amino}-1H-pyrazol-4-yl)cyclopropanecarboxamide;
1-{3-cyano-1-[2,6-dichloro-4-pentafluorothiophenyl]-5-({4-[(methylamino)sulfonyl]benzyl}amino)-1H-pyrazol-4-yl}cyclopropanecarboxamide;
1-{3-cyano-1-[2,6-dichloro-4-pentafluorothiophenyl]-5-({4-[(methylsulfonyl)amino]benzyl}amino)-1H-pyrazol-4-yl}cyclopropanecarboxamide;
1-{3-cyano-1-[2,6-dichloro-4-pentafluorothiophenyl]-5-[(tetrahydro-2H-pyran-4-ylmethyl)amino]-1H-pyrazol-4-yl}cyclopropanecarboxamide;
1-{3-cyano-5-[(cyclopropylmethyl)amino]-1-[2,6-dichloro-4-pentafluorothiophenyl]-1H-pyrazol-4-yl}-N-(3-isopropoxypropyl)cyclopropanecarboxamide;
1-{3-cyano-1-[2,6-dichloro-4-pentafluorothiophenyl]-5-({2-oxo-2-[(2,2,2-trifluoroethyl)amino]ethyl}amino)-1H-pyrazol-4-yl}cyclopropanecarboxamide;
5-amino-1-[2,6-dichloro-4-(trifluoromethyl)phenyl]-4-[2,2-difluoro-1-(methylthio)cyclopropyl]-1H-pyrazole-3-carbonitrile;
S-methyl 5-amino-1-[2,6-dichloro-4-(trifluoromethyl)phenyl]-4-[2,2-difluoro-1-(methylthio)cyclopropyl]-1H-pyrazole-3-carbothioate;
1-{3-cyano-5-[(cyclopropylmethyl)amino]-1-[2,6-dichloro-4-(trifluoromethyl)phenyl]-1H-pyrazol-4-yl}cyclopropanecarboxamide;
1-{5-(benzylamino)-3-cyano-1-[2,6-dichloro-4-(trifluoromethyl)phenyl]-1H-pyrazol-4-yl}cyclopropanecarboxamide;
1-{3-cyano-1-[2,6-dichloro-4-(trifluoromethyl)phenyl]-5-[(pyridin-2-ylmethyl)amino]-1H-pyrazol-4-yl}cyclopropanecarboxamide;
1-{3-cyano-1-[2,6-dichloro-4-(trifluoromethyl)phenyl]-5-[(2,2-dimethylpropyl)amino]-1H-pyrazol-4-yl}cyclopropanecarboxamide;
1-(3-cyano-1-[2,6-dichloro-4-(trifluoromethyl)phenyl]-5-{[4-(methylsulfonyl)benzyl]amino}-1H-pyrazol-4-yl)cyclopropanecarboxamide;
1-{3-cyano-1-[2,6-dichloro-4-(trifluoromethyl)phenyl]-5-[(pyridin-4-ylmethyl)amino]-1H-pyrazol-4-yl}cyclopropanecarboxamide;
1-{3-cyano-1-[2,6-dichloro-4-(trifluoromethyl)phenyl]-5-[(2,2,2-trifluoroethyl)amino]-1H-pyrazol-4-yl}cyclopropanecarboxamide;
1-{3-cyano-1-[2,6-dichloro-4-(trifluoromethyl)phenyl]-5-[(1H-imidazol-2-ylmethyl)amino]-1H-pyrazol-4-yl}cyclopropanecarboxamide;
1-{3-cyano-1-[2,6-dichloro-4-pentafluorothiophenyl]-1H-pyrazol-4-yl}-2,2-difluorocyclopropanecarboxamide;
1-{3-cyano-1-[2,6-dichloro-4-pentafluorothiophenyl]-1H-pyrazol-4-yl}cyclopropanecarboxamide;
1-{5-chloro-3-cyano-1-[2,6-dichloro-4-pentafluorothiophenyl]-1H-pyrazol-4-yl}cyclopropanecarboxamide;
1-{5-chloro-3-cyano-1-[2,6-dichloro-4-pentafluorothiophenyl]-1H-pyrazol-4-yl}-2,2-difluorocyclopropanecarboxamide;
5-amino-1-[2,6-dichloro-4-(trifluoromethyl)phenyl]-4-[1-(5-methyl-1,3,4-oxadiazol-2-yl)cyclopropyl]-1H-pyrazole-3-carbonitrile;
1-{5-amino-3-cyano-1-[2,6-dichloro-4-(trifluoromethyl)phenyl]-1H-pyrazol-4-yl}-2,2-dimethylcyclopropanecarboxylic acid;
1-{3-cyano-1-[2,6-dichloro-4-pentafluorothiophenyl]-5-(methylamino)-1H-pyrazol-4-yl}cyclopropane-carboxamide;
1-{3-cyano-1-[2,6-dichloro-4-pentafluorothiophenyl]-5-(difluoromethyl)-1H-pyrazol-4-yl}cyclopropane-carboxamide; cyclopropylmethyl {4-[1-(aminocarbonyl)cyclopropyl]-3-cyano-1-[2,6-dichloro-4-pentafluorothiophenyl]-1H-pyrazol-5-yl}carbamate;
ethyl {4-[1-(aminocarbonyl)cyclopropyl]-3-cyano-1-[2,6-dichloro-4-pentafluorothiophenyl]-1H-pyrazol-5-yl}methylcarbamate;
1-[({4-[1-(aminocarbonyl)cyclopropyl]-3-cyano-1-[2,6-dichloro-4-pentafluorothiophenyl]-1H-pyrazol-5-yl}amino)methyl]cyclopropanecarboxamide;
1-{3-cyano-1-[2,6-dichloro-4-pentafluorothiophenyl]-5-methyl-1H-pyrazol-4-yl}cyclopropanecarboxamide;
1-{3-cyano-5-[(cyclopropylmethyl)amino]-1-[2,6-dichloro-4-(trifluoromethoxy)phenyl]-1H-pyrazol-4-yl}-cyclopropanecarboxamide;
1-{3-cyano-1-[2,6-dichloro-4-pentafluorothiophenyl]-5-[(2-fluoro-2-methylpropyl)amino]-1H-pyrazol-4-yl}cyclopropanecarboxamide;
methyl {4-[1-(aminocarbonyl)cyclopropyl]-3-cyano-1-[2,6-dichloro-4-pentafluorothiophenyl]-1H-pyrazol-5-yl}carbamate;
1-{5-amino-3-cyano-1-[2,6-dichloro-4-(trifluoromethoxy)phenyl]-1H-pyrazol-4-yl}-2,2-difluorocyclopropane-carboxamide;
ethyl {4-[1-(aminocarbonyl)cyclopropyl]-3-cyano-1-[2,6-dichloro-4-pentafluorothiophenyl]-1H-pyrazol-5-yl}carbamate;
cyclopropylmethyl {4-[1-(aminocarbonyl)cyclopropyl]-3-cyano-1-[2,6-dichloro-4-pentafluorothiophenyl]-1H-pyrazol-5-yl}methylcarbamate;
1-{3-cyano-1-[2,6-dichloro-4-pentafluorothiophenyl]-5-[(4,4,4-trifluorobutyl)amino]-1H-pyrazol-4-yl}-cyclopropanecarboxamide;
1-{3-cyano-1-[2,6-dichloro-4-pentafluorothiophenyl]-5-(ethylamino)-1H-pyrazol-4-yl}cyclopropanecarboxamide;
tert-butyl {1-[({4-[1-(aminocarbonyl)cyclopropyl]-3-cyano-1-[2,6-dichloro-4-pentafluorothiophenyl]-1H-pyrazol-5-yl}amino)methyl]cyclopropyl}carbamate;
1-(3-cyano-1-[2,6-dichloro-4-(trifluoromethyl)phenyl]-5-{[4-(trifluoromethyl)benzyl]amino}-1H-pyrazol-4-yl)cyclopropanecarboxamide;
1-{3-cyano-5-(cyclopropylmethoxy)-1-[2,6-dichloro-4-pentafluorothiophenyl]-1H-pyrazol-4-yl}cyclopropane-carboxamide;
1-{3-cyano-1-[2,6-dichloro-4-pentafluorothiophenyl]-5-[(2-isopropoxyethyl)amino]-1H-pyrazol-4-yl}cyclopropanecarboxamide;
1-{3-cyano-1-[2,6-dichloro-4-pentafluorothiophenyl]-5-vinyl-1H-pyrazol-4-yl}cyclopropanecarboxamide; cyclobutyl {4-[1-(aminocarbonyl)cyclopropyl]-3-cyano-1-[2,6-dichloro-4-pentafluorothiophenyl]-1H-pyrazol-5-yl}carbamate;
1-[5-amino-3-cyano-1-(2,6-dichloro-4-cyanophenyl)-1H-pyrazol-4-yl]cyclopropanecarboxamide;

1-{3-cyano-1-[2,6-dichloro-4-pentafluorothiophenyl]-5-[(4-fluorobenzyl)amino]-1H-pyrazol-4-yl}cyclopropane-carboxamide;

1-{3-cyano-1-[2,6-dichloro-4-pentafluorothiophenyl]-5-(methoxymethyl)-1H-pyrazol-4-yl}cyclopropane-carboxamide;

ethyl {4-[1-(aminocarbonyl)cyclopropyl]-3-cyano-1-[2,6-dichloro-4-(trifluoromethyl)phenyl]-1H-pyrazol-5-yl}carbamate;

1-{3-cyano-5-[(cyclopropylmethyl)amino]-1-[2,6-dichloro-4-pentafluorothiophenyl]-1H-pyrazol-4-yl}cyclopropanecarboxamide;

methyl 1-{5-(benzylamino)-3-cyano-1-[2,6-dichloro-4-(trifluoromethyl)phenyl]-1H-pyrazol-4-yl}cyclopropanecarboxylate;

1-{3-cyano-5-[(cyclopropylmethyl)amino]-1-[2,6-dichloro-4-pentafluorothiophenyl]-1H-pyrazol-4-yl}-2,2-difluoro-cyclopropanecarboxamide;

1-{3-cyano-5-[(cyclopropylmethyl)amino]-1-[2,6-dichloro-4-(trifluoromethyl)phenyl]-1H-pyrazol-4-yl}-2,2-difluorocyclopropanecarboxamide;

4-(1-cyanocyclopropyl)-1-[2,6-dichloro-4-pentafluorothiophenyl]-5-(methylamino)-1H-pyrazole-3-carbonitrile;

1-{5-amino-3-cyano-1-[2,6-dichloro-4-(trifluoromethyl)phenyl]-1H-pyrazol-4-yl}cyclopropanecarbothioamide;

5-amino-1-[2,6-dichloro-4-(trifluoromethyl)phenyl]-4-[1-(1,3-thiazol-2-yl)cyclopropyl]-1H-pyrazole-3-carbonitrile;

1-(3-cyano-1-[2,6-dichloro-4-(trifluoromethyl)phenyl]-5-{[(1-oxidopyridin-4-yl)methyl]amino}-1H-pyrazol-4-yl)cyclopropanecarboxamide;

1-{5-amino-3-cyano-1-[2,6-dichloro-4-pentafluorothiophenyl]-1H-pyrazol-4-yl}-N-(methylsulfonyl)-cyclopropanecarboxamide;

1-{3-cyano-5-[(2-cyclopropylethyl)amino]-1-[2,6-dichloro-4-pentafluorothiophenyl]-1H-pyrazol-4-yl}cyclopropanecarboxamide;

1-[2,6-dichloro-4-pentafluorothiophenyl]-7-methyl-5-oxo-5,6,7,8-tetrahydro-1H-spiro[cyclopropane-1,4-pyrazolo[3,4-d][1,3]diazepine]-3-carbonitrile;

5-amino-1-[2,6-dichloro-4-(trifluoromethyl)phenyl]-4-[2,2-difluoro-1-(methylsulfinyl)cyclopropyl]-1H-pyrazole-3-carbonitrile;

5-amino-1-[2,6-dichloro-4-(trifluoromethyl)phenyl]-4-[2,2-difluoro-1-(methylsulfinyl)cyclopropyl]-1H-pyrazole-3-carbonitrile;

1-{3-cyano-1-[2,6-dichloro-4-pentafluorothiophenyl]-5-(isopropylamino)-1H-pyrazol-4-yl}cyclopropane-carboxamide;

1-{3-cyano-1-[2,6-dichloro-4-(trifluoromethoxy)phenyl]-5-(isopropylamino)-1H-pyrazol-4-yl}-2,2-difluorocyclopropanecarboxamide;

4-(1-cyanocyclopropyl)-5-[(cyclopropylmethyl)amino]-1-[2,6-dichloro-4-pentafluorothiophenyl]-1H-pyrazole-3-carbonitrile;

1-{3-cyano-1-[2,6-dichloro-4-pentafluorothiophenyl]-5-[({1-[(methylsulfonyl)amino]cyclopropyl}methyl)amino]-1H-pyrazol-4-yl}cyclopropanecarboxamide;

1-(5-{[(1-aminocyclopropyl)methyl]amino}-3-cyano-1-[2,6-dichloro-4-pentafluorothiophenyl]-1H-pyrazol-4-yl)cyclopropanecarboxamide;

1-{3-cyano-1-[2,6-dichloro-4-pentafluorothiophenyl]-5-(methylsulfinyl)-1H-pyrazol-4-yl}cyclopropanecarboxamide;

1-{3-cyano-1-[2,6-dichloro-4-pentafluorothiophenyl]-5-(methylsulfonyl)-1H-pyrazol-4-yl}cyclopropanecarboxamide;

4-({4-[1-(aminocarbonyl)cyclopropyl]-3-cyano-1-[2,6-dichloro-4-pentafluorothiophenyl]-1H-pyrazol-5-yl}amino)butanoic acid;

or a pharmaceutically acceptable salt or prodrug thereof.

Even more preferred individual compounds of the present invention are selected from:

1-{3-cyano-5-[(cyclopropylmethyl)amino]-1-[2,6-dichloro-4-pentafluorothiophenyl]-1H-pyrazol-4-yl}cyclopropanecarboxamide; cyclopropylmethyl {4-[1-(aminocarbonyl)cyclopropyl]-3-cyano-1-[2,6-dichloro-4-pentafluorothiophenyl]-1H-pyrazol-5-yl}carbamate;

1-{5-amino-3-cyano-1-[2,6-dichloro-4-pentafluorothiophenyl]-1H-pyrazol-4-yl}cyclopropanecarboxamide;

1-{3-cyano-1-[2,6-dichloro-4-pentafluorothiophenyl]-5-(methylamino)-1H-pyrazol-4-yl}cyclopropanecarboxamide;

1-{3-cyano-5-[(cyclopropylmethyl)amino]-1-[2,6-dichloro-4-(trifluoromethoxy)phenyl]-1H-pyrazol-4-yl}cyclopropanecarboxamide;

1-{5-amino-3-cyano-1-[2,6-dichloro-4-pentafluorothiophenyl]-1H-pyrazol-4-yl}-2,2-dichlorocyclopropane-carboxamide;

1-{5-amino-3-cyano-1-[2,6-dichloro-4-(trifluoromethoxy)phenyl]-1H-pyrazol-4-yl}-2,2-difluorocyclopropane-carboxamide;

1-{3-cyano-1-[2,6-dichloro-4-pentafluorothiophenyl]-5-[(2-fluoroethyl)amino]-1H-pyrazol-4-yl}cyclopropane-carboxamide;

1-{3-cyano-1-[2,6-dichloro-4-pentafluorothiophenyl]-5-(methylamino)-1H-pyrazol-4-yl}-2,2-difluorocyclopropanecarboxamide;

1-[({4-[1-(aminocarbonyl)cyclopropyl]-3-cyano-1-[2,6-dichloro-4-pentafluorothiophenyl]-1H-pyrazol-5-yl}amino)methyl]cyclopropanecarboxamide;

ethyl {4-[1-(aminocarbonyl)cyclopropyl]-3-cyano-1-[2,6-dichloro-4-pentafluorothiophenyl]-1H-pyrazol-5-yl}methylcarbamate;

1-{3-cyano-1-[2,6-dichloro-4-pentafluorothiophenyl]-5-(isobutylamino)-1H-pyrazol-4-yl}cyclopropane-carboxamide;

1-{3-cyano-5-[(cyclopropylmethyl)amino]-1-[2,6-dichloro-4-pentafluorothiophenyl]-1H-pyrazol-4-yl}-N-(pyridin-4-ylmethyl)cyclopropanecarboxamide;

isopropyl {4-[1-(aminocarbonyl)cyclopropyl]-3-cyano-1-[2,6-dichloro-4-pentafluorothiophenyl]-1H-pyrazol-5-yl}carbamate;

1-(3-cyano-1-[2,6-dichloro-4-pentafluorothiophenyl]-5-{[3-(methylthio)propyl]amino}-1H-pyrazol-4-yl)-cyclopropanecarboxamide;

1-{3-cyano-1-[2,6-dichloro-4-pentafluorothiophenyl]-5-[(2-fluoro-2-methylpropyl)amino]-1H-pyrazol-4-yl}cyclopropanecarboxamide;

1-(3-cyano-1-[2,6-dichloro-4-pentafluorothiophenyl]-5-{[2-(1H-1,2,4-triazol-1-yl)ethyl]amino}-1H-pyrazol-4-yl)cyclopropanecarboxamide;

1-{3-cyano-5-[(2-cyanoethyl)amino]-1-[2,6-dichloro-4-pentafluorothiophenyl]-1H-pyrazol-4-yl}cyclopropane-carboxamide;

1-{5-chloro-3-cyano-1-[2,6-dichloro-4-pentafluorothiophenyl]-1H-pyrazol-4-yl}-2,2-difluorocyclopropane-carboxamide;

1-{5-chloro-3-cyano-1-[2,6-dichloro-4-pentafluorothiophenyl]-1H-pyrazol-4-yl}cyclopropanecarboxamide;

1-{3-cyano-1-[2,6-dichloro-4-pentafluorothiophenyl]-5-methyl-1H-pyrazol-4-yl}cyclopropanecarboxamide;
1-{3-cyano-1-[2,6-dichloro-4-pentafluorothiophenyl]-5-(difluoromethyl)-1H-pyrazol-4-yl}cyclopropanecarboxamide;
1-{5-amino-3-cyano-1-[2,6-dichloro-4-pentafluorothiophenyl]-1H-pyrazol-4-yl}-N-isopropylcyclopropane-carboxamide;
1-{5-[(2-amino-2-oxoethyl)amino]-3-cyano-1-[2,6-dichloro-4-pentafluorothiophenyl]-1H-pyrazol-4-yl}-cyclopropanecarboxamide;
methyl {4-[1-(aminocarbonyl)cyclopropyl]-3-cyano-1-[2,6-dichloro-4-pentafluorothiophenyl]-1H-pyrazol-5-yl}carbamate;
5-amino-1-[2,6-dichloro-4-pentafluorothiophenyl]-4-[1-(methylsulfonyl)cyclopropyl]-1H-pyrazole-3-carbonitrile;
1-{3-cyano-5-[(cyclopropylmethyl)(methyl)amino]-1-[2,6-dichloro-4-pentafluorothiophenyl]-1H-pyrazol-4-yl}cyclopropanecarboxamide;
ethyl {4-[1-(aminocarbonyl)cyclopropyl]-3-cyano-1-[2,6-dichloro-4-pentafluorothiophenyl]-1H-pyrazol-5-yl}carbamate;
or a pharmaceutically acceptable salt or prodrug thereof.

Most preferred individual compounds of the present invention are selected from:
1-{3-cyano-5-[(cyclopropylmethyl)amino]-1-[2,6-dichloro-4-pentafluorothiophenyl]-1H-pyrazol-4-yl}cyclopropanecarboxamide; cyclopropylmethyl {4-[1-(aminocarbonyl)cyclopropyl]-3-cyano-1-[2,6-dichloro-4-pentafluorothiophenyl]-1H-pyrazol-5-yl}carbamate;
1-{5-amino-3-cyano-1-[2,6-dichloro-4-(trifluoromethoxy)phenyl]-1H-pyrazol-4-yl}-2,2-difluorocyclopropane-carboxamide;
1-{3-cyano-1-[2,6-dichloro-4-pentafluorothiophenyl]-5-[(2-fluoroethyl)amino]-1H-pyrazol-4-yl}cyclopropane-carboxamide;
1-{3-cyano-1-[2,6-dichloro-4-pentafluorothiophenyl]-5-(methylamino)-1H-pyrazol-4-yl}-2,2-difluoro-cyclopropanecarboxamide;
1-{5-chloro-3-cyano-1-[2,6-dichloro-4-pentafluorothiophenyl]-1H-pyrazol-4-yl}cyclopropanecarboxamide;
or a pharmaceutically acceptable salt or prodrug thereof.

In the compounds according to formula (I) the term 'halo' means a group selected from fluoro, chloro, bromo or iodo. Preferably the term "halo" means a group selected from fluoro, chloro or bromo.

Alkyl, alkenyl, alkynyl and alkoxy groups, containing the requisite number of carbon atoms, can be unbranched or branched. The term lower alkyl shall be taken to mean $C_{1-6}$ alkyl. Examples of alkyl include methyl, ethyl, n-propyl, i-propyl, n-butyl, i-butyl, sec-butyl and t-butyl. Examples of alkoxy include methoxy, ethoxy, n-propoxy, i-propoxy, n-butoxy, i-butoxy, sec-butoxy and t-butoxy. Examples of alkenyl include methylene, 1,1-ethylene, 1,2-ethylene, 1,1-propylene, 1,2-propylene, 1,3-propylene and 2,2-propylene. The term cycloalkyl shall be taken to mean $C_{3-8}$ cycloalkyl. Examples of include cyclopropyl, cyclobutyl, cyclopentyl, cyclohexyl and cycloheptyl.

In the compounds according to formula (I) the term phenyl shall be taken to mean a six membered aromatic carbon ring, which phenyl can be substituted as described for compounds of formula (I).

In the compounds according to formula (I) the term "het" shall be taken to mean those substituents which fall into the definition as set out in claim 1. Preferably the term "het" shall be taken to mean those substituents which represent a five to six membered heterocyclic group, which is aromatic or non-aromatic, unsaturated, partially saturated or saturated and which contains one or more heteroatoms selected from nitrogen, N-oxide, oxygen, and sulphur and wherein said heterocyclic ring is optionally substituted where the valence allows with one or more substituents selected from halo, $C_{1-6}$ alkyl, $C_{1-6}$ haloalkyl, $NR^gR^h$, where $R^g$ and $R^h$ are independently selected from hydrogen, and $C_{1-6}$ alkyl. More preferably the term "het" shall be taken to mean those substituents which represent a five to six membered heterocyclic ring, which is aromatic or non-aromatic, unsaturated, partially saturated or saturated and which contains at least one nitrogen or oxygen atom and optionally up to two further heterocyclic atoms selected from nitrogen, oxygen and sulphur and wherein said heterocyclic ring is optionally substituted where the valence allows with one or more substituents selected from halo, $C_{1-6}$ alkyl, $C_{1-6}$ haloalkyl, $NR^gR^h$, where $R^g$ and $R^h$ are independently selected from hydrogen, and $C_{1-6}$ alkyl.

In the case of substituents $R^2$, $R^a$, or $R^b$ and further optional substituents thereof of compounds of formula (I), the term "het" shall most preferably be taken to mean those substituents which represent a five to six membered heterocyclic ring, which is aromatic, unsaturated, or partially saturated and which contains at least one nitrogen atom and optionally up to two further heterocyclic atoms selected from nitrogen, oxygen and sulphur and wherein said heterocyclic ring is optionally substituted where the valence allows with one or more substituents selected from halo, and $C_{1-6}$ alkyl. Suitable preferred examples of such rings include 1-oxa-3,4-diazolyl, thiazolyl, 5-methyl-1-3,4-oxadiazol-2-yl, pyridinyl, or 1, 2, 4 triazolyl.

In the case of substituents $R^9$, $R^e$, or $R^f$ and further optional substituents thereof of compounds of formula (I), the term "het" shall most preferably be taken to mean those substituents which represent a five to six membered heterocyclic ring, which is aromatic, unsaturated, partially saturated, or saturated and which contains at least one nitrogen atom or one oxygen atom and optionally up to two further heterocyclic atoms selected from nitrogen, oxygen or sulphur and wherein said heterocyclic ring is optionally substituted where the valence allows with one or more substituents selected from halo, and $C_{1-6}$ alkyl. Suitable preferred examples of such rings include pyrazinyl, imidazolyl, pyridinyl, 1-hydroxypyridinyl, 1,2,4-triazolyl, 1,3,4-triazolyl, isoxaolyl, thiazolyl, 2-chloro-1,3-thiazol-4-yl, pyrazolyl, 1-methyl-1H-pyrazol-4-yl, 1-methyl-3-methyl-5-chloro-1H-pyrazol-4-yl, and tretrahydropyranyl.

In the compounds according to formula (I) each phenyl group may be optionally and independently substituted as set out in Claim 1. More preferably each phenyl group may be optionally and independently substituted with one or more further substitutents selected from the group consisting of halo, $C_{1-6}$ alkyl, $C_{1-6}$ haloalkyl, $C_{1-6}$ alkoxy, $C_{1-6}$ haloalkoxy, $-NHS(O)_nR^{11}$, and $S(O)_nR^{11}$. More preferably each phenyl group may be optionally substituted in the 4-position with a substituent selected from the group consisting of halo, $C_{1-6}$ haloalkyl, $-NHS(O)_nR^{11}$, and $S(O)_nR^{11}$.

In the case of substituents $R^9$, $R^e$, or $R^f$ and further optional substituents thereof of compounds of formula (I) it is preferred that each phenyl group may be optionally substituted in the 4-position a substituent selected from the group consisting of halo, $C_{1-6}$ haloalkyl, $-NHS(O)_nR^{11}$, and $S(O)_nR^{11}$. Suitable examples of such phenyl groups include 4-fluorophenyl, 4-trifluoromethylphenyl, (4-methylsulphonyl)phenyl, 4-[(methylsulphonyl)amino]phenyl, and 4-[(methylamino)sulphonyl]phenyl.

It will be understood that compounds of formula (I) may exist as one or more geometric isomers. Thus included within the scope of the present invention are all such possible geometric isomer forms of the compounds of the present invention. Geometric isomers may be separated by conventional techniques well known to those skilled in the art, for example, chromatography and fractional crystallisation.

It will be understood that compounds of formula (I) may exist as one or more tautomeric isomers. Thus included within the scope of the present invention are all such possible tautomeric isomer forms of compounds of the present invention.

It is to be understood that compounds of formula (I) may contain one or more asymmetric carbon atoms, thus compounds of the invention can exist as two or more stereoisomers. Included within the scope of the present invention are all stereoisomers such as enantiomers and diastereomers. Also included are acid addition or base salts wherein the counterion is optically active, for example, D-lactate or L-lysine, or racemic, for example, DL-tartrate or DL-arginine.

Conventional techniques for the preparation/isolation of individual enantiomers include chiral synthesis from a suitable optically pure precursor or resolution of the racemate (or the racemate of a salt or derivative) using, for example, chiral high performance liquid chromatography (HPLC).

Alternatively, the racemate (or a racemic precursor) may be reacted with a suitable optically active compound, for example, an alcohol, or, in the case where the compound of formula (I) contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, using conditions such as on an asymmetric resin with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture.

Stereoisomeric conglomerates may be separated by conventional techniques known to those skilled in the art—see, for example, "Stereochemistry of Organic Compounds" by E L Eliel (Wiley, New York, 1994).

Also included within the scope of the present invention are compounds exhibiting more than one type of isomerism, and mixtures of one or more thereof.

For the avoidance of doubt, it will be understood that throughout the application all references to pharmaceutically acceptable compounds includes references to veterinarily acceptable compounds or agriculturally acceptable compounds. Furthermore it will be understood that throughout the application all references to pharmaceutical activity includes references to veterinary activity or agricultural activity.

Pharmaceutically acceptable salts of the compounds of formula (I) include the acid addition and base salts thereof. Suitable acid addition salts are formed from acids which form non-toxic salts. Examples include the acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts. Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

The pharmaceutically, veterinarily and agriculturally acceptable acid addition salts of certain of the compounds of formula (I) may also be prepared in a conventional manner. For example, a solution of a free base may be treated with the appropriate acid, either neat or in a suitable solvent, and the resulting salt isolated either by filtration or by evaporation under reduced pressure of the reaction solvent. For a review on suitable salts, see "Handbook of Pharmaceutical Salts Properties, Selection, and Use" by Stahl and Wermuth (Wiley-VCH, Weinheim, Germany, 2002).

Hereinafter, and throughout the application, all references to compounds of formula (I) include references to salts, solvates and complexes thereof and to solvates and complexes of salts thereof.

The invention includes all polymorphs of the compounds of formula (I) as hereinbefore defined.

The compounds of the invention may exist in both unsolvated and solvated forms. The term 'solvate' is used herein to describe a molecular complex comprising the compound of the invention and one or more pharmaceutically acceptable solvent molecules, for example, ethanol. The term 'hydrate' is employed when said solvent is water. Pharmaceutically acceptable solvates in accordance with the invention include those wherein the solvent of crystallization may be isotopically substituted, e.g. $D_2O$, $d_6$-acetone, $d_6$-DMSO.

Included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts. The resulting complexes may be ionised, partially ionised, or non-ionised. For a review of such complexes, see J Pharm Sci, 64 (8), 1269-1288 by Haleblian (August 1975).

The present invention includes all pharmaceutically acceptable isotopically-labelled compounds of formula (I) wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Within the scope of the invention are so-called 'prodrugs' of the compounds of formula (I). Thus certain derivatives of compounds of formula (I) which may have little or no pharmacological activity themselves can, when administered into or onto the body, be converted into compounds of formula (I) having the desired activity, for example, by hydrolytic cleavage. Such derivatives are referred to as 'prodrugs'. Further information on the use of prodrugs may be found in 'Prodrugs as Novel Delivery Systems, Vol. 14, ACS Symposium Series (T Higuchi and W Stella) and 'Bioreversible Carriers in Drug Design', Pergamon Press, 1987 (ed. E B Roche, American Pharmaceutical Association).

Prodrugs in accordance with the invention can, for example, be produced by replacing appropriate functionalities present in the compounds of formula (I) with certain moieties known to those skilled in the art as 'pro-moieties' as described, for example, in "Design of Prodrugs" by H Bundgaard (Elsevier, 1985).

Some examples of prodrugs in accordance with the invention include:

(i) where the compound of formula (I) contains a carboxylic acid functionality (—COOH), an ester thereof, for example, replacement of the hydrogen with ($C_1$-$C_8$)alkyl;

(ii) where the compound of formula (I) contains an alcohol functionality (—OH), an ether thereof, for example, replacement of the hydrogen with ($C_1$-$C_6$)alkanoyloxymethyl; and (iii) where the compound of formula (I) contains a primary or secondary amino functionality (—$NH_2$ or —NHR where R≠H), an amide thereof, for example, replacement of one or both hydrogens with ($C_1$-$C_{10}$)alkanoyl.

Prodrugs in accordance with the invention can, for example, be produced by replacing the 5-amino substituent on the pyrazole ring in the compounds of formula (I) with certain moieties known to those skilled in the art as 'pro-drug moieties' as described, for example, in "Design of Prodrugs" by H Bundgaard (Elsevier, 1985); "Design and application of prodrugs," Textbook of Drug Design and Discovery, (3d Edition), 2002, 410-458, (Taylor and Francis Ltd., London); and references therein.

Suitable prodrugs may have an N-containing group at the 5-position of the pyrazole ring of formula (I) and are bound to the ring through N. The 5-N group can be substituted once or twice. Examples of substituents include: alkyl amines, aryl amines, amides, ureas, carbamates, cyclic carbamates, imines, enamines, imides, cyclic imides, sulfenamides, and sulfonamides. The hydrocarbon portion of these groups contain $C_{1-6}$ alkyl, phenyl, heteroaryl such as pyridinyl, $C_{2-6}$ alkenyl, and $C_{3-8}$ cycloalkyl; wherein each of the above groups may include one or more optional substituents where chemically possible independently selected from: halo; hydroxy; $C_{1-6}$ alkyl and $C_{1-6}$ alkoxy.

Further examples of replacement groups in accordance with the foregoing example and examples of other prodrug types may be found in the aforementioned references.

A prodrug according to the invention can be readily identified by administering it to a host animal and sampling a body fluid for a compound of formula (I). Finally, certain compounds of formula (I) may themselves act as prodrugs of other compounds of formula (I). Prodrugs may be cleaved to active drug by metabolism by the host or by the parasite targeting the host.

In a further aspect, the present invention provides processes for the preparation of a compound of formula (I), or a pharmaceutically, veterinarily or agriculturally acceptable salt thereof, or a pharmaceutically, veterinarily or agriculturally acceptable solvate (including hydrate) of either entity, as illustrated below.

It will be apparent to those skilled in the art that sensitive functional groups may need to be protected and deprotected during synthesis of a compound of the invention. This may be achieved by conventional methods, for example as described in "Protective Groups in Organic Synthesis" by T W Greene and P G M Wuts, John Wiley & Sons Inc (1999), and references therein.

The following processes are illustrative of the general synthetic procedures which may be adopted in order to obtain the compounds of the invention.

When one or more of $R^1$, $R^2$, $R^3$, $R^4$, $R^5$, $R^6$, $R^7$, $R^8$, $R^9$, $R^{10}$ and $R^{11}$ contain reactive functional groups then additional protection may be provided according to standard procedures during the synthesis of compounds of formula (I). In the processes described below, for all synthetic precursors used in the synthesis of compounds of formula (I), the definitions of $R^1$, $R^2$, $R^3$, $R^4$ $R^5$, $R^6$, $R^7$, $R^8$, $R^9$, $R^{10}$ and $R^{11}$, wherein $R^1$, $R^2$, $R^3$, $R^4$ $R^5$, $R^6$, $R^7$, $R^8$, $R^9$, $R^{10}$, and $R^{11}$ are as defined for formula (I), are intended to optionally include suitably protected variants, $P^1$, $P^2$, $P^3$, $P^4$ $P^5$, $P^6$, $P^7$, $P^8$, $P^9$, $P^{10}$ and $P^{11}$. Such suitable protecting groups for these functionalities are described in the references listed below and the use of these protecting groups where needed is specifically intended to fall within the scope of the processes described in the present invention for producing compounds of formula (I) and its precursors. When suitable protecting groups are used, then these will need to be removed to yield compounds of formula (I). Deprotection can be effected according to standard procedures including those described in the references listed below. For example, when $R^9$ in formula (I) is an unsubstituted amino group, certain precursors may require protection of the amino group in order to perform the necessary transformations, for example, by an imidoformamide group such as a compound of formula (I), where $R^1$-$R^8$ and $R^{10}$ are as described for formula (I) and $R^9$ represents —N=C(H)—$NR^cR^d$, where $R^c$ and $R^d$ independently represent $C_{1-6}$alkyl, e.g. to form a N,N-dimethyl group. Such imidoformamides may be prepared by standard methods, typically by refluxing the unprotected amine in N,N-dimethylformamide dimethyl acetal for 2-16 hours, usually around 5 hours followed by stirring at room temperature for 5-24 hours, usually overnight. The imidoformamide protecting group may be removed under standard conditions, such as at elevated temperature, with a suitable acid such as hydrochloric acid or para-toluenesulfonic acid in a solvent such as methanol or dioxane.

A compound of formula (I) may be prepared by cyclopropanation of an alkene of formula (II):

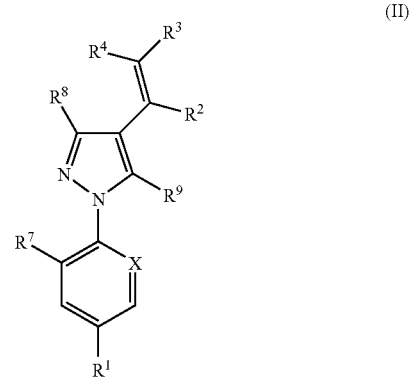

(II)

wherein $R^1$, $R^2$, $R^3$, $R^4$, $R^7$, $R^8$, $R^9$ and X are as previously defined for formula (I). This may be achieved by in situ generation of the required carbenoid species, $CR^5R^6$ in which $R^5$ and $R^6$ are as previously defined for formula (I), in the presence of (II), by an appropriate method.

Such methods may include treatment of a compound of formula (II), with a reactive species such as trimethylsilyl difluoro(fluorosulfonyl)acetate (TFDA) at reflux in the presence of sodium fluoride, as described by Dolbier et al., in J. Fluor Chem., 2004, 125, 459, to yield a product of formula (I). Other methods for in situ carbenoid generation include treatment of chloroform or bromoform with base, preferably under phase transfer catalysis conditions, thermolysis of a suitable organometallic precursor such as an aryl trifluoromethyl, trichloromethyl, tribromomethyl or phenyl(trifluoromethyl) mercury derivative or treatment with a diazoalkane in the presence of a transition metal catalyst and treatment with a diazoalkane in the absence of a transition metal catalyst followed by thermolysis of the intermediate pyrazoline, or generation from a sulphur ylid.

Compounds of formula (II) can be synthesized using an organozinc reagent of formula (III):

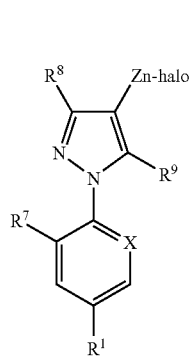

(III)

wherein $R^1$, $R^7$, $R^8$, $R^9$ and X are as previously defined for formula (I). The organozinc reagent formula (III) may be obtained by treatment of (IV) wherein halo is preferably bromo or iodo, with activated zinc (Rieke zinc) in an aprotic solvent such as tetrahydrofuran, for several hours. The organozincate can then be cross coupled to a haloalkene in the presence of a palladium (II) species such as dichlorobis(triphenylphosphine) palladium (II) and a reducing agent such as diisobutylaluminium hydride in an aprotic solvent such as tetrahydrofuran, at elevated temperatures, normally at reflux.

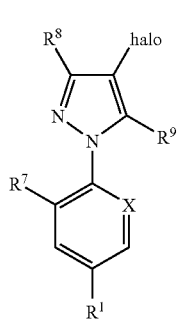

(IV)

Alternatively, a compound of formula (II) may be obtained directly by the reaction of a compound of formula (IV) with an organostannane in the presence of a metal catalyst such as tetrakis(triphenylphosphine)palladium(0) at an elevated temperature for several hours.

Compounds of formula (IV) may be useful for accessing intermediates of formula (V).

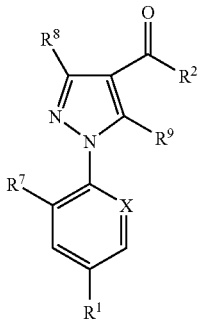

(V)

Thus, compounds of formula (IV) can be treated with a Grignard reagent such as isopropyl-magnesium chloride under inert conditions using an aprotic solvent at reduced temperature before treatment with an acid chloride or acid anhydride, upon warming to room temperature the desired ketone represented by formula (V) is produced.

Compounds of formula (V) can be utilized to access compounds of formula (II) wherein $R^3$ and $R^4$ are H. Thus compounds of formula (V) can be methylenated by treatment with a Wittig reagent under inert conditions at reduced temperature in a solvent such as tetrahydrofuran.

Compounds of formula (II) can also be obtained from compounds of formula (V), by treatment with a haloalkene such as dibromodifluoromethane in the presence of triphenylphosphine and Reike zinc in an aprotic solvent.

Similarly, a compound of formula (II) may be obtained by the reaction of a compound of formula (IV) with an organozinc reagent. A specific example is the compound of formula (VI), prepared as shown in Scheme 1 below. The reaction uses a metal catalyst such as tetrakis(triphenylphosphine)palladium(0) in a suitable solvent such as N,N-dimethylformamide at an elevated temperature, typically 110° C., for several hours, typically 10. Intermediates used in the synthesis of compound (VI) can be obtained using conventional synthetic procedures, in accordance with standard textbooks on organic chemistry or literature precedent.

Scheme 1

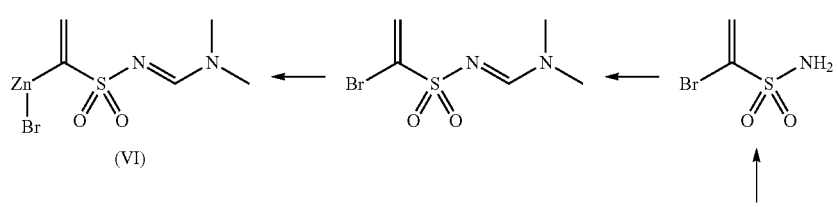

(VI)

-continued

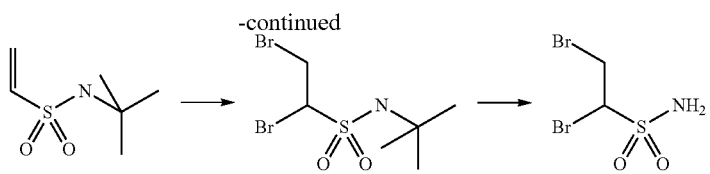

Alternatively, a compound of formula (VII), wherein $R^1$, $R^7$, $R^8$, $R^9$ and X are as previously defined for formula (I) may be obtained by the reaction of a compound of formula (IV) with a suitable Grignard reagent such as isopropylmagnesium chloride followed by the addition of methyl pyruvate in a suitable solvent such as tetrahydrofuran.

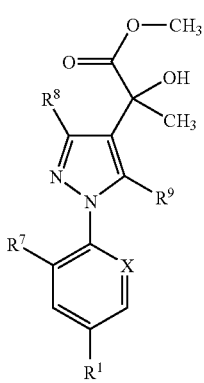

(VII)

Subsequent dehydration using a mild base and an activating agent such as methanesulphonyl chloride gives a compound of formula (II) wherein $R^2$ is $COOCH_3$. Alternatively, dehydration can be achieved using a two step sequence of halogenation using thionyl chloride in acetonitrile followed by dehydrohalogenation by heating in an inert solvent such as para-xylene or by standard base catalysed dehydrohalogenation procedures.

A compound of formula (IV) may be obtained from a compound of formula (VIII):

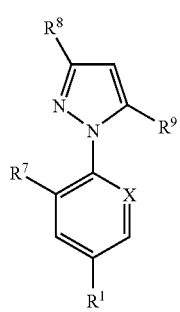

(VIII)

wherein $R^1$, $R^7$, $R^8$, $R^9$ and X are as previously defined for formula (I), by conventional bromination or iodination procedures. For example, when halo is iodo, (VIII) is treated with N-iodosuccinimide in a suitable solvent such as acetonitrile at from about room temperature to about 85° C.

Alternatively, a compound of formula (IV) may be prepared as shown in Scheme 2 below:

Scheme 2

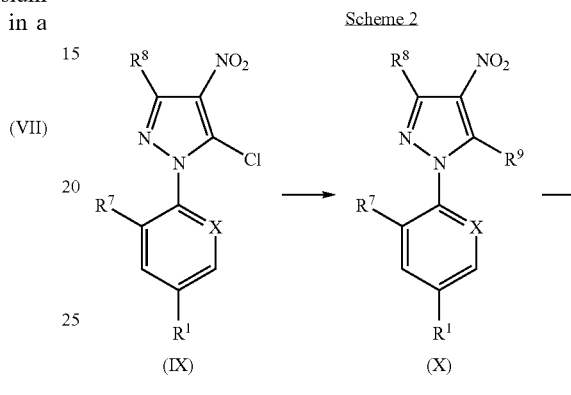

(IX)    (X)

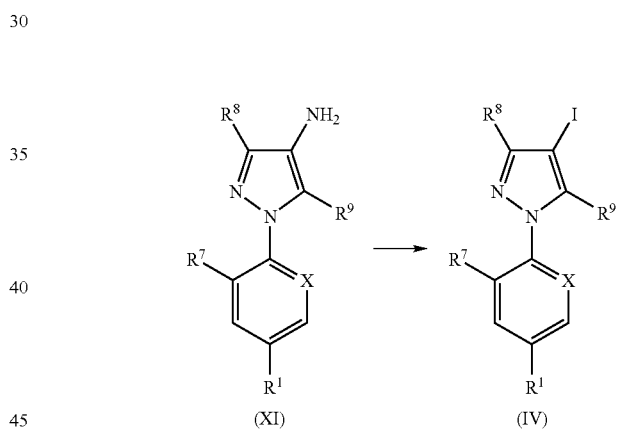

(XI)    (IV)

wherein $R^1$, $R^7$, $R^8$ and X are as previously defined for formula (I) and $R^9$ is $SR^r$, $NR^rR^s$ or $OR^r$ wherein $R^r$ and $R^s$ are each independently H, alkyl, cycloalkyl, aryl, heteroaryl, cycloalkylalkyl, arylalkyl, heteroarylalkyl wherein each alkyl, cycloalkyl, aryl, heteroaryl, cycloalkylalkyl, arylalkyl, heteroarylalkyl may be optionally substituted. Compounds of formula (X) can be prepared from compounds of formula (IX) via standard nucleophilic substitution procedures. The amine (XI) may then be obtained by reduction using a suitable reducing agent, optionally in the presence of a catalyst, typically $SnCl_2/HCl$ or $Fe/CaCl_2$. Compounds of formula (IV) may be prepared from (XI) by conventional Sandmeyer procedures.

A specific method for preparing a compound of formula (I), wherein $R^2$ is $CF_2O$, $R^3$, $R^4$ are F and $R^5$, $R^6$ are H is via an intermediate oxonium ion (XIII) formed by the reaction of a ketone of formula (XII) with TFDA in the presence of sodium fluoride, followed by hydride transfer and carbene insertion at the newly formed olefin to give the cyclopropane.

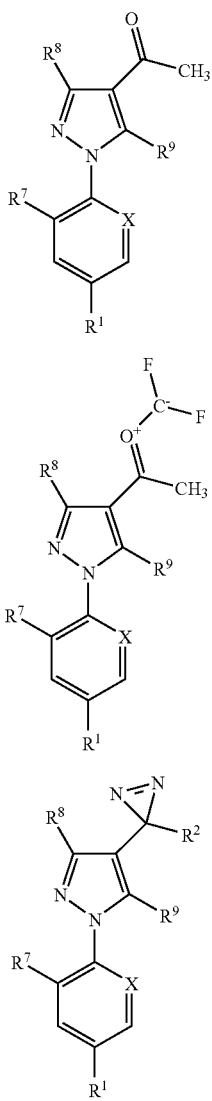

(XII)

(XIII)

(XIV)

Another cyclopropanation procedure is via the reaction of a carbenoid species, generated in situ from compounds of formula (XIV), with alkenes of formula:

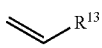

where $R^{13}$ is optionally substituted aryl or heteroaryl. For example, a compound of formula (I) in which $R^2$ is $CF_3$ and $R^3$ is 4-chlorophenyl may be obtained by stirring a compound of formula (XIV), wherein $R^2$ is $CF_3$ with 4-chlorostyrene in a suitable solvent, typically toluene, at 60° C. for an extended period of time, typically 18 hours.

The diazirine (XIV) may be prepared from the corresponding diaziridine using standard oxidising agents, such as iodine or those described in "Handbook of Reagents for Organic Synthesis—Oxidising and Reducing Agents" edited by S. D. Burke and R. L. Danheiser.

The diaziridine may be prepared by reacting compounds of formula (XV), wherein $R^1$, $R^2$, $R^7$, $R^8$, $R^9$ and X are as defined for formula (I)

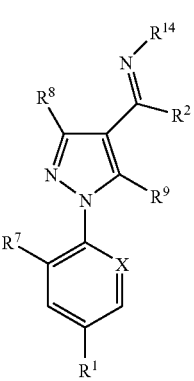

(XV)

and $R^{14}$ is tosyloxy, with ammonia gas at elevated pressure, followed by reaction with a suitable base such as triethylamine.

Furthermore, a compound of formula (I) may be prepared by the ring contraction of a 4,5-dihydropyrazole of formula (XVI), wherein $R^1$, $R^2$, $R^7$, $R^8$, $R^9$ and X are as defined for formula (I) by heating at elevated temperatures in a suitable aprotic solvent such as xylene. An alternative extrusion method uses u.v. light in a suitable solvent, such as dichloromethane, in the presence of an initiator, such as benzophenone. This is particularly appropriate where $R^2$ is $SO_2$alkyl. During the preparation of compounds of formula (I) wherein $R^2$ is $SO_2NH_2$, the sulphamoyl group may need protection as the sulphonimido-formamide.

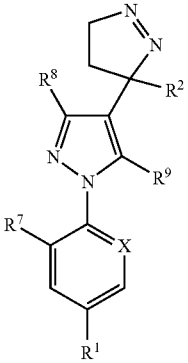

(XVI)

The dihydropyrazoles are prepared from compounds of formula (II), wherein $R^1$, $R^2$, $R^7$, $R^8$, $R^9$ and X are as defined for formula (I), by standard literature procedures.

Arylpyrazoles of formula (I) may also be prepared by the Japp-Klingemann reaction. This reaction is described in Org. React., 1959, 10, 143-178. 3,4,5-Trisubstituted 1-arylpyrazoles may be produced directly in a reaction which involves coupling of an aryldiazonium species with an appropriately substituted precursor bearing a desired substituent. The desired substituent is introduced concomitantly at the C-4 position in a process, which does not involve any rearrangement. Furthermore, a very wide variety of 4-substituents may be introduced conveniently and directly.

Thus, a compound of formula (I) in which $R^9$ is $NH_2$, can be prepared by reacting a compound of formula (XVII)

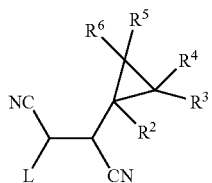

(XVII)

with a compound of formula (XVIII)

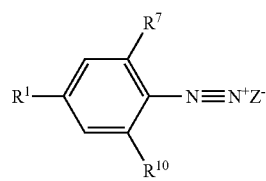

(XVIII)

optionally in the presence of an acid, wherein:
$R^1$ to $R^{10}$ are as defined above in relation to the compounds of formula (I);
L is an activating group; and
Z is a compatible counter ion, followed by removal of group L.

The counter ion $Z^-$ may be any suitable counter ion normally found in diazonium reactions. Preferably, $Z^-$ is halogen, $HSO_4$—, or tetrafluoroborate and most preferably is tetrafluoroborate.

The group L is an electron withdrawing group which stabilises the anion intermediate in the process. Thus, preferably, L is a group which is capable of stabilising a negative charge on an adjacent carbon atom. The group L must also be removable. L can be removed under basic conditions, for example by base hydrolysis or can be removed by reduction and/or elimination. The group L is important as it serves to direct the reaction of the diazonium species with the compound of formula (XVII) but then is removed in the subsequent stages of the reaction. Preferably L is an ester group or a group $COR^{15}$. More preferably, L is a group selected from: —S(O)$_p R^{16}$ where p is 1 or 2, $(R^{16}O)_2PO$, $COOR^{16}$ and —$COR^{15}$, wherein $R^{15}$ is selected from: $C_{1-8}$ alkyl, di-$C_{1-8}$ alkylamino, $C_{1-8}$alkylthio, $C_{3-8}$ cycloalkyl, $(CH_2)_n$Ph and $(CH_2)_n$ heteroaryl wherein n=0, 1 or 2, each of which groups may be optionally substituted on any carbon atom by one or more groups selected independently from: halogen, hydroxy, cyano, nitro, $C_{1-4}$ alkoxy, $C_{1-4}$ haloalkoxy, $C_{1-4}$ alkanoyl, $C_{1-4}$ haloalkanoyl, $C_{1-4}$ alkylsulphinyl, $C_{1-4}$ haloalkylsulphinyl, $C_{1-4}$ alkylsulphonyl, $C_{1-4}$ haloalkylsulphonyl, $C_{3-8}$ cycloalkyl and $C_{3-8}$ halocycloalkyl; and $R^{15}$ can be hydrogen; and wherein $R^{16}$ is selected from: $C_{1-8}$ alkyl, $C_{3-8}$ cycloalkyl, $(CH_2)_n$Ph and $(CH_2)_n$ heteroaryl wherein n=0, 1 or 2, each of which groups may be optionally substituted on any carbon atom by one or more groups selected independently from: halogen, hydroxy, cyano, nitro, $C_{1-4}$ alkoxy, $C_{1-4}$ haloalkoxy, $C_{1-4}$ alkanoyl, $C_{1-4}$ haloalkanoyl, $C_{1-4}$ alkylsulphinyl, $C_{1-4}$ haloalkylsulphinyl, $C_{1-4}$ alkylsulphonyl, $C_{1-4}$ haloalkylsulphonyl, $C_{3-8}$ cycloalkyl and $C_{3-8}$ halocycloalkyl; and $R^{15}$ can be hydrogen. Preferably L is a group selected from $COR^{15}$ and $COOR^{16}$. Most preferably L is —COOMe or —COOEt.

In certain cases, the nature of the leaving group L means that the resulting intermediate is in the wrong oxidation state. Thus, where necessary, one or more reaction steps may be added to ensure the correct oxidation state is reached prior to cyclising to form the aryl pyrazole.

Ideally, for the coupling reaction to form the compound of formula (I), the solvent should be a polar solvent which does not react with either the diazonium salt or cation, or with the compound of formula (XVII). The reaction may optionally be carried out under mildly acidic conditions. The diazonium salt of formula (XVIII) can be produced by conventional means and may be prepared in situ for further reaction or can be isolated and used in a subsequent reaction step. For example, by the dropwise addition of a solution of the corresponding aminobenzenes in glacial acetic acid to a solution of sodium nitrite in concentrated sulphuric/glacial acetic acid mixtures at reduced temperature, typically 10° C., followed by heating at 50° C. for several hours, typically 1 hour and allowing to cool to room temperature. This solution of the diazonium salt is then added dropwise to a solution of a compound of formula (XVII) in a suitable solvent, such as acetic acid followed by stirring at room temperature for up to 1 hour. The reaction mixture is poured into water and extracted with a water immiscible organic solvent such as dichloromethane. Aqueous ammonium hydroxide is added to the organic extract and stirred overnight to give compounds of formula (I). The aminobenzenes are generally commercially available. Others may be prepared by standard literature procedures. For example (XX) is readily prepared from (XIX) by chlorination using N-chlorosuccinimide in acetonitrile.

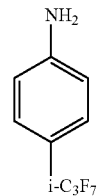

(XIX)

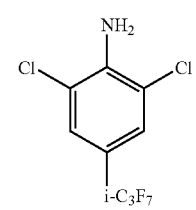

(XX)

Alternatively, compounds of formula (XVII) can be obtained from compounds of formula (XXI) wherein $R^2$, $R^3$, $R^4$, $R^5$, $R^6$ and L are as defined for formula (XVII), for example, by treating a compound of formula (XX!) with a source of cyanide ions.

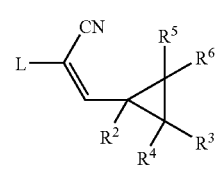

(XXI)

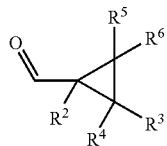
(XXII)

Compounds of the formula (XXI) can be obtained by reducing and then dehydrating a compound of formula (XXIII).

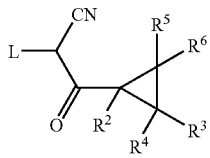
(XXIII)

Compounds of formula (XXIII) can, for example, be made by condensation of an alkyl cyanoalkanoate e.g. methyl cyanoacetate with an acid chloride in an aprotic solvent such as dichloromethane in the presence of a Lewis acid, such as magnesium chloride and a mild base, such as triethylamine, at reduced temperature.

Alternatively, compounds of formula (XXI) can be accessed by Knoevenagel condensation of a suitable aldehyde, such as (XXII) or ketone with an alkyl alkanoate such as methyl cyanoacetate. Compounds of formula (XXII) in which $R^2$=COOalkyl can be prepared by selective reduction of the malonyl esters (XXIV)

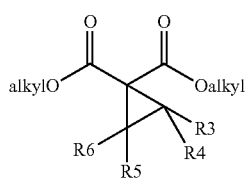
(XXIV)

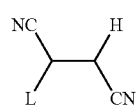
(XXV)

Compounds of formula (XXV) wherein L=$CO_2C_1$ to $C_6$ alkyl are synthesised by the slow addition of glycolonitrile optionally at decreased temperatures to a $C_1$ to $C_6$ alkyl cyanoacetate, in an aprotic solvent such as dimethylformamide, followed by the addition of a base such as potassium carbonate.

In addition, variations to the Japp-Klingemann reaction, utilising standard conditions well-known to those skilled in the art, for producing compounds of formula (I) and its precursors, are also intended to fall within the scope described in the present invention. For example, coupling of an aryldiazonium species with precursors of formula (XXVI):

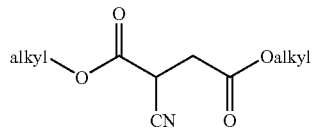
(XXVI)

in the presence of a suitable base, may be useful in accessing compounds in which $R^9$ is OH. These compounds may then undergo standard alkylation, acylation, carbamoylation, sulphonation and other procedures to produce, for example, the corresponding alkoxy derivatives.

Alternatively, arylpyrazoles may be prepared by the reaction of optionally substituted phenylhydrazine derivatives with compounds of formula (XXVII) or (XXVIII):

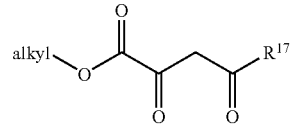
(XXVII)

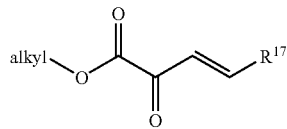
(XXVIII)

in which $R^{17}$ is lower alkyl or cycloalkyl.

In another aspect, the invention provides processes for the preparation of compounds of formula (I) from alternative compounds of formula (I) through functional group interconversion. For example, saponification of a compound of (I) in which $R^2$ is a methyl ester to give the acid, may be achieved using standard ester hydrolysis conditions. A particularly useful procedure involves adding tetrahydrofuran, water and lithium hydroxide and stirring at room temperature for from 1 to 60 h or by the addition of pyridine and lithium iodide and heating at elevated temperatures for an extended period of time. This acid can be further reacted with secondary, tertiary or cyclic amine compounds or ammonia or ammonium hydroxide in the presence of a suitable base such as triethylamine and an activating agent, such as ethyl chloroformate, in a suitable solvent such as tetrahydrofuran to give the amide derivative. For example, to a compound of formula (I) in which $R^2$ is $CO_2H$ in tetrahydrofuran and triethylamine, cooled to 0° C. can be added ethyl chloroformate, cyclopropylmethylamine and in tetrahydrofuran and allowed to warm to room temperature to give a compound of formula (I) in which $R^2$ is cyclopropanecarboxamide.

Compounds of formula (I), in which $R^2$ is a carboxylic acid, can be reduced by standard literature procedures, such as sodium borohydride, to give the corresponding alcohol.

Furthermore, compounds of formula (I), in which $R^2$ is a carboxylic acid, can rearrange under standard Curtius conditions to carbamates which after deprotection gave compounds of formula (I) wherein $R^2$ is $NH_2$.

Using standard reaction conditions, compounds of formula (I), wherein $R^2$ is an alkyl ester may be converted to amides, wherein $R^2$ is $CONH_2$. For example, trimethyl aluminium in hexane is added to ammonium chloride in a suitable solvent, typically toluene, at 0° C., optionally under nitrogen. After stirring for 1-2 h at room temperature, a solution of a compound of formula (I), wherein $R^2$ is COOalkyl, in a suitable solvent is added. Conversion to the amide is achieved by stirring at elevated temperature, typically 50° C. for 15-80 hours. Similarly, transesterifications may be achieved by reaction with a substituted alcohol and hydroxylamides ($R^2$ is CONHOH) prepared by reaction with hydroxylamine. Acylhydrazones and bis-acylhydrazones may be similarly prepared using literature conditions. These bis-acylhydrazones may be converted to 1,2,4-oxadiazoles by reaction with phosphorus oxychloride in a suitable solvent. The acylhydrazones may be converted to 1,2,4-oxadiazoles by refluxing with triethyl orthoformate in the presence of an acid catalyst, typically p-toluenesulphonic acid. These 1,2,4-oxadiazoles can be hydrolysed back to the acylhydrazones by refluxing in a suitable solvent, such as methanol:dioxane mixtures, in the presence of an acid, such as hydrochloric acid.

Compounds of formula (I) in which $R^2$ is an amide may undergo standard alkylation reactions with compounds of formula $R^1$—Y, in which Y is a suitable leaving group, to give the substituted amide. Compounds of formula (I) in which $R^2$ is an amide may undergo a functional group interconversion by refluxing with Lawesson's reagent for several hours in a suitable solvent, typically tetrahydrofuran, to produce the thioamide or be dehydrated by reaction with trifluoroacetic anhydride in pyridine at 0° C. for several hours to give the nitrile, wherein $R^2$ is CN.

In particular, a compound of formula (XXIX), wherein $R^1$-$R^8$ and X are as defined for formula (I), can be cyclised to (XXX) via the acid catalysed addition of an aldehyde to give the imine intermediate followed by the in situ reduction using a suitable reducing agent, such as sodium borohydride.

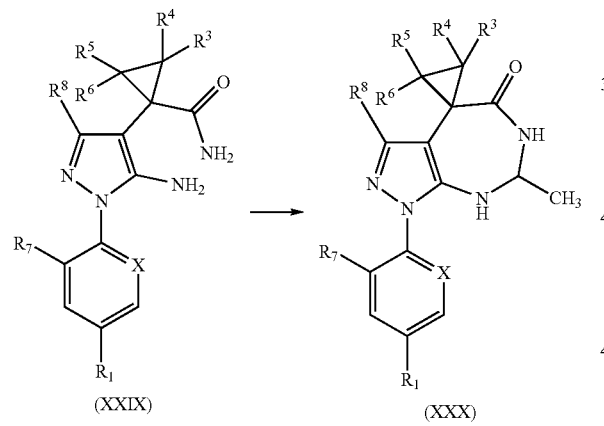

(XXIX)    (XXX)

Compounds of formula (I) in which $R^2$ is aminomethyl may be obtained via formation of the thioalkylated intermediate formed by treatment of (I) in which $R^2$ is a thioamide, with an alkylating agent such as triethyloxonium tetrafluoroborate, in a suitable solvent, typically dichloromethane, at 0° C. and then by being allowed to stir at room temperature for an extended period of time, followed by reduction with sodium borohydride at 0° C.

Compounds of formula (I) in which $R^2$ is thioamide may be reacted with haloketones or haloaldehydes to give (I) in which $R^2$ is substituted thiazole. Similarly, reaction with acylhydrazides to give compounds of formula (I) in which $R^2$ is substituted triazole.

Compounds of formula (I) in which $R^2$ is aminomethyl can be further treated with an acid anhydride, in a suitable solvent, typically dichloromethane and a mild base such as triethylamine and stirring at room temperature for an extended period of time, typically 60 h, to give the corresponding amide.

Furthermore compounds of formula (I) in which $R^2$ is aminomethyl can be monosulphonated or disulphonated with alkyl or aryl sulphonyl halides under standard conditions well-known to those skilled in the art.

Compounds of formula (I) in which $R^2$ is halo can undergo standard nucleophilic substitution reactions by refluxing with a suitable acid catalyst such as p-toluenesulphonic acid and an alkylthiol or alcohol for an extended period of time, typically from 18 hours to several days, to produce the corresponding ether or thioether respectively. Compounds of formula (I) in which $R^2$ is S-alkyl can be oxidised to the corresponding sulphines or sulphones using standard oxidizing agents, such as m-chloroperoxybenzoic acid or those described in "Handbook of Reagents for Organic Synthesis—Oxidising and Reducing Agents" edited by S. D. Burke and R. L. Danheiser Compounds of formula (I) in which $R^2$ is formyl can undergo standard literature procedures for transformation of aldehydes. For example, reaction with (trifluoromethyl)trimethylsilane in a suitable solvent, such as tetrahydrofuran, in the presence of tetrabutylammonium fluoride gives intermediates of formula (XXXI). These intermediates can be desilylated using tetrabutylammonium fluoride in tetrahydrofuran to give secondary alcohols of formula (XXXII)

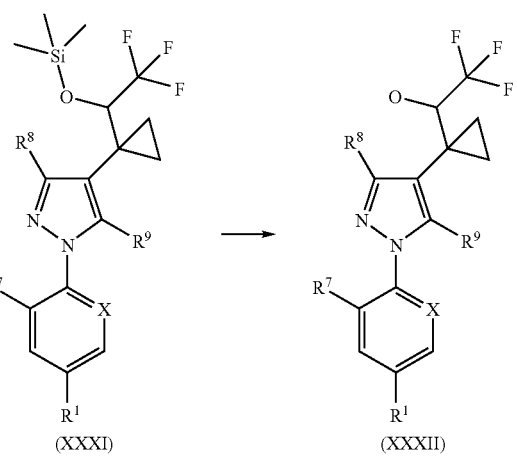

(XXXI)    (XXXII)

Compounds of formula (I) in which $R^2$ contains a secondary alcohol can be oxidized, for example by stirring with Dess Martin Periodinane at room temperature for 30 minutes in a suitable solvent, typically dichloromethane, to produce the corresponding ketone. Compounds of formula (I) in which $R^2$ contains a primary alcohol can be oxidized, for example by stirring with Dess Martin Periodinane at room temperature for 30 minutes in a suitable solvent, typically dichloromethane, to produce the corresponding aldehyde, for example, $R^2$=hydroxymethyl can be readily converted to $R^2$=formyl. Compounds of formula (I), in which $R^2$=hydroxymethyl can be prepared by reduction of the acids of formula (I), wherein $R^2$=—COOH. The acid can be activated by reaction with ethylchloroformate in the presence of a base, such as triethylamine in a suitable solvent, such as tetrahydrofuran; subsequent reduction can be effected using, for example, sodium borohydride.

Compounds of formula (I) in which $R^9$ is $NH_2$ may be used to synthesis imines by reacting the amino functionality of formula (I) with aldehydes and an appropriate acid catalyst, typically p-toluenesulphonic acid at room temperature, for an extended period of time, typically 16 h or with aldehydes in the presence of a mild reducing agent such as sodium triacetoxyborohydride and a mild base to form secondary amines. For example, a compound of formula (I) in which $R^9$ is $NH_2$ undergoes reaction with isonicotinaldehyde and a mild base to give the corresponding imine functionality which can be further reduced by reaction with a suitable reducing agent such as sodium borohydride to give the secondary amine. This can be further oxidized using standard procedures to give the N-oxide. Similarly, compounds of formula (I) in which $R^9$ is $NH_2$ may be reacted with optionally substituted ketones.

N-alkylation, N-arylalkylation and N-heteroarylalkylation of compounds of formula (I) in which $R^9$ is $NH_2$ can also be effected by reaction with the appropriate organic halides using a strong base, such as sodium hydride in a suitable aprotic solvent, for example N-methylpyrrolidone. Reactions are stirred at room temperature for 10-25 hours, typically overnight. Those skilled in the art will recognize that using a suitable sequence of synthetic procedures both mono-N-substituted and di-N-substituted products may be obtained. More reactive alkyl halides need less severe reaction conditions. For example, compounds of formula (I) in which $R^9$ is $NH_2$ will react with tert-butyl bromoacetate in a suitable solvent, such as acetonitrile in the presence of a weak base, typically potassium carbonate at elevated temperatures, typically 55° C.

Compounds of formula (I) in which $R^9$ is $NH_2$ may be carbamoylated by stirring with phosgene in a suitable solvent, typically dichloromethane, in the presence of a base, such as pyridine, at 0° C., followed by reaction with a primary, secondary or tertiary alcohol at room temperature for 10-30 hours, typically overnight. Compounds of formula (I) in which $R^9$ is $NH_2$ may also be carbamoylated by reacting with chloroformates using standard literature conditions.

Reductive amination of compounds in which $R^9$=$NH_2$ can also be achieved with protected aldehydes, such as (XXXIII)

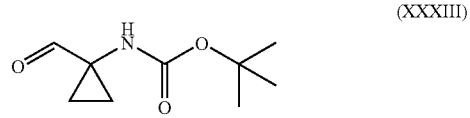
(XXXIII)

The t-BOC protecting group can be removed using standard procedures such as stirring with trifluoroacetic acid in a suitable solvent, such as dichloromethane for several hours, usually 2 hours, at room temperatures yielding compounds of formula (XXXIV)

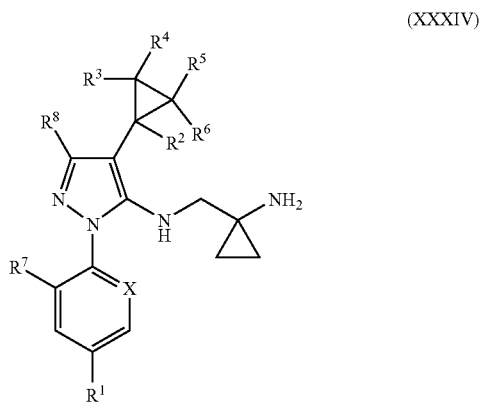
(XXXIV)

The primary amine in compounds of formula (XXXIV) can be alkylated, acylated and sulphonylated using classical literature procedures. Typical sulphonylation procedures are reaction with a sulphonyl chloride in a suitable solvent, such as dichloromethane, in the presence of a base, such as triethylamine.

Reductive amination of compounds in which $R^9$=$NH_2$ can also be achieved with protected aldehydes, such as (XXXV). The t-BOC protecting group can be removed using trifluoroacetic acid in dichloromethane.

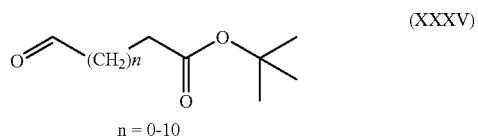
(XXXV)

n = 0-10

Compounds of formula (I) in which $R^9$ is $NH_2$, can undergo reaction with triethyl orthoformate in acidic conditions, by heating at elevated temperatures, typically 60° C., for several hours, typically from 2 to 4 hours, to give (I) in which $R^9$ is —N=$CHOC_2H_5$. This can, in turn, be further reduced by a suitable reducing agent, such as sodium borohydride, to give a compound of formula (I) in which $R^9$ is —$NHCH_3$. Compounds of formula (I) in which $R^9$ is $NH_2$ may be functionalised in a similar manner A compound of formula (I) in which $R^9$ is H, may be prepared by the diazotisation of a compound of formula (I) in which $R^9$ is $NH_2$ by a variety of standard diazotisation procedures.

In a similar manner, compounds of formula (I) in which $R^9$ is —S-alkyl, may be formed by coupling the diazonium species formed from a compound of formula (I) in which $R^9$ is $NH_2$ and an appropriate nucleophile such as $(alkylS)_2$. Furthermore, compounds of formula (I) in which $R^9$ is S-alkyl may be oxidised, using standard oxidising agents, such as hydrogen peroxide, to give the corresponding sulphines and sulphones.

Compounds of formula (I) in which $R^9$ is $NH_2$, can be converted to give a compound of formula (I) wherein $R^9$ is halo, utilising standard Sandmeyer reaction conditions. These halo compounds may be used in standard organometallic coupling procedures, for example in the preparation of a compound of formula (I) in which $R^9$=—$CF_3$.

Compounds of formula (I) in which $R^9$ is $CH_2Y$ or N-alkyl-Y, in which Y is a suitable leaving group such as halo, may, in the presence of a suitable base, undergo a wide range of nucleophilic substitution reactions well known to those skilled in the art. Examples of such nucleophiles are cyanide ion, alcohols, phenols, thiols, primary and secondary amines and heterocycles such as 1,2,4-triazole. A typical leaving group is the mesyl group; such compounds are prepared from compounds in which Y=OH by reaction with methane sulphonyl chloride in acetonitrile in the presence of triethylamine.

Furthermore, compounds of formula (I) in which $R^9$ is —$NH_2$ or aminoalkyl can be monosulphonated or disulphonated with alkyl or aryl sulphonyl halides under standard conditions well-known to those skilled in the art, to give the corresponding sulphonamides.

Furthermore, compounds of formula (I) in which $R^9$ is —$NH_2$ or aminoalkyl can be acylated under standard conditions well known to those skilled in the art. The resulting amides can be reduced to amines by reaction with phosphorus pentachloride in toluene at reflux, cooling to room temperature and pouring into sodium borohydride in a polar hydroxylic solvent, such as methanol.

Compounds of formula (I) in which $R^9$ is —$NH_2$, may also be converted to compounds of formula (I) in which $R^9$ is —$CH_3$ or —$CHF_2$ as shown in Scheme 3 below. Firstly, compounds (XXXVI) may be converted to (XXXVII) by the radical arylation of methyl acrylate with the corresponding diazonium salts. Compounds of formula (XXXVII) can be dehydrobrominated using standard conditions by stirring with base, such as DBU, for several hours, to give enones, (XXXVIII). Conversion of (XXXVIII) to (XXXIX) can be achieved via diol formation, utilising $OsO_4$, followed by oxidative cleavage, using an oxidising agent such as sodium periodate, to generate the aldehyde. Aldehydes of formula (XXXIX) may be reduced to give alcohols of formula (XL) by stirring with a reducing agent, typically sodium borohydride or reacted further with a halogenating reagent such as diethylaminosulfur trifluoride to obtain a compound of formula (I) in which $R^9$ is difluoromethyl. Reaction of (XL) with thionyl chloride and heating at reflux for several hours gives the intermediate chloro derivative from compounds of formula (XLI) may then be obtained by reduction, for example using Rieke zinc.

Compounds of formula (XXXIX) and (XL) may be used to prepare compounds of formula (I) in which $R^9$ encompasses a wide variety of carbon linked substituents. Also, in (XL), activation of the hydroxyl, such as by mesylation or tosylation, gives an intermediate that undergoes a wide range of nucleophilic substitution reactions. Compounds of formula (XL) can also be acylated and alkylated using standard literature procedures. For example by reaction with an alkyl halide, such as iodomethane, in a suitable solvent, typically acetonitrile, in the presence of a base, such as potassium carbonate at room temperature for several days, typically 5 days. The aldehyde, (XXXIX) may be readily converted to the acid, nitrile, esters, amides and thioamides under standard conditions well-known to those skilled in the art. Standard Wittig olefination of the aldehyde (XXXIX) may be followed by routine cyclopropanation procedures to give compounds in which $R^9$ is substituted cyclopropyl. For example, methylenation may be achieved using the Wittig reaction, using a Peterson reagent, using a Tebbe reagent or using the Lombardt procedure. A typical Wittig reaction involves adding n-butyllithium in hexane to a solution of methyltriph-

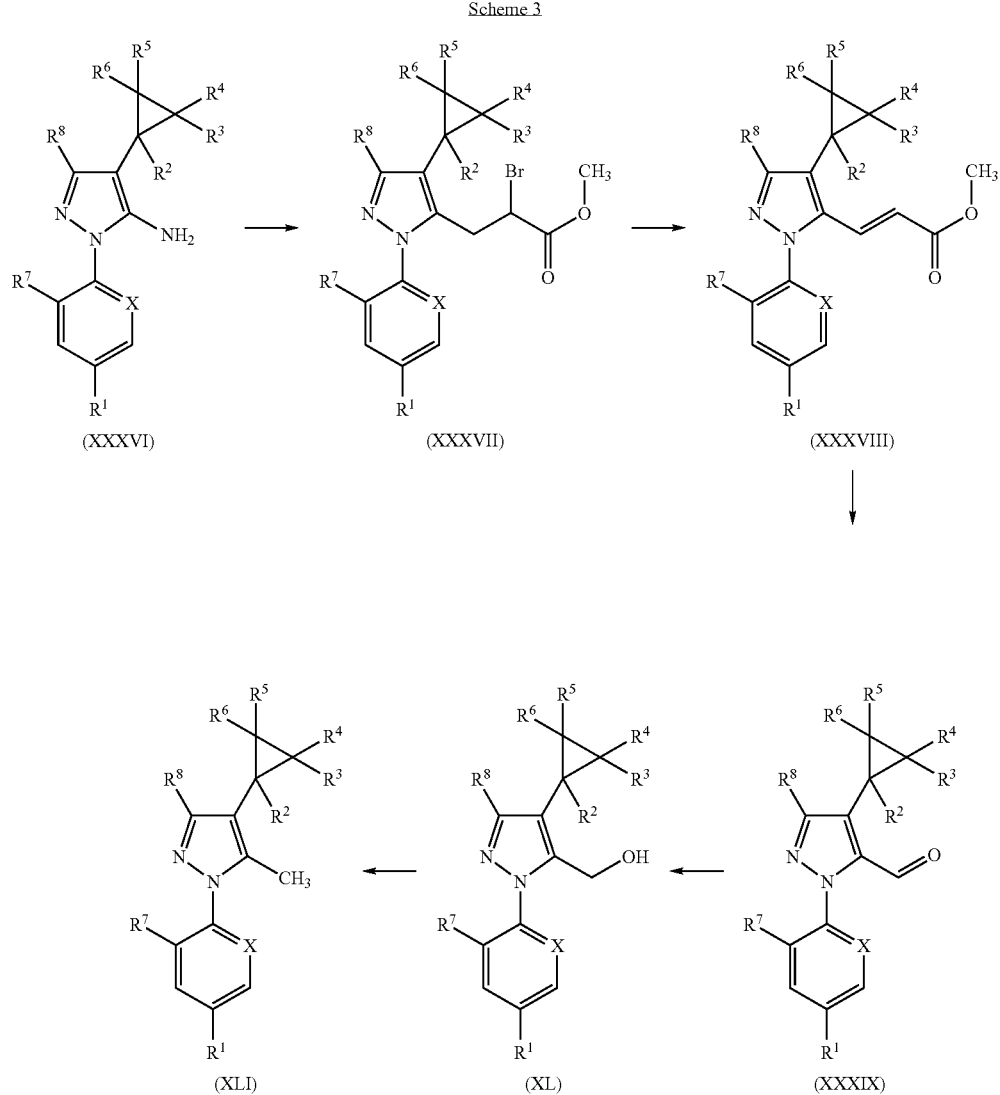

enylphosphonium bromide in tetrahydrofuran at 0° C. followed by addition of a solution of an aldehyde of formula (XXIX) in tetrahydrofuran giving compounds of formula (I) in which $R^9$=vinyl. Organometallic addition to the aldehyde, (XXXIX), followed by oxidation of the secondary alcohol, then Wittig olefination and cyclopropanation may be used to prepare compounds of formula (XLII), for example wherein $R^{12}$=—$CF_3$.

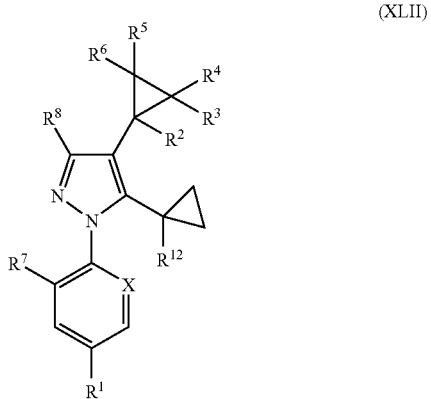

(XLII)

Alternatively, organometallic addition to the aldehyde, (XXXIX), followed by elimination of the hydroxyl group using standard procedures such as reaction with $SOCl_2$ in the presence of a zinc catalyst, may be a means to generate compounds of formula (I) in which $R^9$ is optionally substituted alkyl, optionally substituted aryl or arylalkyl and optionally substituted heteroaryl or heteroarylalkyl. Compounds of formula (XXXIX) may also undergo standard Knovenagel type reactions, followed by reduction and partial hydrolysis and heating at elevated temperature to give the corresponding ester derivative which may be further derivatised. Alternatively, methylenation of compounds of formula (XXXIX) may be readily achieved utilising standard known reactions such as the Wittig or the Horner-Wadsworth-Emmons reaction. The resulting compounds of formula (I) in which $R^9$ is vinyl, may be hydroxylated using standard conditions such as by reaction with hydrogen peroxide and a suitable base to give compounds in which $R^9$ is —$CH_2CH_2OH$. These compounds can, in turn, be further oxidised to give the corresponding aldehydes and acids, i.e. where $R^9$ is —$CH_2CHO$ or —$CH_2COOH$. These aldehydes undergo reactions well known to those skilled in the art, such as Wittig olefination and reductive amination. The acids undergo the Curtius rearrangement to give compounds of formula (I), in which $R^9$ is —$CH_2NH_2$, which may be alkylated, acylated, sulphonylated and other electrophiles.

Furthermore, compounds in which $R^9$ is —$CH_2CH_2OH$ may be activated for example by the addition of $SOCl_2$ or TsCl and further reacted with a wide range of nucleophiles such as $^-CN$, $^-SR$ or $^-OR$ to achieve the corresponding alkylated derivative.

Alternatively, standard known catalysed cross coupling reactions, such as the Heck reaction, may be employed to generate compounds of formula (I) in which $R^9$ is substituted vinyl from the vinyl derivative.

Oxidation of compounds of formula (XXXIX) using standard reaction conditions followed by further derivatisation of the acid formed may be a means of accessing compounds of formula (I) in which $R^9$ is a heterocyclic moiety. For example, the oxidised product may undergo reaction with substituted acyl hydrazides to give oxadiazoles. Those skilled in the art will recognise that a wide variety of optionally substituted heterocycles may be synthesised from the aldehydes (XXXIX) or the corresponding acids. These acids may also be derivatised using standard literature procedures.

A compound of formula (I) in which $R^8$ is —$C(O)SCH_3$ may be prepared from (I) $R^8$=—CN by the acid catalysed addition of methanethiol by heating under pressure at elevated temperatures, typically 80° C. for several hours, typically 16. Compounds of formula (I) in which $R^8$ is —CN may undergo reactions of nitriles as recorded in organic chemistry textbooks and literature precedent.

It will also be appreciated by persons skilled in the art that, within certain of the processes described, the order of the synthetic steps employed may be varied and will depend inter alia on factors such as the nature of other functional groups present in a particular substrate, the availability of key intermediates, and the protecting group strategy (if any) to be adopted. Clearly, such factors will also influence the choice of reagent for use in the said synthetic steps.

The skilled person will appreciate that the compounds of the invention could be made by methods other than those herein described, by adaptation of the methods herein described and/or adaptation of methods known in the art, for example the art described herein, or using standard textbooks such as "Comprehensive Organic Transformations—A Guide to Functional Group Transformations", R C Larock, Wiley-VCH (1999 or later editions).

It is to be understood that the synthetic transformation methods mentioned herein are exemplary only and they may be carried out in various different sequences in order that the desired compounds can be efficiently assembled. The skilled chemist will exercise his judgement and skill as to the most efficient sequence of reactions for synthesis of a given target compound.

The present invention also relates to intermediates of formula (L) below:

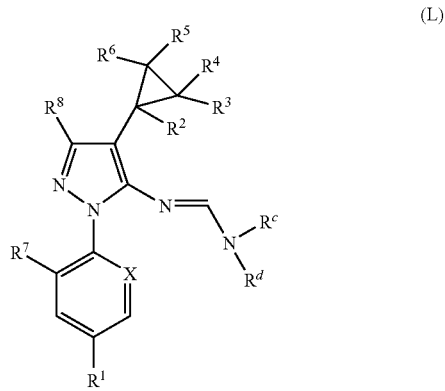

(L)

where:
$R^1$-$R^8$, X, $R^c$, $R^d$, n, $R^{11}$ and het are all as defined for formula (I) above; or a pharmaceutical salt or a prodrug thereof. With reference to formula (L), suitably $R^c$=$R^d$=methyl.

The present invention also relates to further intermediates of formula (LI) below:

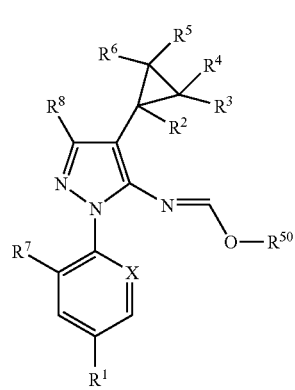

(LI)

where:
$R^1$-$R^8$, X, n, $R^{11}$ and het are all as defined for formula (LI) above; where $R^{50}$ is independently selected from hydrogen, $C_{1-6}$ alkyl, $C_{3-8}$ cycloalkyl, $C_{3-8}$ cycloalkyl$C_{1-6}$ alkyl, $C_{2-6}$ alkenyl, $C_{1-6}$ alkanoyl, $C(O)OC_{1-6}$ alkyl, het, phenyl and S$(O)_n R^{11}$; or a pharmaceutical salt or a prodrug thereof. With reference to formula (IZ), suitably $R^{50}$ is methyl.

It will be understood that throughout the application all references to formula (I) apply equally to compounds of the formulas (L) and (LI). Furthermore, it will be understood that all the suitable groups and preferences applied to $R^1$-$R^8$, X, $R^c$, $R^d$, n, $R^{11}$ and het above for formula (I) apply equally to compounds of the formulas (L) and (LI).

This invention also relates to a pharmaceutical composition comprising a compound of formula (I), or a pharmaceutically acceptable salt thereof, or a pharmaceutically acceptable solvate of either entity, together with a pharmaceutically acceptable diluent or carrier, which may be adapted for oral, parenteral or topical administration.

Pharmaceutical compositions suitable for the delivery of compounds of the present invention and methods for their preparation will be readily apparent to those skilled in the art. Such compositions and methods for their preparation may be found, for example, in 'Remington's Pharmaceutical Sciences', 19th Edition (Mack Publishing Company, 1995).

The compounds may be administered alone or in a formulation appropriate to the specific use envisaged, the particular species of host mammal being treated and the parasite involved or as appropriate for the agricultural pest being treated and the crop designated for treatment. Generally, they will be administered as a formulation in association with one or more pharmaceutically acceptable excipients. The term "excipient" is used herein to describe any ingredient other than the compound(s) of the invention. The choice of excipient will to a large extent depend on factors such as the particular mode of administration, the effect of the excipient on solubility and stability, and the nature of the dosage form.

Compounds of the invention intended for pharmaceutical use may be administered as crystalline or amorphous products, for example, spray-dried dispersions or as produced by melt-extrusion or nano-milling. They may be obtained, for example, as solid plugs, powders, or films (for example, rapid dissolving or mucoadhesive films) by methods such as precipitation, crystallization, freeze drying, or spray drying, or evaporative drying. Microwave or radio frequency drying may be used for this purpose.

The methods by which the compounds may be administered include oral administration by capsule, bolus, tablet, powders, lozenges, chews, multi and nanoparticulates, gels, solid solution, films, sprays, or liquid formulation. Liquid forms include suspensions, solutions, syrups, drenches and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet. Oral drenches are commonly prepared by dissolving or suspending the active ingredient in a suitable medium.

Thus compositions useful for oral administration may be prepared by mixing the active ingredient with a suitable finely divided diluent and/or disintegrating agent and/or binder, and/or lubricant etc. Other possible ingredients include antioxidants, colourants, flavouring agents, preservatives and taste-masking agents.

For oral dosage forms, depending on dose, the drug may make up from 1 wt % to 80 wt % of the dosage form, more typically from 5 wt % to 60 wt % of the dosage form. Examples of suitable disintegrants for use herein include sodium starch glycolate, sodium carboxymethyl cellulose, calcium carboxymethyl cellulose, croscarmellose sodium, crospovidone, polyvinylpyrrolidone, methyl cellulose, lower alkyl-substituted hydroxypropyl cellulose, starch, pregelatinised starch and sodium alginate. Generally, the disintegrant will comprise from 1 wt % to 25 wt %, preferably from 5 wt % to 20 wt % of the dosage form.

Binders are generally used to impart cohesive qualities to a tablet formulation. Examples of suitable binders for use herein include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Examples of diluents include lactose (monohydrate, spray-dried monohydrate, anhydrous and the like), mannitol, xylitol, dextrose, sucrose, sorbitol, microcrystalline cellulose, starch and dibasic calcium phosphate dehydrate.

Oral formulations may also optionally comprise surface active agents, such as sodium lauryl sulfate and polysorbate 80, and glidants such as silicon dioxide and talc. When present, surface active agents may comprise from 0.2 wt % to 5 wt % of the tablet, and glidants may comprise from 0.2 wt % to 1 wt % of the tablet.

Lubricants include magnesium stearate, calcium stearate, zinc stearate, sodium stearyl fumarate, and mixtures of magnesium stearate with sodium lauryl sulphate. Lubricants generally comprise from 0.25 wt % to 10 wt %, preferably from 0.5 wt % to 3 wt % of the tablet.

Exemplary tablets contain up to about 80% drug, from about 10 wt % to about 90 wt % binder, from about 0 wt % to about 85 wt % diluent, from about 2 wt % to about 10 wt % disintegrant, and from about 0.25 wt % to about 10 wt % lubricant.

The formulation of tablets is discussed in "Pharmaceutical Dosage Forms: Tablets, Vol. 1", by H. Lieberman and L. Lachman, Marcel Dekker, N.Y., N.Y., 1980 (ISBN 0-8247-6918-X).

The compounds may be administered topically to the skin, that is dermally or transdermally. The compounds may also be administered via the mucosa or mucous membranes. Typical formulations for this purpose include pour-on, spot-on, dip, spray, mousse, shampoo, powder formulation, gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J Pharm Sci, 88 (10), 955-958 by Finnin and Morgan (October 1999). Pour-on or spot-on formulations may be prepared by dissolving the active ingredient in an acceptable liquid carrier vehicle such as butyl digol, liquid paraffin or a non-volatile ester, optionally with the addition of a volatile component such as propan-2-ol. Alternatively, pour-on, spot-on or spray formulations can be prepared by encapsulation, to leave a residue of active agent on the surface of the animal.

Injectable formulations may be prepared in the form of a sterile solution which may contain other substances, for example enough salts or glucose to make the solution isotonic with blood. Acceptable liquid carriers include vegetable oils such as sesame oil, glycerides such as triacetin, esters such as benzyl benzoate, isopropyl myristate and fatty acid derivatives of propylene glycol, as well as organic solvents such as pyrrolidin-2-one and glycerol formal. The formulations are prepared by dissolving or suspending the active ingredient in the liquid carrier such that the final formulation contains from 0.01 to 10% by weight of the active ingredient. These formulations may be self-preserving, self-sterilising or may be non-sterile to which preservatives may be optionally added.

Equally suitably the compounds can be administered parenterally, or by injection directly into the blood stream, muscle or into an internal organ. Suitable routes for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques. Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as powdered a dried form to be used in conjunction with a suitable vehicle such as sterile, pyrogen-free water. The preparation of parenteral formulations under sterile conditions, for example, by lyophilisation, may readily be accomplished using standard pharmaceutical techniques well known to those skilled in the art. The solubility of compounds of formula (I) used in the preparation of parenteral solutions may be increased by the use of appropriate formulation techniques, such as the incorporation of solubility-enhancing agents.

Such formulations are prepared in a conventional manner in accordance with standard medicinal or veterinary practice.

These formulations will vary with regard to the weight of active compound contained therein, depending on the species of host animal to be treated, the severity and type of infection and the body weight of the host. For parenteral, topical and oral administration, typical dose ranges of the active ingredient are 0.01 to 100 mg per kg of body weight of the animal. Preferably the range is 0.1 to 10 mg per kg.

Formulations may be immediate or be designed to have a controlled or modified release profile. Modified release formulations include those formulations which have a delayed-, sustained-, pulsed-, targeted, or programmed release. Suitable modified release formulations for the purposes of the invention are described in U.S. Pat. No. 6,106,864. Details of other suitable release technologies such as high energy dispersions and osmotic and coated particles are to be found in Verma et al, Pharmaceutical Technology On-line, 25(2), 1-14 (2001). The use of chewing gum to achieve controlled release is described in WO 00/35298. Alternatively, compounds of the invention may be formulated as a solid, semi-solid, or thixotropic liquid for administration as an implanted depot providing modified release of the active compound. Examples of such formulations include drug-coated stents and PGLA microspheres.

As an alternative the compounds may be administered to a non-human animal with the feedstuff and for this purpose a concentrated feed additive or premix may be prepared for mixing with the normal animal feed.

All aqueous dispersions, emulsions or spraying mixtures of the present invention can be applied, for example, to crops by any suitable means, chiefly by spraying, at rates which are generally of the order of about 100 to about 1,200 liters of spraying mixture per hectare, but may be higher or lower (eg. low or ultra-low volume) depending upon the need or application technique. The compounds or compositions according to the invention are conveniently applied to vegetation and in particular to roots or leaves having pests to be eliminated. Another method of application of the compounds or compositions according to the invention is by chemigation, that is to say, the addition of a formulation containing the active ingredient to irrigation water. This irrigation may be sprinkler irrigation for foliar pesticides or it can be ground irrigation or underground irrigation for soil or for systemic pesticides.

Concentrated suspensions, which can be applied by spraying, are prepared so as to produce a stable fluid product which does not settle (fine grinding) and usually contain from about 10 to about 75% by weight of active ingredient, from about 0.5 to about 30% of surface-active agents, from about 0.1 to about 10% of thixotropic agents, from about 0 to about 30% of suitable additives, such as anti-foaming agents, corrosion inhibitors, stabilizers, penetrating agents, adhesives and, as the carrier, water or an organic liquid in which the active ingredient is poorly soluble or insoluble Some organic solids or inorganic salts may be dissolved in the carrier to help prevent settling or as antifreezes for water.

Wettable powers (or powder for spraying) are usually prepared so that they contain from about 10 to about 80% by weight of active ingredient, from about 20 to about 90% of a solid carrier, from about 0 to about 5% of a wetting agent, from about 3 to about 10% of a dispersing agent and, when necessary, from about 0 to about 80% of one or more stabilizers and/or other additives, such as penetrating agents, adhesives, anti-caking agents, colorants, or the like. To obtain these wettable powders, the active ingredient(s) is(are) thoroughly mixed in a suitable blender with additional substances which may be impregnated on the porous filler and is(are) ground using a mill or other suitable grinder. This produces wettable powders, the wettability and the suspendability of which are advantageous. They may be suspended in water to give any desired concentration and this suspension can be employed very advantageously in particular for application to plant foliage.

"Water dispersible granules (WG)" (granules which are readily dispersible in water) have compositions which are substantially close to that of the wettable powders. They may be prepared by granulation of formulations described for the wettable powders, either by a wet route (contacting finely divided active ingredient with the inert filler and a little water, e.g. 1 to 20% by weight, or with an aqueous solution of a dispersing agent or binder, followed by drying and screening), or by a dry route (compacting followed by grinding and screening).

The rates and concentrations of the formulated compositions may vary according to the method of application or the nature of the compositions or use thereof. Generally speaking, the compositions for application to control arthropod, plant nematode, helminth or protozoan pests usually contain from about 0.00001% to about 95%, more particularly from about 0.0005% to about 50% by weight of one or more compounds of formula (I), or pesticidally acceptable salts thereof, or of total active ingredients (that is to say the compound of formula (I), or a pesticidally acceptable salt thereof, together with: other substances toxic to arthropods or plant nematodes, anthelmintics, anticoccidials, synergists, trace elements or stabilizers). The actual compositions employed and their rate of application will be selected to achieve the desired effect(s) by the farmer, livestock producer, medical or veterinary practitioner, pest control operator or other person skilled in the art.

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

Compounds of the present invention may be administered alone or in combination with one or more other compounds of the invention or in combination with one or more other drugs (or as any combination thereof). For example, compounds of the invention can also be mixed with one or more biologically active compounds or agents including insecticides, acaricides, anthelmintics, fungicides, nematocides, antiprotozoals, bactericides, growth regulators, vaccines (including live, attenuated or killed vaccines), entomopathogenic bacteria, viruses or fungi to form a multi-component pesticide giving an even broader spectrum of pharmaceutical, veterinary or agricultural utility. Thus, the present invention also pertains to a composition comprising a biologically effective amount of compounds of the invention and an effective amount of at least one additional biologically active compound or agent and can further comprise one or more of surfactant, a solid diluent or a liquid diluent. Specific further active compounds include those described in International Patent Application No WO 2005/090313, at pages 39 to 44.

Inasmuch as it may desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions.

Thus this invention also relates to a kit comprising two or more separate pharmaceutical compositions, at least one of which contains a compound of formula (I) in accordance with the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically comprises directions for administration and may be provided with a so-called memory aid.

The compounds of the invention, i.e. those of formula (I), possess parasiticidal activity in humans, animals, insects and plants. They are particularly useful in the treatment of ectoparasites.

This invention also relates to a compound of formula (I), or a pharmaceutically acceptable salt thereof, or a pharmaceutically acceptable solvate of either entity, or a pharmaceutical composition containing any of the foregoing, for use as a medicament.

A further aspect of this invention relates to the use of a compound of formula (I), or a pharmaceutically acceptable salt thereof, or a pharmaceutically acceptable solvate of either entity, for the manufacture of a medicament for the treatment of a parasitic infestation.

As used herein the term "long duration of action" shall be taken to mean compounds which have a duration of action of 14 days or greater, more preferably of 21 days or greater and most preferably of 28 days or greater.

In one embodiment this invention is useful for the manufacture of a medicament for the treatment of a parasitic infestation in humans.

In one embodiment this invention is useful for the manufacture of a medicament for the treatment of a parasitic infestation in animals.

An even further aspect of this invention relates to a method of treating a parasitic infestation which comprises treating an animal with an effective amount of a compound of formula (I), or a pharmaceutically acceptable salt thereof, or a pharmaceutically acceptable solvate of either entity, or a pharmaceutical composition containing any of the foregoing.

A yet further aspect of this invention relates to a method of preventing a parasitic infestation which comprises treating an animal with an effective amount of a compound of formula (I), or a pharmaceutically acceptable salt thereof, or a pharmaceutically acceptable solvate of either entity, or a pharmaceutical composition containing any of the foregoing.

In a still further embodiment this invention also relates to a method of controlling disease transmission between animals which comprises treating an animal with an effective amount of a compound of formula (I), or a pharmaceutically acceptable salt thereof, or a pharmaceutically acceptable solvate of either entity, or a pharmaceutical composition containing any of the foregoing.

In one embodiment this invention is useful for the manufacture of a medicament for the treatment of a parasitic infestation in plants.

According to another aspect of the present invention, there is provided a method for the control of arthropod, plant nematode or helminth pests at a locus which comprises the treatment of the locus (e.g. by application or administration) with an effective amount of a compound of general formula (I), or a pesticidally acceptable salt thereof.

According to a yet further aspect of the present invention, there is provided a method for the control or eradication of a parasitic infestation from the environment, for example the living or accommodation areas of an animal, particularly a companion animal, which comprises treating said animal with an effective amount of a compound of formula (I), or a pharmaceutically acceptable salt thereof, or a pharmaceutically acceptable solvate of either entity, or a pharmaceutical composition containing any of the foregoing.

For the avoidance of doubt, references herein to "treatment" as used herein includes references to curative, palliative and prophylactic treatment, references to "control" (of parasites and/or pests etc.) include kill, repel, expel, incapacitate, deter, eliminate, alleviate, minimise, eradicate.

The compounds of the invention have utility in the control of arthropod pests. They may have activity against resistant strains where control is not achievable by known parasiticides or combinations thereof. They may, in particular, be used in the fields of veterinary medicine, livestock husbandry and the maintenance of public health: against arthropods which are parasitic internally or externally upon humans and animals, including mammals, poultry and fish. Examples of mammals include domestic animals such as dogs, cats, cattle, sheep, goats, equines, and swine. Examples of arthropods include *Acarina*, including ticks (e.g. *Ixodes* spp., *Boophilus* spp. e.g. *Boophilus microplus, Amblyomma* spp., *Hyalomma* spp., *Rhipicephalus* spp. e.g. *Rhipicephalus appendiculatus, Haemaphysalis* spp., *Dermacentor* spp., *Ornithodorus* spp. (e.g. *Ornithodorus moubata*), mites (e.g. *Damalinia* spp., *Dermanyssus gallinae, Sarcoptes* spp. e.g. *Sarcoptes scabiei, Psoroptes* spp., *Chorioptes* spp., *Demodex* spp., *Eutrombicula* spp.); *Diptera* (e.g. *Aedes* spp., *Anopheles* spp., *Muscidae* spp. e.g. *Stomoxys calcitrans* and *Haematobia irritans, Hypoderma* spp., *Gastrophilus* spp., *Simulium* spp.); Hemiptera (e.g. *Triatoma* spp.); *Phthiraptera* (e.g. *Damalinia* spp., *Linognathus* spp.); *Siphonaptera* (e.g. *Ctenocephalides* spp.); *Dictyoptera* (e.g. *Periplaneta* spp., *Blatella* spp.) and Hymenoptera (e.g. *Monomorium pharaonis*). The compounds of the present invention also have utility in the field of control of plant pests, soil inhabiting pests and other environmental pests. Specific further arthropod pests include those described in International Patent Application No WO 2005/090313, particularly on pages 57-63.

The present invention is particularly useful in the control of arthropod pests in humans and animals, particularly mammals. Preferably this invention is useful in the control of arthropod pests in animals which includes livestock such as cattle, sheep, goats, equines, swine and companion animals such as dogs and cats.

The compounds of the invention are of particular value in the control of arthropods which are injurious to, or spread or act as vectors of diseases in, man and domestic animals, for example those hereinbefore mentioned, and more especially in the control of ticks, mites, lice, fleas, midges and biting, nuisance and myiasis flies. They are particularly useful in controlling arthropods which are present inside domestic host animals or which feed in or on the skin or suck the blood of the animal, for which purpose they may be administered orally, parenterally, percutaneously or topically.

The compounds of the invention are of value for the treatment and control of the various lifecycle stages of parasites including egg, nymph, larvae, juvenile and adult stages.

According to another aspect of the present invention, there is provided a method for the control of arthropod pests of insects which comprises treatment of the insect with an effective amount of a compound of general formula (I), or a pesticidally acceptable salt thereof. Compounds of the present invention may also be used for the treatment of infections caused by mites, and in particular varoaa mites. In particular compounds of the present invention may also be used for the treatment of varoaa mite infection in bees.

According to another aspect of the present invention, there is provided a method for the control of arthropod pests of plants which comprises treatment of the plant with an effective amount of a compound of general formula (I), or a pesticidally acceptable salt thereof. The compounds of the invention also have utility in the control of arthropod pests of plants. The active compound is generally applied to the locus at which the arthropod infestation is to be controlled at a rate of about 0.005 kg to about 25 kg of active compound per hectare (ha) of locus treated, preferably 0.02 to 2 kg/ha. Under ideal conditions, depending on the pest to be controlled, the lower rate may offer adequate protection. On the other hand, adverse weather conditions and other factors may require that the active ingredient be used in higher proportions. For foliar application, a rate of 0.01 to 1 kg/ha may be used. Preferably, the locus is the plant surface, or the soil around the plant to be treated.

According to another aspect of the present invention, there is provided a method for the protection of timber which comprises treatment of the timber with an effective amount of a compound of general formula (I), or a pesticidally acceptable salt thereof. Compounds of the present invention are also valuable in the protection of timber (standing, felled, converted, stored or structural) from attack by sawflies or beetles or termites. They have applications in the protection of stored products such as grains, fruits, nuts, spices and tobacco, whether whole, milled or compounded into products, from moth, beetle and mite attack. Also protected are stored animal products such as skins, hair, wool and feathers in natural or converted form (e.g. as carpets or textiles) from moth and beetle attack; also stored meat and fish from beetle, mite and fly attack. Solid or liquid compositions for application topically to timber, stored products or household goods usually contain from about 0.00005% to about 90%, more particularly from about 0.001% to about 10%, by weight of one or more compounds of formula (I) or pesticidally acceptable salts thereof.

The liquid compositions of this invention may, in addition to normal agricultural-use applications be used for example to treat substrates or sites infested or liable to infestation by arthropods (or other pests controlled by compounds of this invention) including premises, outdoor or indoor storage or processing areas, containers or equipment or standing or running water.

The present invention also relates to a method of cleaning animals in good health comprising the application to the animal of compound of formula (I) or a veterinarily acceptable salt. The purpose of such cleaning is to reduce or eliminate the infestation of humans with parasites carried by the animal and to improve the environment in which humans inhabit.

The flea membrane feed test is used to measure the biological activities of the compounds claimed. The assay involves in vitro testing against *Ctenocephalides felis* conducted according to the following general procedure.

Fleas are cultured in vitro using dog blood. 25-30 adult *Ctenocephalides felis* (cat flea) were collected and placed in a test chamber (50 ml polystyrene tube with fine nylon mesh sealing the end). Citrated dog blood was prepared by adding aqueous sodium citrate solution (10 ml, 20% w/v, 20 g sodium citrate in 100 ml water) to dog blood (250 ml). Test compounds were dissolved in dimethylsulfoxide to give a working stock solution of 4 mg/ml. The stock solution (12.5 µl) was added to citrated dog blood (5 ml) to give an initial test concentration of 10 µg/ml. For testing at 30 □g/ml, working stock solutions of 12 mg/ml were prepared.

Citrated dog blood containing the test compound (5 ml, 100 µg/ml) was placed into a plastic Petri dish lid, which was kept at 37° C. on a heated pad. Parafilm was stretched over the open top to form a tight membrane for the fleas to feed through. The test chamber containing the fleas was placed carefully onto the parafilm membrane and the fleas commenced feeding.

The fleas were allowed to feed for 2 hours and the test chambers were then removed and stored overnight at room temperature.

The fleas were observed and the percentage of fleas killed recorded. Compounds were initially tested at 100 μg/ml, wherefrom relevant dose responses (100, 30, 10, 3, 1, 0.3, 0.1 μg/ml) were conducted and repeated n=5. Data was plotted to generate ED80, ED90 & ED95 values.

The compounds of the present invention have significantly better activity than the prior art compounds. All the Examples of the present invention have flea ED80 values of less than 100 □g/ml. Results for some of the compounds are presented below.

| Example | Flea feed ED80 results μg/ml |
| --- | --- |
| 1 | ≦1 |
| 2 | ≦1 |
| 11 | ≦1 |
| 16 | ≦1 |
| 18 | ≦1 |
| 19 | ≦1 |
| 20 | ≦1 |
| 27 | ≦1 |
| 32 | ≦1 |
| 37 | ≦1 |
| 45 | ≦1 |
| 86 | ≦1 |
| 101 | ≦1 |

EXAMPLES

The following Examples illustrate the preparation of compounds of the formula (I).

In the following experimental details, nuclear magnetic resonance spectral data were obtained using Varian Inova 300, Varian Inova 400, Varian Mercury 400, Varian Unityplus 400, Bruker AC 300 MHz, Bruker AM 250 MHz or Varian T60 MHz spectrometers, the observed chemical shifts being consistent with the proposed structures. Mass spectral data were obtained on a Finnigan Masslab Navigator, a Fisons Instrument Trio 1000, or a Hewlett Packard GCMS System Model 5971 spectrometer. The calculated and observed ions quoted refer to the isotopic composition of lowest mass. HPLC means high performance liquid chromatography. Room temperature means 20 to 25° C.

Example 1

5-amino-1-[2,6-dichloro-4-pentafluorothiophenyl]-4-[1-(methylsulfonyl)cyclopropyl]-1H-pyrazole-3-carbonitrile

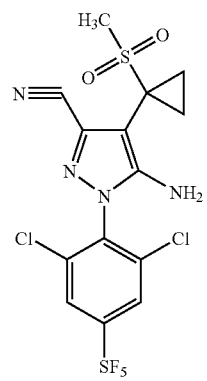

To a solution of Preparation 82 (150 mg, 0.27 mmol) in dioxane (8 ml) and methanol (1 ml) was added hydrochloric acid (10%, 1 ml) and the reaction mixture was heated at 80° C. for 8 h. The mixture was concentrated under a stream of nitrogen and the residue was dissolved in acetonitrile/water (1:1, 2.8 ml) and purified by automated preparative liquid chromatography (Gilson system, 150 mm×30 mm Phenomenex LUNA C18(2) 10 μm column) using an acetonitrile:water gradient [50:50 to 98:2]. The appropriate fractions were combined and concentrated to give the titled compound (75 mg).

Experimental MH⁺ 496.9; expected 497.0

$^1$H-NMR (CDCl$_3$): 1.36-1.43 (2H), 1.85-1.91 (2H), 2.90-2.95 (3H), 4.38-4.48 (2H), 7.89-7.92 (2H)

Example 2

1-{5-amino-3-cyano-1-[2,6-dichloro-4-(trifluoromethyl)phenyl]-1H-pyrazol-4-yl}cyclopropanecarboxamide To a solution of Example 61 (53 mg, 0.12 mmol) in 1,4-dioxane (1 ml) was added methanol (0.3 ml) and hydrochloric acid (1N, 0.3 ml). The reaction mixture was then heated at 100° C. for 2 h. The reaction mixture was concentrated in vacuo and to the residue was added ethyl acetate and saturated aqueous sodium hydrogencarbonate solution. The two layers were separated and the aqueous layer was extracted with ethyl acetate (×2). The combined organic phases were dried (MgSO$_4$) and concentrated in vacuo. The residue was dissolved in acetonitrile (1 ml) and purified by automated preparative liquid chromatography (Gilson system, 150 mm×21.2 mm Phenomenex LUNA C18(2) 5 μm column) using an acetonitrile:water gradient. The appropriate fractions were concentrated in vacuo to give titled compound (16 mg).

Experimental MH$^+$ 404.0; expected 404.0

$^1$H-NMR (Acetone-d$_6$): 1.01-1.07 (2H), 1.46-1.52 (2H), 5.77-5.87 (2H), 6.01-6.15 (1H), 6.34-6.46 (1H), 8.02-8.06 (2H)

Similarly Prepared were:

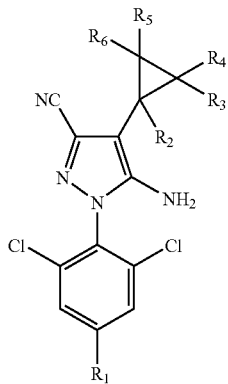

| Example | R1 | R3 | R4 | R5 | R6 | R2 | From |
|---|---|---|---|---|---|---|---|
| Example 3 | CF3 | H | H | H | H | —COOCH$_3$ | Preparation 64 |
| Example 4 | CF3 | H | H | F | F | —SO2CH3 | Preparation 59 |
| Example 5 | CF3 | H | H | H | H | —N=CH—N(CH$_3$)$_2$ | Preparation 51 |
| Example 6 | CF3 | H | H | H | H | —SO2CH3 | Preparation 81 |
| Example 7 | CF3 | H | H | F | F | —NH2 | Preparation 99 |
| Example 8 | CF3 | H | H | F | F | —SO2N(CH3)$_2$ | Preparation 57 |
| Example 9 | CF3 | H | H | H | H | —CO-pyrrolidin-1-yl | Preparation 52 |
| Example 10 | CF3 | H | H | H | H | CN | Preparation 2 |
| Example 11 | SF5 | H | H | H | H | CN | Preparation 1 |

Example 3 methyl 1-{5-amino-3-cyano-1-[2,6-dichloro-4-(trifluoromethyl)phenyl]-1H-pyrazol-4-yl}cyclopropanecarboxylate Experimental MH$^+$ 419.0; expected 419.0

$^1$H-NMR (CDCl$_3$): 1.26-1.30 (2H), 1.67-1.71 (2H), 3.65-3.68 (3H), 3.70-3.83 (2H), 7.72-7.77 (2H)

Example 4

5-amino-1-[2,6-dichloro-4-(trifluoromethyl)phenyl]-4-[2,2-difluoro-1-(methylsulfonyl)cyclopropyl]-1H-pyrazole-3-carbonitrile Experimental MH$^+$ 475.0; expected 475.0

$^1$H-NMR (CDCl$_3$): 1.83-1.95 (3H), 2.94-3.02 (1H), 3.03-3.14 (1H), 4.21-4.51 (2H), 7.77-7.80 (2H)

Example 5

1-{5-amino-3-cyano-1-[2,6-dichloro-4-(trifluoromethyl)phenyl]-1H-pyrazol-4-yl}-N,N-dimethylcyclopropanecarboxamide Experimental MH$^+$ 432.0; expected 432.1

$^1$H-NMR (CDCl$_3$): 1.26-1.30 (2H), 1.31-1.36 (2H), 2.82-2.93 (3H), 3.19-3.32 (3H), 4.57-4.68 (2H), 7.68-7.78 (2H)

Example 6

5-amino-1-[2,6-dichloro-4-(trifluoromethyl)phenyl]-4-[1-(methylsulfonyl)cyclopropyl]-1H-pyrazole-3-carbonitrile Experimental MH$^+$ 438.8; expected 439.0

$^1$H-NMR (CDCl$_3$): 1.37-1.42 (2H), 1.86-1.90 (2H), 2.91-2.94 (3H), 4.38-4.44 (2H), 7.76-7.78 (2H)

Example 7

5-amino-4-(1-amino-2,2-difluorocyclopropyl)-1-[2,6-dichloro-4-(trifluoromethyl)phenyl]-1H-pyrazole-3-carbonitrile $^1$H-NMR (CDCl$_3$): 1.87-1.90 (1H), 1.92-1.95 (2H), 1.97-1.99 (1H), 5.98-6.05 (2H), 7.81-7.84 (2H)

Example 8

1-{5-amino-3-cyano-1-[2,6-dichloro-4-(trifluoromethyl)phenyl]-1H-pyrazol-4-yl}-2,2-difluoro-N,N-dimethylcyclopropanesulfonamide $^1$H-NMR (CDCl$_3$): 1.94-2.01 (1H), 2.40-2.48 (1H), 2.87-2.94 (6H), 4.39-4.49 (2H), 7.76-7.80 (2H)

Example 9

5-amino-1-[2,6-dichloro-4-(trifluoromethyl)phenyl]-4-[1-(pyrrolidin-1-ylcarbonyl)cyclopropyl]-1H-pyrazole-3-carbonitrile Experimental MH$^+$ 458.0; expected 458.1

$^1$H-NMR (CDCl$_3$): 1.21-1.26 (2H), 1.34-1.39 (2H), 1.77-1.84 (2H), 1.89-1.97 (2H), 3.36-3.41 (2H), 3.63-3.69 (2H), 4.55-4.64 (2H), 7.69-7.78 (2H)

Example 10

5-amino-4-(1-cyanocyclopropyl)-1-[2,6-dichloro-4-(trifluoromethyl)phenyl]-1H-pyrazole-3-carbonitrile Experimental MH$^+$ 386.1; expected 386.0

$^1$H-NMR (CDCl$_3$): 1.44-1.50 (2H), 1.71-1.76 (2H), 3.93-4.04 (2H), 7.74-7.77 (2H)

Example 11

5-amino-4-(1-cyanocyclopropyl)-1-[2,6-dichloro-4-pentafluorothiophenyl]-1H-pyrazole-3-carbonitrile $^1$H-NMR (d$_6$-DMSO): 1.24-1.31 (2H), 1.65-1.72 (2H), 6.53-6.62 (2H), 8.42-8.47 (2H)

Example 12

1-{5-amino-3-cyano-1-[2,6-dichloro-4-(trifluoromethyl)phenyl]-1H-pyrazol-4-yl}-2,2-difluorocyclopropanesulfonamide

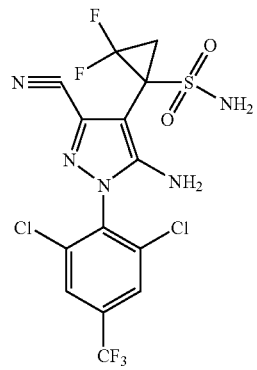

To a solution of Preparation 56 (30 mg, 0.05 mmol) in 1,4-dioxane (4 ml) was added hydrochloric acid (10%, 1 ml). The reaction mixture was then heated at 85° C. for 6 h, cooled to room temperature and concentrated under a stream of nitrogen. The residue was dissolved in acetonitrile/dimethyl sulphoxide (650 µl) and purified by automated preparative liquid chromatography (Gilson system, 150 mm×21.2 mm Phenomenex LUNA C18(2) 5 µm column) using an acetonitrile:water gradient [45:55 to 95:5]. The appropriate fractions were concentrated in vacuo to give titled compound (7 mg).

Experimental MH$^+$ 476.0; expected 476.0

$^1$H-NMR (CDCl$_3$): 2.17-2.31 (1H), 2.65-2.79 (1H), 7.68-7.73 (2H)

Example 13

1-{5-amino-3-cyano-1-[2,6-dichloro-4-pentafluorothiophenyl]-1H-pyrazol-4-yl}-cyclopropanecarboxamide

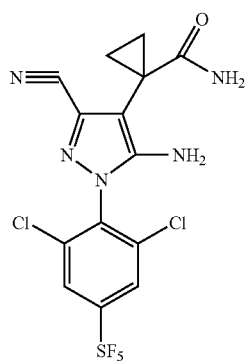

To a solution of Preparation 5 (615 mg, 1.33 mmol) and triethylamine (204 µl, 1.46 mmol) in tetrahydrofuran (20 ml), at −10° C., was added dropwise ethyl chloroformate (140 µl, 1.46 mmol). The mixture was stirred at 0° C. for 1 h, before addition of ammonium hydroxide (35% in water, 737 µl, 13.3 mmol) in tetrahydrofuran. The reaction mixture was then stirred at 0° C. for 1 h. To the reaction mixture was added brine and the mixture was extracted with ethyl acetate. The combined extracts were dried (MgSO$_4$) and concentrated in vacuo to give the crude product. The residue was dissolved in acetonitrile (1 ml) and purified by automated preparative liquid chromatography (Gilson system, 150 mm×50 mm Phenomenex LUNA C18(2) 10m column) using an acetonitrile:water gradient [45:55 to 95:5]. The appropriate fractions were concentrated in vacuo to give titled compound (95 mg).

Experimental MH$^+$ 462.0; expected 462.0

$^1$H-NMR (d$_6$-DMSO): 0.91-0.95 (2H), 1.41-1.46 (2H), 6.12-6.17 (1H), 6.18-6.22 (2H), 7.13-7.18 (1H), 8.39-8.41 (2H)

Example 14

1-[3-cyano-1-[2,6-dichloro-4-pentafluorothiophenyl]-5-(isobutylamino)-1H-pyrazol-4-yl]cyclopropanecarboxamide

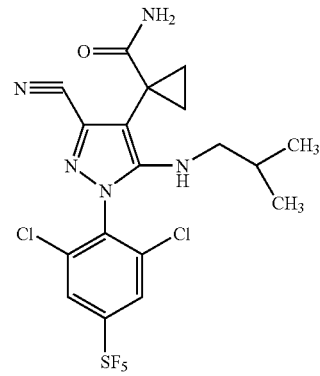

To a solution of Preparation 30 (41 mg, 79 µmol) in tetrahydrofuran (2 ml), at 0° C., was added triethylamine (28 µl, 0.20 mmol) and ethyl chloroformate (48 µl, 87 µmol). After stirring for 20 min, the mixture was warmed to room temperature and stirring continued for 1 h. Anhydrous ammonia was bubbled through the mixture for 15 min, followed by nitrogen for 3 min. The reaction mixture was partitioned between hydrochloric acid (1M) and ethyl acetate and the organic layer was separated, washed with water, dried (MgSO$_4$) and concentrated in vacuo. The residue was dissolved in acetonitrile/water (0.45 ml) and purified by automated preparative liquid chromatography (Gilson system, 150 mm×30 mm LUNA C18(2) 10 µm column) using an acetonitrile:water gradient [55:45 to 95:5]. The appropriate fractions were concentrated in vacuo to give the titled compound (21 mg).

Experimental MH$^+$ 518.0; expected 518.1

$^1$H-NMR (CDCl$_3$): 0.78-0.86 (6H), 1.22-1.29 (2H), 1.56-1.66 (1H), 1.74-1.83 (2H), 2.86-2.92 (2H), 3.49-3.62 (1H), 5.55-5.74 (2H), 7.90-7.95 (2H)

Example 15

1-{5-amino-3-cyano-1-[2,6-dichloro-4-pentafluorothiophenyl]-1H-pyrazol-4-yl}-N-isopropylcyclopropane-carboxamide

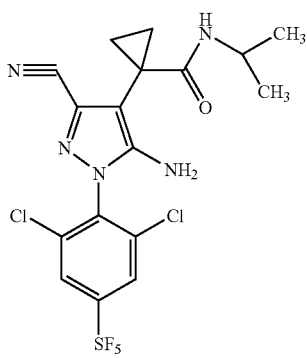

To a solution of Preparation 5 (300 mg, 0.65 mmol) in tetrahydrofuran (6 ml), at 0° C. and under nitrogen, was added triethylamine (227 μl, 1.63 mmol), followed by ethyl chloroformate (69 μl, 0.72 mmol). After stirring at 0° C. for 30 min, the reaction mixture was warmed to room temperature and isopropylamine (278 μl, 3.25 mmol) was added. The reaction mixture was stirred at room temperature for 18 h and then concentrated in vacuo. The residue was dissolved in acetonitrile/dimethyl sulphoxide (1.8 ml) and purified by automated preparative liquid chromatography (Gilson system, 150 mm×50 mm LUNA C18(2) 10 μm column) using an acetonitrile:water gradient [55:45 to 95:5]. The appropriate fractions were concentrated in vacuo to give the titled compound (103 mg).

Experimental $MH^+$ 504.3; expected 504.0

$^1$H-NMR ($d_6$-DMSO): 0.91-0.95 (2H), 0.98-1.03 (6H), 1.37-1.42 (2H), 3.77-3.86 (1H), 5.95-5.99 (1H), 6.26-6.31 (2H), 8.43-8.45 (2H)

Example 16

1-{3-cyano-1-[2,6-dichloro-4-pentafluorothiophenyl]-5-[(2-fluoroethyl)amino]-1H-pyrazol-4-yl}cyclopropanecarboxamide

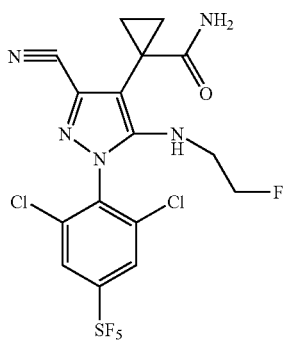

To a solution of Preparation 8 (150 mg, 0.30 mmol) in tetrahydrofuran (5 ml), at 0° C., was added triethylamine (165 μl, 1.20 mmol), followed by ethyl chloroformate (65 μl, 0.60 mmol). After stirring for 30 min, the mixture was quenched by addition of aqueous ammonium hydroxide solution. The reaction mixture was partitioned between water and ethyl acetate and the two layers were separated. The organic layer was washed with hydrochloric acid (10%) and brine, dried (MgSO$_4$) and concentrated in vacuo. The residue was dissolved in acetonitrile/water (9:1, 2 ml) and purified by automated preparative liquid chromatography (Gilson system, 150 mm×30 mm LUNA C18 10 μm column) using an acetonitrile:water gradient [55:45 to 95:5]. The appropriate fractions were combined and concentrated to give the titled compound (61 mg).

Experimental $MH^+$ 508.1; expected 508.0

1H-NMR ($d_6$-Acetone): 1.18-1.23 (2H), 1.54-1.60 (2H), 3.58-3.65 (2H), 4.39-4.50 (2H), 5.50-5.61 (1H), 6.30-6.50 (2H), 8.20-8.22 (2H)

Example 17

1-{5-[(2-amino-2-oxoethyl)amino]-3-cyano-1-[2,6-dichloro-4-pentafluorothiophenyl]-1H-pyrazol-4-yl}cyclopropanecarboxamide

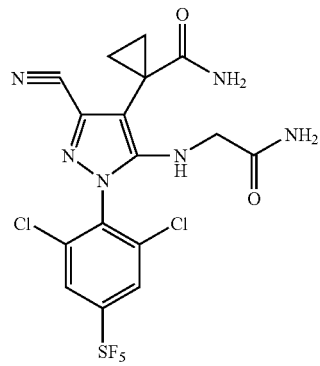

To a solution of crude Preparation 15 (approximately 0.26 mmol) in tetrahydrofuran (6 ml) was added triethylamine (180 μl, 1.31 mmol), followed by ethyl chloroformate (75 μl, 0.79 mmol). After stirring for 30 min, excess ammonium hydroxide solution (30 wt %, 0.37 ml) was added and stirring continued for 1 h. The reaction mixture was then concentrated in vacuo and the residue was partitioned between water (10 ml) and ethyl acetate (20 ml). The organic phase was separated, washed with hydrochloric acid (1N, 10 ml) and brine (10 ml), dried (MgSO$_4$) and concentrated in vacuo. The residue was dissolved in acetonitrile (2 ml) and purified by automated preparative liquid chromatography (Gilson system, 150 mm×30 mm LUNA C18(2) 10 μm column) using an acetonitrile:water gradient [40:60 to 95:5]. The appropriate fractions were concentrated in vacuo to give the titled compound (22 mg).

Experimental $MH^+$ 519.3; expected 519.0

1H-NMR ($d_6$-Acetone): 1.15-1.20 (2H), 1.55-1.60 (2H), 3.85-3.90 (2H), 5.45-5.55 (1H), 6.40-6.55 (2H), 6.95-7.05 (1H), 8.21-8.24 (2H)

Example 18

1-{5-amino-3-cyano-1-[2,6-dichloro-4-pentafluorothiophenyl]-1H-pyrazol-4-yl}-2,2-dichlorocyclopropanecarboxamide

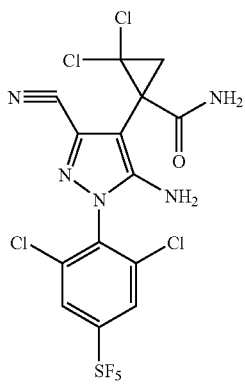

To a solution of Preparation 31 (244 mg, 0.46 mmol) in tetrahydrofuran (10 ml), at room temperature and under nitrogen, was added triethylamine (128 µl, 0.92 mmol), followed by ethyl chloroformate (48 mg, 0.51 mmol) in tetrahydrofuran (0.5 ml). After 30 min, ammonium hydroxide (0.27 ml, 2.30 mmol) was added dropwise and the reaction mixture was stirred for 18 h, before being concentrated in vacuo. The residue was dissolved in acetonitrile/dimethyl sulphoxide (2 ml) and purified by automated preparative liquid chromatography (Gilson system, 150 mm×50 mm Sunfire LUNA C18 10 µm column) using an acetonitrile:water [55:45 to 95:5] gradient. The appropriate fractions were combined and concentrated to give the titled compound (132 mg).

Experimental MH+ 529.9; expected 529.9

$^1$H-NMR (Acetone-$d_6$): 2.35-2.41 (1H), 2.65-2.69 (1H), 6.23-6.33 (2H), 6.95-7.04 (1H), 7.45-7.58 (1H), 8.25-8.28 (2H)

Example 19

1-{3-cyano-5-[(cyclopropylmethyl)amino]-1-[2,6-dichloro-4-pentafluorothiophenyl]-1H-pyrazol-4-yl}-N-(pyridin-4-ylmethyl)cyclopropanecarboxamide

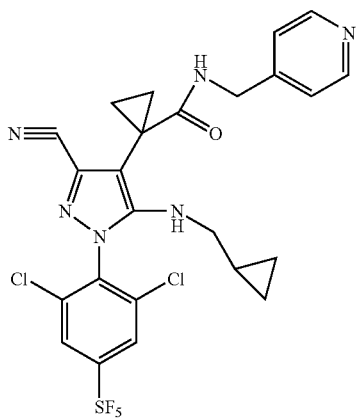

To a solution of Preparation 6 (110 mg, 0.21 mmol) in tetrahydrofuran (6 ml), at 0° C., was added triethylamine (119 µl, 0.85 mmol), followed by ethyl chloroformate (41 µl, 0.43 mmol). The mixture was stirred for 10 min, before addition of 4-aminomethylpyridine (111 µl, 1.05 mmol). After stirring for a further 3 h at 0° C., the reaction mixture was extracted with ethyl acetate and the combined extracts were washed with brine, dried (MgSO$_4$) and concentrated in vacuo. The residue was dissolved in acetonitrile (2 ml) and purified by automated preparative liquid chromatography (Gilson system, 150 mm×30 mm LUNA C18 10 µm column) using an acetonitrile:0.1% trifluoroacetic acid gradient [55:45 to 95:5]. The appropriate fractions were combined and concentrated to give the titled compound (99 mg).

Experimental MH+ 607.3; expected 607.1

$^1$H-NMR ($d_6$-DMSO): 0.00-0.01 (2H), 0.20-0.30 (2H), 0.79-0.83 (1H), 1.02-1.11 (2H), 1.40-1.48 (2H), 2.90-2.99 (2H), 4.38-4.43 (2H), 7.58-7.62 (2H), 8.40-8.44 (2H), 8.62-8.70 (2H)

Example 20 isopropyl {4-[1-(aminocarbonyl)cyclopropyl]-3-cyano-1-[2,6-dichloro-4-pentafluorothiophenyl]-1H-pyrazol-5-yl}carbamate

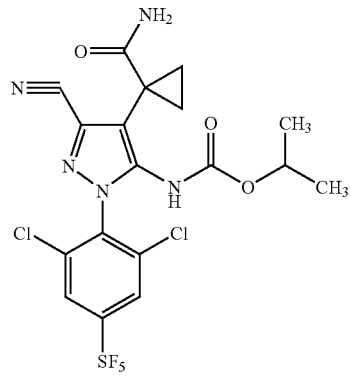

To a solution of crude Preparation 22 (approx. 0.60 mmol) in tetrahydrofuran (2 ml), at 0° C., was added triethylamine (330 µl, 2.40 mmol) and ethyl chloroformate (120 µl, 1.20 mmol). After stirring for 5 min, aqueous ammonium hydroxide solution (18M, 0.5 ml) was added and the reaction mixture was stirred at room temperature for 18 h. The reaction mixture was adjusted to pH 1 by addition of hydrochloric acid (1M) and extracted with ethyl acetate. The combined extracts were washed with water, dried (MgSO$_4$) and concentrated under a stream of nitrogen. The residue was dissolved in acetonitrile/dimethyl sulphoxide (1.5 ml) and purified by automated preparative liquid chromatography (Gilson system, 150 mm×50 mm Sunfire LUNA C18 10 µm column) using an acetonitrile:water gradient [50:50 to 95:5]. The appropriate fractions were combined and concentrated to give the titled compound (143 mg).

Experimental MH+ 547.9; expected 548.0

$^1$H-NMR (CD$_3$OD): 1.09-1.15 (8H), 1.55-1.60 (2H), 4.70-4.80 (1H), 8.19-8.21 (2H)

Example 21

1-(3-cyano-1-[2,6-dichloro-4-pentafluorothiophenyl]-5-{[2-(1H-1,2,4-triazol-1-yl)ethyl]amino}-1H-pyrazol-4-yl)cyclopropanecarboxamide

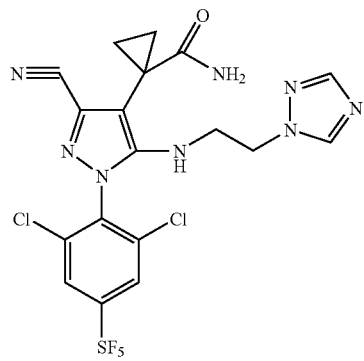

To a solution of Preparation 24 (103 mg, 0.19 mmol) in tetrahydrofuran (5 ml) was added triethylamine (28 mg, 0.28 mmol), followed by ethyl chloroformate (26 mg, 0.24 mmol). After stirring for 30 min, aqueous ammonium hydroxide solution (30 wt %, 0.2 ml) was added and stirring continued for 1 h. The reaction mixture was then concentrated in vacuo and the residue was partitioned between water (10 ml) and ethyl acetate (20 ml). The organic phase was separated, washed with hydrochloric acid (1N, 10 ml) and brine (10 ml), dried-(MgSO$_4$) and concentrated in vacuo. The residue was dissolved in acetonitrile (1.4 ml) and purified by automated preparative liquid chromatography (Gilson system, 150 mm×30 mm LUNA C18 10 □m column) using an acetonitrile:water gradient [40:60 to 98:2]. The appropriate fractions were combined and concentrated to give the titled compound (24 mg).

Experimental MH$^+$ 556.9; expected 557.0

$^1$H-NMR (CDCl$_3$): 1.15-1.20 (2H), 1.60-1.65 (2H), 3.61-3.67 (2H), 4.25-4.31 (2H), 7.90-7.92 (1H), 8.18-8.20 (2H), 8.25-8.27 (1H)

Example 22

1-{3-cyano-5-[(2-cyanoethyl)amino]-1-[2,6-dichloro-4-pentafluorothiophenyl]-1H-pyrazol-4-yl}cyclopropanecarboxamide

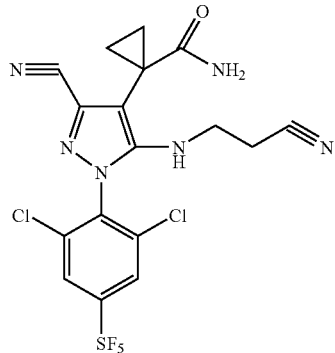

To a solution of Preparation 25 (223 mg, 0.44 mmol) in tetrahydrofuran (5 ml) was added triethylamine (180 µl, 1.31 mmol), followed by ethyl chloroformate (71 mg, 0.65 mmol). After stirring for 30 min, excess ammonium hydroxide solution (0.61 ml) was added and stirring continued for 1 h. The reaction mixture was then concentrated in vacuo and the residue was partitioned between water (10 ml) and ethyl acetate (20 ml). The organic phase was separated, washed with hydrochloric acid (1N, 10 ml) and brine (10 ml), dried (MgSO$_4$) and concentrated in vacuo. The residue was dissolved in acetonitrile (2 ml) and purified by automated preparative liquid chromatography (Gilson system, 150 mm×30 mm LUNA C18 10 µm column) using an acetonitrile:water gradient [45:55 to 95:5]. The appropriate fractions were combined and concentrated to give the titled compound (59 mg).

Experimental MH$^+$ 515.2; expected 515.0

$^1$H-NMR (CD$_3$OD): 1.21-1.26 (2H), 1.61-1.68 (2H), 1.54-1.60 (2H), 3.50-3.56 (2H), 8.19-8.22 (2H)

Example 23

1-(5-amino-3-cyano-1-{2,6-dichloro-4-[1,2,2,2-tetrafluoro-1-(trifluoromethyl)ethyl]phenyl}-1H-pyrazol-4-yl)cyclopropanecarboxamide

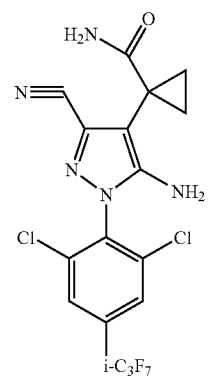

To a solution of Preparation 23 (430 mg, 0.85 mmol) in tetrahydrofuran (10 ml), at 0° C., was added triethylamine (474 g, 3.40 mmol), followed by ethyl chloroformate (162 µl, 1.70 mmol). The mixture was stirred for 5 min, before addition of aqueous ammonium hydroxide solution (2 ml). After stirring for a further 18 h at room temperature, the reaction mixture was diluted with water and extracted with ethyl acetate. The combined extracts were washed with brine, dried (MgSO$_4$) and concentrated in vacuo. The residue was dissolved in acetonitrile/dimethyl sulphoxide (3 ml) and purified by automated preparative liquid chromatography (Gilson system, 150 mm×50 mm Sunfire C18 10 µm column) using an acetonitrile:water gradient [50:50 to 95:5]. The appropriate fractions were combined and concentrated to give the titled compound (184 mg).

Experimental MH$^+$ 503.9; expected 504.0

$^1$H-NMR (CD$_3$OD): 1.07-1.11 (2H), 1.55-1.60 (2H), 7.90-7.92 (2H)

Example 24

1-(3-cyano-1-[2,6-dichloro-4-pentafluorothiophenyl]-5-{[3-(methylthio)propyl]amino}-1H-pyrazol-4-yl)cyclopropanecarboxamide

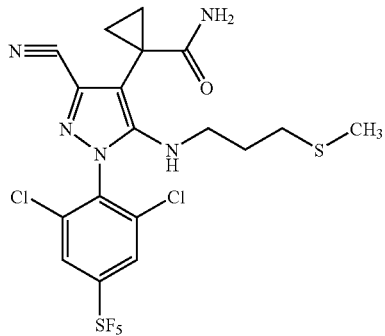

To a solution of crude Preparation 21 (approx. 0.79 mmol) in tetrahydrofuran (10 ml), at 0° C., was added triethylamine (0.27 ml, 1.98 mmol), followed by ethyl chloroformate (0.09 ml, 0.94 mmol). After stirring for 15 min, aqueous ammonium hydroxide solution (6 ml) was added and stirring continued for 30 min. The reaction mixture was adjusted to pH 1 by addition of hydrochloric acid (1M) and the mixture was extracted with ethyl acetate (×3). The combined extracts were washed with water, dried (MgSO$_4$) and concentrated in vacuo. The residue was dissolved in acetonitrile/dimethyl sulphoxide (1.5 ml) and purified by automated preparative liquid chromatography (Gilson system, 150 mm×50 mm Sunfire LUNA C18 10 μm column) using an acetonitrile:water gradient [50:50 to 95:5]. The appropriate fractions were combined and concentrated to give the titled compound (73 mg).

Experimental MH$^+$ 549.9; expected 550.0

$^1$H-NMR (CD$_3$OD): 1.20-1.25 (2H), 1.62-1.67 (2H), 1.70-1.80 (2H), 2.00-2.01 (3H), 2.40-2.45 (2H), 3.30-3.40 (2H), 8.20-8.23 (2H)

Example 25

1-{3-cyano-5-[(cyclopropylmethyl)amino]-1-[2,6-dichloro-4-pentafluorothiophenyl]-1H-pyrazol-4-yl}-N-[(5-methyl-4H-1,2,4-triazol-3-yl)methyl]cyclopropanecarboxamide

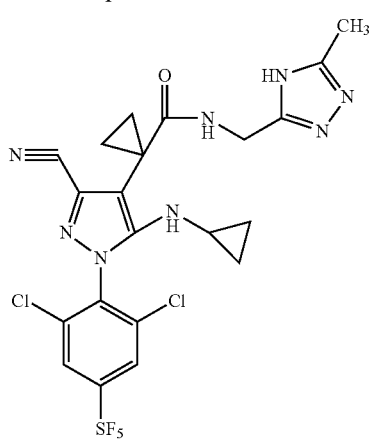

To a solution of Preparation 6 (110 mg, 0.21 mmol) in tetrahydrofuran (6 ml), at 0° C., was added triethylamine (177 μl, 1.27 mmol), followed by ethyl chloroformate (41 μl, 0.43 mmol). The mixture was stirred for 10 min, before addition of 1-[5-methyl-4H-(1,2,4)-triazol-3-yl]methylamine (218 mg, 1.00 mmol). After stirring for a further 1 h at 0° C., the reaction mixture was diluted with water and extracted with ethyl acetate. The combined extracts were washed with brine, dried (MgSO$_4$) and concentrated in vacuo. The residue was dissolved in acetonitrile (0.7 ml) and purified by automated preparative liquid chromatography (Gilson system, 150 mm×30 mm LUNA C18 10 μm column) using an acetonitrile:0.1% trifluoroacetic acid gradient [50:50 to 98:2]. The appropriate fractions were combined and concentrated to give the titled compound (20 mg).

Experimental MH$^+$ 611.3; expected 611.1

$^1$H-NMR (d$_6$-DMSO): 0.00-0.01 (2H), 0.20-0.27 (2H), 0.70-0.85 (1H), 1.05-1.10 (2H), 1.45-1.51 (2H), 2.25-2.30 (3H), 2.90-2.98 (2H), 4.21-4.26 (2H), 8.40-8.42 (2H)

Example 26

1-{3-cyano-5-[(cyclopropylmethyl)(methyl)amino]-1-[2,6-dichloro-4-pentafluorothiophenyl]-1H-pyrazol-4-yl}cyclopropanecarboxamide

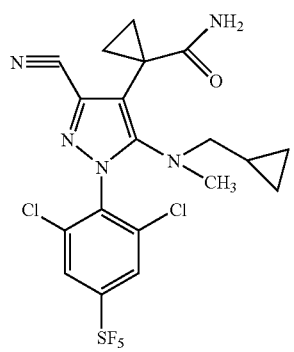

To a solution of Preparation 192 (200 mg, 0.36 mmol) in pyridine (5 ml) was added lithium iodide (482 mg, 3.60 mmol) and the reaction mixture was stirred at 125° C. for 6 h.

The reaction mixture was concentrated in vacuo and the residue was washed with hydrochloric acid (10%) and extracted with dichloromethane. The combined extracts were washed with brine, dried (MgSO$_4$) and concentrated in vacuo to give the acid. To a solution of the acid (500 mg, 0.95 mmol) in tetrahydrofuran (10 ml), at 0° C., was added triethylamine (330 μl, 2.38 mmol), followed by ethyl chloroformate (136 W, 1.43 mmol). After stirring at 0° C. for 30 min, ammonia (0.5 ml) was added and the reaction mixture was stirred for a further 30 min. The mixture was then quenched with water and extracted with ethyl acetate. The combined extracts were washed with brine, dried (MgSO$_4$) and concentrated in vacuo. The residue was dissolved in acetonitrile/dimethyl sulphoxide (0.3 ml) and purified by automated preparative liquid chromatography (Gilson system, 150 mm×30 mm LUNA C18(2) 10 μm column) using an acetonitrile:water gradient [60:40 to 95:5]. The appropriate fractions were combined and concentrated to give the titled compound (182 mg).

Experimental MH$^+$ 530.1; expected 530.1

Example 27

[1-(fluoromethyl)cyclopropyl]methyl {4-[1-(aminocarbonyl)cyclopropyl]-3-cyano-1-[2,6-dichloro-4-pentafluorothiophenyl]-1H-pyrazol-5-yl}carbamate

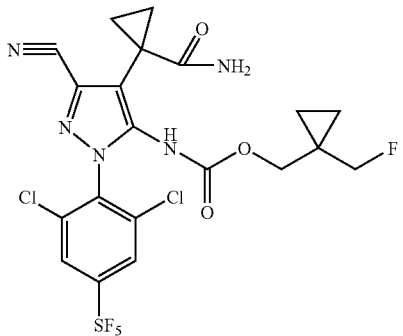

To a solution of crude Preparation 223 (approximately, 0.50 mmol) in tetrahydrofuran (3 ml), at 0° C., was added triethylamine (275 μl, 2.00 mmol), followed by ethyl chloroformate (187 μl, 1.00 mmol). After stirring for 30 min, the mixture was quenched by addition of aqueous ammonium hydroxide solution (2 ml). The reaction mixture was partitioned between water and ethyl acetate and the two layers were separated. The organic layer was washed with hydrochloric acid (10%) and brine, dried (MgSO$_4$) and concentrated in vacuo. The residue was dissolved in acetonitrile/dimethyl sulphoxide (1 ml) and purified by automated preparative liquid chromatography (Gilson system, 150 mm×30 mm LUNA C18 10 μm column) using an acetonitrile:water gradient [50:50 to 98:2]. The appropriate fractions were combined and concentrated to give the titled compound (42 mg).

Experimental MH$^+$ 592.1; expected 592.0

$^1$H-NMR (CDCl$_3$): 0.51-0.62 (4H), 1.18-1.23 (2H), 1.65-1.75 (2H), 4.00-4.06 (3H), 4.18-4.20 (1H), 7.91-7.95 (2H)

Example 28

1-{3-cyano-1-[2,6-dichloro-4-pentafluorothiophenyl]-5-(methylamino)-1H-pyrazol-4-yl}-2,2-difluorocyclopropanecarboxamide

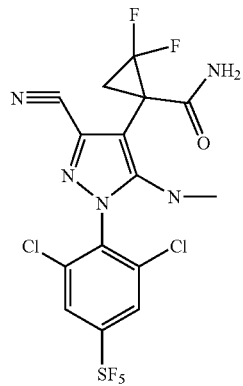

To a solution of Preparation 7 (977 mg, 1.91 mmol) in tetrahydrofuran (20 ml) was added triethylamine (0.79 ml, 5.72 mmol), followed by ethyl chloroformate (0.20 ml, 2.10 mmol), added dropwise. After stirring for 5 min, ammonium hydroxide (30 wt %, 2.20 ml, 19.10 mmol) was added and the reaction mixture was stirred at room temperature for 30 min. To the reaction mixture was added hydrochloric acid (2N, 50 ml) and the mixture was extracted with ethyl acetate (3×30 ml). The combined extracts were dried (MgSO4) and concentrated in vacuo. The residue was dissolved in acetonitrile (3.5 ml) and purified by automated preparative liquid chromatography (Gilson system, 150 mm×50 mm Phenomenex LUNA C18(2) 10 μm column) using an acetonitrile:water [50:50 to 95:5] gradient. The appropriate fractions were combined and concentrated to give the titled compound (700 mg).

Experimental MH$^+$ 512.2; expected 512.0

$^1$H-NMR (d$_6$DMSO): 1.90-2.01 (1H), 2.75-2.83 (4H), 6.05-6.13 (1H), 7.15-7.22 (1H), 7.59-7.66 (1H), 8.40-8.49 (2H)

Similarly Prepared Using the Appropriate Amine were:

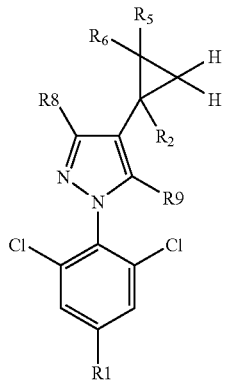

| Example | R1 | R5 | R6 | R8 | R9 | R2 | From |
|---|---|---|---|---|---|---|---|
| Example 29 | $SF_5$ | H | H | CN | 3,3,3-trifluoropropylamino | aminocarbonyl[a] | Preparation 16 |
| Example 30 | $SF_5$ | H | H | CN | [2-chloro(1,3-thiazol-5-yl)]methylamino | aminocarbonyl[a] | Preparation 17 |
| Example 31 | $SF_5$ | H | H | CN | (isoxazol-5-yl)methylamino | aminocarbonyl[a] | Preparation 18 |
| Example 32 | $SF_5$ | H | H | CN | —NH(CH$_2$)$_2$CONH$_2$ | aminocarbonyl[a] | Preparation 19 |
| Example 33 | $SF_5$ | H | H | CN | 5,5,5-trifluoropentylamino | aminocarbonyl[a] | Preparation 20 |
| Example 34 | $SF_5$ | H | H | CN | propylamino | aminocarbonyl[a] | Preparation 41 |
| Example 35 | $SF_5$ | H | H | CN | (cyclobutylmethyl)amino | aminocarbonyl[a] | Preparation 32 |
| Example 36 | $SF_5$ | H | H | CN | dimethylamino | aminocarbonyl[a] | Preparation 33 |
| Example 37 | $OCF_3$ | H | H | CN | ethoxycarbonylamino | aminocarbonyl[a] | Preparation 34 |
| Example 38 | $SF_5$ | Cl | Cl | CN | methylamino | aminocarbonyl[a] | Preparation 39 |
| Example 39 | $OCF_3$ | Cl | Cl | CN | $NH_2$ | aminocarbonyl[a] | Preparation 40 |
| Example 40 | $SF_5$ | H | H | CN | —NHCH$_2$CONHCH$_2$c-Pr | aminocarbonyl[a] | Preparation 42 |
| Example 41 | $SF_5$ | H | H | CN | —NH(CH$_2$)$_3$CONH$_2$ | aminocarbonyl[a] | Preparation 45 |
| Example 42 | $SF_5$ | H | H | CN | (1,3-thiazol-2-ylmethyl)amino | aminocarbonyl[a] | Preparation 46 |
| Example 43 | $SF_5$ | H | H | CN | (cyclopropylmethyl)amino | —CONH(CH$_2$)$_2$OCH$_3$[b] | Preparation 6 |
| Example 44 | $SF_5$ | H | H | CN | (cyclopropylmethyl)amino | —CONH(CH$_2$)$_2$OH[c] | Preparation 6 |
| Example 45 | $SF_5$ | H | H | CN | (cyclopropylmethyl)amino | (pyridin-2-ylmethyl)aminocarbonyl[d] | Preparation 6 |
| Example 46 | $SF_5$ | H | H | CN | (cyclopropylmethyl)amino | (pyridin-3-ylmethyl)aminocarbonyl[e] | Preparation 6 |
| Example 47 | $SF_5$ | H | H | CN | (cyclopropylmethyl)amino | —CONHCH$_2$C(CH$_3$)$_2$OH[f] | Preparation 6 |
| Example 48 | $SF_5$ | H | H | CN | 2-(1-methyl-1H-pyrazol-4-yl)ethylamino | aminocarbonyl[a] | Preparation 47 |
| Example 49 | $SF_5$ | F | F | CN | dimethylamino | aminocarbonyl[a] | Preparation 198 |
| Example 50 | $SF_5$ | H | H | CN | methylthio | aminocarbonyl[a] | Preparation 35 |
| Example 51 | $SF_5$ | H | H | CN | (2-methoxyethyl)(methyl)amino | aminocarbonyl[a] | Preparation 44 |
| Example 52 | $SF_5$ | H | H | CN | [(5-chloro-1,3-dimethyl-1H-pyrazol-4-yl)methyl]amino | aminocarbonyl[a] | Preparation 43 |
| Example 53 | $SF_5$ | F | F | CN | $NH_2$ | aminocarbonyl[a] | Preparation 10 |
| Example 54 | $OCF_3$ | H | H | CN | $NH_2$ | aminocarbonyl[a] | Preparation 11 |
| Example 55 | $CF_3$ | F | F | CN | $NH_2$ | aminocarbonyl[a] | Preparation 94 |
| Example 56 | $SF_5$ | H | H | CN | $NH_2$ | (methylamino)carbonyl[g] | Preparation 5 |
| Example 57 | $CF_3$ | H | H | CN | $NH_2$ | (cyclopropylamino)carbonyl[h] | Preparation 178 |
| Example 58 | $CF_3$ | H | H | CN | $NH_2$ | (cyclopropylmethylamino)carbonyl[i] | Preparation 178 |
| Example 59 | $CF_3$ | H | H | CN | $NH_2$ | (pyridin-2-ylamino)carbonyl[d] | Preparation 178 |
| Example 60 | $CF_3$ | H | H | $CF_3$ | $NH_2$ | aminocarbonyl[a] | Preparation 28 |
| Example 61 | $CF_3$ | H | H | CN | —N=CH—N(CH$_3$)$_2$ | aminocarbonyl[a] | Preparation 27 |
| Example 62 | $SF_5$ | H | H | CN | $NH_2$ | (2,2,2-trifluoroethylamino)carbonyl[j] | Preparation 5 |
| Example 63 | $OCF_3$ | F | F | CN | methylamino | aminocarbonyl[a] | Preparation 50 |
| Example 64 | $OCF_3$ | H | H | CN | methylamino | aminocarbonyl[a] | Preparation 12 |
| Example 65 | $CF_3$ | H | H | CN | (cyclopropylmethyl)amino | (methylamino)carbonyl[g] | Preparation 29 |
| Example 66 | $CF_3$ | CH3 | CH3 | CN | $NH_2$ | aminocarbonyl[a] | Example 89 |
| Example 67 | $SF_5$ | H | H | CN | [(4H-1,2,4-triazol-3-yl)methyl]amino | aminocarbonyl[a] | Preparation 13 |
| Example 68 | $SF_5$ | H | H | CN | [(1-methylcyclopropyl)methyl]amino | aminocarbonyl[a] | Preparation 14 |
| Example 69 | $SF_5$ | H | H | CN | {4-[(methylamino)sulphonyl]benzyl}amino | aminocarbonyl[a] | Preparation 37 |
| Example 70 | $SF_5$ | H | H | CN | {4-[(methylsulphonyl)amino]benzyl}amino | aminocarbonyl[a] | Preparation 36 |
| Example 71 | $SF_5$ | H | H | CN | (tetrahydro-2H-pyran-4-ylmethyl)amino | aminocarbonyl[a] | Preparation 38 |

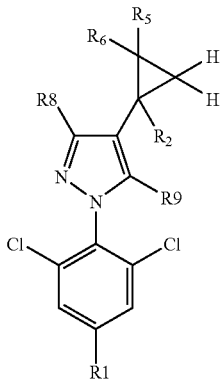

| Example | R1 | R5 | R6 | R8 | R9 | R2 | From |
|---|---|---|---|---|---|---|---|
| Example 72 | $SF_5$ | H | H | CN | (cyclopropylmethyl)amino | —CONH$(CH_2)_3$Oi-Pr[k] | Preparation 6 |
| Example 73 | $SF_5$ | H | H | CN | —NHCH$_2$CONHCH$_2$CF$_3$ | aminocarbonyl[a] | Preparation 225 |

[a]reagent—ammonia;
[b]reagent—methoxymethylamine;
[c]reagent—hydroxyethylamine;
[d]reagent—pyrid-2-ylmethylamine;
[e]reagent—pyrid-3-ylmethylamine;
[f]reagent—2-hydroxyisobutylamine;
[g]reagent—methylamine;
[h]reagent—cyclopropylamine;
[i]reagent—cyclopropylmethylamine;
[j]reagent—2,2,2-trifluoroethylamine;
[k]reagent—isopropyloxypropylamine

Example 29

1-{3-cyano-1-[2,6-dichloro-4-pentafluorothiophenyl]-5-[(3,3,3-trifluoropropyl)amino]-1H-pyrazol-4-yl}cyclopropanecarboxamide Experimental MH$^+$ 558.0; expected 558.0
$^1$H-NMR (d$_6$-DMSO): 1.00-1.06 (2H), 1.42-1.50 (2H), 2.38-2.44 (2H), 3.39-3.44 (2H), 5.85-5.91 (1H), 8.41-8.43 (2H)

Example 30

1-(5-{[(2-chloro-1,3-thiazol-5-yl)methyl]amino}-3-cyano-1-[2,6-dichloro-4-pentafluorothiophenyl]-1H-pyrazol-4-yl)cyclopropanecarboxamide Experimental MH$^+$ 593.1; expected 593.0
$^1$H-NMR (d$_6$-DMSO): 1.00-1.06 (2H), 1.41-1.48 (2H), 4.40-4.49 (2H), 6.43-6.50 (1H), 6.64-6.71 (1H), 7.17-7.23 (1H), 7.39-7.41 (1H), 8.40-8.22 (2H)

Example 31

1-{3-cyano-1-[2,6-dichloro-4-pentafluorothiophenyl]-5-[(isoxazol-5-ylmethyl)amino]-1H-pyrazol-4-yl}cyclopropanecarboxamide Experimental MH$^+$ 542.9; expected 543.0
$^1$H-NMR (d$_6$-DMSO): 0.97-1.02 (2H), 1.39-1.45 (2H), 4.44-4.51 (2H), 6.20-6.23 (1H), 6.57-6.64 (1H), 7.17-7.23 (1H), 8.39-8.43 (3H)

Example 32

N~3~-{4-[1-(aminocarbonyl)cyclopropyl]-3-cyano-1-[2,6-dichloro-4-pentafluorothiophenyl]-1H-pyrazol-5-yl}-beta-alaninamide Experimental MH$^+$ 533.2; expected 533.0
$^1$H-NMR (d$_6$-DMSO): 0.99-1.05 (2H), 1.40-1.45 (2H), 2.15-2.22 (2H), 3.30-3.38 (2H), 8.40-8.42 (2H)

Example 33

1-{3-cyano-1-[2,6-dichloro-4-pentafluorothiophenyl]-5-[(5,5,5-trifluoropentyl)amino]-1H-pyrazol-4-yl}cyclopropanecarboxamide Experimental MH$^+$ 586.2; expected 586.0
$^1$H-NMR (d$_6$-DMSO): 0.95-1.02 (2H), 1.30-1.40 (2H), 1.40-1.48 (4H), 2.01-2.20 (2H), 3.10-3.18 (2H), 8.39-8.42 (2H)

Example 34

1-{3-cyano-1-[2,6-dichloro-4-pentafluorothiophenyl]-5-(propylamino)-1H-pyrazol-4-yl}cyclopropanecarboxamide $^1$H-NMR (d$_6$-Acetone): 0.75-0.80 (3H), 1.10-1.15 (2H), 1.40-1.50 (2H), 1.55-1.60 (2H), 3.20-3.29 (2H), 5.30-5.38 (1H), 6.25-6.55 (2H), 8.20-8.22 (2H)

Example 35

1-{3-cyano-5-[(cyclobutylmethyl)amino]-1-[2,6-dichloro-4-pentafluorothiophenyl]-1H-pyrazol-4-yl}cyclopropanecarboxamide Experimental MH$^+$ 530.1; expected 530.1
$^1$H-NMR (CDCl$_3$): 1.21-1.27 (2H), 1.48-1.58 (2H), 1.75-1.93 (4H), 1.95-2.05 (2H), 2.30-2.40 (1H), 3.05-3.11 (2H), 3.39-3.46 (1H), 5.61-5.72 (2H), 7.89-7.95 (2H)

Example 36

1-{3-cyano-1-[2,6-dichloro-4-pentafluorothiophenyl]-5-(dimethylamino)-1H-pyrazol-4-yl}cyclopropanecarboxamide Experimental MH$^+$ 490.1; expected 490.0
$^1$H-NMR (d$_6$-DMSO): 1.07-1.11 (2H), 1.50-1.54 (2H), 2.63-2.66 (6H), 6.69-6.76 (1H), 7.13-7.20 (1H), 8.48-8.50 (2H)

Example 37 ethyl {4-[1-(aminocarbonyl)cyclopropyl]-3-cyano-1-[2,6-dichloro-4-(trifluoromethoxy)phenyl]-1H-pyrazol-5-yl}carbamate Experimental MH$^+$ 492.3; expected 492.0
$^1$H-NMR (d$_6$-DMSO): 0.90-0.95 (2H), 1.00-1.10 (3H), 1.37-1.42 (2H), 3.95-4.02 (2H), 6.25-6.39 (1H), 7.10-7.21 (1H), 7.95-8.00 (2H), 9.80-9.95 (1H)

Example 38

2,2-dichloro-1-{3-cyano-1-[2,6-dichloro-4-pentafluorothiophenyl]-5-(methylamino)-1H-pyrazol-4-yl}cyclopropanecarboxamide Experimental MH$^+$ 544.2; expected 543.9
$^1$H-NMR (d$_6$-Acetone): 2.22-2.36 (1H), 2.79-2.81 (2H), 2.84-2.89 (3H), 6.99-7.20 (2H), 8.26-8.30 (2H)

Example 39

1-{5-amino-3-cyano-1-[2,6-dichloro-4-(trifluoromethoxy)phenyl]-1H-pyrazol-4-yl}-2,2-dichlorocyclopropanecarboxamide Experimental MH$^+$ 488.2; expected 487.9
$^1$H-NMR (d$_6$-Acetone): 2.30-2.40 (1H), 2.61-2.69 (1H), 6.10-6.30 (2H), 6.90-7.00 (1H), 7.40-7.60 (1H), 7.75-7.80 (2H)

Example 40

1-{3-cyano-5-({2-[(cyclopropylmethyl)amino]-2-oxoethyl}amino)-1-[2,6-dichloro-4-pentafluorothiophenyl]-1H-pyrazol-4-yl}cyclopropanecarboxamide Experimental MH$^+$ 573.3; expected 573.1
$^1$H-NMR (d$_6$-DMSO): 0.05-0.10 (2H), 0.35-0.40 (2H), 0.68-0.75 (1H), 1.00-1.05 (2H), 1.40-1.45 (2H), 2.84-2.90 (2H), 3.62-3.69 (2H), 6.18-6.22 (1H), 6.42-6.49 (1H), 7.19-7.22 (1H), 7.78-7.81 (1H), 8.41-8.43 (2H)

Example 41

1-{5-[(4-amino-4-oxobutyl)amino]-3-cyano-1-[2,6-dichloro-4-pentafluorothiophenyl]-1H-pyrazol-4-yl}cyclopropanecarboxamide Experimental MH$^+$ 547.2; expected 547.1
$^1$H-NMR (d$_6$-DMSO): 0.95-1.02 (2H), 1.39-1.45 (2H), 1.50-1.63 (2H), 1.90-1.99 (2H), 3.10-3.17 (2H), 8.39-8.42 (2H)

Example 42

1-{3-cyano-1-[2,6-dichloro-4-pentafluorothiophenyl]-5-[(1,3-thiazol-2-ylmethyl)amino]-1H-pyrazol-4-yl}cyclopropanecarboxamide Experimental MH$^+$ 558.9; expected 559.0
$^1$H-NMR (d$_6$-DMSO): 0.90-0.99 (2H), 1.35-1.41 (2H), 4.50-4.52 (2H), 7.55-7.63 (2H), 8.37-8.40 (2H)

Example 43

1-{3-cyano-5-[(cyclopropylmethyl)amino]-1-[2,6-dichloro-4-pentafluorothiophenyl]-1H-pyrazol-4-yl}-N-(2-methoxyethyl)cyclopropanecarboxamide Experimental MH$^+$ 574.3; expected 574.1
$^1$H-NMR (d$_6$-DMSO): 0.01-0.07 (2H), 0.30-0.36 (2H), 0.80-0.90 (1H), 1.00-1.05 (2H), 1.40-1.44 (2H), 2.90-2.99 (2H), 3.17-3.19 (3H), 3.20-3.30 (4H), 8.40-8.42 (2H)

Example 44

1-{3-cyano-5-[(cyclopropylmethyl)amino]-1-[2,6-dichloro-4-pentafluorothiophenyl]-1H-pyrazol-4-yl}-N-(2-hydroxyethyl)cyclopropanecarboxamide Experimental MH$^+$ 560.3; expected 560.1
$^1$H-NMR (d$_6$-DMSO): 0.01-0.08 (2H), 0.27-0.32 (2H), 0.80-0.90 (1H), 1.00-1.05 (2H), 1.20-1.25 (2H), 2.90-2.99 (2H), 3.10-3.17 (2H), 3.34-3.38 (2H), 4.60-4.65 (1H), 8.40-8.42 (2H)

Example 45

1-{3-cyano-5-[(cyclopropylmethyl)amino]-1-[2,6-dichloro-4-pentafluorothiophenyl]-1H-pyrazol-4-yl}-N-(pyridin-2-ylmethyl)cyclopropanecarboxamide Experimental MH$^+$ 607.3; expected 607.1
$^1$H-NMR (d$_6$-DMSO): 0.00-0.01 (2H), 0.10-0.14 (2H), 0.79-0.83 (1H), 1.02-1.09 (2H), 1.41-1.46 (2H), 2.90-2.99 (2H), 4.35-4.40 (2H), 7.18-7.23 (2H), 7.60-7.70 (2H), 8.40-8.42 (2H)

Example 46

1-{3-cyano-5-[(cyclopropylmethyl)amino]-1-[2,6-dichloro-4-pentafluorothiophenyl]-1H-pyrazol-4-yl}-N-(pyridin-3-ylmethyl)cyclopropanecarboxamide Experimental MH$^+$ 606.9; expected 607.1
$^1$H-NMR (d$_6$-DMSO): −0.15-0.00 (2H), 0.20-0.30 (2H), 0.70-0.85 (1H), 1.00-1.10 (2H), 1.40-1.50 (2H), 2.80-2.90 (2H), 4.30-4.40 (2H), 7.82-7.95 (2H), 8.35-8.41 (2H), 8.50-8.58 (2H)

Example 47

1-{3-cyano-5-[(cyclopropylmethyl)amino]-1-[2,6-dichloro-4-pentafluorothiophenyl]-1H-pyrazol-4-yl}-N-(2-hydroxy-2-methylpropyl)cyclopropanecarboxamide Experimental MH$^+$ 588.3; expected 588.1
$^1$H-NMR (CD$_3$OD): 0.09-0.15 (2H), 0.41-0.49 (2H), 0.90-1.00 (1H), 1.16-1.18 (6H), 1.25-1.30 (2H), 1.63-1.69 (2H), 3.05-3.10 (2H), 3.19-3.21 (2H), 8.20-8.22 (2H)

Example 48

1-(3-cyano-1-[2,6-dichloro-4-pentafluorothiophenyl]-5-{[2-(1-methyl-1H-pyrazol-4-yl)ethyl]amino}-1H-pyrazol-4-yl)cyclopropanecarboxamide Experimental MH$^+$ 570.2; expected 570.1
$^1$H-NMR (CD$_3$OD): 1.19-1.23 (2H), 1.60-1.65 (2H), 2.59-2.64 (2H), 3.37-3.41 (2H), 3.79-3.81 (3H), 7.21-7.22 (1H), 7.35-7.36 (1H), 8.21-8.23 (2H)

Example 49

1-{3-cyano-1-[2,6-dichloro-4-pentafluorothiophenyl]-5-(dimethylamino)-1H-pyrazol-4-yl}-2,2-difluorocyclopropanecarboxamide Experimental MH$^+$ 526.0; expected 526.0
$^1$H-NMR (CDCl$_3$): 1.96-2.04 (1H), 2.74-2.77 (6H), 2.81-2.90 (1H), 5.74-5.81 (2H), 7.91-7.93 (2H)

Example 50

1-{3-cyano-1-[2,6-dichloro-4-pentafluorothiophenyl]-5-(methylthio)-1H-pyrazol-4-yl}cyclopropanecarboxamide $^1$H-NMR (CDCl$_3$): 1.35-1.38 (2H), 1.85-1.89 (2H), 2.35-2.37 (3H), 7.93-7.94 (2H)

Example 51

1-{3-cyano-1-[2,6-dichloro-4-pentafluorothiophenyl]-5-[(2-methoxyethyl)(methyl)amino]-1H-pyrazol-4-yl}cyclopropanecarboxamide Experimental MH$^+$ 534.1; expected 534.1
$^1$H-NMR (CDCl$_3$): 1.21-1.26 (2H), 1.75-1.80 (2H), 2.90-2.93 (3H), 3.01-3.04 (2H), 3.12-3.14 (3H), 3.20-3.25 (2H), 5.60-5.80 (2H), 7.89-7.92 (2H)

Example 52

1-(5-{[(5-chloro-1,3-dimethyl-1H-pyrazol-4-yl)methyl]amino}-3-cyano-1-[2,6-dichloro-4-pentafluorothiophenyl]-1H-pyrazol-4-yl)cyclopropanecarboxamide Experimental MH$^+$ 604.3; expected 604.0
$^1$H-NMR (d$_6$-DMSO): 1.04-1.11 (2H), 1.42-1.50 (2H), 2.00-2.06 (3H), 3.59-3.62 (3H), 4.16-4.20 (2H), 5.81-5.86 (1H), 8.36-8.40 (2H)

Example 53

1-{5-amino-3-cyano-1-[2,6-dichloro-4-pentafluorothiophenyl]-1H-pyrazol-4-yl}-2,2-difluorocyclopropanecarboxamide Experimental MH$^+$ 497.9; expected 498.0
$^1$H-NMR (d$_6$-DMSO): 1.74-1.84 (1H), 2.51-2.61 (1H), 6.26-6.35 (2H), 7.13-7.22 (1H), 7.44-7.53 (1H), 8.40-8.46 (2H)

Example 54

1-{5-amino-3-cyano-1-[2,6-dichloro-4-(trifluoromethoxy)phenyl]-1H-pyrazol-4-yl}cyclopropanecarboxamide Experimental MH$^+$ 420.0; expected 420.0
$^1$H-NMR (d$_6$-DMSO): 0.87-0.93 (2H), 1.38-1.44 (2H), 6.06-6.11 (1H), 6.12-6.17 (2H), 7.12-7.21 (1H), 7.88-7.92 (2H)

Example 55

1-{5-amino-3-cyano-1-[2,6-dichloro-4-(trifluoromethyl)phenyl]-1H-pyrazol-4-yl}-2,2-difluorocyclopropanecarboxamide Experimental MH$^+$ 440.0; expected 440.0
$^1$H-NMR (Acetone-d$_6$): 1.91-1.99 (1H), 2.60-2.69 (1H), 5.93-6.03 (2H), 6.70-6.88 (2H), 8.03-8.08 (2H)

Example 56

1-{5-amino-3-cyano-1-[2,6-dichloro-4-pentafluorothiophenyl]-1H-pyrazol-4-yl}-N-methylcyclopropanecarboxamide Experimental MH$^+$ 476.3; expected 476.0
$^1$H-NMR (d$_6$-DMSO): 0.84-0.89 (2H), 1.38-1.43 (2H), 2.57-2.61 (3H), 6.14-6.21 (2H), 6.74-6.80 (1H), 8.38-8.41 (2H)

Example 57

1-{5-amino-3-cyano-1-[2,6-dichloro-4-(trifluoromethyl)phenyl]-1H-pyrazol-4-yl}-N-cyclopropylcyclopropanecarboxamide Experimental MH$^+$ 443.9; expected 444.1
$^1$H-NMR (CDCl$_3$): 0.30-0.36 (2H), 0.65-0.72 (2H), 1.05-1.11 (2H), 1.55-1.62 (2H), 2.57-2.64 (1H), 7.71-7.75 (2H)

Example 58

1-{5-amino-3-cyano-1-[2,6-dichloro-4-(trifluoromethyl)phenyl]-1H-pyrazol-4-yl}-N-(cyclopropylmethyl)cyclopropanecarboxamide Experimental MH$^+$ 457.9; expected 458.1
$^1$H-NMR (CDCl$_3$): 0.08-0.13 (2H), 0.40-0.46 (2H), 0.80-0.87 (1H), 1.10-1.14 (2H), 1.64-1.68 (2H), 3.04-3.08 (2H), 3.96-4.02 (2H), 5.68-5.73 (1H), 7.76-7.79 (2H)

Example 59

1-{5-amino-3-cyano-1-[2,6-dichloro-4-(trifluoromethyl)phenyl]-1H-pyrazol-4-yl}-N-pyridin-2-ylcyclopropanecarboxamide Experimental MH$^+$ 481.0; expected 481.1
$^1$H-NMR (CDCl$_3$): 1.28-1.34 (2H), 1.75-1.82 (2H), 4.10-4.31 (2H), 7.09-7.14 (1H), 7.73-7.78 (2H), 7.81-7.87 (1H), 8.14-8.19 (1H), 8.28-8.32 (1H), 9.47-9.60 (1H)

Example 60

1-{5-amino-1-[2,6-dichloro-4-(trifluoromethyl)phenyl]-3-(trifluoromethyl)-1H-pyrazol-4-yl}cyclopropanecarboxamide Experimental MH$^+$ 447.0; expected 447.0
$^1$H-NMR (CDCl$_3$): 1.10-1.15 (2H), 1.65-1.70 (2H), 3.87-4.05 (2H), 5.63-5.72 (2H), 7.74-7.77 (2H)

Example 61

1-(3-cyano-1-[2,6-dichloro-4-(trifluoromethyl)phenyl]-5-{[(dimethylamino)methylene]amino}-1H-pyrazol-4-yl)cyclopropanecarboxamide Experimental MH$^+$ 459.0; expected 459.1
$^1$H-NMR (Acetone-d$_6$): 0.97-1.02 (2H), 1.54-1.58 (2H), 2.74-2.78 (3H), 3.03-3.06 (3H), 6.29-6.42 (1H), 6.45-6.56 (1H), 7.97-8.01 (2H), 8.12-8.15 (1H)

Example 62

1-{5-amino-3-cyano-1-[2,6-dichloro-4-pentafluorothiophenyl]-1H-pyrazol-4-yl}-N-(2,2,2-trifluoroethyl)cyclopropanecarboxamide Experimental MH$^+$ 544.2; expected 544.0
$^1$H-NMR (d$_6$-DMSO): 0.96-1.01 (2H), 1.44-1.49 (2H), 3.82-3.93 (2H), 6.17-6.24 (1H), 7.24-7.29 (1H), 8.40-8.42 (2H)

Example 63

1-{3-cyano-1-[2,6-dichloro-4-(trifluoromethoxy)phenyl]-5-(methylamino)-1H-pyrazol-4-yl}-2,2-difluorocyclopropanecarboxamide Experimental MH$^+$ 470.2; expected 470.0
$^1$H-NMR (d$_6$-DMSO): 1.91-2.00 (1H), 2.71-2.81 (4H), 5.98-6.04 (1H), 7.12-7.19 (1H), 7.58-7.64 (1H), 7.91-7.95 (2H)

Example 64

1-{3-cyano-1-[2,6-dichloro-4-(trifluoromethoxy)phenyl]-5-(methylamino)-1H-pyrazol-4-yl}cyclopropanecarboxamide Experimental MH$^+$ 434.0; expected 434.0
$^1$H-NMR (d$_6$-DMSO): 1.03-1.07 (2H), 1.44-1.48 (2H), 2.78-2.82 (3H), 5.87-5.92 (1H), 6.39-6.45 (1H), 7.20-7.26 (1H), 7.90-7.93 (2H)

Example 65

1-{3-cyano-5-[(cyclopropylmethyl)amino]-1-[2,6-dichloro-4-(trifluoromethyl)phenyl]-1H-pyrazol-4-yl}-N-methylcyclopropanecarboxamide Experimental MH$^+$ 472.1; expected 472.1
$^1$H-NMR (d$_6$-DMSO): −0.01-0.05 (2H), 0.26-0.32 (2H), 0.83-0.88 (1H), 0.95-1.00 (2H), 1.39-1.44 (2H), 2.55-2.60 (3H), 2.88-2.94 (2H), 5.84-5.89 (1H), 7.10-7.16 (1H), 8.20-8.24 (2H)

Example 66

1-{5-amino-3-cyano-1-[2,6-dichloro-4-(trifluoromethyl)phenyl]-1H-pyrazol-4-yl}-2,2-dimethylcyclopropanecarboxamide Experimental MH$^+$ 432.0; expected 432.1
$^1$H-NMR (CDCl$_3$): 1.03-1.14 (3H), 1.24-1.32 (1H), 1.32-1.38 (3H), 1.42-1.52 (1H), 4.72-4.93 (2H), 5.39-5.52 (1H), 5.79-5.92 (1H), 7.74-7.80 (2H)

Example 67

1-{3-cyano-1-[2,6-dichloro-4-pentafluorothiophenyl]-5-[(4H-1,2,4-triazol-3-ylmethyl)amino]-1H-pyrazol-4-yl}cyclopropanecarboxamide Experimental MH$^+$ 543.2; expected 543.0
$^1$H-NMR (d$_6$-DMSO): 1.08-1.12 (2H), 1.42-1.46 (2H), 4.36-4.40 (2H), 6.41-6.47 (1H), 6.75-6.82 (1H), 7.19-7.25 (1H), 8.20-8.30 (1H), 8.34-8.36 (2H)

Example 68

1-(3-cyano-1-[2,6-dichloro-4-pentafluorothiophenyl]-5-{[(1-methylcyclopropyl)methyl]amino}-1H-pyrazol-4-yl)cyclopropanecarboxamide Experimental MH$^+$ 530.0; expected 530.1
$^1$H-NMR (d$_6$-DMSO): 0.00-0.04 (2H), 0.14-0.18 (2H), 0.79-0.83 (3H), 0.88-0.93 (2H), 1.29-1.34 (2H), 2.94-2.98 (2H), 5.58-5.64 (1H), 6.28-6.38 (1H), 6.99-7.09 (1H), 8.26-8.29 (2H).

Example 69

1-{3-cyano-1-[2,6-dichloro-4-pentafluorothiophenyl]-5-({4-[(methylamino)sulfonyl]benzyl}amino)-1H-pyrazol-4-yl}cyclopropanecarboxamide Experimental MH$^+$ 645.1; expected 645.0
$^1$H-NMR (d$_6$-Acetone): 1.10-1.17 (2H), 1.50-1.56 (2H), 2.55-2.59 (3H), 4.60-4.65 (2H), 6.01-6.10 (1H), 6.25-6.30 (1H), 6.35-6.55 (2H), 7.45-7.50 (2H), 7.70-7.75 (2H), 8.20-8.23 (2H)

Example 70

1-{3-cyano-1-[2,6-dichloro-4-pentafluorothiophenyl]-5-({4-[(methylsulfonyl)amino]benzyl}amino)-1H-pyrazol-4-yl}cyclopropanecarboxamide Experimental MH$^+$ 645.2; expected 645.0
$^1$H-NMR (d$_6$-DMSO): 1.18-1.22 (2H), 1.75-1.79 (2H), 2.99-3.01 (3H), 4.02-4.10 (1H), 4.22-4.27 (2H), 5.60-5.80 (2H), 7.00-7.04 (1H), 7.10-7.15 (4H), 7.82-7.87 (2H)

Example 71

1-{3-cyano-1-[2,6-dichloro-4-pentafluorothiophenyl]-5-[(tetrahydro-2H-pyran-4-ylmethyl)amino]-1H-pyrazol-4-yl}cyclopropanecarboxamide Experimental MH$^+$ 560.2; expected 560.1
$^1$H-NMR (d$_6$-Acetone): 1.00-1.10 (2H), 1.18-1.21 (2H), 1.55-1.60 (4H), 1.60-1.75 (1H), 3.15-3.25 (4H), 3.78-3.81 (2H), 5.40-5.50 (1H), 6.35-6.60 (2H), 8.21-8.24 (2H)

Example 72

1-{3-cyano-5-[(cyclopropylmethyl)amino]-1-[2,6-dichloro-4-pentafluorothiophenyl]-1H-pyrazol-4-yl}-N-(3-isopropoxypropyl)cyclopropanecarboxamide Experimental MH+ 616.0; expected 616.1

$^1$H-NMR (d$_6$-DMSO): 0.01-0.08 (2H), 0.29-0.33 (2H), 0.80-0.90 (1H), 0.99-1.05 (6H), 1.41-1.46 (2H), 1.49-1.54 (2H), 2.91-2.98 (2H), 3.03-3.10 (2H), 3.23-3.27 (2H), 3.39-3.44 (1H), 8.40-8.42 (2H)

Example 73

1-{3-cyano-1-[2,6-dichloro-4-pentafluorothiophenyl]-5-({2-oxo-2-[(2,2,2-trifluoroethyl)amino]ethyl}amino)-1H-pyrazol-4-yl}cyclopropanecarboxamide Experimental MH+ 601.1; expected 601.0

$^1$H-NMR (d$_6$-DMSO): 0.90-1.00 (2H), 1.30-1.39 (2H), 3.80-4.00 (2H), 6.00-6.10 (2H), 6.90-7.00 (2H), 8.55-8.65 (2H)

Example 74

5-amino-1-[2,6-dichloro-4-(trifluoromethyl)phenyl]-4-[2,2-difluoro-1-(methylthio)-cyclopropyl]-1H-pyrazole-3-carbonitrile

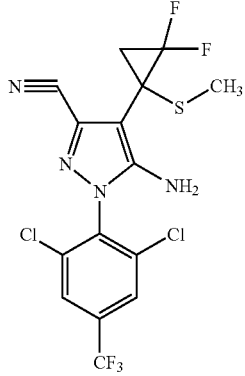

A stirred solution of Preparation 96 (250 mg, 0.60 mmol) and p-toluenesulphonic acid (250 mg, 1.32 mmol) in dichloromethane was saturated with methanethiol (g) at room temperature. After stirring for 80 h, the solution was transferred to a PTFE bomb and heated at 80° C., with stirring, for 16 h. The reaction mixture was concentrated in vacuo and to the residue was added dichloromethane. The solution was washed with aqueous sodium hydrogencarbonate solution, dried (MgSO$_4$) and concentrated in vacuo. The residue was purified using a Biotage column (silica, 10×2.5 cm), eluting with dichloromethane. The appropriate fractions were concentrated and to the residue was added acetonitrile/water (1 ml). This solution was purified by automated preparative liquid chromatography (Gilson system, 250 mm×30 mm Phenomenex LUNA C18(2) 10 μm column) using an acetonitrile:water gradient [55:45 to 95:5]. The appropriate fractions were concentrated in vacuo to give the titled compound (19 mg).

Experimental MH+ 442.9; expected 443.0

$^1$H-NMR (CDCl$_3$): 1.96-2.03 (1H), 2.15-2.23 (4H), 3.86-3.94 (2H), 7.75-7.78 (2H)

Similarly Prepared was

Example 75

S-methyl 5-amino-1-[2,6-dichloro-4-(trifluoromethyl)phenyl]-4-[2,2-difluoro-1-(methylthio)cyclopropyl]-1H-pyrazole-3-carbothioate from Preparation 96

Experimental MH+ 492.0; expected 492.0

$^1$H-NMR (CDCl$_3$): 1.86-1.96 (2H), 2.13-2.16 (3H), 2.36-2.39 (3H), 3.65-3.79 (2H), 7.73-7.76 (2H)

Example 76

1-{3-cyano-5-[(cyclopropylmethyl)amino]-1-[2,6-dichloro-4-(trifluoromethyl)phenyl]-1H-pyrazol-4-yl}cyclopropanecarboxamide

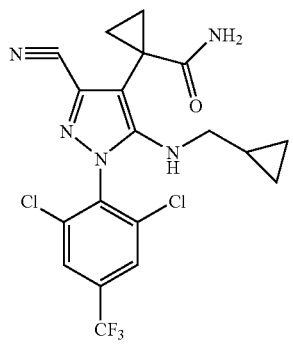

To a suspension of ammonium chloride (373 mg, 6.91 mmol) in toluene (20 ml), at 0° C., was added dropwise trimethyl aluminium (3.51 ml, 7.02 mmol). After stirring at 0° C. for 20 min and then room temperature for 40 min, Preparation 131 (654 mg, 1.38 mmol) in toluene (10 ml) was added dropwise at 0° C. The reaction mixture was stirred at 50° C. for 18 h, before addition of hydrochloric acid (2N, 15 ml), followed by brine (15 ml). The mixture was extracted with ethyl acetate (2×20 ml) and the combined extracts were concentrated in vacuo. The residue was dissolved in acetonitrile (1 ml) and purified by automated preparative liquid chromatography (Gilson system, 250 mm×30 mm Phenomenex LUNA C18(2) 10 μm column) using an acetonitrile:0.1% trifluoroacetic acid gradient [50:50 to 95:5]. The appropriate fractions were concentrated in vacuo to give titled compound (500 mg).

Experimental MH+ 457.9; expected 458.1

$^1$H-NMR (CD$_3$OD): 0.06-0.11 (2H), 0.37-0.43 (2H), 0.88-0.99 (1H), 1.19-1.24 (2H), 1.59-1.63 (2H), 3.02-3.06 (2H), 7.98-8.01 (2H)

Similarly Prepared were:

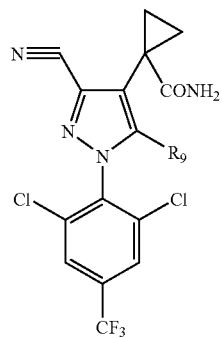

| Example | R9 | From |
|---|---|---|
| Example 77 | benzylamino | Example 115 |
| Example 78 | (pyridin-2-ylmethyl)amino | Preparation 145 |
| Example 79 | (2,2-dimethylpropyl)amino | Preparation 115 |
| Example 80 | [4-(methylsulfonyl)-benzyl]amino | Preparation 116 |
| Example 81 | (pyridin-4-ylmethyl)amino | Preparation 146 |
| Example 82 | (2,2,2-trifluoroethyl)amino | Preparation 147 |
| Example 83 | (1H-imidazol-2-ylmethyl)amino | Preparation 148 |

Example 77

1-{5-(benzylamino)-3-cyano-1-[2,6-dichloro-4-(trifluoromethyl)phenyl]-1H-pyrazol-4-yl}cyclopropanecarboxamide Experimental MH$^+$ 494.0; expected 494.1
$^1$H-NMR (CDCl$_3$): 1.16-1.21 (2H), 1.70-1.74 (2H), 4.21-4.26 (2H), 5.50-5.68 (2H), 7.05-7.10 (2H), 7.22-7.25 (3H), 7.64-7.67 (2H)

Example 78

1-{3-cyano-1-[2,6-dichloro-4-(trifluoromethyl)phenyl]-5-[(pyridin-2-ylmethyl)amino]-1H-pyrazol-4-yl}cyclopropanecarboxamide Experimental MH$^+$ 494.9; expected 495.1
$^1$H-NMR (CDCl$_3$): 1.25-1.29 (2H), 1.74-1.79 (2H), 4.48-4.55 (2H), 5.41-5.48 (1H), 5.77-5.83 (1H), 7.20-7.23 (1H), 7.25-7.35 (1H), 7.71-7.80 (3H), 8.37-8.41 (1H)

Example 79

1-{3-cyano-1-[2,6-dichloro-4-(trifluoromethyl)phenyl]-5-[(2,2-dimethylpropyl)amino]-1H-pyrazol-4-yl}cyclopropanecarboxamide Experimental MH$^+$ 474.0; expected 474.1
$^1$H-NMR (CDCl$_3$): 0.73-0.77 (9H), 1.19-1.23 (2H), 1.73-1.77 (2H), 2.74-2.79 (2H), 3.38-3.46 (1H), 5.47-5.54 (1H), 5.61-5.68 (1H), 7.75-7.77 (2H)

Example 80

1-(3-cyano-1-[2,6-dichloro-4-(trifluoromethyl)phenyl]-5-{[4-(methylsulfonyl)benzyl]amino}-1H-pyrazol-4-yl)cyclopropanecarboxamide Experimental MH$^+$ 572.0; expected 572.1
$^1$H-NMR (CDCl$_3$): 1.17-1.22 (2H), 1.66-1.72 (2H), 2.94-2.98 (3H), 4.13-4.22 (1H), 4.37-4.42 (2H), 5.55-5.69 (2H), 7.26-7.31 (2H), 7.67-7.71 (2H), 7.74-7.79 (2H)

Example 81

1-{3-cyano-1-[2,6-dichloro-4-(trifluoromethyl)phenyl]-5-[(pyridin-4-ylmethyl)amino]-1H-pyrazol-4-yl}cyclopropanecarboxamide Experimental MH$^+$ 495.1; expected 495.1
$^1$H-NMR (d$_6$-DMSO): 0.94-0.99 (2H), 1.36-1.41 (2H), 4.38-4.42 (2H), 6.52-6.56 (1H), 6.56-6.61 (1H), 7.16-7.21 (3H), 8.16-8.18 (2H), 8.40-8.43 (2H)

Example 82

1-{3-cyano-1-[2,6-dichloro-4-(trifluoromethyl)phenyl]-5-[(2,2,2-trifluoroethyl)amino]-1H-pyrazol-4-yl}cyclopropanecarboxamide Experimental MH$^+$ 485.9; expected 486.0
$^1$H-NMR (CDCl$_3$): 1.24-1.29 (2H), 1.74-1.78 (2H), 3.62-3.72 (2H), 3.88-3.95 (1H), 5.51-5.64 (2H), 7.76-7.80 (2H)

Example 83

1-{3-cyano-1-[2,6-dichloro-4-(trifluoromethyl)phenyl]-5-[(1H-imidazol-2-ylmethyl)amino]-1H-pyrazol-4-yl}cyclopropanecarboxamide Experimental MH$^+$ 484.0; expected 484.1
$^1$H-NMR (CDCl$_3$): 1.47-1.52 (2H), 1.55-1.61 (2H), 4.75-4.83 (2H), 5.72-5.82 (1H), 6.06-6.18 (1H), 7.20-7.22 (2H), 7.62-7.66 (2H)

Example 84

1-{3-cyano-1-[2,6-dichloro-4-pentafluorothiophenyl]-1H-pyrazol-4-yl}-2,2-difluorocyclopropanecarboxamide

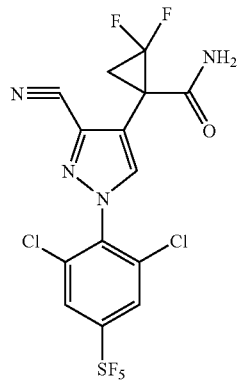

To a stirred solution of Example 53 (100 mg, 0.20 mmol) and copper (II) chloride (41 mg, 0.30 mmol) in acetonitrile (2 ml) was added tert-butyl nitrite (30 μl, 0.24 mmol) in acetonitrile (1 ml). The reaction mixture was stirred at room temperature for 18 h and then partitioned between ethyl acetate and water. The organic phase was separated, dried (MgSO$_4$) and concentrated in vacuo. The residue was dissolved in acetonitrile/water (0.5 ml) and purified by automated preparative liquid chromatography (Gilson system, 150 mm×21.2 mm Phenomenex LUNA C18(2) 5 lm column) using an acetonitrile:water gradient [50:50 to 95:5]. The appropriate fractions were concentrated in vacuo to give titled compound (13 mg) as well as the 5-chloro compound Example 87

$^1$H-NMR (CDCl$_3$): 1.95-2.03 (1H), 2.85-2.94 (1H), 5.53-5.68 (1H), 5.73-5.86 (1H), 7.80-7.84 (1H), 7.91-7.95 (2H)

Similarly Prepared was

Example 85

1-{3-cyano-1-[2,6-dichloro-4-pentafluorothiophenyl]-1H-pyrazol-4-yl}cyclopropane-carboxamide from Example 13

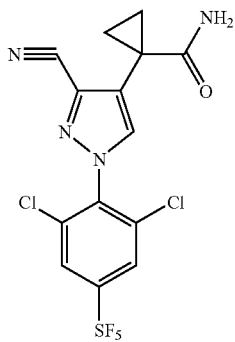

Experimental MH$^+$ acetonitrile adduct 488.1; expected 488.0

$^1$H-NMR (CDCl$_3$): 1.18-1.25 (2H), 1.74-1.80 (2H), 5.32-5.53 (1H), 5.88-6.05 (1H), 7.66-7.70 (1H), 7.89-7.94 (2H)

Example 86

1-{5-chloro-3-cyano-1-[2,6-dichloro-4-pentafluorothiophenyl]-1H-pyrazol-4-yl}cyclopropanecarboxamide

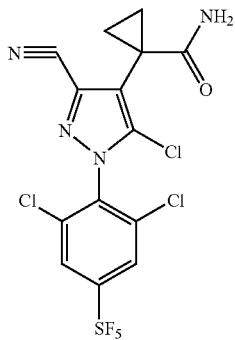

To a stirred solution of Example 13 (100 mg, 0.22 mmol) and copper (II) chloride (43 mg, 0.32 mmol) in acetonitrile (2 ml) was added tert-butyl nitrite (30 μl, 0.26 mmol) in acetonitrile (1 ml). The reaction mixture was stirred at room temperature for 18 h and then partitioned between ethyl acetate and water. The organic phase was separated, dried (MgSO$_4$) and concentrated in vacuo. The residue was dissolved in dimethyl sulphoxide/water (1.4 ml) and purified by automated preparative liquid chromatography (Gilson system, 150 mm×30 mm Phenomenex LUNA C18(2) 10 μm column) using an acetonitrile:water gradient [50:50 to 95:5]. The appropriate fractions were concentrated in vacuo to give the titled compound (20 mg).

Experimental MH$^+$ acetonitrile adduct 522.0; expected 522.0

$^1$H-NMR (CDCl$_3$): 1.24-1.30 (2H), 1.81-1.87 (2H), 5.23-5.44 (1H), 5.76-5.95 (1H), 7.92-7.97 (2H)

Example 87

1-{5-chloro-3-cyano-1-[2,6-dichloro-4-pentafluorothiophenyl]-1H-pyrazol-4-yl}-2,2-difluorocyclopropanecarboxamide

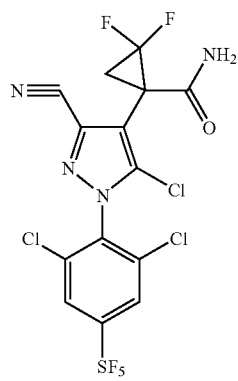

To a stirred solution of Example 53 (370 mg, 0.74 mmol) and copper (II) chloride (250 mg, 1.85 mmol) in acetonitrile (17 ml) was added tert-butyl nitrite (0.11 ml, 0.89 mmol) in acetonitrile (4 ml). The reaction mixture was stirred at room temperature for 3 h and then concentrated in vacuo. The residue was partitioned between ethyl acetate and water and the organic phase was separated, dried (MgSO$_4$) and concentrated in vacuo. The residue was dissolved in acetonitrile/water (0.5 ml) and purified by automated preparative liquid chromatography (Gilson system, 150 mm×30 mm Phenomenex LUNA C18(2) 10 □m column) using an acetonitrile:water gradient [50:50 to 95:5]. The appropriate fractions were concentrated in vacuo to give the titled compound (110 mg).

$^1$H-NMR (CDCl$_3$): 2.04-2.13 (1H), 2.86-2.95 (1H), 5.50-5.63 (1H), 5.64-5.78 (1H), 7.93-7.97 (2H)

Example 88

4-amino-1-[2,6-dichloro-4-(trifluoromethyl)phenyl]-4-[1-(5-methyl-1,3,4-oxadiazol-2-yl)cyclopropyl]-1H-pyrazole-3-carbonitrile

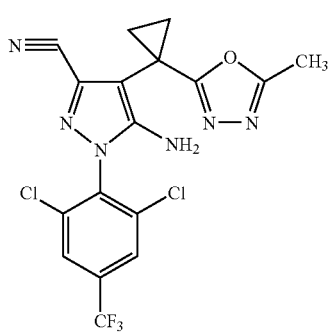

To a solution of acetic acid (0.1 ml) in acetonitrile (10 ml), at room temperature, was added phosphorus oxychloride (0.78 ml, 8.33 mmol), slowly via syringe. After 10 min, 1.16 ml of this solution was added to Preparation 162 (75 mg, 0.18 mmol) in acetonitrile (3 ml). The reaction mixture was heated at reflux for 2 h, cooled to room temperature and quenched with aqueous sodium hydrogencarbonate solution. The mixture was concentrated in vacuo and the residue was partitioned between ethyl acetate and water. The organic phase was separated, dried ($MgSO_4$) and concentrated in vacuo. The residue was dissolved in acetonitrile (0.5 ml) and purified by automated preparative liquid chromatography (Gilson system, 150 mm×30 mm Phenomenex LUNA C18(2) 10 μm column) using an acetonitrile:water gradient. The appropriate fractions were concentrated in vacuo to give the titled compound (3 mg).

Experimental $MH^+$ 442.9; expected 443.0

$^1$H-NMR ($CDCl_3$): 1.57-1.61 (2H), 1.72-1.77 (2H), 2.47-2.51 (3H), 4.05-4.10 (2H), 7.77-7.80 (2H)

Alternative Route

To a solution of Preparation 159 (250 mg, 0.54 mmol) in acetonitrile (20 ml), at room temperature, was added phosphorus oxychloride (0.20 ml, 2.15 mmol). The reaction mixture was heated at reflux for 2 h, cooled to room temperature and quenched with aqueous sodium hydrogencarbonate solution. The mixture was concentrated in vacuo, diluted with water and extracted with ethyl acetate (3×20 ml). The combined extracts were dried ($MgSO_4$) and concentrated in vacuo. The residue was dissolved in acetonitrile (0.5 ml) and purified by automated preparative liquid chromatography (Gilson system, 150 mm×30 mm Phenomenex LUNA C18(2) 10 μm column) using an acetonitrile:water gradient. The appropriate fractions were concentrated in vacuo to give the titled compound (28 mg).

Experimental $MH^+$ 442.9; expected 443.0

$^1$H-NMR ($CDCl_3$): 1.69-1.77 (2H), 2.13-2.18 (2H), 2.45-2.51 (3H), 4.02-4.09 (2H), 7.73-7.79 (2H)

Example 89

1-{5-amino-3-cyano-1-[2,6-dichloro-4-(trifluoromethyl)phenyl]-1H-pyrazol-4-yl}-2,2-dimethylcyclopropanecarboxylic acid

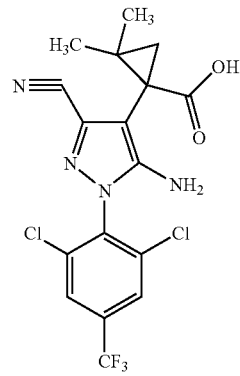

To a solution of Preparation 98 (300 mg, 0.70 mmol) in pyridine (5 ml) at 125° C. was added lithium iodide (1.00 g, 7.00 mmol) and the reaction mixture was heated at 125° C. for 48 h. The reaction mixture was concentrated in vacuo and the residue was partitioned between hydrochloric acid (10%) and dichloromethane. The two layers were separated and the aqueous layer was extracted with dichloromethane. The combined organic phases were dried ($MgSO_4$) and concentrated in vacuo to give the titled compound (300 mg).

Experimental $MH^+$ 433.0; expected 433.1

$^1$H-NMR ($d_6$-acetone): 1.10-1.20 (3H), 1.30-1.34 (1H), 1.39-1.42 (3H), 1.71-1.74 (1H), 5.38-5.55 (2H), 8.02-8.04 (2H)

Example 90

1-[3-cyano-1-[2,6-dichloro-4-pentafluorothiophenyl]-5-(methylamino)-1H-pyrazol-4-yl]cyclopropanecarboxamide

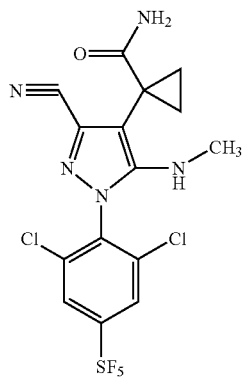

To a solution of Preparation 163 (4.74 g, 9.65 mmol) in tetrahydrofuran/water (4:1, 100 ml) was added lithium hydroxide monohydrate (4.00 g, 96.50 mmol). The reaction mixture was stirred at room temperature for 16 h and then adjusted to pH 1 by addition of hydrochloric acid (1M). The mixture was extracted with ethyl acetate and the combined extracts were washed with water, dried (MgSO$_4$) and concentrated in vacuo. To a solution of the residue and triethylamine (3.4 ml, 24.1 mmol) in tetrahydrofuran (100 ml), at 0° C., was added ethyl chloroformate (1.5 ml, 16.2 mmol). After 20 min at 0° C., the mixture was warmed to room temperature and stirred for 1 h. Anhydrous ammonia (g) was bubbled through the reaction mixture for 15 min, followed by nitrogen for 3 min. The reaction mixture was then partitioned between ethyl acetate and hydrochloric acid (1M) and the organic phase was separated, washed with water, dried (MgSO$_4$) and concentrated in vacuo. The residue was dissolved in acetonitrile (1 ml) and purified by automated preparative liquid chromatography (Gilson system, 150 mm×50 mm Phenomenex LUNA C18(2) 10 μm column) using an acetonitrile:water gradient [45:55 to 95:5]. The appropriate fractions were concentrated in vacuo to give titled compound (3289 mg).

Experimental MH$^+$ 475.9; expected 476.0

$^1$H-NMR (CDCl$_3$): 1.26-1.30 (2H), 1.76-1.81 (2H), 2.88-2.92 (3H), 3.54-3.76 (1H), 5.65-5.75 (2H), 7.91-7:94 (2H)

Example 91

1-{3-cyano-1-[2,6-dichloro-4-pentafluorothiophenyl]-5-(difluoromethyl)-1H-pyrazol-4-yl}cyclopropanecarboxamide

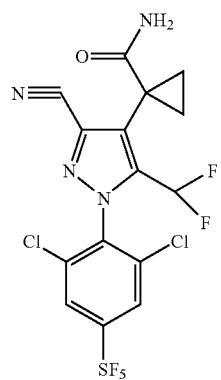

To a solution of Preparation 190 (190 mg, 0.37 mmol) in tetrahydrofuran/water (4:1, 3.7 ml) was added lithium hydroxide monohydrate (155 mg, 3.70 mmol). The reaction mixture was stirred at room temperature for 24 h, acidified with hydrochloric acid (IM) and extracted with ethyl acetate. The combined extracts were washed with water, dried (MgSO$_4$) and concentrated in vacuo to give the acid. To a solution of the acid in tetrahydrofuran (3.7 ml), at 0° C., was added triethylamine (160 μl, 1.11 mmol) and ethyl chloroformate (53 μl, 0.56 mmol). After stirring for 30 min, ammonium hydroxide (3 ml) was added and the solution was warmed to room temperature. The reaction mixture was adjusted to pH 1 by addition of hydrochloric acid (1M) and then extracted with ethyl acetate. The combined extracts were washed with water, dried (MgSO$_4$) and concentrated in vacuo. The residue was dissolved in acetonitrile (1 ml) and purified by automated preparative liquid chromatography (Gilson system, 150 mm×30 mm Phenomenex LUNA C18(2) 10 μm column) using an acetonitrile:water gradient [60:40 to 95:5]. The appropriate fractions were combined and concentrated to give the titled compound (172 mg).

$^1$H-NMR (d$_6$-DMSO): 1.10-1.21 (2H), 1.55-1.62 (2H), 6.70-6.85 (1H), 7.10-7.22 (1H), 7.10-7.40 (1H), 8.56-8.59 (2H)

Example 92 cyclopropylmethyl {4-[1-(aminocarbonyl)cyclopropyl]-3-cyano-1-[2,6-dichloro-4-pentafluorothiophenyl]-1H-pyrazol-5-yl}carbamate

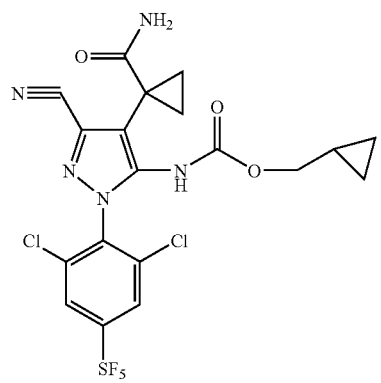

To Preparation 184 (310 mg, 0.52 mmol) in tetrahydrofuran/water (4:1, 5.2 ml) was added lithium hydroxide monohydrate (218 mg, 5.20 mmol) and the reaction mixture was stirred at room temperature for 24 h. The reaction mixture was acidified with hydrochloric acid (IM) and extracted with ethyl acetate. The combined extracts were washed with water, dried (MgSO$_4$) and concentrated in vacuo. To a solution of the residue in tetrahydrofuran (5.20 ml), at 0° C., was added triethylamine (185 μl, 1.30 mmol) and ethyl chloroformate (60 μl, 0.62 mmol). After stirring for 30 min, aqueous ammonium hydroxide solution (3 ml) was added and the reaction mixture was warmed to room temperature. The reaction mixture was adjusted to pH 1 by addition of hydrochloric acid (1M) and extracted with ethyl acetate. The combined extracts were washed with water, dried (MgSO$_4$) and concentrated in vacuo. The residue was dissolved in acetonitrile (1 ml) and purified by automated preparative liquid chromatography (Gilson system, 150 mm×50 mm LUNA C18 10 μm column) using an acetonitrile:water gradient [50:50 to 95:5]. The appropriate fractions were combined and concentrated to give the titled compound (110 mg).

Experimental MH$^+$ 560.0; expected 560.0

$^1$H-NMR (d$_6$-DMSO): −0.00-0.04 (2H), 0.24-0.29 (2H), 0.80-0.86 (3H), 1.25-1.29 (2H), 3.65-3.69 (2H), 6.21-6.29 (1H), 6.97-7.03 (1H), 8.33-8.35 (2H), 9.85-9.92 (1H)

Example 93 ethyl {4-[1-(aminocarbonyl)cyclopropyl]-3-cyano-1-[2,6-dichloro-4-pentafluorothiophenyl]-1H-pyrazol-5-yl}methylcarbamate

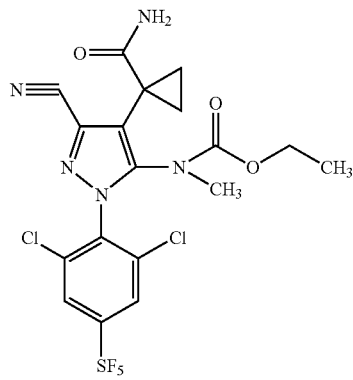

To Preparation 193 (257 mg, 0.46 mmol) in tetrahydrofuran/water (4:1, 4.6 ml) was added lithium hydroxide monohydrate (193 mg, 4.60 mmol) and the reaction mixture was stirred at room temperature for 24 h. The reaction mixture was acidified with hydrochloric acid (1M) and extracted with ethyl acetate. The combined extracts were washed with water, dried ($MgSO_4$) and concentrated in vacuo. To a solution of the residue in tetrahydrofuran (4.60 ml), at 0° C., was added triethylamine (160 μl, 1.15 ml) and ethyl chloroformate (53 μl, 0.55 mmol). After stirring for 30 min, aqueous ammonium hydroxide solution (3 ml) was added and the reaction mixture was warmed to room temperature. The reaction mixture was adjusted to pH 1 by addition of hydrochloric acid (1M) and extracted with ethyl acetate. The combined extracts were washed with water, dried ($MgSO_4$) and concentrated in vacuo. The residue was dissolved in acetonitrile (3 ml) and purified by automated preparative liquid chromatography (Gilson system, 150 mm×30 mm LUNA C18 10 μm column) using an acetonitrile:water gradient [55:45 to 95:5]. The appropriate fractions were combined and concentrated to give the titled compound (96 mg).

Experimental $MH^+$ 548.0; expected 548.0
$^1$H-NMR ($CDCl_3$): 1.09-1.22 (5H), 1.59-1.82 (2H), 3.12-3.15 (3H), 4.07-4.18 (2H), 5.46-6.04 (2H), 7.89-7.92 (2H)

Example 94

1-[({4-[1-(aminocarbonyl)cyclopropyl]-3-cyano-1-[2,6-dichloro-4-pentafluorothiophenyl]-1H-pyrazol-5-yl}amino)methyl]cyclopropanecarboxamide

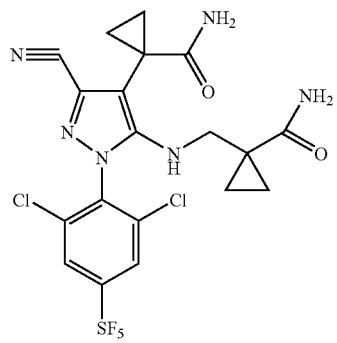

To Preparation 229 (83 mg, 0.14 mmol) in tetrahydrofuran/water (4:1, 2.80 ml) was added lithium hydroxide monohydrate (118 mg, 2.80 mmol) and the reaction mixture was stirred at room temperature for 24 h. The reaction mixture was acidified with hydrochloric acid (1M) and extracted with ethyl acetate. The combined extracts were washed with water, dried ($MgSO_4$) and concentrated in vacuo. To a solution of the residue in tetrahydrofuran (2.80 ml), at 0° C., was added triethylamine (100 μl, 0.73 mmol) and ethyl chloroformate (33 μl, 0.35 mmol). After stirring for 30 min, aqueous ammonium hydroxide solution (1 ml) was added and the reaction mixture was warmed to room temperature. The reaction mixture was adjusted to pH 1 by addition of hydrochloric acid (1M) and extracted with ethyl acetate. The combined extracts were washed with water, dried ($MgSO_4$) and concentrated in vacuo. The residue was dissolved in acetonitrile/dimethyl sulphoxide (1 ml) and purified by automated preparative liquid chromatography (Gilson system, 150 mm×30 mm LUNA C18 10 μm column) using an acetonitrile:water gradient [40:60 to 98:2]. The appropriate fractions were combined and concentrated to give the titled compound (33 mg).

Experimental $MH^+$ 559.1; expected 559.1
$^1$H-NMR ($d_6$-DMSO): 0.60-0.64 (2H), 0.90-0.94 (2H), 1.03-1.07 (2H), 1.44-1.48 (2H), 3.35-3.38 (2H), 5.76-5.81 (1H), 6.68-6.77 (2H), 6.82-6.88 (1H), 7.16-7.21 (1H), 8.41-8.43 (2H)

Example 95

1-{3-cyano-1-[2,6-dichloro-4-pentafluorothiophenyl]-5-methyl-1H-pyrazol-4-yl}cyclopropanecarboxamide

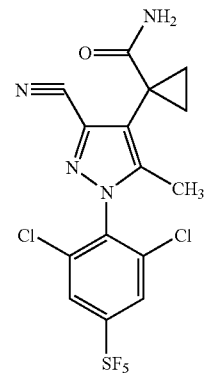

To a solution of Preparation 165 (40 mg, 0.08 mmol) in tetrahydrofuran/water (4:1, 2 ml) was added lithium hydroxide monohydrate (35 mg, 0.84 mmol). The reaction mixture was stirred at room temperature for 16 h and then adjusted to pH 1 by addition of hydrochloric acid (1M). The mixture was extracted with ethyl acetate and the combined extracts were washed with water, dried ($MgSO_4$) and concentrated in vacuo. To a solution of the residue and triethylamine (29 μl, 0.21 mmol) in tetrahydrofuran (1 ml), at 0° C., was added ethyl chloroformate (9 μl, 0.09 mmol). After 20 min at 0° C., the mixture was warmed to room temperature and stirred for 1 h. Anhydrous ammonia (g) was bubbled through the reaction mixture for 15 min, followed by nitrogen for 3 min. The reaction mixture was then partitioned between ethyl acetate and hydrochloric acid (1M) and the organic phase was separated, washed with water, dried ($MgSO_4$) and concentrated in vacuo. The residue was dissolved in acetonitrile (0.3 ml) and purified by automated preparative liquid chromatography (Gilson system, 150 mm×30 mm Phenomenex LUNA C18(2) 10 μm column) using an acetonitrile:water gradient [60:40 to 95:5]. The appropriate fractions were concentrated in vacuo to give the titled compound (12 mg).

Experimental MH+ 461.0; expected 461.0

1H-NMR (CDCl3): 1.18-1.23 (2H), 1.79-1.84 (2H), 2.17-2.22 (3H), 5.30-5.45 (1H), 5.53-5.65 (1H), 7.92-7.96 (2H)

Example 96

1-{3-cyano-5-[(cyclopropylmethyl)amino]-1-[2,6-dichloro-4-(trifluoromethoxy)phenyl]-1H-pyrazol-4-yl}cyclopropanecarboxamide

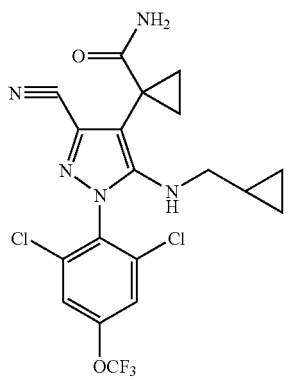

To a solution of Preparation 111 (670 mg, 1.37 mmol) in tetrahydrofuran/water (4:1, 14 ml) was added lithium hydroxide monohydrate (575 mg, 13.70 mmol). The reaction mixture was stirred at room temperature for 16 h and then adjusted to pH 1 by addition of hydrochloric acid (1M). The mixture was extracted with ethyl acetate and the combined extracts were washed with water, dried (MgSO4) and concentrated in vacuo. To a solution of the residue and triethylamine (0.48 ml, 3.43 mmol) in tetrahydrofuran (14 ml), at 0° C., was added ethyl chloroformate (0.16 ml, 1.64 mmol). After 20 min at 0° C., the mixture was warmed to room temperature and stirred for 1 h. Anhydrous ammonia (g) was bubbled through the reaction mixture for 15 min, followed by nitrogen for 3 min. The reaction mixture was then partitioned between ethyl acetate and hydrochloric acid (1M) and the organic phase was separated, washed with water, dried (MgSO4) and concentrated in vacuo. The residue was dissolved in acetonitrile/dimethyl sulphoxide (1 ml) and purified by automated preparative liquid chromatography (Gilson system, 150 mm×50 mm Sunfire LUNA C18 10 μm column) using an acetonitrile:water gradient [55:45 to 98:2]. The appropriate fractions were concentrated in vacuo to give the titled compound (465 mg).

Experimental MH+ 474.0; expected 474.1

1H-NMR (d6-DMSO): −0.01-0.05 (2H), 0.24-0.30 (2H), 0.81-0.90 (1H), 0.95-1.01 (2H), 1.37-1.43 (2H), 2.89-2.95 (2H), 5.74-5.79 (1H), 6.40-6.48 (1H), 7.10-7.20 (1H), 7.85-7.88 (2H)

Example 97

1-{3-cyano-1-[2,6-dichloro-4-pentafluorothiophenyl]-5-[(2-fluoro-2-methylpropyl)amino]-1H-pyrazol-4-yl}cyclopropanecarboxamide

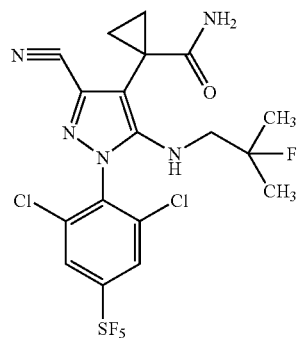

To Preparation 134 (71 mg, 0.13 mmol) in tetrahydrofuran/water (4:1, 2 ml) was added lithium hydroxide monohydrate (54 mg, 1.29 mmol) and the reaction mixture was stirred at room temperature for 18 h. The reaction mixture was adjusted to pH 1 by addition of hydrochloric acid (1M) and extracted with ethyl acetate. The combined extracts were washed with brine, dried (MgSO4) and concentrated in vacuo. To a solution of the residue in tetrahydrofuran (2 ml), at 0° C., was added triethylamine (45 μl, 0.32 mmol) and ethyl chloroformate (15, 0.16 μl mmol). After stirring for 30 min, aqueous ammonium hydroxide solution (1 ml) was added and the reaction mixture was warmed to room temperature. The reaction mixture was adjusted to pH 1 by addition of hydrochloric acid (IM) and extracted with ethyl acetate. The combined extracts were washed with brine, dried (MgSO4) and concentrated in vacuo. The residue was dissolved in acetonitrile (1 ml) and purified by automated preparative liquid chromatography (Gilson system, 150 mm×4.6 mm LUNA C18(2) 5 □m column) using an acetonitrile:water gradient [55:45 to 98:2]. The appropriate fractions were concentrated in vacuo to give the titled compound (34 mg).

Experimental MH+ 535.9; expected 536.1

1H-NMR (d6-DMSO): 1.00-1.10 (2H), 1.15-1.25 (6H), 1.60-1.70 (2H), 3.35-3.40 (2H), 8.38-8.41 (2H)

Example 98

Methyl {4-[1-(aminocarbonyl)cyclopropyl]-3-cyano-1-[2,6-dichloro-4-pentafluorothiophenyl]-1H-pyrazol-5-yl}carbamate

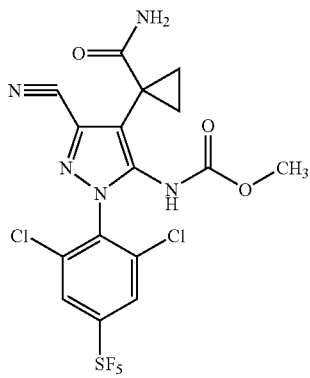

To Preparation 185 (318 mg, 0.59 mmol) in tetrahydrofuran/water (4:1, 5.9 ml) was added lithium hydroxide monohydrate (248 mg, 5.90 mmol) and the reaction mixture was stirred at room temperature for 24 h. The reaction mixture was acidified with hydrochloric acid (IM) and extracted with ethyl acetate. The combined extracts were washed with water, dried (MgSO$_4$) and concentrated in vacuo. To a solution of the residue in tetrahydrofuran (5.90 ml), at 0° C., was added triethylamine (0.21 μl, 1.48 mmol) and ethyl chloroformate (68 μl, 0.71 mmol). After stirring for 30 min, aqueous ammonium hydroxide solution (5 ml) was added and the reaction mixture was warmed to room temperature. The reaction mixture was adjusted to pH 1 by addition of hydrochloric acid (1M) and extracted with ethyl acetate. The combined extracts were washed with water, dried (MgSO$_4$) and concentrated in vacuo. The residue was dissolved in acetonitrile (1 ml) and purified by automated preparative liquid chromatography (Gilson system, 150 mm×30 mm LUNA C18(2) 10 μm column) using an acetonitrile:water gradient [45:55 to 95:5]. The appropriate fractions were combined and concentrated to give the titled compound (169 mg).

Experimental MH$^+$ 520.0; expected 520.0
$^1$H-NMR (d$_6$-DMSO): 1.54-1.58 (2H), 1.95-1.99 (2H), 4.06-4.08 (3H), 6.68-6.92 (2H), 8.72-8.73 (2H)

Example 99

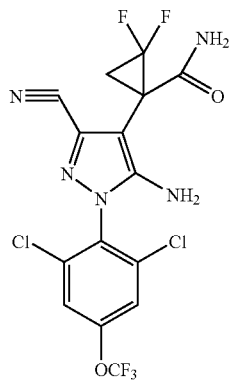

To a solution of lithium hydroxide monohydrate (415 mg, 10.60 mmol) in water (4 ml) and tetrahydrofuran (16 ml) was added Preparation 93 (500 mg, 1.06 mmol). The reaction mixture was stirred at room temperature for 4 h, acidified with hydrochloric acid (concentrated) and extracted with ethyl acetate. The combined extracts were dried (MgSO$_4$) and concentrated in vacuo to give the acid. To a solution of the acid (500 mg, 1.09 mmol) in tetrahydrofuran (15 ml) and triethylamine (379 μl, 2.73 mmol), at 0° C., was added ethyl chloroformate (114 μl, 1.20 mmol). After stirring for 20 min, the reaction mixture was warmed to room temperature and stirred for 1 h. To the reaction mixture was added ammonium hydroxide (0.5 ml, 5.45 mmol) and the solution was stirred for 15 min, before nitrogen (g) was bubbled through for 5 min. The reaction mixture was adjusted to pH 1 by addition of hydrochloric acid and then extracted with ethyl acetate. The combined extracts were washed with sodium hydroxide solution, dried (MgSO$_4$) and concentrated in vacuo. The residue was dissolved in acetonitrile/dimethyl sulphoxide (1 ml) and purified by automated preparative liquid chromatography (Gilson system, 150 mm×30 mm Phenomenex LUNA C18(2) 10 μm column) using an acetonitrile:water [45:55 to 95:5] gradient. The appropriate fractions were combined and concentrated to give the titled compound (62 mg).

Experimental MH$^+$ 455.9; expected 456.0
$^1$H-NMR (d$_6$-DMSO): 1.74-1.82 (1H), 2.49-2.58 (1H), 6.19-6.27 (2H), 7.12-7.19 (1H), 7.44-7.51 (1H), 7.89-7.93 (2H)

Example 100 ethyl {4-[1-(aminocarbonyl)cyclopropyl]-3-cyano-1-[2,6-dichloro-4-pentafluorothiophenyl]-1H-pyrazol-5-yl}carbamate

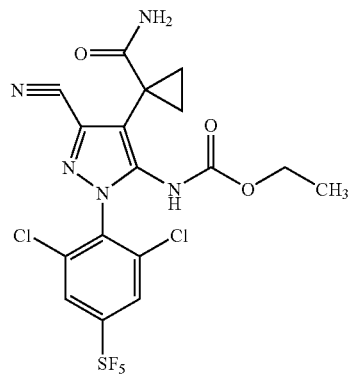

To Preparation 188 (474 mg, 0.86 mmol) in tetrahydrofuran/water (4:1, 8.6 ml) was added lithium hydroxide monohydrate (360 mg, 8.60 mmol) and the reaction mixture was stirred at room temperature for 24 h. The reaction mixture was acidified with hydrochloric acid (1M) and extracted with ethyl acetate. The combined extracts were washed with water, dried (MgSO$_4$) and concentrated in vacuo. To a solution of the residue in tetrahydrofuran (8.6 ml), at 0° C., was added triethylamine (0.30 ml, 2.15 mmol) and ethyl chloroformate (0.98 ml, 1.03 mmol). After stirring for 30 min, aqueous ammonium hydroxide solution (5 ml) was added and the reaction mixture was warmed to room temperature. The reaction mixture was adjusted to pH 1 by addition of hydrochloric acid (1M) and extracted with ethyl acetate. The combined extracts were washed with water, dried (MgSO$_4$) and concentrated in vacuo. The residue was dissolved in acetonitrile/dimethyl sulphoxide (1.3 ml) and purified by automated preparative liquid chromatography (Gilson system, 150 mm×50 mm LUNA C18(2) 10 μm column) using an acetonitrile:

water gradient [45:55 to 95:5]. The appropriate fractions were combined and concentrated to give the titled compound (396 mg).

Experimental MH⁺ 534.3; expected 534.0

¹H-NMR (DMSO): 0.93-0.97 (2H), 1.03-1.07 (3H), 1.36-1.41 (2H), 3.93-4.01 (2H), 6.40-6.50 (1H), 7.07-7.14 (1H), 8.45-8.47 (2H), 9.92-9.96 (1H)

Similarly Prepared were:

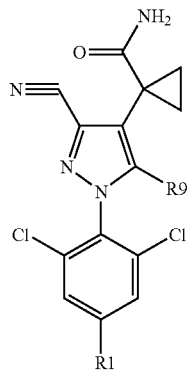

| Example | R1 | R9 | From |
|---|---|---|---|
| Example 101 | SF₅ | (cyclopropylmethoxycarbonyl)(methyl)amino | Preparation 194 |
| Example 102 | SF₅ | (4,4,4-trifluorobutyl)amino | Preparation 127 |
| Example 103 | SF₅ | ethylamino | Preparation 128 |
| Example 104 | SF₅ | (1-t-BOC-amino-cyclopropyl)methylamino | Preparation 205 |
| Example 105 | CF₃ | (4-trifluoromethyl)benzylamino | Preparation 124 |
| Example 106 | SF₅ | cyclopropylmethoxy | Preparation 65 |
| Example 107 | SF₅ | isopropoxyethylamino | Preparation 136 |
| Example 108 | SF₅ | vinyl | Preparation 227 |
| Example 109 | SF₅ | cyclobutyloxycarbonylamino | Preparation 186 |
| Example 110 | CN | NH₂ | Preparation 173 |
| Example 111 | SF₅ | (4-fluoro)benzylamino | Preparation 117 |
| Example 112 | SF₅ | methoxymethyl | Preparation 197 |

Example 101 cyclopropylmethyl {4-[1-(aminocarbonyl)cyclopropyl]-3-cyano-1-[2,6-dichloro-4-pentafluorothiophenyl]-1H-pyrazol-5-yl}methylcarbamate Experimental MH⁺ 574.2; expected 574.1

¹H-NMR (CDCl₃): 0.10-0.21 (2H), 0.40-0.50 (2H), 0.90-1.00 (1H), 1.05-1.25 (2H), 1.70-1.90 (2H), 3.10-3.12 (3H), 3.90-3.99 (2H), 7.92-7.95 (2H)

Example 102

1-{3-cyano-1-[2,6-dichloro-4-pentafluorothiophenyl]-5-[(4,4,4-trifluorobutyl)amino]-1H-pyrazol-4-yl}cyclopropanecarboxamide Experimental MH⁺ 571.9; expected 572.0

¹H-NMR (d₆-DMSO): 0.95-1.01 (2H), 1.39-1.42 (2H), 1.50-1.60 (2H), 2.05-2.20 (2H), 3.18-3.25 (2H), 8.39-8.41 (2H)

Example 103

1-{3-cyano-1-[2,6-dichloro-4-pentafluorothiophenyl]-5-(ethylamino)-1H-pyrazol-4-yl}cyclopropanecarboxamide Experimental MH⁺ 489.8; expected 490.0

¹H-NMR (d₆-Acetone): 1.01-1.09 (3H), 1.15-1.18 (2H), 1.65-1.68 (2H), 3.30-3.40 (2H), 5.24-5.32 (1H), 6.30-6.50 (2H), 8.20-8.22 (2H)

Example 104 tert-butyl {1-[({4-[1-(aminocarbonyl)cyclopropyl]-3-cyano-1-[2,6-dichloro-4-pentafluorothiophenyl]-1H-pyrazol-5-yl}amino)methyl]cyclopropyl}carbamate Experimental MH⁺ 631.4; expected 631.1

Example 105

1-(3-cyano-1-[2,6-dichloro-4-(trifluoromethyl)phenyl]-5-{[4-(trifluoromethyl)benzyl]amino}-1H-pyrazol-4-yl)cyclopropanecarboxamide Experimental MH⁺ 562.0; expected 562.1

¹H-NMR (CDCl₃): 1.19-1.23 (2H), 1.70-1.74 (2H), 4.01-4.20 (1H), 4.29-4.33 (2H), 5.59-5.70 (2H), 7.18-7.22 (2H), 7.42-7.46 (2H), 7.60-7.62 (2H)

Example 106

1-{3-cyano-5-(cyclopropylmethoxy)-1-[2,6-dichloro-4-pentafluorothiophenyl]-1H-pyrazol-4-yl}cyclopropanecarboxamide Experimental MH⁺ 517.3; expected 517.0

¹H-NMR (CDCl₃): 0.18-0.22 (2H), 0.50-0.60 (2H), 1.00-1.10 (1H), 1.25-1.30 (2H), 1.78-1.82 (2H), 4.15-4.20 (2H), 5.60-5.70 (2H), 7.89-7.92 (2H)

Example 107

1-{3-cyano-1-[2,6-dichloro-4-pentafluorothiophenyl]-5-[(2-isopropoxyethyl)amino]-1H-pyrazol-4-yl}cyclopropanecarboxamide Experimental MH⁺ 548.1; expected 548.1

¹H-NMR (d₆-Acetone): 0.98-1.03 (6H), 1.15-1.21 (2H), 1.58-1.61 (2H), 3.40-3.55 (5H), 5.13-5.20 (1H), 6.30-6.50 (2H), 8.26-8.30 (2H)

Example 108

1-{3-cyano-1-[2,6-dichloro-4-pentafluorothiophenyl]-5-vinyl-1H-pyrazol-4-yl}cyclopropanecarboxamide ¹H-NMR (d₆-Acetone): 1.16-1.20 (2H), 1.67-1.72 (2H), 5.65-5.70 (1H), 5.82-5.88 (1H), 6.21-6.32 (1H), 6.45-6.58 (2H), 8.32-8.36 (2H)

Example 109

Cyclobutyl {4-[1-(aminocarbonyl)cyclopropyl]-3-cyano-1-[2,6-dichloro-4-pentafluorothiophenyl]-1H-pyrazol-5-yl}carbamate Experimental MH⁺ 560.0; expected 560.0
¹H-NMR (d₆-DMSO): 1.54-1.60 (2H), 1.94-2.08 (3H), 2.10-2.20 (1H), 2.33-2.44 (2H), 2.61-2.71 (2H), 5.22-5.31 (1H), 6.66-6.92 (2H), 8.70-8.75 (2H), 9.33-9.45 (1H)

Example 110

1-[5-amino-3-cyano-1-(2,6-dichloro-4-cyanophenyl)-1H-pyrazol-4-yl]cyclopropanecarboxamide Experimental MH⁺ 361.3; expected 361.0
¹H-NMR (d₆-DMSO): 0.85-0.90 (2H), 1.38-1.42 (2H), 6.10-6.20 (3H), 8.38-8.40 (2H)

Example 111

1-{3-cyano-1-[2,6-dichloro-4-pentafluorothiophenyl]-5-[(4-fluorobenzyl)amino]-1H-pyrazol-4-yl}cyclopropanecarboxamide Experimental MH⁺ 570.0; expected 570.0
¹H-NMR (CDCl₃): 1.12-1.17 (2H), 1.66-1.71 (2H), 3.89-4.03 (1H), 4.15-4.20 (2H), 5.48-5.64 (2H), 6.85-6.92 (2H), 6.97-7.03 (2H), 7.72-7.75 (2H)

Example 112

1-{3-cyano-1-[2,6-dichloro-4-pentafluorothiophenyl]-5-(methoxymethyl)-1H-pyrazol-4-yl}cyclopropanecarboxamide Experimental MH⁺ 491.0; expected 491.0
¹H-NMR (d₆-Acetone): 1.01-1.05 (2H), 1.52-1.57 (2H), 4.16-4.20 (3H), 5.41-5.46 (2H), 6.30-6.43 (2H), 8.06-8.10 (2H)

Example 113

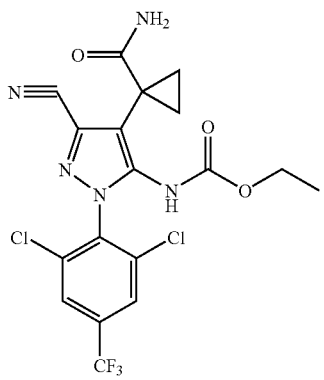

To a solution of Preparation 183 (379 mg, 0.74 mmol) in tetrahydrofuran/water (4:1, 7.4 ml) was added lithium hydroxide monohydrate (311 mg, 7.40 mmol). The reaction mixture was stirred at room temperature for 24 h, acidified with hydrochloric acid (1M) and extracted with ethyl acetate. The combined extracts were washed with water, dried (MgSO4) and concentrated in vacuo to give the acid. To a solution of the acid in tetrahydrofuran (3.2 ml), at 0° C., was added triethylamine (260 µl, 1.85 mmol) and ethyl chloroformate (85 µl, 0.89 mmol). After stirring for 30 min, ammonium hydroxide (3 ml) was added and the solution was warmed to room temperature. The reaction mixture was adjusted to pH 1 by addition of hydrochloric acid (1M) and then extracted with ethyl acetate. The combined extracts were washed with water, dried (MgSO4) and concentrated in vacuo. The residue was dissolved in acetonitrile (1 ml) and purified by automated preparative liquid chromatography (Gilson system, 150 mm×30 mm Phenomenex LUNA C18(2) 10 µm column) using an acetonitrile:water gradient [45:55 to 95:5. The appropriate fractions were combined and concentrated to give the titled compound (182 mg).
¹H-NMR (CDCl₃): 1.15-1.23 (5H), 1.68-1.74 (2H), 4.07-4.14 (2H), 5.60-5.79 (2H), 6.87-7.01 (1H), 7.75-7.79 (2H)

Example 114

1-{3-cyano-5-[(cyclopropylmethyl)amino]-1-[2,6-dichloro-4-pentafluorothiophenyl]-1H-pyrazol-4-yl}cyclopropanecarboxamide

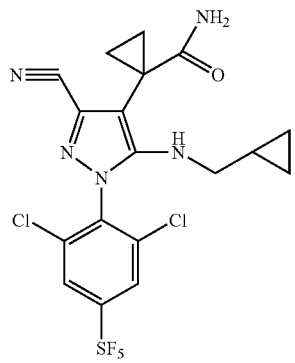

A mixture of Example 13 (276 mg, 0.59 mmol), 4 Å molecular sieves, p-toluenesulphonic acid (2 mg) and cyclopropane carboxaldehyde (134 µl, 1.79 mmol) in toluene (10 ml) was heated in a sealed tube at 90° C. for 4 days. The reaction mixture was cooled to room temperature, washed with aqueous sodium hydrogencarbonate solution (10%, 10 ml) and extracted with ethyl acetate (3×10 ml). The combined extracts were dried (MgSO₄) and concentrated in vacuo. To a solution of the residue (250 mg, 0.49 mmol) in methanol (10 ml), at 0° C. and under nitrogen, was added sodium borohydride (20 mg, 0.53 mmol). The reaction mixture was then allowed to warm to room temperature and stirred for 2 h. To the reaction mixture was added brine and the mixture was extracted with ethyl acetate (3×10 ml). The combined extracts were then dried (MgSO₄) and concentrated in vacuo. The residue was dissolved in acetonitrile (4 ml) and purified by automated preparative liquid chromatography (Gilson system, 150 mm×30 mm Phenomenex LUNA C18(2) 10 µm column) using an acetonitrile:water gradient [55:45 to 95:5]. The appropriate fractions were concentrated in vacuo to give the titled compound (93 mg).
Experimental MH⁺ 516.0; expected 516.0
¹H-NMR (d₆-DMSO): −0.02-0.04 (2H), 0.24-0.31 (2H), 0.82-0.90 (1H), 0.94-1.00 (2H), 1.35-1.41 (2H), 2.91-2.99 (2H), 5.83-5.89 (1H), 6.45-6.52 (1H), 7.10-7.17 (1H), 8.34-8.39 (2H)

Alternative Route

To a solution of Preparation 6 (3.60 g, 7.00 mmol) in acetonitrile (50 ml) was added O-benzotriazol-1-yl-N,N,N',N'-tetramethyluronium hexafluorophosphate (4.00 g, 10.50 mmol) and triethylamine (2.0 ml, 14.00 mmol). The mixture was stirred at room temperature, under nitrogen, for 20 min, before addition of hexamethyldisilazane (5.90 ml, 28.00 mmol). The reaction mixture was stirred at room temperature for a further 18 h and then hydrochloric acid (2N, 50 ml) was added. After stirring for 1 h, the mixture was diluted with water and extracted with ethyl acetate (2×150 ml). The combined extracts were washed with aqueous sodium hydroxide solution (2N), water and saturated brine solution, dried ($MgSO_4$) and concentrated in vacuo. The residue was dissolved in acetonitrile (1 ml) and purified by automated preparative liquid chromatography (Gilson system, 150 mm×50 mm Sunfire LUNA C18 10 μm column) using an acetonitrile:water gradient [50:50 to 95:5]. The appropriate fractions were concentrated in vacuo to give the titled compound (911 mg).

Experimental $MH^+$ 515.9; expected 516.0

$^1$H-NMR ($CDCl_3$): −0.01-0.05 (2H), 0.38-0.44 (2H), 0.77-0.86 (1H), 1.12-1.17 (2H), 1.65-1.70 (2H), 2.78-2.82 (2H), 5.47-5.63 (2H), 7.80-7.84 (2H)

Similarly Prepared were

Example 115 methyl 1-{5-(benzylamino)-3-cyano-1-[2,6-dichloro-4-(trifluoromethyl)phenyl]-1H-pyrazol-4-yl}cyclopropanecarboxylate from Preparation 152

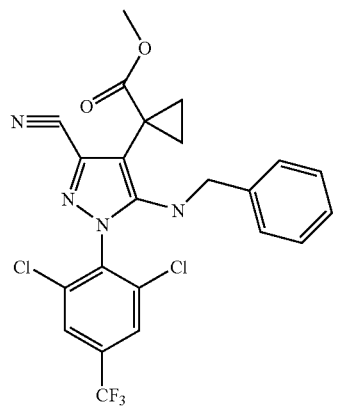

Experimental $MH^+$ 508.8; expected 509.1

$^1$H-NMR ($CDCl_3$): 1.21-1.25 (2H), 1.62-1.67 (2H), 3.60-3.61 (3H), 3.78-3.82 (1H), 4.12-4.17 (2H), 7.07-7.10 (2H), 7.19-7.23 (3H), 7.60-7.61 (2H)

Example 116

1-{3-cyano-5-[(cyclopropylmethyl)amino]-1-[2,6-dichloro-4-pentafluorothiophenyl]-1H-pyrazol-4-yl}-2,2-difluorocyclopropanecarboxamide from Preparation 150

Experimental $MH^+$ 552.1; expected 552.0

$^1$H-NMR ($d_6$-DMSO): 0.77-0.87 (1H), 1.79-1.88 (1H), 2.66-2.74 (1H), 2.76-2.83 (1H), 2.88-2.96 (1H), 5.97-6.02 (1H), 7.23-7.27 (1H), 7.54-7.58 (1H), 8.38-8.41 (2H)

Example 117

1-{3-cyano-5-[(cyclopropylmethyl)amino]-1-[2,6-dichloro-4-(trifluoromethyl)phenyl]-1H-pyrazol-4-yl}-2,2-difluorocyclopropanecarboxamide from Preparation 157

Experimental $MH^+$ 494.2; expected 494.1

Example 118

4-(1-cyanocyclopropyl)-1-[2,6-dichloro-4-pentafluorothiophenyl]-5-(methylamino)-1H-pyrazole-3-carbonitrile

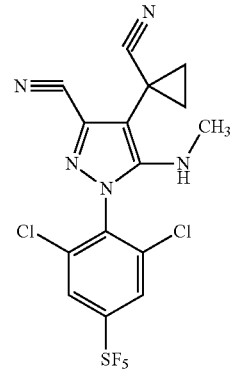

To a solution of Preparation 141 (209 mg, 0.43 mmol) in ethanol (4 ml) and 1,4-dioxane (1 ml) was added sodium borohydride (36 mg, 0.94 mmol). The reaction mixture was stirred at room temperature for 10 h and then quenched with hydrochloric acid (2N). The mixture was concentrated in vacuo and the residue was partitioned between ethyl acetate (10 ml) and water (10 ml). The organic layer was separated, washed with brine, dried ($MgSO_4$) and concentrated in vacuo. The residue was dissolved in acetonitrile (1.2 ml) and purified by automated preparative liquid chromatography (Gilson system, 150 mm×30 mm Phenomenex LUNA C18(2) 10 μm column) using an acetonitrile:water gradient [60:40 to 95:5]. The appropriate fractions were concentrated in vacuo to give the titled compound (86 mg).

Experimental $MH^+$ 457.9; expected 458.0

$^1$H-NMR ($CDCl_3$): 1.52-1.57 (2H), 1.76-1.83 (2H), 3.06-3.13 (3H), 3.47-3.59 (1H), 7.90-7.94 (2H)

Example 119

1-{5-amino-3-cyano-1-[2,6-dichloro-4-(trifluoromethyl)phenyl]-1H-pyrazol-4-yl}cyclopropanecarbothioamide

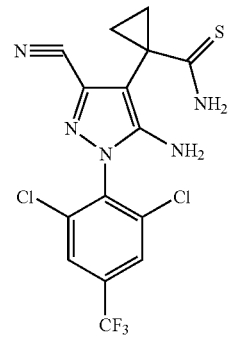

To a solution of Example 2 (400 mg, 0.99 mmol) in tetrahydrofuran (32 ml), under nitrogen, was added Lawesson's reagent (2,4-bis(4-methoxyphenyl)-1,3-dithia-2,4-disulphide, 240 mg, 0.59 mmol). The reaction mixture was heated at reflux for 3 h, cooled to room temperature and diluted with water. The mixture was extracted with ethyl acetate (×3) and the combined extracts were dried (MgSO$_4$) and concentrated in vacuo. The residue was dissolved in acetonitrile (1.2 ml) and purified by automated preparative liquid chromatography (Gilson system, 150 mm×30 mm Phenomenex LUNA C18(2) 10 μm column) using an acetonitrile:water gradient [45:55 to 95:5]. The appropriate fractions were concentrated in vacuo to give the titled compound (64 mg).

Experimental MH$^+$ 420.0; expected 420.0

$^1$H-NMR (CDCl$_3$): 1.36-1.41 (2H), 2.03-2.08 (2H), 3.99-4.08 (2H), 6.89-6.97 (1H), 7.38-7.48 (1H), 7.76-7.79 (2H)

Example 120

5-amino-1-[2,6-dichloro-4-(trifluoromethyl)phenyl]-4-[1-(1,3-thiazol-2-yl)cyclopropyl]-1H-pyrazole-3-carbonitrile

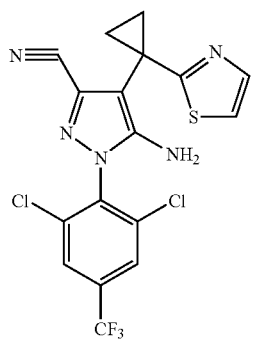

A mixture of Example 119 (100 mg, 0.24 mmol) and chloroacetaldehyde (22 mg, 0.28 mmol) in N,N-dimethylformamide (2 ml) was heated at 90° C. for 2 h. The reaction mixture was cooled to room temperature, diluted with water and extracted with dichloromethane (×3). The combined extracts were dried (MgSO$_4$) and concentrated in vacuo. The residue was dissolved in acetonitrile (2 ml) and purified by automated preparative liquid chromatography (Gilson system, 150 mm×30 mm Phenomenex LUNA C18(2) 10 μm column) using an acetonitrile:water gradient [50:50 to 98:2]. The appropriate fractions were concentrated in vacuo to give the titled compound (10 mg).

Experimental MH$^+$ 444.0; expected 444.0

$^1$H-NMR (CDCl$_3$): 1.50-1.56 (2H), 1.83-1.89 (2H), 4.00-4.10 (2H), 7.10-7.14 (1H), 7.61-7.66 (1H), 7.77-7.81 (2H)

Example 121

1-(3-cyano-1-[2,6-dichloro-4-(trifluoromethyl)phenyl]-5-{[(1-oxidopyridin-4-yl)methyl]amino}-1H-pyrazol-4-yl)cyclopropanecarboxamide

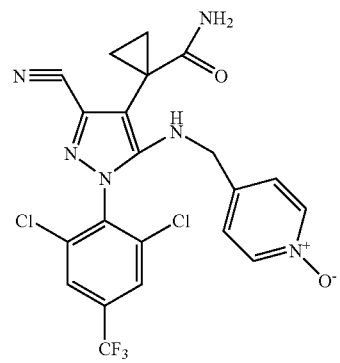

To a solution of Example 81 (57 mg, 0.12 mmol) in dichloromethane (0.5 ml) was added 3-chloroperoxybenzoic acid (77%, 38 mg, 0.17 mmol). The reaction mixture was stirred at room temperature for 48 h, before addition of aqueous sodium hydrogencarbonate solution. The organic layer was separated, washed with water, dried (MgSO$_4$) and concentrated in vacuo. The residue was dissolved in acetonitrile (0.4 ml) and purified by automated preparative liquid chromatography (Gilson system, 250 mm×21.2 mm Phenomenex LUNA C18(2) 50m column) using an acetonitrile:water gradient [30:70 to 95:5]. The appropriate fractions were concentrated in vacuo to give the titled compound (14 mg).

Experimental MH$^+$ 511.1; expected 511.1

$^1$H-NMR (CDCl$_3$): 1.23-1.28 (2H), 1.72-1.77 (2H), 4.25-4.29 (1H), 4.33-4.37 (2H), 5.54-5.68 (2H), 7.03-7.08 (2H), 7.75-7.78 (2H), 8.02-8.07 (2H)

Example 122

1-{5-amino-3-cyano-1-[2,6-dichloro-4-pentafluorothiophenyl]-1H-pyrazol-4-yl}-N-(methylsulfonyl)cyclopropanecarboxamide

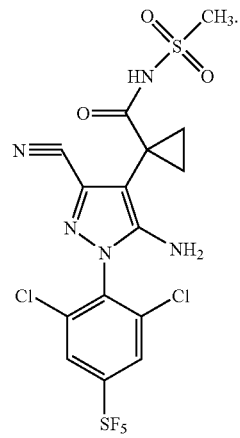

To a solution of Example 13 (100 mg, 0.22 mmol) in N,N-dimethylformamide (1.1 ml) was added sodium hydride (60% in oil, 9 mg, 0.22 mmol). After stirring for 20 min, methanesulphonyl chloride (34 μl, 0.44 mmol) was added and the reaction mixture was stirred at room temperature for 16 h. The mixture was then partitioned between ethyl acetate and brine and the organic layer was separated, washed with water, dried (MgSO$_4$) and concentrated in vacuo. The residue was dissolved in acetonitrile (2.4 ml) and purified by automated preparative liquid chromatography (Gilson system, 150 mm×30 mm Phenomenex LUNA C18(2) 10 μm column) using an acetonitrile:water gradient [50:50 to 95:5]. The appropriate fractions were concentrated in vacuo to give the titled compound (52 mg).

Experimental MH$^+$ 540.0; expected 540.0

$^1$H-NMR (d$_6$-DMSO): 1.61-1.65 (2H), 1.93-1.98 (2H), 3.11-3.14 (3H), 5.43-5.50 (2H), 8.05-8.06 (2H), 10.40-10.43 (1H)

Example 123

1-{3-cyano-5-[(2-cyclopropylethyl)amino]-1-[2,6-dichloro-4-pentafluorothiophenyl]-1H-pyrazol-4-yl}cyclopropanecarboxamide

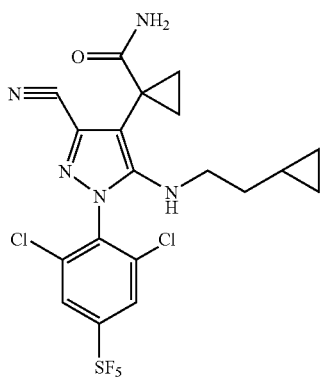

To a solution of Example 13 (150 mg, 0.32 mmol) in toluene (3.2 ml) was added cyclopropylacetaldehyde (54 mg, 0.64 mmol), p-toluenesulphonic acid (3 mg) and 4 Å molecular sieves (120 mg). After stirring for 16 h, the mixture was filtered, washed with toluene and concentrated in vacuo. The residue was dissolved in ethanol and the solution was cooled to 0° C. Sodium borohydride (27 mg) was added and the mixture was stirred at 0° C. for 15 min and then quenched with hydrochloric acid (1M). The mixture was extracted with ethyl acetate and the combined extracts were dried (MgSO$_4$) and concentrated in vacuo. The residue was dissolved in acetonitrile (1.2 ml) and purified by automated preparative liquid chromatography (Gilson system, 150 mm×21.2 mm Phenomenex LUNA C18(2) 5 μm column) using an acetonitrile:0.1% trifluoroacetic acid gradient [60:40 to 95:5]. The appropriate fractions were concentrated in vacuo to give the titled compound (1.5 mg).

Experimental MH$^+$ 530.0; expected 530.1

Example 124

1'-[2,6-dichloro-4-pentafluorothiophenyl]-7'-methyl-5'-oxo-5',6',7',8'-tetrahydro-1'H-spiro[cyclopropane-1,4'-pyrazolo[3,4-d][1,3]diazepine]-3'-carbonitrile

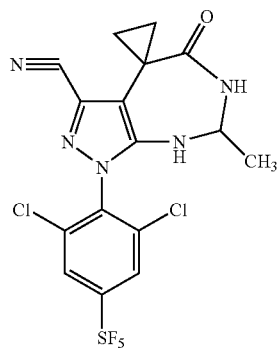

To a solution of Example 13 (150 mg, 0.32 mmol) in toluene (3.2 ml) was added acetaldehyde (0.18 ml, 3.2 mmol), p-toluenesulphonic acid (3 mg) and 4 Å molecular sieves (120 mg). After stirring for 16 h, the mixture was filtered, washed with dichloromethane and concentrated in vacuo. The residue was dissolved in ethanol (6 ml) and the solution was cooled to 0° C. Sodium borohydride (20 mg) was added and the mixture was stirred at 0° C. for 1 h and then quenched with hydrochloric acid (1M). The mixture was extracted with ethyl acetate and the combined extracts were dried (MgSO$_4$) and concentrated in vacuo. The residue was dissolved in acetonitrile/water (9:1, 1.2 ml) and purified by automated preparative liquid chromatography (Gilson system, 150 mm×30 mm Phenomenex LUNA C18(2) 10 μm column) using an acetonitrile:water gradient [45:55 to 95:5]. The appropriate fractions were concentrated in vacuo to give the titled compound (51 mg).

Experimental MH$^+$ 488.1; expected 488.0

$^1$H-NMR (d$_6$-DMSO): 0.93-0.99 (1H), 1.09-1.16 (1H), 1.29-1.34 (3H), 1.55-1.62 (1H), 1.78-1.85 (1H), 5.31-5.40 (1H), 6.99-7.03 (1H), 8.25-8.30 (1H), 8.44-8.50 (2H)

Example 125

5-amino-1-[2,6-dichloro-4-(trifluoromethyl)phenyl]-4-[2,2-difluoro-1-(methylsulfinyl)cyclopropyl]-1H-pyrazole-3-carbonitrile

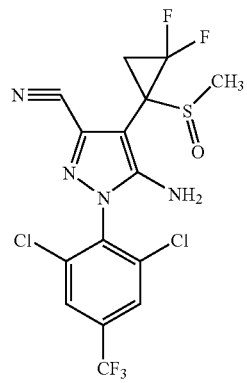

To a solution of Example 74 (100 mg, 0.23 mmol) in dichloromethane (5 ml) was added 3-chloroperoxybenzoic acid (77%, 53 mg, 0.25 mmol). The reaction mixture was stirred at room temperature for 18 h, diluted with dichloromethane (10 ml) and washed with saturated aqueous sodium hydrogencarbonate solution (2×5 ml). The organic layer was separated, dried (MgSO₄) and concentrated in vacuo. The residue was dissolved in acetonitrile/dimethyl sulphoxide (1:1, 1 ml) and purified by automated preparative liquid chromatography (Gilson system, 250 mm×30 mm Phenomenex LUNA C18(2) 101m column) using an acetonitrile:water gradient [45:55 to 95:5]. The appropriate fractions were concentrated in vacuo to give the titled compound (9 mg) and a second diastereoisomer, Example 126

Experimental MH⁺ 459.0; expected 459.0
¹H-NMR (CDCl₃): 2.06-2.14 (1H), 2.39-2.46 (1H), 2.56-2.61 (3H), 4.66-4.80 (2H), 7.75-7.79 (2H)

Similarly Prepared was

Example 126

5-amino-1-[2,6-dichloro-4-(trifluoromethyl)phenyl]-4-[2,2-difluoro-1-(methylsulfinyl)cyclopropyl]-1H-pyrazole-3-carbonitrile from Example 74

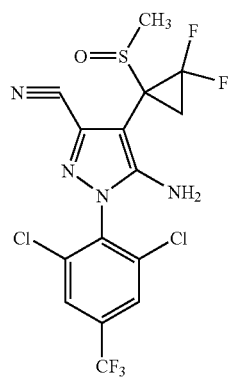

Experimental MH⁺ 459.0; expected 459.0
¹H-NMR (CDCl₃): 2.11-2.18 (1H), 2.60-2.68 (4H), 4.46-4.57 (2H), 7.75-7.79 (2H)

Example 127

1-[3-cyano-1-[2,6-dichloro-4-pentafluorothiophenyl]-5-(isopropylamino)-1H-pyrazol-4-yl]cyclopropanecarboxamide

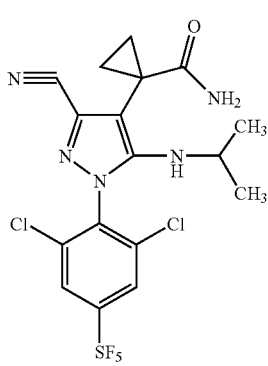

Example 13 (300 mg, 0.65 mmol), citric acid (50 mg, 0.26 mmol) and 2,2-dimethoxypropane (2.54 g, 24.40 mmol) were placed in a sealed CEM microwave tube and microwaved at 300 Watts at 120° C. for 60 min. The mixture was concentrated under a stream of nitrogen and to the residue was added sodium cyanoborohydride (1M in tetrahydrofuran, 3.0 ml, 3.00 mmol). After stirring at room temperature for 18 h, the reaction mixture was poured into water (10 ml) and extracted with dichloromethane (3×5 ml). The combined extracts were washed with sodium hydrogencarbonate solution (3×10 ml) and water (2×10 ml), dried (MgSO₄) and concentrated in vacuo. The residue was purified by flash chromatography to give the titled compound (190 mg).

Experimental MH⁺ 503.9; expected 504.0
¹H-NMR (CDCl₃): 1.08-1.13 (6H), 1.24-1.28 (2H), 1.76-1.81 (2H), 3.21-3.29 (1H), 3.43-3.55 (1H), 5.44-5.52 (1H), 5.68-5.75 (1H), 7.91-7.94 (2H)

Similarly Prepared was

Example 128

1-[3-cyano-1-[2,6-dichloro-4-(trifluoromethoxy)phenyl]-5-(isopropylamino)-1H-pyrazol-4-yl]-2,2-difluorocyclopropanecarboxamide from Example 99

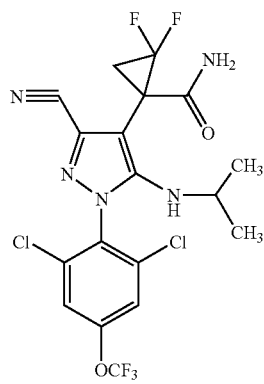

Experimental MH⁺ 498.3; expected 498.1
¹H-NMR (d₆-DMSO): 0.95-1.00 (3H), 1.05-1.11 (3H), 1.80-1.89 (1H), 2.66-2.75 (1H), 3.40-3.52 (1H), 5.53-5.58 (1H), 7.26-7.33 (1H), 7.57-7.63 (1H), 7.91-7.94 (2H)

Example 129

4-(1-cyanocyclopropyl)-5-[(cyclopropylmethyl)amino]-1-[2,6-dichloro-4-pentafluorothiophenyl]-1H-pyrazole-3-carbonitrile

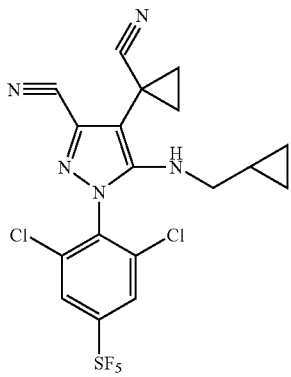

To a solution of Example 114 (100 mg, 0.19 mmol) in 1,4-dioxane (3 ml), at 0° C., was added trifluoroacetic anhydride (80 μl, 0.57 mmol) and pyridine (0.15 ml, 1.90 mmol). The reaction mixture was stirred at 0° C. for 2 h and then at room temperature for 30 min, before being partitioned between ethyl acetate and hydrochloric acid (1M). The organic phase was separated, washed with water, dried (MgSO$_4$) and concentrated in vacuo to give the titled compound (206 mg).

Experimental MH$^-$ 495.5; expected 496.0

$^1$H-NMR (d$_6$-DMSO): −0.01-0.05 (2H), 0.22-0.28 (2H), 0.79-0.86 (1H), 1.25-1.31 (2H), 1.62-1.68 (2H), 3.02-3.08 (2H), 6.14-6.19 (1H), 8.30-8.33 (2H).

Example 130

1-{3-cyano-1-[2,6-dichloro-4-pentafluorothiophenyl]-5-[({1-[(methylsulfonyl)amino]cyclopropyl}methyl)amino]-1H-pyrazol-4-yl}cyclopropanecarboxamide

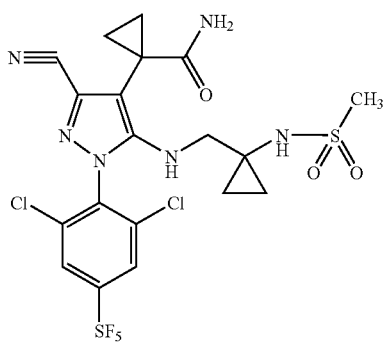

To a solution of Example 131 (50 mg, 0.08 mmol) in dichloromethane (2 ml) was added triethylamine (43 μl, 0.31 mmol), followed by methanesulphonyl chloride (61, 0.08 mmol). The reaction mixture was stirred for 18 h at room temperature and then concentrated in vacuo. The residue was dissolved in acetonitrile (1 ml) and purified by automated preparative liquid chromatography (Gilson system, 150 mm×30 mm LUNA C18(2) 10 μm column) using an acetonitrile:water gradient [50:50 to 98:2]. The appropriate fractions were concentrated in vacuo to give the titled compound (35 mg).

Experimental MH$^-$ 607.1; expected 607.0

$^1$H-NMR (d$_6$-Acetone): 0.79-0.83 (2H), 0.95-1.00 (2H), 1.15-1.20 (2H), 1.55-1.60 (2H), 2.85-2.90 (3H), 3.45-3.50 (2H), 8.22-8.25 (2H)

Example 131

1-(5-{[(1-aminocyclopropyl)methyl]amino}-3-cyano-1-[2,6-dichloro-4-pentafluorothiophenyl]-1H-pyrazol-4-yl)cyclopropanecarboxamide

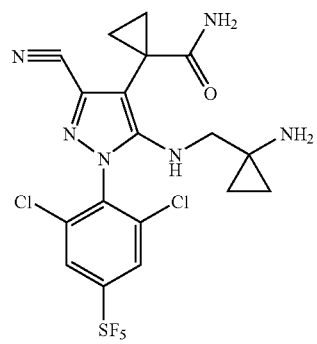

To a solution of Preparation 216 (68 mg, 0.11 mmol) in dichloromethane (2.4 ml), at 0° C., was added trifluoroacetic acid (1.2 ml). The reaction mixture was stirred at room temperature for 2 h and then concentrated in vacuo. The residue was dissolved in acetonitrile (0.25 ml) and purified by automated preparative liquid chromatography (Gilson system, 150 mm×21.2 mm LUNA C18(2) 5 μm column) using an acetonitrile:water gradient [50:50 to 95:5]. The appropriate fractions were concentrated in vacuo to give the titled compound (4 mg).

Experimental MH$^+$ 531.4; expected 531.1

Example 132

1-{3-cyano-1-[2,6-dichloro-4-pentafluorothiophenyl]-5-(methylsulfinyl)-1H-pyrazol-4-yl}cyclopropanecarboxamide

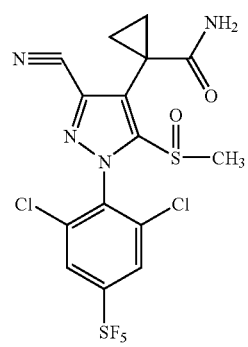

To a solution of Example 50 (40 mg, 0.08 mmol) in glacial acetic acid (1 ml) was added hydrogen peroxide (30 wt. %, 1 ml, 9.79 mmol) and the reaction mixture was stirred at room temperature for 60 h. The mixture was extracted with dichloromethane and the combined extracts were washed with aqueous sodium hydrogen carbonate solution and brine, dried (Na$_2$SO$_4$) and concentrated in vacuo. The residue was dissolved in acetonitrile/dimethyl sulphoxide (1 ml) and purified by automated preparative liquid chromatography (Gilson system, 150 mm×21.2 mm LUNA C18(2) 5 μm column) using an acetonitrile:water gradient [50:50 to 98:2]. The appropriate fractions were concentrated in vacuo to give the titled compound (4 mg) as one of several products.

Experimental MH$^+$ 509.2; expected 509.0

1H-NMR (CDCl$_3$): 1.55-1.60 (2H), 1.78-1.88 (2H), 3.09-3.14 (3H), 5.40-5.50 (2H), 7.85-7.90 (2H)

Example 133

-{3-cyano-1-[2,6-dichloro-4-pentafluorothiophenyl]-5-(methylsulfonyl)-1H-pyrazol-4-yl}cyclopropanecarboxamide

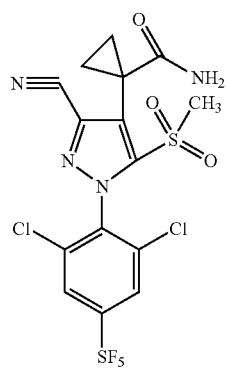

To a solution of Example 50 (40 mg, 0.08 mmol) in glacial acetic acid (1 ml) was added hydrogen peroxide (30 wt. %, 1 ml, 9.79 mmol) and the reaction mixture was stirred at room temperature for 60 h. The mixture was extracted with dichloromethane and the combined extracts were washed with aqueous sodium hydrogen carbonate solution and brine, dried (Na$_2$SO$_4$) and concentrated in vacuo. The residue was dissolved in acetonitrile/dimethyl sulphoxide (1 ml) and purified by automated preparative liquid chromatography (Gilson system, 150 mm×21.2 mm LUNA C18(2) 5 μm column) using an acetonitrile:water gradient [50:50 to 98:2]. The appropriate fractions were concentrated in vacuo to give the titled compound (12 mg) as one of several products.

Experimental MH$^+$ 525.2; expected 525.0

$^1$H-NMR (d$_6$Acetone): 1.50-1.55 (2H), 1.78-1.81 (2H), 3.39-3.41 (3H), 6.45-6.60 (2H), 8.24-8.27 (2H)

Example 134

4-({4-[1-(aminocarbonyl)cyclopropyl]-3-cyano-1-[2,6-dichloro-4-pentafluorothiophenyl]-1H-pyrazol-5-yl}amino)butanoic acid

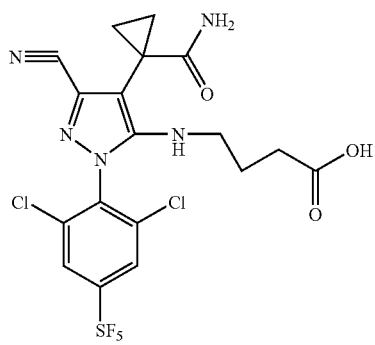

To a solution of Preparation 4 (390 mg, 0.64 mmol) in dichloromethane (5 ml) was added dropwise trifluoroacetic acid (5 ml). The reaction mixture was stirred at room temperature for 2.5 h and then concentrated in vacuo. The residue was extracted with ethyl acetate and the combined extracts were washed with brine, dried (MgSO$_4$) and concentrated in vacuo. The residue was dissolved in acetonitrile (2 ml) and purified by automated preparative liquid chromatography (Gilson system, 150 mm×30 mm LUNA C18 10 μm column) using an acetonitrile:0.1% trifluoroacetic acid [45:55 to 95:5] gradient. The appropriate fractions were combined and concentrated to give the titled compound (30 mg).

Experimental MH$^+$ 548.2; expected 548.0

$^1$H-NMR (d$_6$-DMSO): 0.98-1.03 (2H), 1.40-1.45 (2H), 1.55-1.62 (2H), 2.05-2.12 (2H), 3.10-3.19 (2H), 8.40-8.42 (2H)

Preparations

The following Preparations illustrate the synthesis of certain intermediates used in the preparation of the preceding Examples.

Preparation 1

N'-{3-cyano-4-(1-cyanocyclopropyl)-1-[2,6-dichloro-4-pentafluorothiophenyl]-1H-pyrazol-5-yl}-N,N-dimethylimidoformamide To a solution of Preparation 3 (1.75 g, 3.38 mmol) in 1,4-dioxane (50 ml), at 0° C., was added pyridine (2.7 ml, 33.80 mmol) and trifluoroacetic anhydride (1.4 ml, 10.20 mmol). After 2 h at 0° C., the reaction mixture was warmed to room temperature and stirred for a further 30 min. The mixture was partitioned between hydrochloric acid (1M) and ethyl acetate and the organic layer was separated, washed with water, dried (MgSO$_4$) and concentrated in vacuo to give the titled compound (2.88 g).

Experimental MH$^+$ 499.0; expected 499.0

Similarly Prepared was

Preparation 2

N'-{3-cyano-4-(1-cyanocyclopropyl)-1-[2,6-dichloro-4-(trifluoromethyl)phenyl]-1H-pyrazol-5-yl}-N,N-dimethylimidoformamide from Example 61

Experimental MH$^+$ 441.0; expected 441.1

Preparation 3

1-(3-cyano-1-[2,6-dichloro-4-pentafluorothiophenyl]-5-{[(dimethylamino)methylene]amino}-1H-pyrazol-4-yl)cyclopropanecarboxamide To a mixture of Preparation 9 (1.95 g, 3.76 mmol) and triethylamine (1.3 ml, 9.40 mmol) in tetrahydrofuran (38 ml), at 0° C., was added ethyl chloroformate (0.39 ml, 4.14 mmol). After 20 minutes, the reaction mixture was warmed to room temperature and stirred for 1 h. Anhydrous ammonia (g) was then bubbled through the mixture for 15 min, followed by nitrogen (g) for 3 min. The reaction mixture was partitioned between ethyl acetate and hydrochloric acid (1M) and the organic phase was separated, washed with water, dried (MgSO4) and concentrated in vacuo to give the titled compound (1.96 g).

Experimental MH$^+$ 517.0; expected 517.0

Similarly Prepared was

Preparation 4 tert-butyl 4-({4-[1-(aminocarbonyl)cyclopropyl]-3-cyano-1-[2,6-dichloro-4-pentafluorothiophenyl]-1H-pyrazol-5-yl}amino)butanoate from Preparation 48

Experimental MH$^+$ 604.1; expected 604.1

Preparation 5

1-{5-amino-3-cyano-1-[2,6-dichloro-4-pentafluorothiophenyl]-1H-pyrazol-4-yl}cyclopropanecarboxylic acid To a solution of Preparation 91 (600 mg, 1.26 mmol) in tetrahydrofuran (30 ml) was added lithium hydroxide monohydrate (69 mg, 1.64 mmol). The reaction mixture was then stirred at room temperature for 24 h. To the reaction mixture was added hydrochloric acid (2M) and the mixture was concentrated in vacuo. The residue was extracted with ethyl acetate and the combined extracts were washed with hydrochloric acid (2M), dried (Na$_2$SO$_4$) and concentrated in vacuo to give the titled compound (615 mg).

Experimental MH$^+$ 462.9; expected 463.0

Preparation 6

1-{3-cyano-5-[(cyclopropylmethyl)amino]-1-[2,6-dichloro-4-pentafluorothiophenyl]-1H-pyrazol-4-yl}cyclopropanecarboxylic acid To a solution of Preparation 143 (3.90 g, 7.34 mmol) in tetrahydrofuran (100 ml) was added lithium hydroxide (1.40 g, 33.10 mmol) in water (25 ml). The reaction mixture was stirred at room temperature for 18 h and then quenched with hydrochloric acid (2N). The mixture was extracted with ethyl acetate (2×150 ml) and the combined extracts were washed with water and saturated brine solution, dried (MgSO$_4$) and concentrated in vacuo to give the titled compound (3.60 g).

Experimental MH$^+$ 517.0; expected 517.0

Preparation 7

1-[3-cyano-1-[2,6-dichloro-4-pentafluorothiophenyl]-5-(methylamino)-1H-pyrazol-4-yl]-2,2-difluorocyclopropanecarboxylic acid A mixture of Preparation 138 (960 mg, 1.83 mmol) and lithium hydroxide monohydrate (383 mg, 9.13 mmol) in tetrahydrofuran (30 ml) and water (10 ml) was stirred at room temperature for 18 h. The reaction mixture was concentrated in vacuo and the residue was partitioned between hydrochloric acid (2N, 50 ml) and ethyl acetate (50 ml). The organic layer was separated, washed with brine (50 ml), dried (MgSO$_4$) and concentrated in vacuo to give the titled compound (977 mg).

Experimental MH$^+$ 512.9; expected 513.0

Preparation 8

1-{3-cyano-1-[2,6-dichloro-4-pentafluorothiophenyl]-5-[(2-fluoroethyl)amino]-1H-pyrazol-4-yl}cyclopropanecarboxylic acid To a solution of Preparation 135 (100 mg, 0.20 mmol) in tetrahydrofuran (5 ml) was added lithium hydroxide monohydrate (80 mg, 2.00 mmol) in water (1 ml). The reaction mixture was stirred at room temperature for 22 h and then concentrated in vacuo. The residue was partitioned between ethyl acetate and hydrochloric acid (10%) and the organic layer was separated. The aqueous layer was extracted with ethyl acetate and the combined organic phases were dried (MgSO$_4$) and concentrated in vacuo to give the titled compound (100 mg).

Experimental MH$^+$ 509.1; expected 509.0

Similarly Prepared were

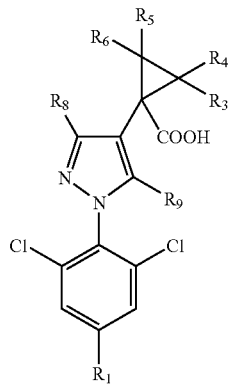

| Prep | R1 | R3 | R4 | R5 | R6 | R8 | R9 | From |
|---|---|---|---|---|---|---|---|---|
| Preparation 9 | $SF_5$ | H | H | H | H | CN | —N=CH—N($CH_3$)$_2$ | Preparation 61 |
| Preparation 10 | $SF_5$ | H | H | F | F | CN | $NH_2$ | Preparation 92 |
| Preparation 11 | $CF_3O$ | H | H | H | H | CN | $NH_2$ | Preparation 95 |
| Preparation 12 | $CF_3O$ | H | H | H | H | CN | —$NHCH_3$ | Preparation 137 |
| Preparation 13 | $SF_5$ | H | H | H | H | CN | [(4H-1,2,4-triazol-3-yl)methyl]amino | Preparation 144 |
| Preparation 14 | $SF_5$ | H | H | H | H | CN | [(1-methyl-cyclopropyl)methyl]amino | Preparation 125 |
| Preparation 15 | $SF_5$ | H | H | H | H | CN | —$NHCH_2COOH$ | Preparation 49 |
| Preparation 16 | $SF_5$ | H | H | H | H | CN | —NH($CH_2$)$_2$$CF_3$ | Preparation 130 |
| Preparation 17 | $SF_5$ | H | H | H | H | CN | [(2-chloro-1,3-thiazol-5-yl)methyl]amino | Preparation 112 |
| Preparation 18 | $SF_5$ | H | H | H | H | CN | (isoxazol-5-yl)methylamino | Preparation 113 |
| Preparation 19 | $SF_5$ | H | H | H | H | CN | —NH($CH_2$)$_2$COOH | Preparation 133 |
| Preparation 20 | $SF_5$ | H | H | H | H | CN | —NH($CH_2$)$_4$$CF_3$ | Preparation 132 |
| Preparation 21 | $SF_5$ | H | H | H | H | CN | —NH($CH_2$)$_3$$SCH_3$ | Preparation 114 |
| Preparation 22 | $SF_5$ | H | H | H | H | CN | —NHCOOi-Pr | Preparation 189 |
| Preparation 23 | i-$C_3F_7$ | H | H | H | H | CN | $NH_2$ | Preparation 171 |
| Preparation 24 | $SF_5$ | H | H | H | H | CN | [2-(4H-1,2,4-triazol-1-yl)ethyl]amino | Preparation 213 |
| Preparation 25 | $SF_5$ | H | H | H | H | CN | —NH($CH_2$)$_2$CN | Preparation 214 |
| Preparation 26 | CF3 | H | H | F | F | CN | —N=CH—N($CH_3$)$_2$ | Preparation 55 |
| Preparation 27 | CF3 | H | H | H | H | CN | —N=CH—N($CH_3$)$_2$ | Preparation 64 |
| Preparation 28 | CF3 | H | H | H | H | CF3 | NH2 | Preparation 97 |
| Preparation 29 | CF3 | H | H | H | H | CN | (cyclopropylmethyl)amino- | Preparation 131 |
| Preparation 30 | SF5 | H | H | H | H | CN | isobutylamino | Preparation 110 |
| Preparation 31 | SF5 | H | H | Cl | Cl | CN | NH2 | Preparation 170 |
| Preparation 32 | CF3 | H | H | H | H | CN | cyclobutylmethylamino | Preparation 199 |
| Preparation 33 | SF5 | H | H | H | H | CN | dimethylamino | Preparation 195 |
| Preparation 34 | $CF_3O$ | H | H | H | H | CN | ethoxycarbonylamino | Preparation 187 |
| Preparation 35 | SF5 | H | H | H | H | CN | methylthio | Preparation 196 |
| Preparation 36 | SF5 | H | H | H | H | CN | {4-[(methylsulphonyl)amino]benzyl}amino | Preparation 126 |
| Preparation 37 | SF5 | H | H | H | H | CN | {4[(methylamino)sulphonyl]benzyl}amino | Preparation 118 |
| Preparation 38 | SF5 | H | H | H | H | CN | (tetrahydro-2H-pyran-4-ylmethyl)amino | Preparation 119 |
| Preparation 39 | SF5 | H | H | Cl | Cl | CN | methylamino | Preparation 164 |
| Preparation 40 | $CF_3O$ | H | H | Cl | Cl | CN | $NH_2$ | Preparation 172 |
| Preparation 41 | SF5 | H | H | H | H | CN | propylamino | Preparation 129 |
| Preparation 42 | SF5 | H | H | H | H | CN | —$NHCH_2CONHCH_2$c-Pr | Preparation 206 |
| Preparation 43 | SF5 | H | H | H | H | CN | [(5-chloro1,3-dimethyl-1H-pyrazol-4-yl)methyl]amino | Preparation 120 |
| Preparation 44 | SF5 | H | H | H | H | CN | —N($CH_3$)($CH_2$)$_2$$OCH_3$ | Preparation 210 |
| Preparation 45 | SF5 | H | H | H | H | CN | —NH($CH_2$)$_3$COOH | Preparation 212 |
| Preparation 46 | SF5 | H | H | H | H | CN | (1,3-thiazol-2-ylmethyl)amino | Preparation 122 |
| Preparation 47 | SF5 | H | H | H | H | CN | 2-(1-methyl-1H-pyrazol-4-yl)ethylamino | Preparation 123 |
| Preparation 48 | SF5 | H | H | H | H | CN | t-BOC-propylamino | Preparation 121 |

Preparation 9

1-(3-cyano-1-[2,6-dichloro-4-pentafluorothiophenyl]-5-{[(dimethylamino)methylene]amino}-1H-pyrazol-4-yl)cyclopropanecarboxylic acid Experimental $MH^+$ 518.0; expected 518.0

Preparation 10

1-{5-amino-3-cyano-1-[2,6-dichloro-4-pentafluorothiophenyl]-1H-pyrazol-4-yl}-2,2-difluorocyclopropanecarboxylic acid Experimental $MH^+$ 499.1; expected 499.0

Preparation 11

1-{5-amino-3-cyano-1-[2,6-dichloro-4-(trifluoromethoxy)phenyl]-1H-pyrazol-4-yl}cyclopropanecarboxylic acid Experimental M⁻ 418.7; expected 419.0

Preparation 12

1-{3-cyano-1-[2,6-dichloro-4-(trifluoromethoxy)phenyl]-5-(methylamino)-1H-pyrazol-4-yl}cyclopropanecarboxylic acid Experimental MH⁺ 434.9; expected 435.0

Preparation 13

1-{3-cyano-1-[2,6-dichloro-4-pentafluorothiophenyl]-5-[(4H-1,2,4-triazol-3-ylmethyl)amino]-1H-pyrazol-4-yl}cyclopropanecarboxylic acid Experimental MH⁺ 543.9; expected 544.0

Preparation 14

1-(3-cyano-1-[2,6-dichloro-4-pentafluorothiophenyl]-5-{[(1-methylcyclopropyl)methyl]amino}-1H-pyrazol-4-yl)cyclopropanecarboxylic acid

Preparation 15

1-{5-[(carboxymethyl)amino]-3-cyano-1-[2,6-dichloro-4-pentafluorothiophenyl]-1H-pyrazol-4-yl}cyclopropanecarboxylic acid Experimental MH⁺ 520.8; expected 521.0

Preparation 16

1-{3-cyano-1-[2,6-dichloro-4-pentafluorothiophenyl]-5-[(3,3,3-trifluoropropyl)amino]-1H-pyrazol-4-yl}cyclopropanecarboxylic acid Experimental MH⁺ 559.1; expected 559.0

Preparation 17

1-(5-{[(2-chloro-1,3-thiazol-5-yl)methyl]amino}-3-cyano-1-[2,6-dichloro-4-pentafluorothiophenyl]-1H-pyrazol-4-yl)cyclopropanecarboxylic acid Experimental MH⁺ 594.0; expected 593.9

Preparation 18

1-{3-cyano-1-[2,6-dichloro-4-pentafluorothiophenyl]-5-[(isoxazol-5-ylmethyl)amino]-1H-pyrazol-4-yl}cyclopropanecarboxylic acid Experimental MH⁺ 544.0; expected 544.0

Preparation 19

N-{4-(1-carboxycyclopropyl)-3-cyano-1-[2,6-dichloro-4-pentafluorothiophenyl]-1H-pyrazol-5-yl}-beta-alanine Experimental MH⁺ 535.0; expected 535.0

Preparation 20

1-{3-cyano-1-[2,6-dichloro-4-pentafluorothiophenyl]-5-[(5,5,5-trifluoropentyl)amino]-1H-pyrazol-4-yl}cyclopropanecarboxylic acid Experimental MH⁺ 587.0; expected 587.0

Preparation 21

1-(3-cyano-1-[2,6-dichloro-4-pentafluorothiophenyl]-5-{[3-(methylthio)propyl]amino}-1H-pyrazol-4-yl)cyclopropanecarboxylic acid Experimental MH⁺ 550.9; expected 551.0

Preparation 22

1-{3-cyano-1-[2,6-dichloro-4-pentafluorothiophenyl]-5-[(isopropoxycarbonyl)amino]-1H-pyrazol-4-yl}cyclopropanecarboxylic acid Experimental MH⁺ 549.0; expected 549.0

Preparation 23

1-(5-amino-3-cyano-1-{2,6-dichloro-4-[1,2,2,2-tetrafluoro-1-(trifluoromethyl)ethyl]phenyl}-1H-pyrazol-4-yl)cyclopropanecarboxylic acid ¹H-NMR (CDCl₃): 1.37-1.40 (2H), 1.68-1.71 (2H), 7.71-7.74 (2H)

Preparation 24

1-(3-cyano-1-[2,6-dichloro-4-pentafluorothiophenyl]-5-{[2-(1H-1,2,4-triazol-1-yl)ethyl]amino}-1H-pyrazol-4-yl)cyclopropanecarboxylic acid Experimental MH⁺ 557.9; expected 558.0

Preparation 25

1-{3-cyano-5-[(2-cyanoethyl)amino]-1-[2,6-dichloro-4-pentafluorothiophenyl]-1H-pyrazol-4-yl}cyclopropanecarboxylic acid Experimental MH⁺ 515.9; expected 516.0

Preparation 26

1-(3-cyano-1-[2,6-dichloro-4-(trifluoromethyl)phenyl]-5-{[(dimethylamino)methylene]amino}-1H-pyrazol-4-yl)-2,2-difluorocyclopropanecarboxylic acid Experimental MH⁺ 495.9; expected 496.0

Preparation 27

1-(3-cyano-1-[2,6-dichloro-4-(trifluoromethyl)phenyl]-5-{[(dimethylamino)methylene]amino}-1H-pyrazol-4-yl)cyclopropanecarboxylic acid Experimental MH$^+$ 460.0; expected 460.1

Preparation 28

1-{5-amino-1-[2,6-dichloro-4-(trifluoromethyl)phenyl]-3-(trifluoromethyl)-1H-pyrazol-4-yl}cyclopropanecarboxylic acid Experimental MH$^+$ 448.0; expected 448.0

Preparation 29

1-{3-cyano-5-[(cyclopropylmethyl)amino]-1-[2,6-dichloro-4-(trifluoromethyl)phenyl]-1H-pyrazol-4-yl}cyclopropanecarboxylic acid Experimental MH$^+$ 459.1; expected 459.1

Preparation 30

1-{3-cyano-1-[2,6-dichloro-4-pentafluorothiophenyl]-5-(isobutylamino)-1H-pyrazol-4-yl}cyclopropanecarboxylic acid Experimental M$^-$ 517.0; expected 517.0

Preparation 31

1-{5-amino-3-cyano-1-[2,6-dichloro-4-pentafluorothiophenyl]-1H-pyrazol-4-yl}-2,2-dichlorocyclopropanecarboxylic acid Experimental MH$^+$ 530.8; expected 530.9

Preparation 32

1-{3-cyano-5-[(cyclobutylmethyl)amino]-1-[2,6-dichloro-4-pentafluorothiophenyl]-1H-pyrazol-4-yl}cyclopropanecarboxylic acid Experimental MH$^+$ 531.0; expected 531.0

Preparation 33

1-{3-cyano-1-[2,6-dichloro-4-pentafluorothiophenyl]-5-(dimethylamino)-1H-pyrazol-4-yl}cyclopropanecarboxylic acid Experimental MH$^+$ 491.0; expected 491.0

Preparation 34

1-{3-cyano-1-[2,6-dichloro-4-(trifluoromethoxy)phenyl]-5-[(ethoxycarbonyl)amino]-1H-pyrazol-4-yl}cyclopropanecarboxylic acid

Preparation 35

1-{3-cyano-1-[2,6-dichloro-4-pentafluorothiophenyl]-5-(methylthio)-1H-pyrazol-4-yl}cyclopropanecarboxylic acid $^1$H-NMR (CDCl$_3$): 1.39-1.53 (2H), 1.77-1.93 (2H), 2.29-2.41 (3H), 7.89-7.91 (2H)

Preparation 36

1-{3-cyano-1-[2,6-dichloro-4-pentafluorothiophenyl]-5-({4-[(methylsulfonyl)amino]benzyl}amino)-1H-pyrazol-4-yl}cyclopropanecarboxylic acid Experimental MH$^+$ 646.1; expected 646.0

Preparation 37

1-{3-cyano-1-[2,6-dichloro-4-pentafluorothiophenyl]-5-({4-[(methylamino)sulfonyl]benzyl}amino)-1H-pyrazol-4-yl}cyclopropanecarboxylic acid Experimental MH$^+$ 645.9; expected 646.0

Preparation 38

1-{3-cyano-1-[2,6-dichloro-4-pentafluorothiophenyl]-5-[(tetrahydro-2H-pyran-4-ylmethyl)amino]-1H-pyrazol-4-yl}cyclopropanecarboxylic acid Experimental MH$^+$ 560.9; expected 561.0

Preparation 39

2,2-dichloro-1-{3-cyano-1-[2,6-dichloro-4-pentafluorothiophenyl]-5-(methylamino)-1H-pyrazol-4-yl}cyclopropanecarboxylic acid Experimental MH$^+$ 545.0; expected 544.9

Preparation 40

1-{5-amino-3-cyano-1-[2,6-dichloro-4-(trifluoromethoxy)phenyl]-1H-pyrazol-4-yl}-2,2-dichlorocyclopropanecarboxylic acid Experimental MH$^+$ 489.0; expected 488.9

Preparation 41

1-{3-cyano-1-[2,6-dichloro-4-pentafluorothiophenyl]-5-(propylamino)-1H-pyrazol-4-yl}cyclopropanecarboxylic acid Experimental MH$^+$ 504.8; expected 505.0

Preparation 42

1-{3-cyano-5-({2-[(cyclopropylmethyl)amino]-2-oxoethyl}amino)-1-[2,6-dichloro-4-pentafluorothiophenyl]-1H-pyrazol-4-yl}cyclopropanecarboxylic acid Experimental MH$^+$ 573.9; expected 574.1

Preparation 43

1-(5-{[(5-chloro-1,3-dimethyl-1H-pyrazol-4-yl)methyl]amino}-3-cyano-1-[2,6-dichloro-4-pentafluorothiophenyl]-1H-pyrazol-4-yl)cyclopropanecarboxylic acid Experimental MH$^+$ 605.0; expected 605.0

Preparation 44

1-{3-cyano-1-[2,6-dichloro-4-pentafluorothiophenyl]-5-[(2-methoxyethyl)(methyl)amino]-1H-pyrazol-4-yl}cyclopropanecarboxylic acid Experimental MH$^+$ 535.2; expected 535.0

Preparation 45

1-{5-[(3-carboxypropyl)amino]-3-cyano-1-[2,6-dichloro-4-pentafluorothiophenyl]-1H-pyrazol-4-yl}cyclopropanecarboxylic acid Experimental MH$^+$ 549.1; expected 549.0

Preparation 46

1-{3-cyano-1-[2,6-dichloro-4-pentafluorothiophenyl]-5-[(1,3-thiazol-2-ylmethyl)amino]-1H-pyrazol-4-yl}cyclopropanecarboxylic acid Experimental MH$^+$ 560.1; expected 560.0

Preparation 47

1-(3-cyano-1-[2,6-dichloro-4-pentafluorothiophenyl]-5-{[2-(1-methyl-1H-pyrazol-4-yl)ethyl]amino}-1H-pyrazol-4-yl)cyclopropanecarboxylic acid Experimental MH$^+$ 570.9; expected 571.1

Preparation 48

1-{5-[(4-tert-butoxy-4-oxobutyl)amino]-3-cyano-1-[2,6-dichloro-4-pentafluorothiophenyl]-1H-pyrazol-4-yl}cyclopropanecarboxylic acid Experimental MH$^+$ 605.1; expected 605.1

Preparation 49

N-{3-cyano-1-[2,6-dichloro-4-pentafluorothiophenyl]-4-[1-(methoxycarbonyl)cyclopropyl]-1H-pyrazol-5-yl}glycine A solution of Preparation 207 (380 mg, 0.64 mmol) in trifluoroacetic acid (10 ml) was stirred at room temperature for 2 h and then concentrated in vacuo. The residue was partitioned between ethyl acetate (30 ml) and water (30 ml) and the organic phase was separated, washed with brine (30 ml), dried (MgSO$_4$) and concentrated in vacuo to give the titled compound (350 mg).

Experimental MH$^+$ 534.8; expected 535.0

Preparation 50

1-[3-cyano-1-[2,6-dichloro-4-(trifluoromethoxy)phenyl]-5-(methylamino)-1H-pyrazol-4-yl]-2,2-difluorocyclopropanecarboxylic acid To a solution of Preparation 93 (180 mg, 0.38 mmol) in triethylorthoformate (5 ml) was added hydrochloric acid (concentrated, 0.2 ml). The reaction mixture was heated at reflux for 1 h, toluene was added and the mixture was concentrated in vacuo. This process was repeated three times and the residue was dissolved in acetic acid. To the solution was added sodium cyanoborohydride (53 mg, 0.84 mmol) over a period of 2 h. The reaction mixture was partitioned between water and dichloromethane and the organic phase was separated, dried (MgSO$_4$) and concentrated in vacuo to give the methyl ester (200 mg). To a solution of the methyl ester (200 mg, 0.41 mmol) in tetrahydrofuran (9 ml) and water (3 ml) was added lithium hydroxide monohydrate (172 mg, 4.10 mmol). The reaction mixture was stirred at room temperature for 2 h and then acidified with hydrochloric acid. The mixture was extracted with ethyl acetate and the combined extracts were dried (MgSO$_4$) and concentrated in vacuo to give the titled compound (200 mg).

Experimental MH$^+$ 471.0; expected 471.0

Preparation 51

1-(3-cyano-1-[2,6-dichloro-4-(trifluoromethyl)phenyl]-5-{[(dimethylamino)methylene]amino}-1H-pyrazol-4-yl)-N,N-dimethylcyclopropanecarboxamide To a solution of Preparation 27 (107 mg, 0.23 mmol) in N,N-dimethylformamide (5 ml) was added magnesium sulphate, followed by 1-hydroxybenzotriazole monohydrate (33 mg, 0.25 mmol), dimethylamine hydrochloride (29 mg, 0.35 mmol), N-methylmorpholine (64 µl, 0.58 mmol) and 1-(3-dimethylaminopropyl)-3-ethylcarbodiimide hydrochloride (49 mg, 0.26 mmol). The reaction mixture was stirred at room temperature for 1 h and a catalytic amount of 4-dimethylaminopyridine was added. The reaction mixture was then stirred for a further 3 h. To the reaction mixture was added water (30 ml) and the mixture was extracted with ethyl acetate (3×10 ml). The combined extracts were dried (MgSO$_4$) and concentrated in vacuo to give the titled compound (68 mg).

Experimental MH$^+$ 487.1; expected 487.1

Similarly Prepared was

Preparation 52

N'-{3-cyano-1-[2,6-dichloro-4-(trifluoromethyl)phenyl]-4-[1-(pyrrolidin-1-ylcarbonyl)cyclopropyl]-1H-pyrazol-5-yl}-N,N-dimethylimidoformamide from Preparation 27 and Pyrrolidine Experimental MH$^+$ 513.1; expected 513.1

Preparation 53 methyl 1-(3-cyano-1-[2,6-dichloro-4-pentafluorothiophenyl]-5-{[(dimethylamino)methylene]amino}-1H-pyrazol-4-yl)-2,2-difluorocyclopropanecarboxylate To a mixture of Preparation 66 (2.24 g, 4.32 mmol) and sodium fluoride (3 mg) in toluene (5.4 ml) at reflux was added trimethylsilyl-2,2-difluoro-2-(fluorosulphonyl)acetate (3.4 ml, 17.30 mmol), via syringe. After heating at reflux for 4 h, the reaction mixture was cooled to room temperature and stirred for 16 h. The reaction mixture was concentrated in vacuo and the residue was purified by column chromatography (silica) with gradient elution, ethyl acetate:hexane [10:90 to 35:65]. The appropriate fractions were combined and concentrated in vacuo to give the titled compound (1.96 g).

Experimental MH$^+$ 568.1; expected 568.0

Preparation 54 methyl 1-(3-cyano-1-[2,6-dichloro-4-(trifluoromethoxy)phenyl]-5-{[(dimethylamino)methylene]amino}-1H-pyrazol-4-yl)-2,2-difluorocyclopropanecarboxylate To a suspension of Preparation 69 (7.50 g, 15.80 mmol) in toluene (10 ml) was added potassium fluoride (20 mg) and trimethylsilyl-2,2-difluoro-2-(fluorosulphonyl)acetate (Dolbier Reagent, 10 ml), via syringe over 6 h. The reaction mixture was loaded on to a column (silica) and eluted with toluene. The appropriate fractions were combined and concentrated to give the titled compound (7.20 g).

Experimental MH$^+$ 526.0; expected 526.0

Similarly Prepared were:

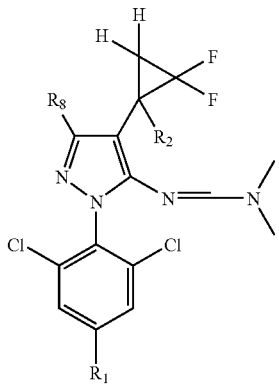

| Prep | R1 | R8 | R2 | From |
|---|---|---|---|---|
| Preparation 55 | CF3 | CN | —COOCH$_3$ | Preparation 67 |
| Preparation 56 | CF3 | CN | —SO2NCHN(CH3)2 | Preparation 70 |
| Preparation 57 | CF3 | CN | —SO2N(CH3)2 | Preparation 86 |
| Preparation 58 | CF3 | CN | F | Preparation 72 |
| Preparation 59 | CF3 | CN | —SO2CH3 | Preparation 85 |

Preparation 55 methyl 1-(3-cyano-1-[2,6-dichloro-4-(trifluoromethyl)phenyl]-5-{[(dimethylamino)methylene]amino}-1H-pyrazol-4-yl)-2,2-difluorocyclopropanecarboxylate Experimental MH$^+$ 509.9; expected 510.1

Preparation 56

1-(3-cyano-1-[2,6-dichloro-4-(trifluoromethyl)phenyl]-5-{[(dimethylamino)methylene]amino}-1H-pyrazol-4-yl)-N—[(dimethylamino)methylene]-2,2-difluorocyclopropanesulfonamide Experimental MH$^+$ 585.9; expected 586.1

Preparation 57

1-(3-cyano-1-[2,6-dichloro-4-(trifluoromethyl)phenyl]-5-{[(dimethylamino)methylene]amino}-1H-pyrazol-4-yl)-2,2-difluoro-N,N-dimethylcyclopropanesulfonamide Experimental MH$^+$ 559.0; expected 559.1

Preparation 58

N-{3-cyano-1-[2,6-dichloro-4-(trifluoromethyl)phenyl]-4-(1,2,2-trifluorocyclopropyl)-1H-pyrazol-5-yl}-N,N-dimethylimidoformamide Experimental MH$^+$ 470.2; expected 470.0

Preparation 59

N-{3-cyano-1-[2,6-dichloro-4-(trifluoromethyl)phenyl]-4-[2,2-difluoro-1-(methylsulfonyl)cyclopropyl]-1H-pyrazol-5-yl}-N,N-dimethylimidoformamide Experimental MH$^+$ 530.0; expected 530.0

Preparation 60 methyl 1-(3-cyano-1-[2,6-dichloro-4-(trifluoromethyl)phenyl]-5-{[(dimethylamino)methylene]amino}-1H-pyrazol-4-yl)-2,2-dimethylcyclopropanecarboxylate To a suspension of Preparation 191 (632 mg, 2.00 mmol) in ethylene glycol dimethyl ether (5 ml) and dichloromethane (100 μl), at −78° C. and under nitrogen, was added lithium diisopropylamide (1.8N in tetrahydrofuran, 1.1 ml, 2.00 mmol). After stirring for 30 min, a solution of Preparation 67 (460 mg, 1.00 mmol) in ethylene glycol dimethyl ether (9 ml) was added. The reaction mixture was stirred at −78° C. for 1 h and then allowed to warm to room temperature. To the reaction mixture was added hydrochloric acid (10%) and the mixture was extracted with ethyl acetate (3×25 ml). The combined extracts were washed with hydrochloric acid (10%), dried (MgSO$_4$) and concentrated in vacuo. The residue was purified by column chromatography (silica), eluting with diethyl ether/pentane [1:1]. The appropriate fractions were combined and concentrated to give the titled compound (350 mg).

Experimental MH$^+$ 502.0; expected 502.1

Preparation 61 methyl 1-(3-cyano-1-[2,6-dichloro-4-pentafluorothiophenyl]-5-{[(dimethylamino)methylene]amino}-1H-pyrazol-4-yl)cyclopropanecarboxylate To trimethylsulphoxonium iodide (892 mg, 4.05 mmol) and sodium hydride (60% in oil, 150 mg, 3.76 mmol) was added dimethyl sulphoxide (20 ml). After stirring for 1 h, the mixture was added to a solution of Preparation 66 (1.5 g, 2.89 mmol) in dimethyl sulphoxide (20 ml) at 0° C. The reaction mixture was allowed to warm to room temperature and stirred overnight. To the reaction mixture was added hydrochloric acid (1M) and the mixture was extracted with ethyl acetate. The combined organic phases were washed with water, dried (Na$_2$SO$_4$) and concentrated in vacuo. The residue was purified on a Biotage column (silica, 100 g) eluting with dichloromethane. The appropriate fractions were combined and concentrated to give the titled compound (1.0 g).

Experimental MH$^+$ 532.0; expected 532.0

Similarly Prepared were

Preparation 62 methyl 1-{1-[2,6-dichloro-4-(trifluoromethyl)phenyl]-5-{[(dimethylamino)methylene]amino}-3-(trifluoromethyl)-1H-pyrazol-4-yl}cyclopropanecarboxylate Experimental MH$^+$ 516.8; expected 517.1 from Preparation 68

Preparation 63 methyl 1-(3-cyano-1-[2,6-dichloro-4-(trifluoromethoxy)phenyl]-5-{[(dimethylamino)methylene]amino}-1H-pyrazol-4-yl)cyclopropanecarboxylate from Preparation 69

Experimental MH$^+$ 462.8; expected 462.9

Preparation 64 methyl 1-(3-cyano-1-[2,6-dichloro-4-(trifluoromethyl)phenyl]-5-{[(dimethylamino)methylene]amino}-1H-pyrazol-4-yl)cyclopropanecarboxylate from Preparation 67

$^1$H-NMR (CDCl$_3$): 1.13-1.17 (2H), 1.64-1.68 (2H), 2.72-2.75 (3H), 2.92-2.95 (3H), 3.67-3.69 (3H), 7.62-7.65 (2H), 7.73-7.75 (1H)

Preparation 65 methyl 1-{3-cyano-5-(cyclopropylmethoxy)-1-[2,6-dichloro-4-pentafluorothiophenyl]-1H-pyrazol-4-yl}cyclopropanecarboxylate from Preparation 201

Experimental MH$^+$ 532.1; expected 532.0

Preparation 66 methyl 2-(3-cyano-1-[2,6-dichloro-4-pentafluorothiophenyl]-5-{[(dimethylamino)methylene]amino}-1H-pyrazol-4-yl)acrylate To a solution of Preparation 73 (3.5 g, 6.54 mmol) in dichloromethane (30 ml) was added triethylamine (5.28 ml, 37.93 mmol) and methanesulphonyl chloride (1.81 ml, 23.54 mmol). The reaction mixture was then stirred at room temperature for 24 h. To the reaction mixture was added hydrochloric acid (2M) and ice and the mixture was extracted with dichloromethane. The combined extracts were dried (Na$_2$SO$_4$) and concentrated in vacuo. The residue was purified on a Biotage column (silica, 100 g), eluting with dichloromethane. The appropriate fractions were combined and concentrated to give the titled compound (1.5 g).

Experimental MH$^+$ 518.0; expected 518.0

Similarly Prepared was

Preparation 67 methyl 2-(3-cyano-1-[2,6-dichloro-4-(trifluoromethyl)phenyl]-5-{[(dimethylamino)methylene]amino}-1H-pyrazol-4-yl)acrylate from Preparation 75

Experimental MH$^+$ 460.1; expected 460.1

$^1$H-NMR (CDCl$_3$): 2.72-2.75 (3H), 2.88-2.92 (3H), 3.73-3.76 (3H), 6.02-6.05 (1H), 6.48-6.51 (1H), 7.50-7.53 (1H), 7.64-7.69 (2H)

Preparation 68 methyl 2-[1-[2,6-dichloro-4-(trifluoromethyl)phenyl]-5-{[(dimethylamino)methylene]amino}-3-(trifluoromethyl)-1H-pyrazol-4-yl]acrylate from Preparation 76

Experimental MH$^+$ 502.8; expected 503.0

Preparation 69 methyl 2-(3-cyano-1-[2,6-dichloro-4-(trifluoromethoxy)phenyl]-5-{[(dimethylamino)methylene]amino}-1H-pyrazol-4-yl)acrylate To a solution of Preparation 74 (24.50 g, 49.60 mmol) in acetonitrile (100 ml) was added dropwise thionyl chloride (30 ml). After stirring at 50° C. for 2 days, the reaction mixture was concentrated in vacuo. The residue was purified by column chromatography (silica), eluting with dichloromethane. The appropriate fractions were combined and concentrated to give the titled compound (19.1 g).

Experimental MH$^+$ 476.0; expected 476.1

Preparation 70

1-(3-cyano-1-[2,6-dichloro-4-(trifluoromethyl)phenyl]-5-{[(dimethylamino)methylene]amino}-1H-pyrazol-4-yl)-N—[(dimethylamino)methylene]-ethylenesulfonamide To a solution of Preparation 219 (670 mg, 1.30 mmol) in N,N-dimethylformamide (5 ml), under nitrogen, was added tetrakis(triphenylphosphine)palladium(0) (10%, 150 mg), followed by the solution of Preparation 101 (approximately 2.00 mmol). The reaction mixture was heated at 110° C. for 10 h, before addition of hydrochloric acid (10%) and water. The mixture was extracted with diethyl ether (3×15 ml) and the combined extracts were washed with water (15 ml), dried (MgSO$_4$) and concentrated in vacuo. The residue was purified by column chromatography (silica) with gradient elution, ethyl acetate:hexane [1:0 to 0:1]. The appropriate fractions were combined and concentrated to give the titled compound (300 mg) as a mixture of isomers.

Experimental MH$^+$ 536.0; expected 536.1

Similarly Prepared were

Preparation 71

N'-{3-cyano-1-[2,6-dichloro-4-pentafluorothiophenyl]-4-[1-(methylsulfonyl)-vinyl]-1H-pyrazol-5-yl}-N,N-dimethylimidoformamide from Preparation 78 and Preparation 180

Experimental MH$^+$ 538.0; expected 538.0

Preparation 72

N'-[3-cyano-1-[2,6-dichloro-4-(trifluoromethyl)phenyl]-4-(1-fluorovinyl)-1H-pyrazol-5-yl]-N,N-dimethylimidoformamide from Preparation 219 and Preparation 234

$^1$H-NMR (CDCl$_3$): 2.76-2.78 (3H), 2.99-3.01 (3H), 4.92-5.10 (2H), 7.66-7.68 (2H), 7.70-7.73 (1H)

Preparation 73 methyl 2-(3-cyano-1-[2,6-dichloro-4-pentafluorothiophenyl]-5-{[(dimethylamino)methylene]amino}-1H-pyrazol-4-yl)-2-hydroxypropanoate To a solution of Preparation 78 (3.15 g, 5.62 mmol) in dry tetrahydrofuran (20 ml), at −78° C., was added isopropylmagnesium chloride (2M, 3.09 ml, 6.19 mmol). The mixture was stirred at −78° C. for 30 min and then added to methyl pyruvate (0.76 ml, 8.44 mmol) in tetrahydrofuran (5 ml) at −30° C. The reaction mixture was then stirred overnight at room temperature. The reaction mixture was acidified with hydrochloric acid (2M) and extracted with ethyl acetate (200 ml). The combined extracts were dried (Na$_2$SO$_4$) and concentrated in vacuo to give the titled compound (3.5 g).

Experimental MH$^+$ 536.0; expected 536.0

Preparation 74 methyl 2-(3-cyano-1-[2,6-dichloro-4-(trifluoromethoxy)phenyl]-5-{[(dimethylamino)methylene]amino}-1H-pyrazol-4-yl)-2-hydroxypropanoate To a solution of Preparation 79 (41.00 g, 79.00 mmol) in anhydrous tetrahydrofuran (250 ml), at −30° C. and under nitrogen, was added dropwise isopropylmagnesium chloride (2M in tetrahydrofuran, 4.5 ml, 90.00 mmol). After stirring at −30° C. for 1 h, methyl pyruvate (90%, 15.5 ml, 135.00 mmol) was added and the reaction mixture was stirred for 1 h and then allowed to warm to room temperature. The reaction mixture was quenched on ice/hydrochloric acid (2N) and extracted with ethyl acetate (3×200 ml). The combined extracts were dried (MgSO$_4$) and concentrated in vacuo. The residue was purified by column chromatography (silica), eluting with dichloromethane, followed by ethyl acetate. The appropriate fractions were combined and concentrated to give the titled compound (24.50 g)

Experimental MH$^+$ 494.0; expected 494.1.

Similarly Prepared were

Preparation 75 methyl 2-(3-cyano-1-[2,6-dichloro-4-(trifluoromethyl)phenyl]-5-{[(dimethylamino)methylene]amino}-1H-pyrazol-4-yl)-2-hydroxypropanoate from Preparation 219

Experimental MH$^+$ 478.1; expected 478.1

Preparation 76 methyl 2-[1-[2,6-dichloro-4-(trifluoromethyl)phenyl]-5-{[(dimethylamino)methylene]amino}-3-(trifluoromethyl)-1H-pyrazol-4-yl]-2-hydroxypropanoate from Preparation 80

Experimental MH$^+$ 521.1; expected 521.1

Preparation 77 methyl 2-{3-cyano-5-(cyclopropylmethoxy)-1-[2,6-dichloro-4-pentafluorothiophenyl]-1H-pyrazol-4-yl}-2-hydroxypropanoate from Preparation 106

Experimental MH$^+$ 536.1; expected 536.0

Preparation 78

N'-{3-cyano-1-[2,6-dichloro-4-pentafluorothiophenyl]-4-iodo-1H-pyrazol-5-yl}-N,N-dimethylimidoformamide A solution of Preparation 105. (52 g, 103 mmol) in N,N-dimethylformamide dimethyl acetal (300 ml) was heated at reflux for 5 h, cooled to room temperature and stirred overnight. The reaction mixture was purified by column chromatography (silica, 1 kg) with gradient elution, hexane:ethyl acetate [6:1 to 4:1]. The appropriate fractions were combined and concentrated to give the titled compound (45 g) as a light brown solid.

$^1$H-NMR (CDCl$_3$): 2.77-2.81 (3H), 3.02-3.05 (3H), 7.78-7.81 (2H), 8.21-8.24 (1H)

Preparation 79

N'-{3-cyano-1-[2,6-dichloro-4-(trifluoromethoxy)phenyl]-4-iodo-1H-pyrazol-5-yl}-N,N-dimethylimidoformamide To a solution of Preparation 107 (6.8 g, 14.7 mmol) in dichloromethane (100 ml) was added N,N-dimethylformamide dimethyl acetal (1.93 g, 16.2 mmol). The reaction mixture was then stirred at room temperature overnight. The reaction mixture was concentrated in vacuo and the residue was purified by flash chromatography (silica) with gradient elution, toluene:dichloromethane [1:0 to 1:1]. The appropriate fractions were combined and concentrated to give the titled compound (6.2 g).

¹H-NMR (CDCl₃): 2.76-2.79 (3H), 3.01-3.04 (3H), 7.27-7.30 (2H), 8.17-8.20 (1H)

Preparation 80

N'-[1-[2,6-dichloro-4-(trifluoromethyl)phenyl]-4-iodo-3-(trifluoromethyl)-1H-pyrazol-5-yl]-N,N-dimethylimidoformamide A solution of Preparation 109 (13.0 g, 26.53 mmol) in N,N-dimethylformamide dimethyl acetal (100 ml) was heated at reflux for 5 h. The reaction mixture was concentrated in vacuo and the residue was partitioned between dichloromethane and water. The organic phase was separated, dried (MgSO₄) and concentrated in vacuo. The residue was purified by column chromatography (silica), eluting with cyclohexane/dichloromethane [4:1]. The appropriate fractions were combined and concentrated to give the titled compound (12.0 g).
Experimental MH⁺ 544.7; expected 544.9

Preparation 81

N'-{3-cyano-1-[2,6-dichloro-4-(trifluoromethyl)phenyl]-4-[1-(methylsulfonyl)cyclopropyl]-1H-pyrazol-5-yl}-N,N-dimethylimidoformamide A solution of Preparation 83 (110 mg, 0.20 mmol) in xylene (5 ml) was heated at 130° C. for 4 h. The reaction mixture was concentrated in vacuo to give the titled compound (150 mg).
Experimental MH⁺ 493.8; expected 494.0

Similarly Prepared was

Preparation 82

N'-{3-cyano-1-[2,6-dichloro-4-pentafluorothiophenyl]-4-[1-(methylsulfonyl)cyclopropyl]-1H-pyrazol-5-yl}-N,N-dimethylimidoformamide from Preparation 84

Experimental MH⁺ 552.0; expected 552.0

Preparation 83

N'-[3'-cyano-1'-[2,6-dichloro-4-(trifluoromethyl)phenyl]-3-(methylsulfonyl)-4,5-dihydro-1'H,3H-3,4'-bipyrazol-5'-yl]-N,N-dimethylimidoformamide Diazald® (2.5 g, 11.4 mmol) was used to generate diazomethane in diethyl ether (15 ml), using Aldrich Technical Bulletin AL-180. To Preparation 85 (150 mg, 0.3 mmol) in diethyl ether (10 ml) was added the diazomethane solution and the reaction mixture was allowed to stand at room temperature overnight. The reaction mixture was concentrated in vacuo to give the titled compound (130 mg).
Experimental MH⁺ 522.0; expected 522.1

Similarly Prepared was

Preparation 84

N'-[3'-cyano-1'-[2,6-dichloro-4-pentafluorothiophenyl]-3-(methylsulfonyl)-4,5-dihydro-1'H,3H-3,4'-bipyrazol-5'-yl]-N,N-dimethylimidoformamide from Preparation 71

Experimental MH⁺ 579.9; expected 580.0

Preparation 85

N'-{3-cyano-1-[2,6-dichloro-4-(trifluoromethyl)phenyl]-4-[1-(methylsulfonyl)-vinyl]-1H-pyrazol-5-yl}-N,N-dimethylimidoformamide To a solution of tetrakis(triphenylphosphine)palladium(0) (100 mg) in tetrahydrofuran (3 ml), purged with nitrogen, was added 1-bromo-1-(methylsulfonyl)ethylene (555 mg, 3.0 mmol), followed by a solution of Preparation 142 in tetrahydrofuran (0.2M, 10 ml, 2.0 mmol), added via syringe. The reaction mixture was then heated at reflux for 60 h. The reaction mixture was filtered through Celite® and the filtrate was concentrated in vacuo to give the titled compound (150 mg).
Experimental MH⁺ 480.0; expected 480.0

Similarly Prepared was

Preparation 86

1-(3-cyano-1-[2,6-dichloro-4-(trifluoromethyl)phenyl]-5-{[(dimethylamino)methylene]amino}-1H-pyrazol-4-yl)-N,N-dimethylethylenesulfonamide from Preparation 142 and Preparation 88

Experimental MH⁺ 509.0; expected 509.1

Preparation 87

1-bromoethylenesulfonamide

To a solution of 1,2-dibromoethanesulfonamide Preparation 103 (8.00 g, 30.00 mmol) in toluene (100 ml) and ethyl acetate (10 ml) was added dropwise triethylamine (4.6 ml, 36.00 mmol). The reaction mixture was stirred for 18 h at room temperature and then filtered. The filtrate was washed with hydrochloric acid (10%, 10 ml) and water (20 ml), dried (MgSO₄) and concentrated in vacuo to give the titled compound (5.00 g).
¹H-NMR (CDCl₃): 4.88-5.05 (2H), 6.11-6.14 (1H), 6.83-6.86 (1H)

Similarly Prepared was

Preparation 88

1-bromo-N,N-dimethylethylenesulfonamide from Preparation 90

¹H-NMR (CDCl₃): 2.90-3.00 (6H), 6.20-6.25 (1H), 6.76-6.80 (1H)

Preparation 89

1,2-dibromo-N-(tert-butyl)ethanesulfonamide

To a solution of Preparation 104 (6.00 g, 36.00 mmol) in dichloromethane (50 ml) was added bromine (3.6 ml, 72.00 mmol) and the reaction mixture was stirred at room temperature for 48 h. The reaction mixture was then concentrated in vacuo to give the titled compound (12.00 g) together with other impurities.
¹H-NMR (CDCl₃): 1.83-1.86 (3H), 3.80-3.84 (1H), 4.12-4.17 (1H), 5.00-5.05 (1H)

129

Similarly Prepared was

Preparation 90

1,2-dibromo-N,N-dimethylethanesulfonamide from Preparation 181

$^1$H-NMR (CDCl$_3$): 2.95-3.05 (6H), 3.60-3.70 (1H), 4.15-2.05 (1H), 4.90-5.00 (1H)

Preparation 91 methyl 1-{5-amino-3-cyano-1-[2,6-dichloro-4-(pentafluorothiophenyl]-1H-pyrazol-4-yl}cyclopropanecarboxylate To Preparation 61 (1.0 g, 1.88 mmol) in 1,4-dioxane (12.5 ml) and methanol (3.5 ml) was added hydrochloric acid (1M, 3.5 ml). The reaction mixture was then heated at reflux overnight. The reaction mixture was concentrated in vacuo and the residue was extracted with ethyl acetate. The combined extracts were washed with water, dried and concentrated in vacuo to give the titled compound (600 mg).

Experimental MH$^+$ 477.0; expected 477.0

Preparation 92 methyl 1-{5-amino-3-cyano-1-[2,6-dichloro-4-pentafluorothiophenyl]-1H-pyrazol-4-yl}-2,2-difluoro-cyclopropanecarboxylate A solution of Preparation 53 (3.00 g, 5.28 mmol) in p-toluenesulphonic acid (10% in methanol, 80 ml) was heated at reflux for 18 h. The reaction mixture was concentrated in vacuo and the residue was partitioned between saturated aqueous sodium hydrogencarbonate solution and ethyl acetate. The organic phase was separated, washed with brine, dried (MgSO$_4$) and concentrated in vacuo. The residue was triturated with cold ethanol to give the titled compound (500 mg).

Experimental MH$^+$ 513.0; expected 513.0

Preparation 93 methyl 1-{5-amino-3-cyano-1-[2,6-dichloro-4-(trifluoromethoxy)phenyl]-1H-pyrazol-4-yl}-2,2-difluorocyclopropanecarboxylate A mixture of Preparation 54 (7.20 g, 13.70 mmol) and hydrochloric acid (4N, 20 ml) in methanol (50 ml) was heated at reflux for 18 h. The reaction mixture was concentrated in vacuo to give the titled compound (6.50 g).

Experimental MH$^+$ 470.9; expected 471.0

130

Similarly Prepared were:

| Preparation | R1 | R3 | R4 | R5 | R6 | R8 | R2 | From |
|---|---|---|---|---|---|---|---|---|
| Preparation 94 | CF3 | H | H | F | F | CN | COOH | Preparation 26 |
| Preparation 95 | CF3O | H | H | H | H | CN | COOCH3 | Preparation 63 |
| Preparation 96 | CF3 | H | H | F | F | CN | F | Preparation 58 |
| Preparation 97 | CF3 | H | H | H | H | CF3 | COOCH3 | Preparation 62 |
| Preparation 98 | CF3 | H | H | CH3 | CH3 | CN | COOCH3 | Preparation 60 |

Preparation 94

1-{5-amino-3-cyano-1-[2,6-dichloro-4-(trifluoromethyl)phenyl]-1H-pyrazol-4-yl}-2,2-difluorocyclopropanecarboxylic acid Experimental MH$^+$ 440.8; expected 441.0

Preparation 95 methyl 1-{5-amino-3-cyano-1-[2,6-dichloro-4-(trifluoromethoxy)phenyl]-1H-pyrazol-4-yl}cyclopropanecarboxylate Experimental MH$^+$ 435.0; expected 435.0

Preparation 96

5-amino-1-[2,6-dichloro-4-(trifluoromethyl)phenyl]-4-(1,2,2-trifluorocyclopropyl)-1H-pyrazole-3-carbonitrile Experimental MH$^+$ 415.1; expected 415.0

Preparation 97 methyl 1-{5-amino-1-[2,6-dichloro-4-(trifluoromethyl)phenyl]-3-(trifluoromethyl)-1H-pyrazol-4-yl}cyclopropanecarboxylate Experimental MH$^+$ 462.0; expected 462.0

Preparation 98 methyl 1-{5-amino-3-cyano-1-[2,6-dichloro-4-(trifluoromethyl)phenyl]-1H-pyrazol-4-yl}-2,2-dimethylcyclopropanecarboxylate Experimental MH$^+$ 447.0; expected 447.1

Preparation 99

N'-{4-(1-amino-2,2-difluorocyclopropyl)-3-cyano-1-[2,6-dichloro-4-(trifluoromethyl)phenyl]-1H-pyrazol-5-yl}-N,N-dimethylimidoformamide To a solution of Preparation 100 (30 mg, 0.05 mmol) in dichloromethane (1.5 ml) was added slowly trifluoroacetic acid (500 μl). The reaction mixture was then sealed and stirred for 3 h. The reaction mixture was concentrated under nitrogen to give the titled compound (30 mg) which was used directly

Preparation 100 tert-butyl [1-(3-cyano-1-[2,6-dichloro-4-(trifluoromethyl)phenyl]-5-{[(dimethylamino)methylene]amino}-1H-pyrazol-4-yl)-2,2-difluorocyclopropyl] carbamate To a solution of Preparation 26 (180 mg, 0.35 mmol) in tert-butanol (5 ml) was added diphenylphosphoryl azide (77 μl, 0.35 mmol) and triethylamine (50 μl, 0.35 mmol). The reaction mixture was then heated at 90° C. for 3 h. To the reaction mixture was added aqueous sodium hydrogencarbonate solution and the mixture was extracted with ethyl acetate. The combined extracts were washed with brine, dried (MgSO$_4$) and concentrated in vacuo. The residue was purified by column chromatography (silica) with gradient elution, ethyl acetate:cyclohexane [0:1 to 1:1]. The appropriate fractions were combined and concentrated to give the titled compound (30 mg).

Experimental MH$^+$ 567.1; expected 567.1

Preparation 101 bromo[1-({[(dimethylamino)methylene]amino}sulfonyl)vinyl]zinc

To a solution of Preparation 102 (480 mg, 1.94 mmol) in N,N-dimethylformamide (2 ml), under nitrogen, was added Rieke® Zinc (0.8N in N,N-dimethylformamide, 5 ml, 4.00 mmol). The reaction mixture was stirred under nitrogen for 4 h and then filtered (Waterman 0.45μ to give a solution of the titled compound, which was used directly

Preparation 102

1-bromo-N-[(dimethylamino)methylene]ethylenesulfonamide

To a solution of Preparation 87 (930 mg, 5.00 mmol) in dichloromethane (5 ml) was added N,N-dimethylformamide dimethyl acetal (595 mg, 5.00 mmol). The reaction mixture was heated at 50° C. for 1 h and then concentrated in vacuo. The residue was purified by column chromatography (silica) with gradient elution, ethyl acetate:hexane [0:1 to 1:0]. The appropriate fractions were combined and concentrated to give the titled compound (1.20 g).

$^1$H-NMR (CDCl$_3$): 3.05-3.13 (3H), 3.15-3.23 (3H), 6.01-6.10 (1H), 6.83-6.91 (1H), 8.01-8.09 (1H)

Preparation 103

1,2-dibromoethanesulfonamide

To a solution of Preparation 89 (12.00 g, 56.00 mmol) in dichloromethane (30 ml) was added trifluoroacetic acid (30 ml) and the reaction mixture was stirred at room temperature for 14 h. The reaction mixture was then concentrated in vacuo to give the titled compound (8.00 g).

$^1$H-NMR (CDCl$_3$): 3.79-3.84 (1H), 4.11-4.17 (1H), 5.00-5.03 (1H), 5.03-5.11 (2H)

Preparation 104

N-(tert-butyl)ethylenesulfonamide

To a solution of 2-chloroethylsulphonyl chloride (9.20 g, 55.00 mmol) in diethyl ether (50 ml), at −78° C., was added a 1:1 mixture of tert-butylamine (5.8 ml, 55.00 mmol) and triethylamine (7.6 ml, 55.00 mmol). After complete addition, hydrochloric acid (10%, 10 ml) was added and the two layers were separated. The aqueous layer was extracted with dichloromethane (×3) and the combined organic phases were washed with water, dried (MgSO$_4$) and concentrated in vacuo to give the titled compound (6.00 g).

$^1$H-NMR (CDCl$_3$): 1.28-1.34 (9H), 4.26-4.36 (1H), 5.77-5.82 (1H), 6.15-6.22 (1H), 6.52-6.60 (1H)

Preparation 105

5-amino-1-[2,6-dichloro-4-pentafluorothiophenyl]-4-iodo-1H-pyrazole-3-carbonitrile To a solution of Preparation 108 (40.0 g, 106 mmol) in acetonitrile (400 ml) was added N-iodosuccinimide (26.4 g, 117 mmol) and the reaction mixture was stirred at room temperature overnight. The reaction mixture was diluted with ethyl acetate (1 l) and washed with aqueous sodium thiosulphate solution (10%, 3×500 ml) and brine (500 ml). The organic phase was dried (MgSO$_4$) and concentrated in vacuo to give the titled compound (53 g) as a brown solid.

$^1$H-NMR (CDCl$_3$): 3.87-3.94 (2H), 7.88-7.90 (2H)

Preparation 106

5-(cyclopropylmethoxy)-1-[2,6-dichloro-4-pentafluorothiophenyl]-4-iodo-1H-pyrazole-3-carbonitrile To a solution of Preparation 204 (2.97 g, 6.84 mmol) in ethanol (68 ml) was added silver sulphate (4.30 g, 13.70 mmol), followed by iodine (3.50 g, 13.70 mmol). After stirring for 3 h, the solution was filtered and the precipitate partitioned between aqueous sodium hydroxide solution (1M) and dichloromethane. The two layers were separated and the organic layer was washed with brine, dried (MgSO$_4$) and concentrated in vacuo. The residue was filtered through silica, washing through with ethyl acetate, and the filtrate was concentrated in vacuo to give the titled compound (3.53 g)

Experimental MH$^+$ (acetonitrile adduct) 600.8; expected 600.9.

Preparation 107

5-amino-1-[2,6-dichloro-4-(trifluoromethoxy)phenyl]-4-iodo-1H-pyrazole-3-carbonitrile Reference: WO-9804530A1; WO-9707102A1

Preparation 108

5-amino-1-[2,6-dichloro-4-pentafluorothiophenyl]-1H-pyrazole-3-carbonitrile

Reference: WO 9306089 A1, EP 605469 A1

Preparation 109

1-[2,6-dichloro-4-(trifluoromethyl)phenyl]-4-iodo-3-(trifluoromethyl)-1H-pyrazol-5-amine Reference: WO9707102A1

Preparation 110 methyl 1-[3-cyano-1-[2,6-dichloro-4-pentafluorothiophenyl]-5-(isobutylamino)-1H-pyrazol-4-yl]cyclopropanecarboxylate To a mixture of Preparation 91 (300 mg, 0.63 mmol), p-toluenesulphonic acid (12 mg) and 4 Å molecular sieves (300 mg) in toluene (17 ml) was added isobutyraldehyde (2.9 ml, 31.50 mmol). The reaction mixture was stirred at room temperature for 16 h, washed with ethyl acetate and concentrated in vacuo. To a solution of the residue in methanol, at 0° C., was added sodium borohydride (75 mg) and the mixture was stirred at room temperature for 14 h. Hydrochloric acid (1M, 50 ml) was added and the mixture was extracted with ethyl acetate. The combined extracts were washed with water, dried (MgSO$_4$) and concentrated in vacuo. The residue was dissolved in acetonitrile (1 ml) and purified by automated preparative liquid chromatography (Gilson system, 150 mm×50 mm Phenomenex LUNA C18(2) 10 µm column) using an acetonitrile:water gradient. The appropriate fractions were concentrated in vacuo to give the titled compound (43 mg).

Experimental MH$^+$ 532.9; expected 533.1

Similarly Prepared from the Appropriate Aldehydes were:

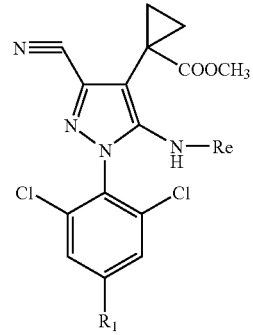

| Preparation | R1 | Re | Experimental MH$^+$ | Expected MH$^+$ | From |
|---|---|---|---|---|---|
| Preparation 111 | CF$_3$O | cyclopropylmethyl | 489.0 | 489.1 | Preparation 95 |
| Preparation 112 | SF$_5$ | (2-chloro-1,2-thiazol-5-yl)methyl | 607.9 | 608.0 | Preparation 91 |
| Preparation 113 | SF$_5$ | Isoxazol-5-ylmethyl | 558.1 | 558.0 | Preparation 91 |
| Preparation 114 | SF$_5$ | methylthiopropyl | 565.1 | 565.0 | Preparation 91 |
| Preparation 115 | CF$_3$ | 2,2-dimethylpropyl | 489.1 | 489.1 | Example 3 |
| Preparation 116 | CF$_3$ | (4-methylsulphonyl)benzyl | 587.0 | 587.1 | Example 3 |
| Preparation 117 | SF$_5$ | 4-fluorobenzyl | 585.1 | 585.0 | Preparation 91 |
| Preparation 118 | SF$_5$ | 4[(methylamino)sulphonyl]benzyl | 660.0 | 660.0 | Preparation 91 |
| Preparation 119 | SF$_5$ | (tetrahydro-2H-pyran-4-yl)methyl | 574.9 | 575.1 | Preparation 91 |
| Preparation 120 | SF$_5$ | (5-chloro-1,3-dimethyl-1H-pyrazol-4-yl)methyl | 619.0 | 619.0 | Preparation 91 |
| Preparation 121 | SF$_5$ | t-BOC-propyl | 619.1 | 619.1 | Preparation 91 |
| Preparation 122 | SF$_5$ | (1,3-thiazol-2-yl)methyl | 574.0 | 574.0 | Preparation 91 |
| Preparation 123 | SF$_5$ | 2-(1-methyl-1H-pyrazol-4-yl)ethyl | 585.0 | 585.1 | Preparation 91 |
| Preparation 124 | CF$_3$ | (4-trifluoromethyl)benzyl | 577.1 | 577.1 | Example 3 |
| Preparation 125 | SF$_5$ | (1-methylcyclopropyl)methyl | 545.0 | 545.1 | Preparation 91 |
| Preparation 126 | SF$_5$ | 4-[(methylsulphonyl)amino]benzyl | 660.1 | 660.0 | Preparation 91 |
| Preparation 127 | SF$_5$ | 4,4,4-trifluorobutyl | 586.9 | 587.0 | Preparation 91 |
| Preparation 128 | SF$_5$ | ethyl | 505.3 | 505.1 | Preparation 91 |
| Preparation 129 | SF$_5$ | propyl | 518.8 | 519.0 | Preparation 91 |

Also Similarly Prepared

Preparation 130 methyl 1-{3-cyano-1-[2,6-dichloro-4-pentafluorothiophenyl]-5-[(3,3,3-trifluoropropyl)amino]-1H-pyrazol-4-yl}cyclopropanecarboxylate from Preparation 91

1H-NMR (CDCl$_3$): 1.35-1.40 (2H), 1.78-1.82 (2H), 2.19-2.30 (2H), 3.25-3.31 (2H), 3.40-3.49 (1H), 3.70-3.72 (3H), 7.90-7.93 (2H)

Preparation 131 methyl 1-{3-cyano-5-[(cyclopropylmethyl)amino]-1-[2,6-dichloro-4-(trifluoromethyl)phenyl]-1H-pyrazol-4-yl}cyclopropanecarboxylate To a solution of Example 3 (150 mg, 0.36 mmol) in 1-methyl-2-pyrrolidinone (5 ml) was added sodium hydride (60% in oils, 16 mg, 0.40 mmol). After stirring for 30 min, (bromomethyl)cyclopropane (53 mg, 0.40 mmol) was added and the reaction mixture was stirred for 18 h at room temperature. The reaction mixture was concentrated in vacuo and the residue was dissolved in acetonitrile (1 ml) and purified by automated preparative liquid chromatography (Gilson system, 150 mm×50 mm Phenomenex LUNA C18(2) 10 µm column) using an acetonitrile:water gradient. The appropriate fractions were concentrated in vacuo to give the titled compound (32 mg).

Experimental MH$^+$ 472.9; expected 473.1

Similarly Prepared was

Preparation 132 methyl 1-{3-cyano-1-[2,6-dichloro-4-pentafluorothiophenyl]-5-[(5,5,5-trifluoropentyl)amino]-1H-pyrazol-4-yl}cyclopropanecarboxylate from Preparation 91 and 5-iodo-1,1,1-trifluoropentane Experimental MH$^+$ 601.0; expected 601.0

Preparation 133

Methyl N-{3-cyano-1-[2,6-dichloro-4-pentafluorothiophenyl]-4-[1-(methoxycarbonyl)cyclopropyl]-1H-pyrazol-5-yl}-beta-alaninate A solution of Preparation 91 (250 mg, 0.52 mmol), p-toluenesulphonic acid (20 mg), 4 A molecular sieves and methyl 3,3-dimethoxypropanoate (223 µl, 1.57 mmol) in anhydrous dichloromethane (4 ml) was stirred at room temperature for 18 h. The reaction mixture was then filtered and the filtrate was added to a solution of sodium borohydride (200 mg, 5.20 mmol) in methanol (10 ml) at 0° C. After stirring for 18 h, the mixture was quenched with water and extracted with ethyl acetate. The combined extracts were washed with brine, dried (MgSO$_4$) and concentrated in vacuo. The residue was purified by column chromatography (silica), eluting with cyclohexane/ethyl acetate [3:2]. The appropriate fractions were combined and concentrated to give the titled compound (131 mg)

Experimental MH$^+$ 563.0; expected 563.0.

Preparation 134 methyl 1-{3-cyano-1-[2,6-dichloro-4-pentafluorothiophenyl]-5-[(2-fluoro-2-methylpropyl)amino]-1H-pyrazol-4-yl}cyclopropanecarboxylate To a mixture of Preparation 91 (200 mg, 0.42 mmol), (1,1,1-triacetoxy)-1,1-dihydro-1,2-benziodoxol-3(1H)-one (863 mg, 2.04 mmol) and p-toluenesulphonic acid (20 mg) in dichloromethane (3 ml) was added dropwise Preparation 231 (0.5 ml). After stirring for 10 min, the mixture was added dropwise to a solution of sodium borohydride (154 mg, 4.07 mmol) in methanol (5 ml) at 0° C. After stirring at 0° C. for 30 min, the mixture was partitioned between water and ethyl acetate. The two layers were separated and the organic layer was washed with saturated aqueous sodium hydrogen carbonate solution and brine, dried (MgSO$_4$) and concentrated in vacuo. The residue was dissolved in acetonitrile (2 ml) and purified by automated preparative liquid chromatography (Gilson system, 150 mm×50 mm LUNA C18(2) 10 µm column) using an acetonitrile:water gradient [65:35 to 98:2]. The appropriate fractions were concentrated in vacuo to give the titled compound (72 mg). This was used directly.

Preparation 135 methyl 1-{3-cyano-1-[2,6-dichloro-4-pentafluorothiophenyl]-5-[(2-fluoroethyl)amino]-1H-pyrazol-4-yl}cyclopropanecarboxylate To a solution of Preparation 91 (250 mg, 0.50 mmol) in dichloromethane (5 ml) was added 2-fluoroethanol (160 mg, 2.50 mmol), followed by Dess-Martin periodinane (1.15 g, 2.50 mmol). After stirring at room temperature for 5 h, the solution was filtered through Celite® and the filtrate was added carefully to a solution of sodium borohydride (200 mg, 5.00 mmol) in methanol (5 ml) at 0° C. The reaction mixture was stirred at 0° C. for 30 min, before addition of water and ethyl acetate, and the organic layer was separated. The aqueous layer was extracted with ethyl acetate and the combined organic phases were washed with aqueous sodium hydrogen carbonate solution and brine, dried (MgSO$_4$) and concentrated in vacuo to give the titled compound (100 mg).

1H-NMR (CDCl$_3$): 1.35-1.40 (2H), 1.71-1.78 (2H), 3.20-3.32 (2H), 3.65-3.67 (3H), 4.30-4.45 (2H), 7.90-7.94 (2H)

Similarly Prepared was

Preparation 136 methyl 1-{3-cyano-1-[2,6-dichloro-4-pentafluorothiophenyl]-5-[(2-isopropoxyethyl)amino]-1H-pyrazol-4-yl}cyclopropanecarboxylate from Preparation 91 and Isopropoxyethanol Experimental MH$^+$ 563.1; expected 563.1

Preparation 137 methyl 1-[3-cyano-1-[2,6-dichloro-4-(trifluoromethoxy)phenyl]-5-(methylamino)-1H-pyrazol-4-yl]cyclopropanecarboxylate To a solution of Preparation 139 (280 mg, 0.58 mmol) in ethanol (10 ml) was added sodium borohydride (54 mg, 1.44 mmol) and the reaction mixture was stirred at room temperature for 18 h. To the reaction mixture was added hydrochloric acid (2N) and the solution was concentrated in vacuo. The residue was partitioned between ethyl acetate (15 ml) and water (15 ml) and the two layers were separated. The organic phase was dried (MgSO$_4$) and concentrated in vacuo to give the titled compound (200 mg) as a mixture of products.
Experimental MH$^+$ 448.9; expected 449.0

Similarly Prepared was

Preparation 138 methyl 1-{3-cyano-1-[2,6-dichloro-4-pentafluorothiophenyl]-5-(methylamino)-1H-pyrazol-4-yl}-2,2-difluorocyclopropanecarboxylate from Preparation 140

Experimental MH$^+$ 526.9; expected 527.0

Preparation 139 methyl 1-(3-cyano-1-[2,6-dichloro-4-(trifluoromethoxy)phenyl]-5-{[ethoxymethylene]amino}-1H-pyrazol-4-yl)cyclopropanecarboxylate A mixture of Preparation 95 (250 mg, 0.58 mmol) and hydrochloric acid (concentrated, 2 drops) in triethylorthoformate (8 ml) was heated at 50° C. for 30 min and then stirred at room temperature overnight. The reaction mixture was concentrated in vacuo and the residue was azeotroped with toluene to give the titled compound (280 mg).
Experimental MH$^+$ 490.7; expected 491.1

Preparation 140 methyl 1-(3-cyano-1-[2,6-dichloro-4-pentafluorothiophenyl]-5-{[ethoxymethylene]amino}-1H-pyrazol-4-yl)-2,2-difluorocyclopropanecarboxylate A mixture of Preparation 92 (223 mg, 0.44 mmol) and hydrochloric acid (1 drop) in triethyl orthoformate (6 ml) was heated at 50° C. for 2 h and then stirred at room temperature for 18 h. The reaction mixture was concentrated in vacuo and the residue was dissolved in toluene and re-concentrated to give the titled compound (250 mg).
Experimental MH$^+$ 568.9; expected 569.0

Similarly Prepared was

Preparation 141 methyl {3-cyano-4-(1-cyanocyclopropyl)-1-[2,6-dichloro-4-pentafluorothiophenyl]-1H-pyrazol-5-yl}imidoformate from Example 11

Experimental MH$^+$ 486.3; expected 486.0

Preparation 142

(3-cyano-1-[2,6-dichloro-4-(trifluoromethyl)phenyl]-5-{[(dimethylamino)methylene]amino}-1H-pyrazol-4-yl)(iodo)zinc To a solution of Preparation 219 (5.02 g, 10.0 mmol) in tetrahydrofuran (24 ml), under nitrogen, was added Rieke® zinc (1.31 g, 20.0 mmol) as a slurry in tetrahydrofuran (26 ml). The reaction mixture was then stirred overnight at room temperature. The excess zinc metal was allowed to settle and the solution containing the titled compound (0.2 mol per litre) was used directly in the next stage.

Preparation 143 methyl 1-{3-cyano-5-[(cyclopropylmethyl)amino]-1-[2,6-dichloro-4-pentafluorothiophenyl]-1H-pyrazol-4-yl}cyclopropanecarboxylate A mixture of Preparation 151 (22.00 g, 44.00 mmol) and borane-pyridine complex (6.7 ml, 66.00 mmol) in methanol (250 ml) was stirred at room temperature for 2 h. Additional borane-pyridine complex (6.7 ml, 66.00 mmol) was added and the reaction mixture was stirred for 48 h. The reaction mixture was quenched with hydrochloric acid (2N) and partitioned between ethyl acetate and water. The two layers were separated and the aqueous layer was extracted with ethyl acetate. The combined organic phases were washed with water and saturated brine solution, dried (MgSO$_4$) and concentrated in vacuo. The residue was absorbed on to silica and purified by column chromatography (silica), eluting with dichloromethane. The appropriate fractions were combined and concentrated to give the titled compound (11.00 g).
Similarly Prepared were:

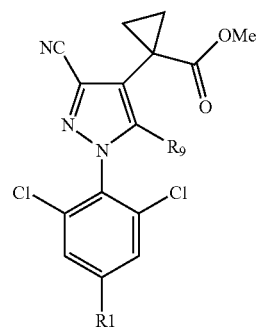

| Prep | R1 | R9 | Experimental MH$^+$ | Expected MH$^+$ | From |
|---|---|---|---|---|---|
| Preparation 144 | SF$_5$ | [(4h-1,2,4-triazol-3-yl)methyl]amino | 558.0 | 558.0 | Preparation 149 |

| | | | | | |
|---|---|---|---|---|---|
| Preparation 145 | CF₃ | (pyridin-2-ylmethyl)amino | 510.0 | 510.1 | Preparation 153 |
| Preparation 146 | CF₃ | (pyridin-4-ylmethyl)amino | 510.0 | 510.1 | Preparation 154 |
| Preparation 147 | CF₃ | (2,2,2-trifluoroethyl)amino | 501.0 | 501.0 | Preparation 155 |
| Preparation 148 | CF₃ | (1H-iimidazol-2-ylmethyl)amino | 499.1 | 499.1 | Preparation 156 |

Preparation 149 methyl 1-(3-cyano-1-[2,6-dichloro-4-pentafluorothiophenyl]-5-{[1H-1,2,4-triazol-5-ylmethylene]amino}-1H-pyrazol-4-yl)cyclopropanecarboxylate A mixture of Preparation 91 (500 mg, 1.04 mmol), p-toluenesulphonic acid (20 mg, 0.11 mmol) and 4H-1,2,4-triazole-3-carboxaldehyde (302 mg, 3.12 mmol) in toluene (50 ml) was heated at reflux for 3 h. The reaction mixture was concentrated in vacuo to give the titled compound (500 mg), which was used directly.

Preparation 150

1-{3-cyano-5-{[(cyclopropylmethylene]amino}-1-[2,6-dichloro-4-pentafluorothiophenyl]-1H-pyrazol-4-yl}-2,2-difluorocyclopropanecarboxamide A mixture of Example 53 (100 mg, 0.20 mmol), p-toluenesulphonic acid (4 mg, 0.02 mmol), 4 Å molecular sieves and cyclopropane carboxaldehyde (42 mg, 0.60 mmol) was heated at 115° C. for 18 h. The reaction mixture was then concentrated in vacuo to give the titled compound (111 mg).

Experimental MH⁺ 550.1; expected 550.0

Preparation 151 methyl 1-{3-cyano-5-[(cyclopropylmethylene)amino]-1-[2,6-dichloro-4-pentafluorothiophenyl]-1H-pyrazol-4-yl}cyclopropanecarboxylate A mixture of Preparation 91 (21.00 g, 44.00 mmol), cyclopropane carboxaldehyde (9.85 ml, 132.00 mmol) and 4 Å molecular sieves (21.00 g) in toluene (210 ml) was stirred at room temperature for 60 h. The reaction mixture was filtered through Celite® and concentrated in vacuo to give the titled compound (22.00 g).

Similarly Prepared were:

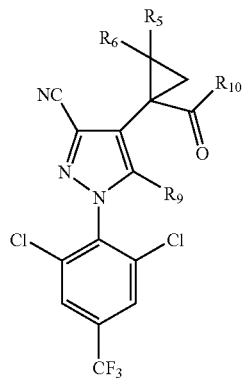

| Prep | R5 | R6 | R9 | R10 | Experimental MH⁺ | Expected MH⁺ | From |
|---|---|---|---|---|---|---|---|
| Preparation 152 | H | H | phenylmethyleneamino | OCH3 | 506.8 | 507.1 | Example 3 |
| Preparation 153 | H | H | (pyridin-2-yl)methyleneamino | OCH3 | 508.0 | 508.1 | Example 3 |
| Preparation 154 | H | H | (pyridin-4-yl)methyleneamino | OCH3 | 508.0 | 508.1 | Example 3 |
| Preparation 155 | H | H | (2,2,2-trifluoroethylidene)amino | OCH3 | | | Example 3 |
| Preparation 156 | H | H | (1H-imidazol-2 ylmethylene)amino | OCH3 | 497.0 | 497.1 | Example 3 |
| Preparation 157 | F | F | cyclopropylmethyleneamino | NH2 | 492.2 | 492.0 | Example 55 |

Preparation 158 tert-butyl 2-{[1-(3-cyano-1-[2,6-dichloro-4-(trifluoromethyl)phenyl]-5-{[(dimethylamino)methylene]amino}-1H-pyrazol-4-yl)cyclopropyl]carbonyl}hydrazinecarboxylate A mixture of Preparation 27 (500 mg, 1.10 mmol), 1-hydroxybenzotriazole hydrate (178 mg, 1.32 mmol), 1-(3-dimethylaminopropyl)-3-ethylcarbodiimide (253 mg, 1.32 mmol), t-butylcarbazate (174 mg, 1.32 mmol) and N-methylmorpholine (0.30 ml, 2.75 mmol) in N,N-dimethylformamide (8 ml) was stirred at room temperature for 18 h. The reaction mixture was then poured into water (40 ml) and the product was extracted with ethyl acetate (3×30 ml). The combined extracts were washed with brine (50 ml), dried (MgSO$_4$) and concentrated in vacuo. The residue was purified by column chromatography (silica) with gradient elution, cyclohexane:ethyl acetate [3:1 to 1:1]. The appropriate fractions were combined and concentrated to give the titled compound (692 mg).

Experimental MH$^+$ 573.9; expected 574.1

Similarly Prepared was

Preparation 159

N'-acetyl-1-{5-amino-3-cyano-1-[2,6-dichloro-4-(trifluoromethyl)phenyl]-1H-pyrazol-4-yl}cyclopropanecarbohydrazide from Preparation 178

Experimental MH$^+$ 460.9; expected 461.1

Preparation 160

N'-{3-cyano-1-[2,6-dichloro-4-(trifluoromethyl)phenyl]-4-[1-(hydrazine-carbonyl)-cyclopropyl]-1H-pyrazol-5-yl}-N,N-dimethylimidoformamide To a solution of Preparation 158 (60 mg, 0.11 mmol) in 1,4-dioxane (1 ml), at 0° C., was added hydrogen chloride (4N in 1,4-dioxane, 1 ml). The reaction mixture was allowed to warm to room temperature and stirred for 4 h. The solution was then concentrated in vacuo to give the titled compound as a mixture of product and starting material.

Experimental MH$^+$ 473.9; expected 474.1

Preparation 161

N'-{3-cyano-1-[2,6-dichloro-4-(trifluoromethyl)phenyl]-4-[1-(1,3,4-oxadiazol-2-yl)cyclopropyl]-1H-pyrazol-5-yl}-N,N-dimethylimidoformamide A mixture of Preparation 160 (approximately 0.11 mmol), triethyl orthoformate (3 ml) and p-toluenesulphonic acid (2 mg) was heated at reflux for 4 h. The reaction mixture was then concentrated in vacuo to give the titled compound (50 mg).

Experimental MH$^+$ 483.9; expected 484.1

Preparation 162

1-{5-amino-3-cyano-1-[2,6-dichloro-4-(trifluoromethyl)phenyl]-1H-pyrazol-4-yl}cyclopropanecarbohydrazide A mixture of Preparation 161 (250 mg, 0.52 mmol) and hydrochloric acid (5N, 1 ml) in methanol (2 ml) and 1,4-dioxane (8 ml) was heated at reflux for 2 h. The reaction mixture was concentrated in vacuo and the residue was partitioned between ethyl acetate (10 ml) and water (10 ml). The organic phase was separated, dried (MgSO$_4$) and concentrated in vacuo. The residue was dissolved in acetonitrile (1 ml) and purified by automated preparative liquid chromatography (Gilson system, 150 mm×50 mm Phenomenex LUNA C18(2) 10 μm column) using an acetonitrile:water gradient. The appropriate fractions were concentrated in vacuo to give the titled compound (75 mg).

Experimental MH$^+$ 418.9; expected 419.0

Preparation 163 methyl 1-[3-cyano-1-[2,6-dichloro-4-pentafluorothiophenyl]-5-(methylamino)-1H-pyrazol-4-yl]cyclopropanecarboxylate To a solution of Preparation 91 (6.84 g, 14.30 mmol) in triethylorthoformate (180 ml) was added hydrochloric acid (concentrated, 0.5 ml) and the reaction mixture was heated at 50° C. for 2 h. The mixture was concentrated in vacuo and to the residue was added ethanol (120 ml). The solution was cooled to 0° C. and sodium borohydride (1.20 g, 31.50 mmol) was added over 5 min. After stirring for 16 h at room temperature, acetic acid (2.5 ml) was added, followed by water (300 ml). After a further 10 min, the mixture was extracted with ethyl acetate and the combined extracts were dried (MgSO$_4$) and concentrated in vacuo. The residue was purified by column chromatography (silica), eluting with ethyl acetate/hexane [1:3]. The appropriate fractions were combined and concentrated to give the titled compound (4.74 g).

Experimental MH$^+$ 491.0; expected 491.0

Similarly Prepared was

Preparation 164 ethyl 2,2-dichloro-1-{3-cyano-1-[2,6-dichloro-4-pentafluorothiophenyl]-5-(methylamino)-1H-pyrazol-4-yl}cyclopropanecarboxylate from Preparation 170

Experimental MH$^+$ 573.0; expected 572.9

Preparation 165 methyl 1-{3-cyano-1-[2,6-dichloro-4-pentafluorothiophenyl]-5-methyl-1H-pyrazol-4-yl}cyclopropanecarboxylate A mixture of Preparation 166 (232 mg, 0.47 mmol) and thionyl chloride (69 μl, 0.94 mmol) was heated at reflux for 2 h. The mixture was concentrated in vacuo and to the residue was added tetrahydrofuran (4.7 ml). This solution was cooled to 0° C. and Rieke® Zinc (0.76M in tetrahydrofuran, 3.1 ml, 2.35 mmol) was added. After stirring for 30 min, the reaction mixture was warmed to room temperature and additional Rieke® Zinc (0.76M in tetrahydrofuran, 15.5 ml, 11.78 mmol) was added. After stirring for another 18 h, the reaction mixture was poured slowly into ice/hydrochloric acid (1M). The mixture was extracted with ethyl acetate and the combined extracts were dried (MgSO$_4$) and concentrated in vacuo.

The residue was purified by column chromatography (silica) with gradient elution, ethyl acetate:cyclohexane [5:95 to 15:85]. The appropriate fractions were combined and concentrated to give the titled compound (40 mg).
Experimental MH$^+$ 475.9; expected 476.0

Preparation 166 methyl 1-[3-cyano-1-[2,6-dichloro-4-pentafluorothiophenyl]-5-(hydroxymethyl)-1H-pyrazol-4-yl] cyclopropanecarboxylate To a solution of Preparation 167 (671 mg, 1.21 mmol) in methanol (12 ml), at 0° C., was added sodium borohydride (60 mg, 1.57 mmol) portionwise. After 1 h, the reaction mixture was warmed to room temperature and poured into hydrochloric acid (1M, excess). The mixture was extracted with ethyl acetate and the combined extracts were dried (MgSO$_4$) and concentrated in vacuo. The residue was purified by column chromatography (silica) with gradient elution, ethyl acetate:cyclohexane [1:9 to 3:7]. The appropriate fractions were combined and concentrated to give the titled compound (406 mg).
Experimental MH$^+$ 491.9; expected 492.0

Preparation 167 methyl 1-{3-cyano-1-[2,6-dichloro-4-pentafluorothiophenyl]-5-formyl-1H-pyrazol-4-yl}cyclopropanecarboxylate To a solution of Preparation 168 (663 mg, 1.21 mmol) in aqueous acetone (10%, 10 ml) was added osmium tetroxide (1.5 ml, 0.12 mmol), followed by sodium periodate (2.60 g, 12.1 mmol), added over a period of 4 h. After stirring at room temperature for 14 h, the reaction mixture was filtered, washing through with acetone, and the filtrate was concentrated in vacuo. The residue was passed through a silica plug, eluting with ethyl acetate/cyclohexane [1:1]. The appropriate fractions were combined and concentrated to give the titled compound (0.98 g) as a 4:1 mixture with the starting material.
$^1$H-NMR (CDCl$_3$): 1.48-1.53 (2H), 1.94-1.98 (2H), 3.70-3.74 (3H), 7.88-7.91 (2H), 9.94-9.95 (1H)

Preparation 168 methyl 1-{3-cyano-1-[2,6-dichloro-4-pentafluorothiophenyl]-5-[3-methoxy-3-oxoprop-1-en-1-yl]-1H-pyrazol-4-yl}cyclopropanecarboxylate To a solution of Preparation 169 (0.96 g, 1.53 mmol) in toluene (7.5 ml), at 0° C., was added 1,8-diazabicyclo[5.4.0] undec-7-ene (DBU, 250 µl, 1.68 mmol). The reaction mixture was allowed to warm to room temperature and stirred for 2 h. The reaction mixture was partitioned between hydrochloric acid (1M) and ethyl acetate and the organic phase was separated, washed with water, dried (MgSO$_4$) and concentrated in vacuo. The residue was purified using a silica plug, eluting with ethyl acetate/cyclohexane [3:7]. The appropriate fractions were combined and concentrated to give the titled compound (0.84 g).
Experimental MH$^+$ 545.8; expected 546.0

Preparation 169 methyl 1-{5-(2-bromo-3-methoxy-3-oxopropyl)-3-cyano-1-[2,6-dichloro-4-pentafluorothiophenyl]-1H-pyrazol-4-yl}cyclopropanecarboxylate To a mixture of methyl acrylate (4.5 ml, 50.00 mmol), copper (II) bromide (0.84 g, 3.75 mmol) and tert-butyl nitrite (0.48 ml, 4.00 mmol) in acetonitrile (25 ml), at 0° C., was added dropwise Preparation 91 (1.20 g, 2.50 mmol) in acetonitrile (12 ml). The reaction mixture was stirred at 0° C. for 10 min and then at room temperature for 1 h. The reaction mixture was concentrated in vacuo and the residue was partitioned between water and ethyl acetate. The organic phase was separated, dried (MgSO$_4$) and concentrated in vacuo. The residue was purified by column chromatography (silica) with gradient elution, ethyl acetate:cyclohexane [2:98 to 10:90]. The appropriate fractions were combined and concentrated to give the titled compound (0.98 g).
Experimental MH$^+$ 625.7; expected 625.9

Preparation 170 ethyl 1-{5-amino-3-cyano-1-[2,6-dichloro-4-pentafluorothiophenyl]-1H-pyrazol-4-yl}-2,2-dichlorocyclopropanecarboxylate To a solution of Preparation 182 (1.00 g, 3.50 mmol) in ethanol (5 ml), at 0° C., was added tetrafluoroboric acid (48% in water, 1.0 ml, 7.35 mmol), followed by isoamylnitrite (0.32 ml, 3.85 mmol). The reaction mixture was then stirred for 40 min. The product was collected by filtration and dried to give 2,6-dichloro-4-pentafluorothiobenzenediazonium tetrafluoroborate A solution of Preparation 187 (100 mg, 0.31 mmol) and pyridine (75 µl) in methanol (2 ml), at 0° C., was stirred for 15 min, before addition of 2,6-dichloro-4-pentafluorothiobenzenediazonium tetrafluoroborate (121 mg, 0.31 mmol). The reaction mixture was then stirred at room temperature for 30 min. To the reaction mixture was added diethyl ether (20 ml) and the solution was washed with water and brine. The organic layer was separated, dried (Na$_2$SO$_4$) and concentrated in vacuo to give the titled compound (220 mg).
Experimental MH$^+$ 558.8; expected 558.9

Similarly Prepared were

Preparation 171 ethyl 1-(5-amino-3-cyano-1-{2,6-dichloro-4-[1,2,2,2-tetrafluoro-1-(trifluoromethyl)ethyl]phenyl}-1H-pyrazol-4-yl)cyclopropanecarboxylate from Preparation 216 and Preparation 220

$^1$H-NMR (CDCl$_3$): 1.19-1.22 (3H), 1.27-1.30 (2H), 1.65-1.70 (2H), 4.09-4.14 (2H), 7.71-7.74 (2H)

Preparation 172 ethyl 1-{5-amino-3-cyano-1-[2,6-dichloro-4-(trifluoromethoxy)phenyl]-1H-pyrazol-4-yl}-2,2-dichlorocyclopropanecarboxylate from Preparation 209 and Preparation 174

Experimental MH$^+$ 516.9; expected 517.0

Preparation 173 ethyl 1-[5-amino-3-cyano-1-(2,6-dichloro-4-cyanophenyl)-1H-pyrazol-4-yl]cyclopropanecarboxylate from Preparation 208 and Preparation 220

Experimental MH$^+$ 390.0; expected 390.1

Preparation 174 ethyl 2,2-dichloro-1-(1,2-dicyano-3-methoxy-3-oxo-propyl)cyclopropane-carboxylate To a solution of Preparation 175 (1.00 g, 3.42 mmol) in methanol (15 ml), at 0° C. and under nitrogen, was added potassium cyanide (267 mg, 4.10 mmol) and the reaction mixture was stirred for 1 h. Glacial acetic acid (390 µl) and silica (1.00 g) were added and the mixture was concentrated in vacuo. The product/silica mix was purified by column chromatography (silica) with gradient elution, diethyl ether: cyclohexane [3:7 to 1:1]. The appropriate fractions were combined and concentrated to give the titled compound (440 mg).

$^1$H-NMR (CDCl$_3$): 1.39-1.41 (3H), 1.65-2.00 (1H), 2.42-2.70 (1H), 3.32-3.41 (1H), 3.89-3.99 (3H), 4.21-4.27 (1H), 4.35-4.42 (2H)

Preparation 175 ethyl 2,2-dichloro-1-[2-cyano-3-methoxy-3-oxo-prop-1-en-1-yl]-cyclopropanecarboxylate A mixture of Preparation 176 (8.60 g, 40.00 mmol), methyl cyanoacetate (3.5 ml, 40.00 mmol) and piperidine (1.2 ml, 12.00 mmol) in acetic acid (30 ml) was heated at reflux, under nitrogen, for 60 h. The reaction mixture was poured into water (500 ml) and extracted with dichloromethane (2×150 ml). The combined extracts were washed with saturated aqueous sodium hydrogencarbonate solution (200 ml), dried (Na$_2$SO$_4$) and concentrated in vacuo. The residue was purified by column chromatography (silica), eluting with diethyl ether/cyclohexane [2:8]. The appropriate fractions were combined and concentrated to give the titled compound (6.00 g).

$^1$H-NMR (CDCl$_3$): 1.19-1.28 (3H), 2.25-2.30 (1H), 2.81-2.85 (1H), 3.91-3.94 (3H), 4.29-4.41 (2H), 7.89-7.92 (1H)

Preparation 176 ethyl 2,2-dichloro-1-formylcyclopropanecarboxylate

A solution of Preparation 177 (5.00 g, 19.67 mmol) in dichloromethane (50 ml) was purged with nitrogen and cooled to −78° C. To the solution was added dropwise diisobutylaluminium hydride (1M in dichloromethane, 39.4 ml, 39.40 mmol), ensuring that the temperature did not rise above −65° C. After stirring at this temperature for 2 h, saturated aqueous ammonium chloride solution was added, followed by hydrochloric acid (2N, 5 ml), and the mixture was allowed to warm to room temperature. The reaction mixture was filtered, washed with brine, dried (Na$_2$SO$_4$) and concentrated in vacuo. The residue was purified by column chromatography (silica) eluting with diethyl ether/cyclohexane [2:8]. The appropriate fractions were combined and concentrated to give the titled compound (900 mg).

$^1$H-NMR (CDCl$_3$): 1.35-1.38 (3H), 2.40-2.50 (2H), 4.31-4.39 (2H), 9.96-9.99 (1H)

Preparation 177 diethyl 2,2-dichlorocyclopropane-1,1-dicarboxylate

Reference: Synthetic Communications (1989), 19(1-2), 141-6.

Preparation 178

1-{5-amino-3-cyano-1-[2,6-dichloro-4-(trifluoromethyl)phenyl]-1H-pyrazol-4-yl}cyclopropanecarboxylic acid To Preparation 179 (33 mg, 0.06 mmol) in 1,4-dioxane (2 ml) and methanol (0.5 ml) was added hydrochloric acid (0.5N, 0.5 ml). The reaction mixture was then heated at 80° C. overnight. The reaction mixture was concentrated in vacuo and the residue was partitioned between water (5 ml) and ethyl acetate (5 ml). The two layers were separated and the aqueous layer was extracted with ethyl acetate (2×5 ml). The combined organic layers were then dried (MgSO$_4$) and concentrated in vacuo. The crude product was dissolved in a mixture of acetonitrile/water (1:1, 650 µl) and purified by automated preparative liquid chromatography (Gilson system, 250 mm×21.2 mm Phenomenex LUNA C18(2) 5 µm column) using an acetonitrile:water (containing 0.1% trifluoroacetic acid) gradient [45:55 to 98:2]. The appropriate fractions were concentrated in vacuo to give the titled compound (8 mg).

Preparation 179 tert-butyl 1-(3-cyano-1-[2,6-dichloro-4-(trifluoromethyl)phenyl]-5-{[(dimethylamino)methylene]amino}-1H-pyrazol-4-yl)cyclopropanecarboxylate A suspension of potassium tert-butoxide (575 mg, 5.13 mmol) in water (50 µl) and diethyl ether (10 ml) was cooled to 0° C. and stirred for 30 min. To this solution was added dropwise Preparation 64 (303 mg, 0.64 mmol) in diethyl ether (5 ml) and tetrahydrofuran (1 ml). The reaction mixture was then stirred for 10 min. The reaction mixture was poured into ice/water (30 ml). The mixture was then acidified by addition of hydrochloric acid (2N) and extracted with ethyl acetate (3×20 ml). The combined extracts were dried (MgSO$_4$) and concentrated in vacuo. The residue was purified by column chromatography (silica) with gradient elution, hexane:ethyl acetate [3:1 to 1:3]. The appropriate fractions were combined and concentrated to give the titled compound (33 mg).

Preparation 180

1-bromo-1-(methylsulfonyl)ethylene

Reference: JACS (1972), 94(3), 1012-1013

Preparation 181

N,N-dimethylethylenesulfonamide

Reference: US 2004013980 A1, WO 9206973 A1

Preparation 182

2,6-dichloro-4-pentafluorothioaniline

Reference: WO 9306089 A1

Preparation 183 methyl 1-{3-cyano-1-[2,6-dichloro-4-(trifluoromethyl)phenyl]-5-[(ethoxycarbonyl)amino]-1H-pyrazol-4-yl}cyclopropanecarboxylate To a mixture of Example 3 (310 mg, 0.74 mmol) and pyridine (0.30 ml, 3.70 mmol) in dichloromethane (7.4 ml), at 0° C., was added phosgene (1.7M in toluene, 4.4 ml, 7.40 mmol). After stirring for 1 h, ethanol (10 ml) was added and the reaction mixture was then stirred at room temperature for 16 h. The reaction mixture was concentrated in vacuo and the residue was partitioned between hydrochloric acid (1M) and ethyl acetate. The organic phase was separated, washed with water, dried (MgSO$_4$) and concentrated in vacuo to give the titled compound (379 mg).

Experimental MH$^+$ 491.0; expected 491.1

Preparation 184 methyl 1-(3-cyano-5-{[(cyclopropylmethoxy)carbonyl]amino}-1-[2,6-dichloro-4-pentafluorothiophenyl]-1H-pyrazol-4-yl)cyclopropanecarboxylate To a solution of Preparation 91 (250 mg, 0.52 mmol) and pyridine (0.21 ml, 2.60 mmol) in dichloromethane (5.2 ml), at 0° C., was added phosgene (20% in toluene, 2.70 ml, 5.20 mmol). After stirring at 0° C. for 1 h, cyclopropylmethanol (2 ml) was added and the reaction mixture was stirred at room temperature for 16 h. The reaction mixture was concentrated in vacuo and the residue was partitioned between hydrochloric acid (1M) and ethyl acetate. The organic phase was separated, washed with water, dried (MgSO$_4$) and concentrated in vacuo to give the titled compound (310 mg).

Experimental MH$^+$ 575.0; expected 575.0

Similarly Prepared were

Preparation 185 methyl 1-{3-cyano-1-[2,6-dichloro-4-pentafluorothiophenyl]-5-[(methoxycarbonyl)amino]-1H-pyrazol-4-yl}cyclopropanecarboxylate from Preparation 91 and Methanol Experimental MH$^+$ 535.0; expected 535.0

Preparation 186 methyl 1-(3-cyano-5-{[(cyclobutyloxy)carbonyl]amino}-1-[2,6-dichloro-4-pentafluorothiophenyl]-1H-pyrazol-4-yl)cyclopropanecarboxylate from Preparation 91 and Cyclobutanol Experimental MH$^+$ 575.0; expected 575.0

Preparation 187 methyl 1-{3-cyano-1-[2,6-dichloro-4-(trifluoromethoxy)phenyl]-5-[(ethoxycarbonyl)amino]-1H-pyrazol-4-yl}cyclopropanecarboxylate from Preparation 95 and Ethanol Experimental MH$^+$ 506.9; expected 507.0

Preparation 188 methyl 1-{3-cyano-1-[2,6-dichloro-4-pentafluorothiophenyl]-5-[(ethoxycarbonyl)amino]-1H-pyrazol-4-yl}cyclopropanecarboxylate from Preparation 91 and ethanol Experimental MH$^+$ 549.0; expected 549.0

Preparation 189 methyl 1-{3-cyano-1-[2,6-dichloro-4-pentafluorothiophenyl]-5-[(isopropoxycarbonyl)amino]-1H-pyrazol-4-yl}cyclopropanecarboxylate from Preparation 91 and Isopropanol Experimental MH$^+$ 563.0; expected 563.0

Preparation 190 methyl 1-[3-cyano-1-[2,6-dichloro-4-pentafluorothiophenyl]-5-(difluoromethyl)-1H-pyrazol-4-yl]cyclopropanecarboxylate To a solution of Preparation 167 (400 mg, 0.82 mmol), at −78° C., was added (diethylamino)sulphur trifluoride (DAST, 120 μl, 0.90 mmol). The reaction mixture was allowed to warm to room temperature and stirred for 16 h. The reaction mixture was extracted with dichloromethane and the combined extracts were dried (MgSO$_4$) and concentrated in vacuo. The residue was purified by column chromatography (silica) eluting with cyclohexane/ethyl acetate [9:1]. The appropriate fractions were combined and concentrated to give the titled compound (190 mg).

$^1$H-NMR (CDCl$_3$): 1.41-1.45 (2H), 1.84-1.87 (2H), 3.70-3.72 (3H), 6.54-6.82 (1H), 7.90-7.93 (2H)

Preparation 191 isopropyl(diphenyl)sulfonium tetrafluoroborate

Reference: Synthesis (1982), (4), 291-4.

Preparation 192 methyl 1-{3-cyano-5-[(cyclopropylmethyl)(methyl)amino]-1-[2,6-dichloro-4-pentafluorothiophenyl]-1H-pyrazol-4-yl}cyclopropanecarboxylate To a solution of Preparation 143 (500 mg, 0.95 mmol) in glacial acetic acid (20 ml) was added paraformaldehyde (143 mg, 4.75 mmol) and sodium cyanoborohydride (298 mg, 4.75 mmol). The reaction mixture was stirred at room temperature for 60 h and then quenched with water. After stirring for a further 20 min, the mixture was extracted with ethyl acetate and the combined extracts were washed with brine, dried (MgSO4) and concentrated in vacuo to give the titled compound (200 mg) which was used directly.

Similarly Prepared were

Preparation 193 methyl 1-{3-cyano-1-[2,6-dichloro-4-pentafluorothiophenyl]-5-[(ethoxycarbonyl)(methyl)amino]-1H-pyrazol-4-yl}cyclopropanecarboxylate from Preparation 188

Experimental MH$^+$ 563.0; expected 563.0

Preparation 194 methyl 1-(3-cyano-5-{[(cyclopropylmethoxy)carbonyl](methyl)amino}-1-[2,6-dichloro-4-pentafluorothiophenyl]-1H-pyrazol-4-yl)cyclopropanecarboxylate from Preparation 184

Experimental MH$^+$ 589.1; expected 589.1

Preparation 195 methyl 1-{3-cyano-1-[2,6-dichloro-4-pentafluorothiophenyl]-5-(dimethylamino)-1H-pyrazol-4-yl}cyclopropanecarboxylate To a solution of Preparation 91 (500 mg, 1.05 mmol) in glacial acetic acid (15 ml) was added paraformaldehyde (158 mg, 5.25 mmol), followed by sodium cyanoborohydride (330 mg, 5.25 mmol). The reaction mixture was stirred at room temperature for 18 h and then concentrated in vacuo. To the residue was added water (30 ml) and the mixture was extracted with ethyl acetate (3×50 ml). The combined extracts were dried (MgSO$_4$) and concentrated in vacuo and the residue was re-dissolved in toluene and concentrated (×3) to give the titled compound (450 mg).

Experimental MH$^+$ 504.9; expected 505.0

Preparation 196 methyl 1-{3-cyano-1-[2,6-dichloro-4-pentafluorothiophenyl]-5-(methylthio)-1H-pyrazol-4-yl}cyclopropanecarboxylate To a solution of Preparation 91 (500 mg, 1.05 mmol) and dimethyl disulphide (0.19 ml, 2.10 mmol) in dichloromethane (15 ml), at 0° C., was added dropwise t-butyl nitrite (0.32 ml, 2.72 mmol). The reaction mixture was stirred at 0° C. for 1 h and then at room temperature for 18 h. To the reaction mixture was added dichloromethane (25 ml) and the organic phase was separated, washed with brine (50 ml), dried (MgSO$_4$) and concentrated in vacuo. The residue was purified by column chromatography with gradient elution, ethyl acetate:cyclohexane [8:92 to 60:40]. The appropriate fractions were combined and concentrated to give the titled compound (300 mg).

Experimental MH$^+$ 549.1 (acetonitrile adduct); expected 549.0

Preparation 197 methyl 1-{3-cyano-1-[2,6-dichloro-4-pentafluorothiophenyl]-5-(methoxymethyl)-1H-pyrazol-4-yl}cyclopropanecarboxylate To a solution of Preparation 166 (300 mg, 0.61 mmol) in acetonitrile (3 ml) was added iodomethane (2.76 ml, 44.64 mmol) and potassium carbonate (169 mg, 1.22 mmol). The reaction mixture was stirred at room temperature for 5 days and then concentrated in vacuo. The residue was partitioned between ethyl acetate and water and the organic phase was separated, dried (MgSO4) and concentrated in vacuo. The residue was purified by column chromatography (silica) with gradient elution, ethyl acetate:cyclohexane [5:95 to 12:88]. The appropriate fractions were combined and concentrated to give the titled compound (125 mg)

Experimental MH$^+$ 506.0; expected 506.0.

Preparation 198

1-{3-cyano-1-[2,6-dichloro-4-pentafluorothiophenyl]-5-(dimethylamino)-1H-pyrazol-4-yl}-2,2-difluorocyclopropanecarboxylic acid A mixture of the Preparation 228 (100 mg, 0.19 mmol) and lithium hydroxide monohydrate (78 mg, 1.85 mmol) in tetrahydrofuran/water (4:1, 4 ml) was stirred at room temperature for 2 h. To the reaction mixture was added hydrochloric acid (2N, 5 ml) and the mixture was extracted with ethyl acetate (2×5 ml). The combined extracts were dried (MgSO4) and concentrated in vacuo to give the titled compound (100 mg).

Experimental MH$^+$ 527.0; expected 527.0

Preparation 199 methyl 1-{3-cyano-5-[(cyclobutylmethyl)amino]-1-[2,6-dichloro-4-pentafluorothiophenyl]-1H-pyrazol-4-yl}cyclopropanecarboxylate A mixture of Preparation 200 (100 mg, 0.18 mmol) and phosphorus pentachloride (40 mg, 19.00 mmol) in toluene (5 ml) was heated at reflux for 2 h, cooled to room temperature and then poured into a solution of sodium borohydride (20 mg, 0.50 mmol) in methanol (5 ml). After stirring for 30 min, the reaction mixture was quenched with water (10 ml) and concentrated in vacuo. The residue was extracted with ethyl acetate (3×10 ml) and the combined extracts were dried (MgSO$_4$) and concentrated in vacuo to give the titled compound (30 mg).

Experimental MH$^+$ 545.0; expected 545.1

Preparation 200 methyl 1-{3-cyano-5-[(cyclobutylcarbonyl)amino]-1-[2,6-dichloro-4-pentafluorothiophenyl]-1H-pyrazol-4-yl}cyclopropanecarboxylate To a solution of Preparation 91 (500 mg, 1.00 mmol) and pyridine (0.20 ml, 2.50 mmol) in dichloromethane (5 ml), at 0° C. and under nitrogen, was added cyclobutanecarbonyl chloride (0.23 ml, 2.00 mmol). The reaction mixture was heated in a microwave (300 W) at 55° C. for 40 min and then concentrated in vacuo to give the titled compound (100 mg).

Experimental MH$^+$ 559.0; expected 559.0

Preparation 201 methyl 2-{3-cyano-5-(cyclopropylmethoxy)-1-[2,6-dichloro-4-pentafluorothiophenyl]-1H-pyrazol-4-yl}acrylate A solution of Preparation 202 (420 mg, 0.76 mmol) in para-xylene (15 ml) was heated at reflux for 16 h. The reaction mixture was concentrated in vacuo and the residue was purified by column chromatography with gradient elution, ethyl acetate:cyclohexane [5:95 to 25:75]. The appropriate fractions were combined and concentrated to give the titled compound (159 mg).

Experimental MH$^+$ 517.9; expected 518.0

Preparation 202 methyl 2-chloro-2-{3-cyano-5-(cyclopropyl-methoxy)-1-[2,6-dichloro-4-pentafluorothiophenyl]-1H-pyrazol-4-yl}propanoate To a solution of Preparation 77 (1.24 g, 2.31 mmol) in acetonitrile (23 ml) was added thionyl chloride (0.51 ml, 6.93 mmol). The reaction mixture was heated at 50° C. for 3 h and then concentrated in vacuo. The residue was purified by column chromatography with gradient elution, ethyl acetate:cyclohexane [3:97 to 15:85]. The appropriate fractions were combined and concentrated to give the titled compound (850 mg).

Experimental $MH^+$ 554.0; expected 554.0

Preparation 203 tert-butyl {1-[({4-[1-(aminocarbonyl)cyclopropyl]-3-cyano-1-[2,6-dichloro-4-pentafluorothiophenyl]-1H-pyrazol-5-yl}amino)methyl]cyclopropyl}carbamate To Preparation 205 (226 mg, 0.35 mmol) in tetrahydrofuran/water (4:1, 3.5 ml) was added lithium hydroxide monohydrate (147 mg, 3.5 mmol) and the reaction mixture was stirred at room temperature for 24 h. The reaction mixture was acidified with hydrochloric acid (1M) and extracted with ethyl acetate. The combined extracts were washed with water, dried (MgSO4) and concentrated in vacuo. To a solution of the residue in tetrahydrofuran (3.5 ml), at 0° C., was added triethylamine (120 µl, 0.88 mmol) and ethyl chloroformate (40 µl, 0.42 mmol). After stirring for 30 min, aqueous ammonium hydroxide solution (1 ml) was added and the reaction mixture was warmed to room temperature. The reaction mixture was adjusted to pH 1 by addition of hydrochloric acid (1M) and extracted with ethyl acetate. The combined extracts were washed with water, dried (MgSO4) and concentrated in vacuo. The residue was dissolved in acetonitrile/dimethyl sulphoxide (1.5 ml) and purified by automated preparative liquid chromatography (Gilson system, 150 mm×50 mm LUNA C18(2) 10 µm column) using an acetonitrile:water gradient [55:45 to 95:5]. The appropriate fractions were concentrated in vacuo to give the titled compound (72 mg).

Experimental $MH^+$ 631.4; expected 631.1

Preparation 204

5-(cyclopropylmethoxy)-1-[2,6-dichloro-4-pentafluorothiophenyl]-1H-pyrazole-3-carbonitrile To a mixture of Preparation 222 (6.37 g, 16.80 mmol) and potassium carbonate (7.00 g, 50.40 mmol) in acetonitrile (75 ml) was added (bromomethyl)cyclopropane (6.5 ml, 67.20 mmol). The reaction mixture was stirred at room temperature for 1 h and then heated at 50° C. for 3 h. The reaction mixture was concentrated in vacuo and the residue was partitioned between hydrochloric acid (1M) and ethyl acetate. The two layers were separated and the organic layer was washed with water, dried (MgSO4) and concentrated in vacuo. The residue was purified by column chromatography with gradient elution, ethyl acetate:cyclohexane [2:98 to 20:80]. The appropriate fractions were combined and concentrated to give the titled compound (2.97 g).

Experimental $MH^+$ 433.9; expected 434.0

Preparation 205 methyl 1-{5-[({1-[(tert-butoxycarbonyl)amino]cyclopropyl}methyl)amino]-3-cyano-1-[2,6-dichloro-4-pentafluorothiophenyl]-1H-pyrazol-4-yl}cyclopropanecarboxylate A solution of Preparation 91 (425 mg, 0.89 mmol) in toluene/dichloroethane (4:1, 12 ml) was heated at 90° C. for 5 min, before addition of (1-formyl-cyclopropyl)-carbamic acid tert-butyl ester (0.50 g, 2.70 mmol) and p-toluenesulphonic acid (17 mg). The reaction mixture was heated at 90° C. for 1 h and then at reflux for 2 h, using a Dean-Stark apparatus. The mixture was concentrated in vacuo and the residue was azeotroped with toluene. To a solution of the residue in methanol (16 ml), at 0° C., was added sodium borohydride (85 mg, 2.23 mmol) and the reaction mixture was stirred at 0° C. for 30 min and then at room temperature for 1 h. To the mixture was added hydrochloric acid (1M) and ethyl acetate. The organic phase was separated, dried (MgSO4) and concentrated in vacuo to give the titled compound (226 mg).

Experimental $MH^+$ 646.2; expected 646.1

Preparation 206 methyl 1-{3-cyano-5-({2-[(cyclopropylmethyl)amino]-2-oxoethyl}amino)-1-[2,6-dichloro-4-pentafluorothiophenyl]-1H-pyrazol-4-yl}cyclopropanecarboxylate To a solution of Preparation 49 (145 mg, 0.27 mmol) in tetrahydrofuran (6 ml) was added triethylamine (0.15 ml, 1.09 mmol), followed by ethyl chloroformate (31 µl, 0.33 mmol) in tetrahydrofuran (0.5 ml). After stirring for 30 min, (aminomethyl)cyclopropane hydrochloride (88 mg, 0.82 mmol) was added and the reaction mixture was stirred at room temperature for 1 h. The mixture was concentrated in vacuo and the residue was partitioned between hydrochloric acid (0.5N, 20 ml) and ethyl acetate (20 ml). The organic phase was separated, washed with brine (20 ml), dried (MgSO4) and concentrated in vacuo to give the titled compound (150 mg).

Experimental $MH^+$ 587.9; expected 588.1

Preparation 207 methyl 1-{5-[(2-tert-butoxy-2-oxoethyl)amino]-3-cyano-1-[2,6-dichloro-4-pentafluorothiophenyl]-1H-pyrazol-4-yl}cyclopropanecarboxylate A mixture of Preparation 91 (487 mg, 1.02 mmol), tert-butyl bromoacetate (0.23 ml, 1.53 mmol) and potassium carbonate (423 mg, 3.10 mmol) in acetonitrile (20 ml) was heated at 55° C. for 48 h and then concentrated in vacuo. The residue was partitioned between ethyl acetate (50 ml) and water (50 ml) and the organic phase was separated, washed with brine (30 ml), dried (MgSO4) and concentrated in vacuo.

The residue was purified by column chromatography with gradient elution, cyclohexane:ethyl acetate [4:1 to 2:1]. The appropriate fractions were combined and concentrated to give the titled compound (380 mg).

Experimental $MH^+$ 590.8; expected 591.1

Preparation 208

2,6-dichloro-4-cyanobenzenediazonium tetrafluoroborate

To a solution of 4-amino-3,5-dichlorobenzonitrile (2.00 g, 10.63 mmol) in acetonitrile (12 ml) was added dropwise tetrafluoroboric acid (2.80 ml, 21.27 mmol). After stirring for 10 min, isoamyl nitrite (1.50 ml, 10.63 mmol) was added and the reaction mixture was cooled to 0° C. After a further 10 min, diethyl ether (50 ml) was added and the resulting precipitate was collected by filtration and dried to give the titled compound (1.9 g).
1H-NMR (D2O): 8.36-8.40 (2H)

Similarly Prepared was

Preparation 209

2,6-dichloro-4-(trifluoromethoxy)benzenediazonium tetrafluoroborate from 2,6-dichloro-4-trifluoromethoxyaniline

Preparation 210 methyl 1-{3-cyano-1-[2,6-dichloro-4-pentafluorothiophenyl]-5-[(2-methoxyethyl)(methyl)amino]-1H-pyrazol-4-yl}cyclopropanecarboxylate To a solution of Preparation 211 (120 mg, 0.23 mmol) in dimethyl sulphoxide (2 ml) was added potassium hydroxide (103 mg, 1.84 mmol), followed by methyl iodide (1.1 ml, 1.84 mmol). After stirring at room temperature for 1 h, diethyl ether (20 ml) and water (15 ml) were added and the two layers were separated. The organic layer was washed with brine, dried ((MgSO4)) and concentrated in vacuo to give the titled compound (95 mg).
Experimental MH+ 549.1; expected 549.1

Preparation 211 methyl 1-{3-cyano-1-[2,6-dichloro-4-pentafluorothiophenyl]-5-[(2-hydroxyethyl)amino]-1H-pyrazol-4-yl}cyclopropanecarboxylate To a solution of Preparation 49 (330 mg, 0.62 mmol) in tetrahydrofuran (5 ml), at 0° C., was added triethylamine (150 µl, 1.05 mmol), followed by ethyl chloroformate (100 µl, 1.05 mmol). The mixture was stirred at 0° C. for 15 min and then at room temperature for 20 min. The mixture was filtered through Celite® and added to a solution of sodium borohydride (70 mg, 1.85 mmol) in tetrahydrofuran (3 ml). Methanol (4 ml) was then added carefully and the reaction mixture was allowed to warm to room temperature. After 1 h, hydrochloric acid (2N, 5 ml) was added and the mixture was concentrated in vacuo. To the residue was added ethyl acetate (25 ml) and the solution was washed with hydrochloric acid (2N, 15 ml), sodium hydrogen carbonate solution (15 ml) and brine (15 ml), dried (MgSO4) and concentrated in vacuo to give the titled compound (304 mg).
Experimental MH+ 520.8; expected 521.0

Preparation 212

4-({3-cyano-1-[2,6-dichloro-4-pentafluorothiophenyl]-4-[1-(methoxycarbonyl)cyclopropyl]-1H-pyrazol-5-yl}amino)butanoic acid To a solution of Preparation 121 (159 mg, 0.25 mmol) in dichloromethane (5 ml) was added dropwise trifluoroacetic acid (5 ml). After stirring for 1 h, the reaction mixture was concentrated in vacuo to give the titled compound (180 mg).
Experimental MH+ 563.1; expected 563.0

Preparation 213 methyl 1-(3-cyano-1-[2,6-dichloro-4-pentafluorothiophenyl]-5-{[2-(1H-1,2,4-triazol-1-yl)ethyl]amino}-1H-pyrazol-4-yl)cyclopropanecarboxylate To a solution of Preparation 215 (190 mg, 0.32 mmol) in acetonitrile (4 ml) was added 1,2,4-triazole (55 mg, 0.79 mmol) followed by potassium carbonate (132 mg, 0.95 mmol). The reaction mixture was heated at 60° C. for 1 h, cooled and concentrated in vacuo to give the titled compound (150 mg), which was used directly.
Experimental MH+ 571.9; expected 572.0

Similarly Prepared was

Preparation 214 methyl 1-{3-cyano-5-[(2-cyanoethyl)amino]-1-[2,6-dichloro-4-pentafluorothiophenyl]-1H-pyrazol-4-yl}cyclopropanecarboxylate from Preparation 215 and 2-cyanoethylamine Experimental MH+ 529.9; expected 530.0

Preparation 215 methyl 1-{3-cyano-1-[2,6-dichloro-4-pentafluorothiophenyl]-5-({2-[(methylsulfonyl)oxy]ethyl}amino)-1H-pyrazol-4-yl}cyclopropanecarboxylate To a solution of Preparation 211 (295 mg, 0.57 mmol) in dichloromethane (10 ml) was added triethylamine (0.12 ml, 0.85 mmol), followed by methanesulphonyl chloride (78 mg, 0.68 mmol). After stirring at room temperature for 2 h, dichloromethane was added and the solution was washed with hydrochloric acid (0.5N, 25 ml) and brine (25 ml), dried (MgSO4) and concentrated in vacuo to give the titled compound (300 mg).
Experimental MH+ 598.8; expected 599.0

Preparation 216

2,6-dichloro-4-[1,2,2,2-tetrafluoro-1-(trifluoromethyl)ethyl]aniline

To a solution of Preparation 217 (1.00 g, 3.33 mmol) in acetonitrile (10 ml) was added N-chlorosuccinimide (1.02 g, 6.66 mmol). The reaction mixture was heated at 50° C. for 5 h, diluted with water and then extracted with ethyl acetate. The combined extracts were washed with water, dried (MgSO$_4$) and concentrated in vacuo. The residue was purified by column chromatography (silica), eluting with ethyl acetate/cyclohexane [2:3]. The appropriate fractions were combined and concentrated to give the titled compound (630 mg).
1H-NMR (CDCl$_3$): 4.65-4.80 (2H), 7.38-7.41 (2H)

Preparation 217

4-[1,2,2,2-tetrafluoro-1-(trifluoromethyl)ethyl]aniline

To a solution of aniline (1.32 g, 14.19 mmol) in tert-butyl methyl ether (25 ml) and water (25 ml) was added sequentially 2-iodoheptafluoropropane (5.00 g, 17.06 mmol), sodium thiosulphate (3.50 g, 17.06 mmol), sodium hydrogen carbonate (1.73 g, 17.06 mmol) and tetrabutylammonium hydrogen sulphate (0.53 g, 17.06 mmol). The reaction mixture was stirred at room temperature for 18 h and the two layers were separated. The aqueous layer was extracted with ethyl acetate and the combined organic phases were washed with hydrochloric acid (2N), aqueous sodium hydrogen carbonate solution and brine, dried ($MgSO_4$) and concentrated in vacuo to give the titled compound (1.00 g).

1H-NMR ($CDCl_3$): 6.65-4.78 (2H), 7.30-7.35 (2H)

Preparation 218

2-fluoro-2-methylpropan-1-ol

Reference: Zeitschrift fuer Chemie (1965), 5(10), 380-1

Preparation 219

N'-{3-cyano-1-[2,6-dichloro-4-(trifluoromethyl)phenyl]-4-iodo-1H-pyrazol-5-yl}-N,N-dimethylimidoformamide Reference: WO-9828078

Preparation 220 ethyl 1-(1,2-dicyano-3-methoxy-3-oxopropyl)cyclopropanecarboxylate

To a mixture of Preparation 221 (9.35 g, 65.80 mmol), piperidine (0.65 ml, 6.58 mmol), methyl cyanoacetate (5.80 ml, 65.80 mmol) and potassium carbonate (0.91 g, 6.58 mmol) in isopropyl alcohol (120 ml) was added potassium cyanide (4.30 g, 65.80 mmol). The reaction mixture was stirred at room temperature for 18 h and then concentrated in vacuo. The residue was partitioned between hydrochloric acid (1M) and ethyl acetate and the two layers were separated. The aqueous layer was extracted with ethyl acetate and the combined extracts were washed with brine, dried ($MgSO_4$) and concentrated in vacuo.

The residue was purified by column chromatography with gradient elution, ethyl acetate:cyclohexane [5:95 to 35:65]. The appropriate fractions were combined and concentrated to give the titled compound (13.44 g).

1H-NMR ($CDCl_3$): 1.20-1.25 (3H), 1.40-1.60 (4H), 3.89-3.92 (3H), 4.20-4.30 (2H), 4.50-4.65 (1H)

Preparation 221 ethyl 1-formylcyclopropanecarboxylate

To a solution of Preparation 232 1-hydroxymethyl-cyclopropanecarboxylic acid ethyl ester (3.00 g, 21.00 mmol) in dichloromethane (50 ml), at 0° C., was added saturated sodium hydrogen carbonate solution (50 ml), followed by TEMPO (659 mg, 4.00 mmol) and sodium bromide (400 mg, 4.00 mmol). After stirring for 5 min, sodium hypochlorite solution (10%, 14.00 mmol) was added slowly, followed by saturated sodium thiosulphate solution (50 ml). The two layers were separated and the aqueous layer was extracted with dichloromethane. The combined organic phases were dried ($MgSO_4$) and concentrated in vacuo to give the titled compound (3.00 g).

1H-NMR ($CDCl_3$): 1.25-1.35 (3H), 1.55-1.64 (4H), 4.21-4.30 (2H), 10.39-10.41 (1H)

Preparation 222

1-[2,6-dichloro-4-pentafluorothiophenyl]-5-hydroxy-1H-pyrazole-3-carbonitrile

Sodium nitrite (1.32 g, 19.1 mmol) was added carefully to sulphuric acid (concentrated, 6.8 ml), whilst cooling the solution to 0° C. The solution was heated to 60° C. for 30 min, allowed to cool and then diluted with acetic acid (12 ml). To the solution was added Preparation 182 (5.0 mg, 17.4 mmol) in acetic acid (11 ml) and the reaction mixture was heated at 55° C. for 1 h. To a solution of Preparation 248 (3.09 g, 18.1 mmol) in acetic acid (24 ml) and water (36 ml) was added dropwise the solution of the diazonium salt, followed by sodium acetate (24.2 g) in water (42 ml). The reaction mixture was then stirred at room temperature for 30 min. The reaction mixture was poured into ice/water (200 ml) and the mixture was extracted with dichloromethane (4×60 ml). The combined extracts were then washed with ammonium hydroxide (48 ml), dried and concentrated in vacuo. To a solution of sodium methoxide (25 wt. %, 11.5 ml, 50.1 mmol) in methanol (450 ml) was added dropwise a solution of the residue in methanol (100 ml). The reaction mixture was then stirred at room temperature for 2 h. The reaction mixture was concentrated in vacuo and to the residue was added water. This solution was adjusted to pH 1 by addition of hydrochloric acid (4N) and the mixture was extracted with dichloromethane (3×100 ml). The combined extracts were dried ($MgSO_4$) and concentrated in vacuo.

The residue was purified by column chromatography, eluting with hexane/ethyl acetate [3:1]. The appropriate fractions were combined and concentrated to give the titled compound (4.5 g).

Experimental $MH^+$ 379.8; expected 380.0

Preparation 223

1-{3-cyano-1-[2,6-dichloro-4-pentafluorothiophenyl]-5-[({[1-(fluoromethyl)cyclopropyl]methoxy}carbonyl)amino]-1H-pyrazol-4-yl}cyclopropanecarboxylic acid To Preparation 224 (300 mg, 0.50 mmol) in tetrahydrofuran/water (10:1, 5 ml) was added lithium hydroxide monohydrate (200 mg, 5.00 mmol) and the reaction mixture was stirred at room temperature for 24 h. The reaction mixture was acidified with hydrochloric acid (1M) and extracted with ethyl acetate. The combined extracts were washed with water, dried ($MgSO_4$) and concentrated in vacuo to give the titled compound (295 mg).

Experimental $MH^+$ 593.0; expected 593.0

Preparation 224 methyl 1-{3-cyano-1-[2,6-dichloro-4-pentafluorothiophenyl]-5-[({[1-(fluoromethyl)cyclopropyl]methoxy}carbonyl)amino]-1H-pyrazol-4-yl}cyclopropanecarboxylate To a solution of Preparation 91 (250 mg, 0.50 mmol) in dichloromethane (5 ml) was added pyridine (450 mg, 5.00 mmol). The mixture was cooled to 0° C., before addition of phosgene (20% in toluene, 5.5 ml, 2.50 mmol), followed by Preparation 230 (100 mg, 1.00 mmol). The reaction mixture was allowed to warm to room temperature, with stirring, over 2 h and water was added. The mixture was extracted with ethyl acetate and the combined extracts were washed with brine, dried (MgSO$_4$) and concentrated in vacuo to give the titled compound (300 mg).

Experimental MH$^+$ 607.1; expected 607.0

Preparation 225

1-{3-cyano-1-[2,6-dichloro-4-pentafluorothiophenyl]-5-({2-oxo-2-[(2,2,2-trifluoroethyl)amino]ethyl}amino)-1H-pyrazol-4-yl}cyclopropanecarboxylic acid To a solution of Preparation 226 (180 mg, 0.34 mmol) in tetrahydrofuran (4 ml) and water (0.5 ml) was added lithium hydroxide monohydrate (80 mg, 1.91 mmol) and the reaction mixture was stirred at room temperature for 18 h. The mixture was quenched with hydrochloric acid (0.5N) and extracted with ethyl acetate (2×10 ml). The combined extracts were dried (MgSO$_4$) and concentrated in vacuo to give the titled compound (75 mg).

Experimental MH$^+$ 602.0; expected 602.0

Preparation 226 methyl 1-{3-cyano-1-[2,6-dichloro-4-pentafluorothiophenyl]-5-({2-oxo-2-[(2,2,2-trifluoroethyl)amino]ethyl}amino)-1H-pyrazol-4-yl}cyclopropanecarboxylate To a solution of Preparation 49 (180 mg, 0.34 mmol) in tetrahydrofuran (8 ml) was added triethylamine (0.19 ml, 1.35 mmol), followed by ethyl chloroformate (44 mg, 0.41 mmol), added dropwise. After 15 min, 2,2,2-trifluoroethylamine hydrochloride (137 mg, 1.02 mmol) was added and the reaction mixture was stirred at room temperature for 8 h. The mixture was diluted with hydrochloric acid (0.5N, 20 ml) and extracted with ethyl acetate (2×20 ml). The combined extracts were dried (MgSO$_4$) and concentrated in vacuo.

The residue was purified by column chromatography with gradient elution, ethyl acetate:cyclohexane [1:2 to 2:1]. The appropriate fractions were combined and concentrated to give the titled compound (80 mg).

Experimental MH$^+$ 616.0; expected 616.0

Preparation 227 methyl 1-{3-cyano-1-[2,6-dichloro-4-pentafluorothiophenyl]-5-vinyl-1H-pyrazol-4-yl}cyclopropanecarboxylate To a solution of methyltriphenylphosphonium bromide (241 mg, 0.67 mmol) in tetrahydrofuran (12.2 ml), at –78° C., was added n-butyllithium (1.34M in hexanes, 0.48 ml, 0.64 mmol). After 10 min, the mixture was warmed to 0° C. and Preparation 167 (300 mg, 0.61 mmol) in tetrahydrofuran (12.2 ml), at –78° C., was added using a cannular. The reaction mixture was stirred at –78° C. for 20 min and then allowed to warm to room temperature. To the reaction mixture was added water and the mixture was extracted with ethyl acetate. The combined extracts were then dried (MgSO$_4$) and concentrated in vacuo. The residue was purified by column chromatography (silica) with gradient elution, ethyl acetate:cyclohexane [4:96 to 12:88]. The appropriate fractions were combined and concentrated to give the titled compound (30 mg).

1H-NMR (CDCl$_3$): 1.31-1.36 (2H), 1.81-1.86 (2H), 3.68-3.71 (3H), 5.51-5.60 (2H), 6.15-6.23 (1H), 7.89-7.92 (2H)

Preparation 228 methyl 1-{3-cyano-1-[2,6-dichloro-4-pentafluorothiophenyl]-5-(dimethylamino)-1H-pyrazol-4-yl}-2,2-difluorocyclopropanecarboxylate To a solution of Preparation 92 (100 mg, 0.20 mmol) in glacial acetic acid (4 ml), under nitrogen, was added paraformaldehyde (30 mg, 0.98 mmol) and sodium cyanoborohydride (60 mg, 0.98 mmol). The reaction mixture was stirred at room temperature for 60 h and then quenched with water (50 ml). After stirring for a further 30 min, the mixture was extracted with ethyl acetate (50 ml) and the combined extracts were washed with brine, dried (MgSO$_4$) and concentrated in vacuo to give the titled compound (100 mg).

Experimental MH$^+$ 540.9; expected 541.0

Preparation 229

1-[({4-[1-(aminocarbonyl)cyclopropyl]-3-cyano-1-[2,6-dichloro-4-pentafluorothiophenyl]-1H-pyrazol-5-yl}amino)methyl]cyclopropanecarboxylate To a solution of Preparation 91 (434 mg, 0.91 mmol) and p-toluenesulphonic acid (17 mg, 91 μmol) in toluene (43 ml) was added Preparation 221 (390 mg, 2.74 mmol). The reaction mixture was heated at reflux for 3 h, using a Dean-Stark apparatus, and then cooled and concentrated in vacuo. The residue was dissolved in methanol (17 ml) and the solution was cooled to 0° C. Sodium borohydride (86 mg, 2.28 mmol) was added portionwise and the mixture was stirred at 0° C. for 1 h. The mixture was partitioned between hydrochloric acid (1M) and ethyl acetate and the two layers were separated. The aqueous layer was extracted with ethyl acetate and the combined extracts were washed with water, dried (MgSO$_4$) and concentrated in vacuo. The residue was dissolved in acetonitrile/dimethyl sulphoxide (2 ml) and purified by automated preparative liquid chromatography (Gilson system, 150 mm×50 mm LUNA C18(2) 10 μm column) using an acetonitrile:water gradient [70:30 to 95:5]. The appropriate fractions were concentrated in vacuo to give the titled compound (83 mg) which was used directly.

Preparation 230

[1-(fluoromethyl)cyclopropyl]methanol

To a solution of Preparation 231 (3.00 g, 20.00 mmol) in diethyl ether (50 ml), at 0° C., was added lithium aluminium hydride (1M in diethyl ether, 20 ml, 20.00 mmol). After stirring at 0° C. for 30 min, water was added carefully and the mixture was diluted with diethyl ether. Hydrochloric acid (3 drops) was added and the two layers were separated. The aqueous layer was extracted with diethyl ether and the combined organic phases were washed with brine, dried (MgSO$_4$) and concentrated in vacuo. The residue was purified by column chromatography, eluting with diethyl ether/pentane and the appropriate fractions were combined and concentrated to give the titled compound (1.00 g).

1H-NMR (CDCl$_3$): 0.59-0.63 (4H), 3.59-3.62 (2H), 4.25-4.45 (2H)

Preparation 231 ethyl 1-(fluoromethyl)cyclopropanecarboxylate

To a solution of Preparation 232 (3.00 g, 20.00 mmol) in dichloromethane (50 ml), at −78° C. and under nitrogen, was added (diethylamino)sulphur trifluoride (DAST, 3.56 g, 22.00 mmol). The reaction mixture was allowed to warm to room temperature over 2 h and then stirred for 18 h. To the mixture was added hydrochloric acid (10%, 5 drops) and water (50 ml) and the two layers were separated. The aqueous layer was extracted with dichloromethane and the combined organic phases were washed with water and brine, dried (MgSO$_4$) and concentrated in vacuo to give the titled compound (3.00 g).

1H-NMR (CDCl$_3$): 0.92-1.00 (2H), 1.20-1.28 (3H), 1.35-1.40 (2H), 4.10-4.21 (2H), 4.42-4.59 (2H)

Preparation 232

1-hydroxymethyl-cyclopropanecarboxylic acid ethyl ester

Reference: Tetrahedron Letters (1999), 40(30), 5467-5470.

Preparation 233

2-Cyano-succinic acid dimethyl ester

Reference: WO-2005090313

Preparation 234

Tributyl-(1-fluoro-vinyl)-stannane

Reference: WO-0560749

The invention claimed is:

1. A pharmaceutical composition comprising a compound of Formula (I)

(I)

wherein:
X is CR$^{10}$;
R$^1$ is C$_{1-6}$ haloalkyl, C$_{1-6}$ haloalkoxy, or SF$_5$;
R$^2$ is cyano, C(O)OH, het, S(O)$_n$R$^{11}$, C(O)NR$^a$R$^b$, C(S) NR$^a$R$^b$, or C(O)OC$_{1-6}$ alkyl;
R$^a$ and R$^b$ are each independently hydrogen or S(O)$_n$R$^{11}$;
or either one or both of R$^a$ and R$^b$ are independently C$_{1-6}$ alkyl, C$_{2-6}$ alkenyl, C$_{3-8}$ cycloalkyl, C$_{3-8}$ cycloalkylC$_{1-6}$ alkyl, alkanoyl, or C(O)OC$_{1-6}$ alkyl, each of which R$^a$ or R$^b$ may be optionally and independently further substituted by one or more substituents selected from the group consisting of, where chemically possible, cyano, nitro, halo, oxo, hydroxy, C(O)OH, C(O)NR$^c$R$^d$, NR$^c$C(O)R$^d$, C$_{1-6}$ alkyl, C$_{2-6}$ alkenyl, C$_{2-6}$ alkynyl, C$_{3-8}$ cycloalkyl, C$_{3-8}$ cycloalkylC$_{1-6}$ alkyl, C$_{3-8}$ cycloalkylC$_{1-6}$ haloalkyl, C$_{1-6}$ alkoxy, C$_{1-6}$ alkanoyl, —C(O)OC$_{1-6}$ alkyl, C$_{1-6}$ haloalkyl, C$_{3-8}$ halocycloalkyl, C$_{1-6}$ haloalkoxy, C$_{1-6}$ haloalkanoyl, —C(O)OC$_{1-6}$ haloalkyl, amino, NR$^c$R$^d$, het, phenyl and S(O)$_n$R$^{11}$;
R$^3$, R$^4$, R$^5$ and R$^6$ are each independently selected from hydrogen, halo, cyano, hydroxy, C(O)OH, nitro, phenyl, or S(O)$_n$R$^{11}$;
R$^7$ is fluoro or chloro;
R$^8$ is cyano;
R$^9$ is hydrogen, halo, —S(O)$_n$R$^{11}$, NR$^e$R$^f$, C$_{1-6}$ alkyl, C$_{2-6}$ alkenyl, C$_{1-6}$ alkoxy, or —C$_{3-8}$ cycloalkylC$_{1-6}$ alkoxy;
R$^e$ and R$^f$ are each independently hydrogen, het, phenyl or S(O)$_n$R$^{11}$;
or either one or both of R$^e$ and R$^f$ are independently C$_{1-6}$ alkyl, C$_{2-6}$ alkenyl, C$_{3-8}$ cycloalkyl, C$_{3-8}$ cycloalkylC$_{1-6}$ alkyl, C$_{1-6}$ alkanoyl, C(O)OC$_{1-6}$ alkyl, —C(O)OC$_{1-6}$ alkylC$_{3-8}$ cycloalkyl, or —C(O)OC$_{3-8}$ cycloalkyl, each of which R$^e$ or R$^f$ may be optionally and independently further substituted by one or more substituents selected from the group consisting of, where chemically possible, cyano, nitro, halo, oxo, hydroxy, C(O)OH, —C(O)NR$^c$R$^d$, NR$^c$C(O)R$^d$, C$_{1-6}$ alkyl, C$_{2-6}$ alkenyl, C$_{2-6}$ alkynyl, C$_{3-8}$ cycloalkyl, C$_{3-8}$ cycloalkylC$_{1-6}$ alkyl, C$_{3-8}$ cycloalkylC$_{1-6}$ haloalkyl, C$_{1-6}$ alkoxy, C$_{1-6}$ alkanoyl, —C(O)OC$_{1-6}$ alkyl, C$_{1-6}$ haloalkyl, C$_{3-8}$ halocycloalkyl, C$_{1-6}$ haloalkoxy, C$_{1-6}$ haloalkanoyl, —C(O)OC$_{1-6}$ haloalkyl, amino, NR$^c$R$^d$, het, phenyl, and S(O)$_n$R$^{11}$;
R$^{10}$ is halo, C$_{1-6}$ alkyl, or C$_{1-6}$ alkoxy and when R$^{10}$ is C$_{1-6}$ alkyl or C$_{1-6}$ alkoxy it may optionally be substituted with one or more halo substituents;
each of R$^c$ and R$^d$ are independently hydrogen, C$_{1-6}$ alkyl, C$_{2-6}$ alkenyl, C$_{3-8}$ cycloalkyl, C$_{3-8}$ cycloalkylC$_{1-6}$ alkyl, C$_{1-6}$ haloalkyl, C$_{3-8}$ cycloalkylC$_{1-6}$ haloalkyl, C$_{1-6}$ alkanoyl, C$_{1-6}$ haloalkanoyl, C(O)OC$_{1-6}$ alkyl, het, phenyl or S(O)$_n$R$^{11}$;
n is independently 0, 1 or 2;
R$^{11}$ is independently hydrogen, hydroxy, C$_{1-6}$ alkyl, C$_{1-6}$ haloalkyl, amino, C$_{1-6}$ alkyl amino, or di C$_{1-6}$ alkyl amino;
each phenyl may be optionally substituted by one or more further substitutents selected from the group consisting of halo, cyano, nitro, hydroxy, C$_{1-6}$ alkyl, C$_{1-6}$ haloalkyl, C$_{1-6}$ alkoxy, C$_{1-6}$ haloalkoxy, amino, C$_{1-6}$ alkyl amino, di C$_{1-6}$ alkyl amino, —NHS(O)$_n$R$^{11}$, and S(O)$_n$R$^{11}$;
and each het independently represents a four to seven membered heterocyclic ring, which is aromatic or non-aromatic, unsaturated, partially saturated or saturated and which contains one or more heteroatoms selected from nitrogen, N-oxide, oxygen, and sulphur and wherein said heterocyclic ring is optionally substituted, where the valence allows, with one or more substituents selected from the group consisting of halo, cyano, nitro, C$_{1-6}$ alkyl, C$_{1-6}$ haloalkyl, C$_{1-6}$ alkoxy, OC(O)C$_{1-6}$ alkyl, C$_{1-6}$ alkanoyl, C(O)OC$_{1-6}$ alkyl and NR$^g$R$^h$, where R$^g$ and R$^h$ are each independently selected from hydrogen, C$_{1-6}$ alkyl or C$_{2-6}$ alkenyl, and where each of the above groups may include one or more optional substituents where chemically possible independently selected from the group consisting of cyano, nitro, halo, oxo, hydroxy, C(O)OH, C(O)NR$^c$R$^d$, NR$^c$C(O)R$^d$, C$_{1-6}$ alkyl, C$_{2-6}$ alkenyl, C$_{2-6}$ alkynyl, C$_{3-8}$ cycloalkyl, C$_{3-8}$ cycloalkylC$_{1-6}$ alkyl, C$_{3-8}$ cycloalkylC$_{1-6}$ haloalkyl, C$_{1-6}$ alkoxy, C$_{1-6}$ alkanoyl, —C(O)OC$_{1-6}$ alkyl, C$_{1-6}$ haloalkyl, C$_{3-8}$ halocycloalkyl, $C_{1-6}$ haloalkoxy, $C_{1-6}$ haloalkanoyl, —C(O)O$C_{1-6}$ haloalkyl, amino, $C_{1-6}$ alkyl amino, di $C_{1-6}$ alkyl amino, phenyl and $S(O)_nR^{11}$; or a pharmaceutically acceptable salt thereof; and a pharmaceutically acceptable carrier.

2. The composition of claim 1 wherein the compound of Formula (I) is selected from:

5-amino-1-[2,6-dichloro-4-pentafluorothiophenyl]-4-[1-(methylsulfonyl)cyclopropyl]-1H-pyrazole-3-carbonitrile;

1-{5-amino-3-cyano-1-[2,6-dichloro-4-(trifluoromethyl)phenyl]-1H-pyrazol-4-yl}cyclopropanecarboxamide;

methyl 1-{5-amino-3-cyano-1-[2,6-dichloro-4-(trifluoromethyl)phenyl]-1H-pyrazol-4-yl}cyclopropane-carboxylate;

5-amino-1-[2,6-dichloro-4-(trifluoromethyl)phenyl]-4-[2,2-difluoro-1-(methylsulfonyl)cyclopropyl]-1H-pyrazole-3-carbonitrile;

1-{5-amino-3-cyano-1-[2,6-dichloro-4-(trifluoromethyl)phenyl]-1H-pyrazol-4-yl}-N,N-dimethylcyclopropanecarboxamide;

5-amino-1-[2,6-dichloro-4-(trifluoromethyl)phenyl]-4-[1-(methylsulfonyl)cyclopropyl]-1H-pyrazole-3-carbonitrile;

methyl 1-{5-amino-3-cyano-1-[2,6-dichloro-4-(trifluoromethyl)phenyl]-1H-pyrazol-4-yl}cyclopropane-carboxylate;

1-{5-amino-3-cyano-1-[2,6-dichloro-4-(trifluoromethyl)phenyl]-1H-pyrazol-4-yl}-2,2-difluoro-N,N-dimethylcyclopropanesulfonamide;

5-amino-4-(1-cyanocyclopropyl)-1-[2,6-dichloro-4-(trifluoromethyl)phenyl]-1H-pyrazole-3-carbonitrile;

5-amino-4-(1-cyanocyclopropyl)-1-[2,6-dichloro-4-pentafluorothiophenyl]-1H-pyrazole-3-carbonitrile;

1-{5-amino-3-cyano-1-[2,6-dichloro-4-(trifluoromethyl)phenyl]-1H-pyrazol-4-yl}-2,2-difluorocyclopropanesulfonamide;

1-{5-amino-3-cyano-1-[2,6-dichloro-4-pentafluorothiophenyl]-1H-pyrazol-4-yl}cyclopropanecarboxamide;

1-{3-cyano-1-[2,6-dichloro-4-pentafluorothiophenyl]-5-(isobutylamino)-1H-pyrazol-4-yl}cyclopropanecarboxamide;

1-{5-amino-3-cyano-1-[2,6-dichloro-4-pentafluorothiophenyl]-1H-pyrazol-4-yl}-N-isopropylcyclopropanecarboxamide;

1-{3-cyano-1-[2,6-dichloro-4-pentafluorothiophenyl]-5-[(2-fluoroethyl)amino]-1H-pyrazol-4-yl}cyclopropanecarboxamide;

1-{5-[(2-amino-2-oxoethyl)amino]-3-cyano-1-[2,6-dichloro-4-pentafluorothiophenyl]-1H-pyrazol-4-yl}-cyclopropanecarboxamide;

1-{5-amino-3-cyano-1-[2,6-dichloro-4-pentafluorothiophenyl]-1H-pyrazol-4-yl}-2,2-dichlorocyclopropane-carboxamide;

1-{3-cyano-5-[(cyclopropylmethyl)amino]-1-[2,6-dichloro-4-pentafluorothiophenyl]-1H-pyrazol-4-yl}-N-(pyridin-4-ylmethyl)cyclopropanecarboxamide;

isopropyl {4-[1-(aminocarbonyl)cyclopropyl]-3-cyano-1-[2,6-dichloro-4-pentafluorothiophenyl]-1H-pyrazol-5-yl}carbamate;

1-(3-cyano-1-[2,6-dichloro-4-pentafluorothiophenyl]-5-{[2-(1H-1,2,4-triazol-1-yl)ethyl]amino}-1H-pyrazol-4-yl)cyclopropanecarboxamide;

1-{3-cyano-5-[(2-cyanoethyl)amino]-1-[2,6-dichloro-4-pentafluorothiophenyl]-1H-pyrazol-4-yl}cyclopropanecarboxamide;

1-(5-amino-3-cyano-1-{2,6-dichloro-4-[1,2,2,2-tetrafluoro-1-(trifluoromethyl)ethyl]phenyl}-1H-pyrazol-4-yl)cyclopropanecarboxamide;

1-(3-cyano-1-[2,6-dichloro-4-pentafluorothiophenyl]-5-{[3-(methylthio)propyl]amino}-1H-pyrazol-4-yl)-cyclopropanecarboxamide;

1-{3-cyano-5-[(cyclopropylmethyl)amino]-1-[2,6-dichloro-4-pentafluorothiophenyl]-1H-pyrazol-4-yl}-N-[(5-methyl-4H-1,2,4-triazol-3-yl)methyl]cyclopropanecarboxamide;

1-{3-cyano-5-[(cyclopropylmethyl)(methyl)amino]-1-[2,6-dichloro-4-pentafluorothiophenyl]-1H-pyrazol-4-yl}cyclopropanecarboxamide;

[1-(fluoromethyl)cyclopropyl]methyl {4-[1-(aminocarbonyl)cyclopropyl]-3-cyano-1-[2,6-dichloro-4-pentafluorothiophenyl]-1H-pyrazol-5-yl}carbamate;

1-{3-cyano-1-[2,6-dichloro-4-pentafluorothiophenyl]-5-(methylamino)-1H-pyrazol-4-yl}-2,2-difluorocyclopropanecarboxamide;

1-{3-cyano-1-[2,6-dichloro-4-pentafluorothiophenyl]-5-[(3,3,3-trifluoropropyl)amino]-1H-pyrazol-4-yl}cyclopropanecarboxamide;

1-(5-{[(2-chloro-1,3-thiazol-5-yl)methyl]amino}-3-cyano-1-[2,6-dichloro-4-pentafluorothiophenyl]-1H-pyrazol-4-yl)cyclopropanecarboxamide;

1-{3-cyano-1-[2,6-dichloro-4-pentafluorothiophenyl]-5-[(isoxazol-5-ylmethyl)amino]-1H-pyrazol-4-yl}cyclopropanecarboxamide;

N-3-{4-[1-(aminocarbonyl)cyclopropyl]-3-cyano-1-[2,6-dichloro-4-pentafluorothiophenyl]-1H-pyrazol-5-yl}-beta-alaninamide;

1-{3-cyano-1-[2,6-dichloro-4-pentafluorothiophenyl]-5-[(5,5,5-trifluoropentyl)amino]-1H-pyrazol-4-yl}cyclopropanecarboxamide;

1-{3-cyano-1-[2,6-dichloro-4-pentafluorothiophenyl]-5-(propylamino)-1H-pyrazol-4-yl}cyclopropanecarboxamide;

1-{3-cyano-5-[(cyclobutylmethyl)amino]-1-[2,6-dichloro-4-pentafluorothiophenyl]-1H-pyrazol-4-yl}cyclopropanecarboxamide;

1-{3-cyano-5-[(cyclobutylmethyl)amino]-1-[2,6-dichloro-4-pentafluorothiophenyl]-1H-pyrazol-4-yl}cyclopropanecarboxamide;

1-{3-cyano-1-[2,6-dichloro-4-pentafluorothiophenyl]-5-(dimethylamino)-1H-pyrazol-4-yl}cyclopropanecarboxamide;

ethyl {4-[1-(aminocarbonyl)cyclopropyl]-3-cyano-1-[2,6-dichloro-4-(trifluoromethoxy)phenyl]-1H-pyrazol-5-yl}carbamate;

2,2-dichloro-1-{3-cyano-1-[2,6-dichloro-4-pentafluorothiophenyl]-5-(methylamino)-1H-pyrazol-4-yl}cyclopropanecarboxamide;

1-{5-amino-3-cyano-1-[2,6-dichloro-4-(trifluoromethoxy)phenyl]-1H-pyrazol-4-yl}-2,2-dichlorocyclopropanecarboxamide;

1-(3-cyano-5-({2-[(cyclopropylmethyl)amino]-2-oxoethyl}amino)-1-[2,6-dichloro-4-pentafluorothiophenyl]-1H-pyrazol-4-yl)cyclopropanecarboxamide;

1-{5-[(4-amino-4-oxobutyl)amino]-3-cyano-1-[2,6-dichloro-4-pentafluorothiophenyl]-1H-pyrazol-4-yl}cyclopropanecarboxamide;

1-{3-cyano-1-[2,6-dichloro-4-pentafluorothiophenyl]-5-[(1,3-thiazol-2-ylmethyl)amino]-1H-pyrazol-4-yl}-cyclopropanecarboxamide;

1-{3-cyano-5-[(cyclopropylmethyl)amino]-1-[2,6-dichloro-4-pentafluorothiophenyl]-1H-pyrazol-4-yl}-N-(2-methoxyethyl)cyclopropanecarboxamide;
1-{3-cyano-5-[(cyclopropylmethyl)amino]-1-[2,6-dichloro-4-pentafluorothiophenyl]-1H-pyrazol-4-yl}-N-(2-hydroxyethyl)cyclopropanecarboxamide;
1-{3-cyano-5-[(cyclopropylmethyl)amino]-1-[2,6-dichloro-4-pentafluorothiophenyl]-1H-pyrazol-4-yl}-N-(pyridin-2-ylmethyl)cyclopropanecarboxamide;
1-{3-cyano-5-[(cyclopropylmethyl)amino]-1-[2,6-dichloro-4-pentafluorothiophenyl]-1H-pyrazol-4-yl}-N-(pyridin-3-ylmethyl)cyclopropanecarboxamide;
1-{3-cyano-5-[(cyclopropylmethyl)amino]-1-[2,6-dichloro-4-pentafluorothiophenyl]-1H-pyrazol-4-yl}-N-(2-hydroxy-2-methylpropyl)cyclopropanecarboxamide;
1-(3-cyano-1-[2,6-dichloro-4-pentafluorothiophenyl]-5-{[2-(1-methyl-1H-pyrazol-4-yl)ethyl]amino}-1H-pyrazol-4-yl)cyclopropanecarboxamide;
1-{3-cyano-1-[2,6-dichloro-4-pentafluorothiophenyl]-5-(dimethylamino)-1H-pyrazol-4-yl}-2,2-difluorocyclopropanecarboxamide;
1-{3-cyano-1-[2,6-dichloro-4-pentafluorothiophenyl]-5-(methylthio)-1H-pyrazol-4-yl}cyclopropanecarboxamide;
1-{3-cyano-1-[2,6-dichloro-4-pentafluorothiophenyl]-5-[(2-methoxyethyl)(methyl)amino]-1H-pyrazol-4-yl}cyclopropanecarboxamide;
1-(5-{[(5-chloro-1,3-dimethyl-1H-pyrazol-4-yl)methyl]amino}-3-cyano-1-[2,6-dichloro-4-pentafluorothiophenyl]-1H-pyrazol-4-yl)cyclopropanecarboxamide;
1-{5-amino-3-cyano-1-[2,6-dichloro-4-pentafluorothiophenyl]-1H-pyrazol-4-yl}-2,2-difluorocyclopropanecarboxamide;
1-{5-amino-3-cyano-1-[2,6-dichloro-4-(trifluoromethoxy)phenyl]-1H-pyrazol-4-yl}cyclopropanecarboxamide;
1-{5-amino-3-cyano-1-[2,6-dichloro-4-(trifluoromethyl)phenyl]-1H-pyrazol-4-yl}-2,2-difluorocyclopropanecarboxamide;
1-{5-amino-3-cyano-1-[2,6-dichloro-4-pentafluorothiophenyl]-1H-pyrazol-4-yl}-N-methylcyclopropane-carboxamide;
1-{5-amino-3-cyano-1-[2,6-dichloro-4-(trifluoromethyl)phenyl]-1H-pyrazol-4-yl}-N-cyclopropylcyclopropane-carboxamide;
1-{5-amino-3-cyano-1-[2,6-dichloro-4-(trifluoromethyl)phenyl]-1H-pyrazol-4-yl}-N-(cyclopropylmethyl)-cyclopropanecarboxamide;
1-{5-amino-3-cyano-1-[2,6-dichloro-4-(trifluoromethyl)phenyl]-1H-pyrazol-4-yl}-N-pyridin-2-ylcyclopropane-carboxamide;
1-(3-cyano-1-[2,6-dichloro-4-(trifluoromethyl)phenyl]-5-{[(1E)-(dimethylamino)methylene]amino}-1H-pyrazol-4-yl)cyclopropanecarboxamide;
1-{5-amino-3-cyano-1-[2,6-dichloro-4-pentafluorothiophenyl]-1H-pyrazol-4-yl}-N-(2,2,2-trifluoroethyl)-cyclopropanecarboxamide;
1-{3-cyano-1-[2,6-dichloro-4-(trifluoromethoxy)phenyl]-5-(methylamino)-1H-pyrazol-4-yl}-2,2-difluoro-cyclopropanecarboxamide;
1-{3-cyano-1-[2,6-dichloro-4-(trifluoromethoxy)phenyl]-5-(methylamino)-1H-pyrazol-4-yl}cyclopropane-carboxamide;
1-{3-cyano-5-[(cyclopropylmethyl)amino]-1-[2,6-dichloro-4-(trifluoromethyl)phenyl]-1H-pyrazol-4-yl}-N-methylcyclopropanecarboxamide;
1-{5-amino-3-cyano-1-[2,6-dichloro-4-(trifluoromethyl)phenyl]-1H-pyrazol-4-yl}-2,2-dimethylcyclopropanecarboxamide;
1-{3-cyano-1-[2,6-dichloro-4-pentafluorothiophenyl]-5-[(4H-1,2,4-triazol-3-ylmethyl)amino]-1H-pyrazol-4-yl}cyclopropanecarboxamide;
1-(3-cyano-1-[2,6-dichloro-4-pentafluorothiophenyl]-5-{[(1-methylcyclopropyl)methyl]amino}-1H-pyrazol-4-yl)cyclopropanecarboxamide;
1-{3-cyano-1-[2,6-dichloro-4-pentafluorothiophenyl]-5-({4-[(methylamino)sulfonyl]benzyl}amino)-1H-pyrazol-4-yl}cyclopropanecarboxamide;
1-{3-cyano-1-[2,6-dichloro-4-pentafluorothiophenyl]-5-({4-[(methylsulfonyl)amino]benzyl}amino-1H-pyrazol-yl}cyclopropanecarboxamide;
1-{3-cyano-1-[2,6-dichloro-4-pentafluorothiophenyl]-5-[(tetrahydro-2H-pyran-4-ylmethyl)amino]-1H-pyrazol-4-yl}cyclopropanecarboxamide;
1-{3-cyano-5-[(cyclopropylmethyl)amino]-1-[2,6-dichloro-4-pentafluorothiophenyl]-1H-pyrazol-4-yl}-N-(3-isopropoxypropyl)cyclopropanecarboxamide;
1-{3-cyano-1-[2,6-dichloro-4-pentafluorothiophenyl]-5-({2-oxo-2-[(2,2,2-trifluoroethyl)amino]ethyl}amino)-1H-pyrazol-4-yl}cyclopropanecarboxamide;
5-amino-1-[2,6-dichloro-4-(trifluoromethyl)phenyl]-4-[2,2-difluoro-1-(methylthio)cyclopropyl]-1H-pyrazole-3-carbonitrile;
1-{3-cyano-5-[(cyclopropylmethyl)amino]-1-[2,6-dichloro-4-(trifluoromethyl)phenyl]-1H-pyrazol-4-yl}cyclopropanecarboxamide;
1-{5-(benzylamino)-3-cyano-1-[2,6-dichloro-4-(trifluoromethyl)phenyl]-1H-pyrazol-4-yl}cyclopropanecarboxamide;
1-{3-cyano-1-[2,6-dichloro-4-(trifluoromethyl)phenyl]-5-[(pyridin-2-ylmethyl)amino]-1H-pyrazol-4-yl}cyclopropanecarboxamide;
1-{3-cyano-1-[2,6-dichloro-4-(trifluoromethyl)phenyl]-5-[(2,2-dimethylpropyl)amino]-1H-pyrazol-4-yl}cyclopropanecarboxamide;
1-(3-cyano-1-[2,6-dichloro-4-(trifluoromethyl)phenyl]-5-{[4-(methylsulfonyl)benzyl]amino}-1H-pyrazol-4-yl)cyclopropanecarboxamide;
1-{3-cyano-1-[2,6-dichloro-4-(trifluoromethyl)phenyl]-5-[(pyridin-4-ylmethyl)amino]-1H-pyrazol-4-yl}cyclopropanecarboxamide;
1-{3-cyano-1-[2,6-dichloro-4-(trifluoromethyl)phenyl]-5-[(2,2,2-trifluoroethyl)amino]-1H-pyrazol-4-yl}cyclopropanecarboxamide;
1-{3-cyano-1-[2,6-dichloro-4-(trifluoromethyl)phenyl]-5-[(1H-imidazol-2-ylmethyl)amino]-1H-pyrazol-4-yl}cyclopropanecarboxamide;
1-{3-cyano-1-[2,6-dichloro-4-pentafluorothiophenyl]-1H-pyrazol-4-yl}-2,2-difluorocyclopropanecarboxamide;
1-{3-cyano-1-[2,6-dichloro-4-pentafluorothiophenyl]-1H-pyrazol-4-yl}cyclopropanecarboxamide;
1-{5-chloro-3-cyano-1-[2,6-dichloro-4-pentafluorothiophenyl]-1H-pyrazol-4-yl}cyclopropanecarboxamide;
1-{5-chloro-3-cyano-1-[2,6-dichloro-4-pentafluorothiophenyl]-1H-pyrazol-4-yl}-2,2-difluorocyclopropane-carboxamide;

1-{5-amino-3-cyano-1-[2,6-dichloro-4-(trifluoromethyl)phenyl]-1H-pyrazol-4-yl}-2,2-dimethylcyclopropanecarboxylic acid;

1-{3-cyano-1-[2,6-dichloro-4-pentafluorothiophenyl]-5-(methylamino)-1H-pyrazol-4-yl}cyclopropane-carboxamide;

cyclopropylmethyl {4-[1-(aminocarbonyl)cyclopropyl]-3-cyano-1-[2,6-dichloro-4-pentafluorothiophenyl]-1H-pyrazol-5-yl}carbamate;

ethyl {4-[1-(aminocarbonyl)cyclopropyl]-3-cyano-1-[2,6-dichloro-4-pentafluorothiophenyl]-1H-pyrazol-5-yl}methylcarbamate;

1-[({4-[1-(aminocarbonyl)cyclopropyl]-3-cyano-1-[2,6-dichloro-4-pentafluorothiophenyl]-1H-pyrazol-5-yl}amino)methyl]cyclopropanecarboxamide;

1-{3-cyano-1-[2,6-dichloro-4-pentafluorothiophenyl]-5-methyl-1H-pyrazol-4-yl}cyclopropanecarboxamide;

1-{3-cyano-5-[(cyclopropylmethyl)amino]-1--[2,6-dichloro-4-(trifluoromethoxy)phenyl]-1H-pyrazol-4-yl}-cyclopropanecarboxamide;

1-{3-cyano-1-[2,6-dichloro-4-pentafluorothiophenyl]-5-[(2-fluoro-2-methylpropyl)amino]-1H-pyrazol-4-yl}cyclopropanecarboxamide;

methyl {4-[1-(aminocarbonyl)cyclopropyl]-3-cyano-1-[2,6-dichloro-4-pentafluorothiophenyl]-1H-pyrazol-5-yl}carbamate;

1-{5-amino-3-cyano-1-[2,6-dichloro-4-(trifluoromethoxy)phenyl]-1H-pyrazol-4-yl}-2,2-difluorocyclopropane-carboxamide;

ethyl {4-[1-(aminocarbonyl)cyclopropyl]-3-cyano-1-[2,6-dichloro-4-pentafluorothiophenyl]-1H-pyrazol-5-yl}carbamate;

cyclopropylmethyl {4-[1-(aminocarbonyl)cyclopropyl]-3-cyano-1-[2,6-dichloro-4-pentafluorothiophenyl]-1H-pyrazol-5-yl}methylcarbamate;

1-{3-cyano-1-[2,6-dichloro-4-pentafluorothiophenyl]-5-[(4,4,4-trifluorobutyl)amino]-1H-pyrazol-4-yl}-cyclopropanecarboxamide;

1-{3-cyano-1-[2,6-dichloro-4-pentafluorothiophenyl]-5-(ethylamino)-1H-pyrazol-4-yl}cyclopropanecarboxamide;

tert-butyl {1-[({4-[1-(aminocarbonyl)cyclopropyl]-3-cyano-1-[2,6-dichloro-4-pentafluorothiophenyl]-1H-pyrazol-5-yl}amino)methyl]cyclopropyl}carbamate;

1-(3-cyano-1-[2,6-dichloro-4-(trifluoromethyl)phenyl]-5-{[4-(trifluoromethyl)benzyl]amino}-1H-pyrazol-4-yl)cyclopropanecarboxamide;

1-{3-cyano-1-[2,6-dichloro-4-pentafluorothiophenyl]-5-[(2-isopropoxyethyl)amino]-1H-pyrazol-4-yl}cyclopropanecarboxamide;

1-{3-cyano-1-[2,6-dichloro-4-pentafluorothiophenyl]-5-vinyl-1H-pyrazol-4-yl}cyclopropanecarboxamide;

cyclobutyl {4-[1-(aminocarbonyl)cyclopropyl]-3-cyano-1-[2,6-dichloro-4-pentafluorothiophenyl]-1H-pyrazol-5-yl}carbamate;

1-{3-cyano-1-[2,6-dichloro-4-pentafluorothiophenyl]-5-[(4-fluorobenzyl)amino]-1H-pyrazol-4-yl}cyclopropane-carboxamide;

ethyl {4-[1-(aminocarbonyl)cyclopropyl]-3-cyano-1-[2,6-dichloro-4-(trifluoromethyl)phenyl]-1H-pyrazol-5-yl}carbamate;

1-{3-cyano-5-[(cyclopropylmethyl)amino]-1-[2,6-dichloro-4-pentafluorothiophenyl]-1H-pyrazol-4-yl}cyclopropanecarboxamide;

methyl 1-{5-(benzylamino)-3-cyano-1-[2,6-dichloro-4-(trifluoromethyl)phenyl]-1H-pyrazol-4-yl}cyclopropanecarboxylate;

1-{3-cyano-5-[(cyclopropylmethyl)amino]-1-[2,6-dichloro-4-pentafluorothiophenyl]-1H-pyrazol-4-yl}-2,2-difluorocyclopropanecarboxamide;

1-{3-cyano-5-[(cyclopropylmethyl)amino]-1-[2,6-dichloro-4-(trifluoromethyl)phenyl]-1H-pyrazol-4-yl}-2,2-difluorocyclopropanecarboxamide;

4-(1-cyanocyclopropyl)-1-[2,6-dichloro-4-pentafluorothiophenyl]-5-(methylamino)-1H-pyrazole-3-carbonitrile;

1-{5-amino-3-cyano-1-[2,6-dichloro-4-(trifluoromethyl)phenyl]-1H-pyrazol-4-yl}cyclopropanecarbothioamide;

5-amino-1-[2,6-dichloro-4-(trifluoromethyl)phenyl]-4-[1-(1,3-thiazol-2-yl)cyclopropyl]-1H-pyrazole-3-carbonitrile;

1-{5-amino-3-cyano-1-[2,6-dichloro-4-pentafluorothiophenyl]-1H-pyrazol-4-yl}-N-(methylsulfonyl)-cyclopropanecarboxamide;

1-{3-cyano-5-[(2-cyclopropylethyl)amino]-1-[2,6-dichloro-4-pentafluorothiophenyl]-1H-pyrazol-4-yl}cyclopropanecarboxamide;

5 amino-1-[2,6-dichloro-4-(trifluoromethyl)phenyl]-4-[2,2-difluoro-1-(methylsulfinyl)cyclopropyl]-1H-pyrazole-3-carbonitrile;

5-amino-1-[2,6-dichloro-4-(trifluoromethyl)phenyl]-4-[2,2-difluoro-1-(methylsulfinyl)cyclopropyl]-1H-pyrazole-3-carbonitrile;

1-{3-cyano-1-[2,6-dichloro-4-pentafluorothiophenyl]-5-(isopropylamino)-1H-pyrazol-4-yl}cyclopropane-carboxamide;

1-{3-cyano-1-[2,6-dichloro-4-(trifluoromethoxy)phenyl]-5-(isopropylamino)-1H-pyrazol-4-yl}-2,2-difluorocyclopropanecarboxamide;

4-(1-cyanocyclopropyl)-5-[(cyclopropylmethyl)amino]-1-[2,6-dichloro-4-pentafluorothiophenyl]-1H-pyrazole-3-carbonitrile;

1-{3-cyano-1-[2,6-dichloro-4-pentafluorothiophenyl]-5-[({1-[(methylsulfonyl)amino]cyclopropyl}methyl)amino]-1H-pyrazol-4-yl}cyclopropanecarboxamide;

1-(5-{[(1-aminocyclopropyl)methyl]amino}-3-cyano-1-[2,6-dichloro-4-pentafluorothiophenyl]-1H-pyrazol-4-yl)cyclopropanecarboxamide;

1-{3-cyano-1-[2,6-dichloro-4-pentafluorothiophenyl]-5-(methylsulfinyl)-1H-pyrazol-4-yl}cyclopropanecarboxamide;

1-{3-cyano-1-[2,6-dichloro-4-pentafluorothiophenyl]-5-(methylsulfonyl)-1H-pyrazol-4-yl}cyclopropanecarboxamide; and 4-({4-[1-(aminocarbonyl)cyclopropyl]-3-cyano-1-[2,6-dichloro-4-pentafluorothiophenyl]-1H-pyrazol-5-yl}amino)butanoic acid;

or a pharmaceutically acceptable salt thereof, and a pharmaceutically acceptable carrier.

3. A method of treating a parasitic infection comprising treating an animal with an effective amount of a compound of Formula (I)

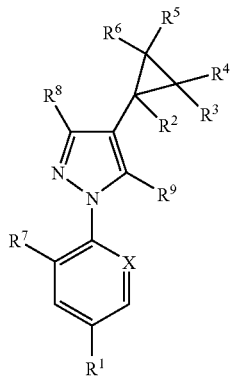

wherein
X is $CR^{10}$;
$R^1$ is $C_{1-6}$ haloalkyl, $C_{1-6}$ haloalkoxy, or $SF_5$;
$R^2$ is cyano, C(O)OH, het, $S(O)_nR^{11}$, $C(O)NR^aR^b$, $C(S)NR^aR^b$, or $C(O)OC_{1-6}$ alkyl;
$R^a$ and $R^b$ are each independently hydrogen or $S(O)_nR^{11}$;
or either one or both of $R^a$ and $R^b$ are independently $C_{1-6}$ alkyl, $C_{2-6}$ alkenyl, $C_{3-8}$ cycloalkyl, $C_{3-8}$ cycloalkyl$C_{1-6}$ alkyl, $C_{1-6}$ alkanoyl, or $C(O)OC_{1-6}$ alkyl, each of which $R^a$ or $R^b$ may be optionally and independently further substituted by one or more substituents selected from the group consisting of, where chemically possible, cyano, nitro, halo, oxo, hydroxy, C(O)OH, $C(O)NR^cR^d$, $NR^cC(O)R^d$, $C_{1-6}$ alkyl, $C_{2-6}$ alkenyl, $C_{2-6}$ alkynyl, $C_{3-8}$ cycloalkyl, $C_{3-8}$ cycloalkyl$C_{1-6}$ alkyl, $C_{3-8}$ cycloalkyl$C_{1-6}$ haloalkyl, $C_{1-6}$ alkoxy, $C_{1-6}$ alkanoyl, —$C(O)OC_{1-6}$ alkyl, $C_{1-6}$ haloalkyl, $C_{3-8}$ halocycloalkyl, $C_{1-6}$ haloalkoxy, $C_{1-6}$ haloalkanoyl, —$C(O)OC_{1-6}$ haloalkyl, amino, $NR^cR^d$, het, phenyl, and $S(O)_nR^{11}$;
$R^3$, $R^4$, $R^5$ and $R^6$ are each independently selected from hydrogen, halo, cyano, hydroxy, C(O)OH, nitro, phenyl, or $S(O)_nR^{11}$;
$R^7$ is fluoro or chloro;
$R^8$ is cyano;
$R^9$ is hydrogen, halo, —$S(O)_nR^{11}$, $NR^eR^f$, $C_{1-6}$ alkyl, $C_{2-6}$ alkenyl, $C_{1-6}$ alkoxy, or —$C_{3-8}$ cycloalkyl$C_{1-6}$ alkoxy;
$R^e$ and $R^f$ are each independently hydrogen, het, phenyl or $S(O)_nR^{11}$;
or either one or both of $R^e$ and $R^f$ are independently $C_{1-6}$ alkyl, $C_{2-6}$ alkenyl, $C_{3-8}$ cycloalkyl, $C_{3-8}$ cycloalkyl$C_{1-6}$ alkyl, $C_{1-6}$ alkanoyl, $C(O)OC_{1-6}$ alkyl, —$C(O)OC_{1-6}$ alkyl$C_{3-8}$ cycloalkyl, or —$C(O)OC_{3-8}$ cycloalkyl, each of which $R^e$ or $R^f$ may be optionally and independently further substituted by one or more substituents selected from the group consisting of, where chemically possible, cyano, nitro, halo, oxo, hydroxy, C(O)OH, —$C(O)NR^cR^d$, $NR^cC(O)R^d$, $C_{1-6}$ alkyl, $C_{2-6}$ alkenyl, $C_{2-6}$ alkynyl, $C_{3-8}$ cycloalkyl, $C_{3-8}$ cycloalkyl$C_{1-6}$ alkyl, $C_{3-8}$ cycloalkyl$C_{1-6}$ haloalkyl, $C_{1-6}$ alkoxy, $C_{1-6}$ alkanoyl, —$C(O)OC_{1-6}$ alkyl, $C_{1-6}$ haloalkyl, $C_{3-8}$ halocycloalkyl, $C_{1-6}$ haloalkoxy, $C_{1-6}$ haloalkanoyl, —$C(O)OC_{1-6}$ haloalkyl, amino, $NR^cR^d$, het, phenyl, and $S(O)_nR^{11}$;
$R^{10}$ is halo, $C_{1-6}$ alkyl, or $C_{1-6}$ alkoxy and when $R^{10}$ is $C_{1-6}$ alkyl or $C_{1-6}$ alkoxy it may optionally be substituted with one or more halo substituents;
each of $R^c$ and $R^d$ are independently hydrogen, $C_{1-6}$ alkyl, $C_{2-6}$ alkenyl, $C_{3-8}$ cycloalkyl, $C_{3-8}$ cycloalkyl$C_{1-6}$ alkyl, haloalkyl, $C_{3-8}$ cycloalkyl$C_{1-6}$ haloalkyl, $C_{1-6}$ alkanoyl, $C_{1-6}$ haloalkanoyl, $C(O)OC_{1-6}$ alkyl, het, phenyl or $S(O)_nR^{11}$;
n is independently 0, 1 or 2;
$R^{11}$ is independently hydrogen, hydroxy, $C_{1-6}$ alkyl, $C_{1-6}$ haloalkyl, amino, $C_{1-6}$ alkyl amino, or di $C_{1-6}$ alkyl amino;
each phenyl may be optionally substituted by one or more further substitutents selected from the group consisting of halo, cyano, nitro, hydroxy, $C_{1-6}$ alkyl, $C_{1-6}$ haloalkyl, $C_{1-6}$ alkoxy, $C_{1-6}$ haloalkoxy, amino, $C_{1-6}$ alkyl amino, di $C_{1-6}$ alkyl amino, —$NHS(O)_nR^{11}$, and $S(O)_nR^{11}$;
and each het independently represents a four to seven membered heterocyclic ring, which is aromatic or non-aromatic, unsaturated, partially saturated or saturated and which contains one or more heteroatoms selected from nitrogen, N-oxide, oxygen, and sulphur and wherein said heterocyclic ring is optionally substituted, where the valence allows, with one or more substituents selected from the group consisting of halo, cyano, nitro, $C_{1-6}$ alkyl, $C_{1-6}$ haloalkyl, $C_{1-6}$ alkoxy, $OC(O)C_{1-6}$ alkyl, $C_{1-6}$ alkanoyl, $C(O)OC_{1-6}$ alkyl and $NR^gR^h$, where $R^g$ and $R^h$ are each independently selected from hydrogen, $C_{1-6}$ alkyl or $C_{2-6}$ alkenyl, and where each of the above groups may include one or more optional substituents where chemically possible independently selected from the group consisting of cyano, nitro, halo, oxo, hydroxy, C(O)OH, $C(O)NR^cR^d$, $NR^cC(O)R^d$, $C_{1-6}$ alkyl, $C_{2-6}$ alkenyl, $C_{2-6}$ alkynyl, $C_{3-8}$ cycloalkyl, $C_{3-8}$ cycloalkyl$C_{1-6}$ alkyl, $C_{3-8}$ cycloalkyl$C_{1-6}$ haloalkyl, $C_{1-6}$ alkoxy, $C_{1-6}$ alkanoyl, —$C(O)OC_{1-6}$ alkyl, $C_{1-6}$ haloalkyl, $C_{3-8}$ halocycloalkyl, $C_{1-6}$ haloalkoxy, $C_{1-6}$ haloalkanoyl, —$C(O)OC_{1-6}$ haloalkyl, amino, $C_{1-6}$ alkyl amino, di $C_{1-6}$ alkyl amino, phenyl and $S(O)_nR^{11}$; or a pharmaceutically acceptable salt thereof.

* * * * *